United States Patent
Huang et al.

(10) Patent No.: US 11,958,805 B2
(45) Date of Patent: Apr. 16, 2024

(54) SOLID FORMS COMPRISING AN OXIME ETHER COMPOUND, COMPOSITIONS AND METHODS OF USE THEREOF

(71) Applicant: Novartis AG, Basel (CH)

(72) Inventors: Lianfeng Huang, Basking Ridge, NJ (US); Daozhong Zou, Raritan, NJ (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/996,720

(22) Filed: Aug. 18, 2020

(65) Prior Publication Data
US 2020/0377454 A1 Dec. 3, 2020

Related U.S. Application Data

(63) Continuation of application No. 15/915,958, filed on Mar. 8, 2018, now abandoned.

(60) Provisional application No. 62/572,137, filed on Oct. 13, 2017, provisional application No. 62/469,154, filed on Mar. 9, 2017.

(51) Int. Cl.
| C07D 205/04 | (2006.01) |
| A61P 17/06 | (2006.01) |
| A61P 21/00 | (2006.01) |
| A61P 25/00 | (2006.01) |

(52) U.S. Cl.
CPC .......... C07D 205/04 (2013.01); A61P 17/06 (2018.01); A61P 21/00 (2018.01); A61P 25/00 (2018.01); C07B 2200/13 (2013.01)

(58) Field of Classification Search
None
See application file for complete search history.

(56) References Cited

U.S. PATENT DOCUMENTS

| 7,939,519 B2 | 5/2011 | Pan et al. |
| 8,173,634 B2 | 5/2012 | Liu et al. |
| 8,486,930 B2 * | 7/2013 | De La Cruz ......... A61K 31/397 |
| | | 548/953 |
| 8,697,682 B2 * | 4/2014 | De La Cruz ............ A61P 21/00 |
| | | 514/210.17 |
| 11,434,200 B2 | 9/2022 | Huang et al. |
| 11,629,124 B2 | 4/2023 | Huang et al. |
| 2012/0115840 A1 * | 5/2012 | Ciszewski ............... A61P 29/00 |
| | | 514/210.17 |
| 2019/0047951 A1 * | 2/2019 | Zhang .................. C07D 205/04 |
| 2021/0323915 A1 | 10/2021 | Ciszewski et al. |
| 2022/0402870 A1 | 12/2022 | Ciszewski et al. |

FOREIGN PATENT DOCUMENTS

WO WO2017009437 * 1/2017

OTHER PUBLICATIONS

"Table II—FDA-Approved Commercially Marketed Salts", Remington's Pharmaceutical Science, (17th Edition), Gennaro, A. R., Editor, Mack Publishing COmpany, Easton, PA 18042, (1985), p. 1418.*
Berge et al., Pharmaceutical Salts. Journal of Pharmaceutical Sciences, 1977, 66, 1-19.*
Aitipamula et al., Polymorphs, Salts, and Cocrystals: What's in a Name? Crystal Growth & Design, 2012, 12, 2147-2152.*
Prescribing Information for Mayzent® (siponimod) tablets 26 pages (first accessed online on Aug. 13, 2022.).

* cited by examiner

*Primary Examiner* — Po-Chih Chen
(74) *Attorney, Agent, or Firm* — Adil R. Zhugralin

(57) ABSTRACT

Provided herein are formulations, processes, solid forms and methods of use relating to (E)-1-(4-(1-(((4-cyclohexyl-3-(trifluoromethyl)benzyl)oxy)imino)ethyl)-2-ethylbenzyl)azetidine-3-carboxylic acid.

38 Claims, 132 Drawing Sheets

SOLID FORMS COMPRISING AN OXIME ETHER COMPOUND, COMPOSITIONS AND METHODS OF USE THEREOF

This application is a Continuation of U.S. Non-provisional application Ser. No. 15/915,958, filed on Mar. 8, 2018, which claims the benefit of U.S. Provisional Application No. 62/572,137, filed on Oct. 13, 2017, and U.S. Provisional Application No. 62/469,154, filed on Mar. 9, 2017, each of which is incorporated herein by reference in its entirety.

1. FIELD

Provided herein are solid forms comprising salts of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. Pharmaceutical compositions comprising such solid forms and methods of use of such solid forms for treating, preventing, and managing various disorders are also provided herein.

2. BACKGROUND

When the immune system functions normally, it produces a response intended to protect against harmful or foreign substances such as bacteria, parasites, and cancerous cells. Autoimmune diseases arise when the immune system attacks one or more of the body's normal constituents as if they were a foreign substance. These attacks cause inflammation and tissue damage that may lead to autoimmune disorders. There are more than 80 diseases that occur as a result of the body's autoimmune response to various harmful or foreign substances, affecting more than 23.5 million people in the United States. Some of the most common types of autoimmune or chronic inflammatory diseases include Graves' disease, Type 1 diabetes, multiple sclerosis, inflammatory bowel disease, systemic lupus, polymyositis, dermatomyositis, lupus nephritis, rheumatoid arthritis, and psoriasis.

Multiple Sclerosis ("MS") is an autoimmune disease of the central nervous system, characterized by degeneration of the protective sheath ("myelin") that covers nerve fibers in the brain and spinal cord. More than 2.5 million people in the world suffer from MS, and it is the most common neurologic, disabling disease in young adults. Diagnosis is generally made between 15 and 50 years of age, with symptoms either occurring in recurring, isolated attacks (i.e., relapsing forms) or symptoms increasing over time (i.e., progressive forms). Permanent neurological dysfunction can result from incomplete recovery from acute relapses or as a consequence of slow progression of disability.

There is a need in the art for novel drug products for the treatment of MS and other autoimmune diseases of the central nervous systems. Alternative solid forms of pharmaceutical compounds have emerged as a possible approach to modulate or enhance the physical and chemical properties of drug products. The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solid forms include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Notably, it is not possible to predict apriori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

The type of salt form of a particular active pharmaceutical ingredient may affect certain properties of the active pharmaceutical ingredient. These properties include solubility, stability, and bioavailability. Accordingly, solubility and stability assays of the salts described herein are provided in Section 6.3.

3. SUMMARY

Provided herein are solid forms comprising salts of Compound 1 (e.g., crystalline forms, amorphous forms, polymorphs or mixtures thereof):

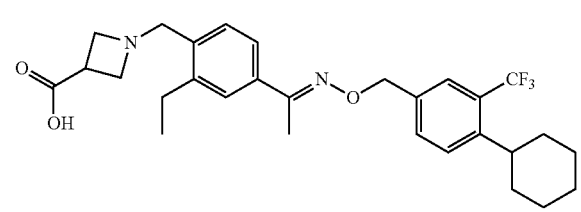

1 having the name (E)-1-(4-(1-(((4-cyclohexyl-3-(trifluoromethyl)benzyl)oxy)imino)ethyl)-2-ethylbenzyl)azetidine-3-carboxylic acid, including tautomers thereof. Also provided herein are methods of preparing, isolating, and characterizing the solid forms.

Provided herein is a solid form comprising Compound 2, or tautomer thereof, which is an HCl salt of (E)-1-(4-(1-(((4-cyclohexyl-3-(trifluoromethyl)benzyl)oxy)imino)

ethyl)-2-ethylbenzyl)azetidine-3-carboxylic acid, which has an X-ray powder diffraction pattern comprising at least three characteristic peaks at about 8.2, 12.3, 15.8 or 20.5° 2θ (±0.2° 2θ). In certain embodiments, the solid form has an X-ray powder diffraction pattern comprising four characteristic peaks at about 8.2, 12.3, 15.8 or 20.5° 2θ (±0.2° 2θ). In certain embodiments, the solid form has an X-ray powder diffraction pattern substantially as shown in FIG. 5. In certain embodiments, the solid form has a DSC thermogram comprising multiple endotherms with onset temperatures at 32.7° C., 81.3° C., and 146.6° C. In certain embodiments, the solid form is hydrated.

In another embodiment, provided herein is solid form comprising Compound 4, or tautomer thereof, which is an oxalate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.5, 7.0, 16.1, 18.1 or 30.1° 2θ (±0.2° 2θ). In certain embodiments, the solid form has an X-ray powder diffraction pattern comprising at least four characteristic peaks at about 3.5, 7.0, 16.1, 18.1 or 30.1° 2θ (±0.2° 2θ). In certain embodiments, the solid form has an X-ray powder diffraction pattern comprising five characteristic peaks at about 3.5, 7.0, 16.1, 18.1 or 30.1° 2θ (±0.2° 2θ). In certain embodiments, the solid form has an X-ray powder diffraction pattern substantially as shown in FIG. 21. In certain embodiments, the solid form has a DSC thermogram comprising multiple endotherms with onset temperatures at 102.6° C. and 139.2° C. In certain embodiments, the solid form is non-solvated.

In another embodiment, provided herein is a solid form comprising Compound 4, or tautomer thereof, which is an oxalate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 2.4, 4.8, 9.6, 14.3, 21.6 or 24.0° 2θ (±0.2° 2θ). In certain embodiments, the solid form has an X-ray powder diffraction pattern comprising at least four characteristic peaks at about 2.4, 4.8, 9.6, 14.3, 21.6 or 24.0° 2θ (±0.2° 2θ). In certain embodiments, the solid form has an X-ray powder diffraction pattern comprising at least five characteristic peaks at about 2.4, 4.8, 9.6, 14.3, 21.6 or 24.0° 2θ (±0.2° 2θ). In certain embodiments, the solid form has an X-ray powder diffraction pattern substantially as shown in FIG. 25. In certain embodiments, the solid form has a DSC thermogram comprising an endotherm with an onset temperature at 90.8° C. In certain embodiments, the solid form is hydrated. In certain embodiments, the solid form is solvated by tetrahydrofuran.

In another embodiment, provided herein is a solid form comprising Compound 5, or tautomer thereof, which is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 2.7, 5.2, 6.7, 13.4 or 20.2° 2θ (±0.2° 2θ). In certain embodiments, the solid form has an X-ray powder diffraction pattern comprising at least four characteristic peaks at about 2.7, 5.2, 6.7, 13.4 or 20.2° 2θ (±0.2° 2θ). In certain embodiments, the solid form has an X-ray powder diffraction pattern comprising five characteristic peaks at about 2.7, 5.2, 6.7, 13.4 or 20.2° 2θ (±0.2° 2θ). In certain embodiments, the solid form has an X-ray powder diffraction pattern substantially as shown in FIG. 33. In certain embodiments, the solid form has a DSC thermogram comprising multiple endotherms with onset temperatures at 39° C. and 131° C. In certain embodiments, the solid form is hydrated.

In another embodiment, provided herein is a solid form comprising Compound 5, or tautomer thereof, which is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.4, 6.9, 10.5, 13.9, or 20.8° 2θ (±0.2° 2θ). In certain embodiments, the solid form has an X-ray powder diffraction pattern comprising at least four characteristic peaks at about 3.4, 6.9, 10.5, 13.9, or 20.8° 2θ (±0.2° 2θ). In certain embodiments, the solid form has an X-ray powder diffraction pattern comprising at least five characteristic peaks at about 3.4, 6.9, 10.5, 13.9, or 20.8° 2θ (±0.2° 2θ). In certain embodiments, the solid form has an X-ray powder diffraction pattern substantially as shown in FIG. 94. In certain embodiments, the solid form has a DSC thermogram comprising an endotherm with an onset temperature at 65° C. In certain embodiments, the solid form is hydrated.

In another embodiment, provided herein is a solid form comprising Compound 5, or tautomer thereof, which is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 12.5, 13.8, 14.8, 16.8, 23.8, 25.2, or 33.6° 2θ (±0.2° 2θ). In certain embodiments, the solid form has an X-ray powder diffraction pattern comprising at least four characteristic peaks at about 12.5, 13.8, 14.8, 16.8, 23.8, 25.2, or 33.6° 2θ (±0.2° 2θ). In certain embodiments, the solid form has an X-ray powder diffraction pattern comprising at least five characteristic peaks at about 12.5, 13.8, 14.8, 16.8, 23.8, 25.2, or 33.6° 2θ (±0.2° 2θ). In certain embodiments, the solid form has an X-ray powder diffraction pattern comprising at least six characteristic peaks at about 12.5, 13.8, 14.8, 16.8, 23.8, 25.2, or 33.6° 2θ (±0.2° 2θ). In certain embodiments, the solid form has an X-ray powder diffraction pattern comprising at least seven characteristic peaks at about 12.5, 13.8, 14.8, 16.8, 23.8, 25.2, or 33.6° 2θ (±0.2° 2θ). In certain embodiments, the solid form has an X-ray powder diffraction pattern substantially as shown in FIG. 98. In certain embodiments, the solid form has a DSC thermogram comprising an endotherm with an onset temperature at 107° C. In certain embodiments, the solid form is hydrated.

In another embodiment, provided herein is a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 5.4, 7.1, 8.1, 13.5, 15.8, 17.5, 21.4, or 23.5° 2θ (±0.2° 2θ). In certain embodiments, the solid form has an X-ray powder diffraction pattern comprising at least four characteristic peaks at about 5.4, 7.1, 8.1, 13.5, 15.8, 17.5, 21.4, or 23.5° 2θ (±0.2° 2θ). In certain embodiments, the solid form has an X-ray powder diffraction pattern comprising at least five characteristic peaks at about 5.4, 7.1, 8.1, 13.5, 15.8, 17.5, 21.4, or 23.5° 2θ (±0.2° 2θ). In certain embodiments, the solid form has an X-ray powder diffraction pattern comprising at least six characteristic peaks at about 5.4, 7.1, 8.1, 13.5, 15.8, 17.5, 21.4, or 23.5° 2θ (±0.2° 2θ). In certain embodiments, the solid form has an X-ray powder diffraction pattern substantially as shown in FIG. 45. In certain embodiments, the solid form has a DSC thermogram comprising an endotherm with an onset temperature at 122.7° C.

In another embodiment, provided herein is a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 2.8, 11.1, 19.4, 20.8, 22.3, or 23.4° 2θ (±0.2° 2θ). In certain embodiments, the solid form has an X-ray powder diffraction pattern comprising at least four characteristic peaks at about 2.8, 11.1, 19.4, 20.8, 22.3, or 23.4° 2θ (±0.2° 2θ). In certain embodiments, the solid form has an X-ray powder diffraction pattern comprising at least five characteristic peaks at about 2.8, 11.1, 19.4, 20.8, 22.3, or 23.4° 2θ (±0.2° 2θ). In certain embodiments, the solid form has an X-ray powder diffraction pattern comprising at least six characteristic peaks at about 2.8, 11.1, 19.4, 20.8, 22.3, or 23.4° 2θ (±0.2° 2θ). In certain embodiments, the solid form has an X-ray powder diffraction pattern substantially as shown in FIG. 102. In certain embodiments, the solid form has a DSC thermogram comprising an endotherm between 50 and 110° C. with a peak temperature at 91° C., and a large endotherm with an onset temperature at 143° C.

In another embodiment, provided herein is a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.0, 18.1, 19.5, 19.9, or 21.5° 2θ (±0.2° 2θ). In certain embodiments, the solid form has an X-ray powder diffraction pattern comprising at least four characteristic peaks at about 7.0, 18.1, 19.5, 19.9, or 21.5° 2θ (±0.2° 2θ). In certain embodiments, the solid form has an X-ray powder diffraction pattern comprising at least five characteristic peaks at about 7.0, 18.1, 19.5, 19.9, or 21.5° 2θ (±0.2° 2θ). In certain embodiments, the solid form has an X-ray powder diffraction pattern substantially as shown in FIG. 106. In certain embodiments, the solid form has a DSC thermogram comprising an endotherm with an onset temperature at 134° C.

In another embodiment, provided herein is a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.0, 15.8, 17.6, 21.8, or 23.9° 2θ (±0.2° 2θ). In certain embodiments, the solid form has an X-ray powder diffraction pattern comprising at least four characteristic peaks at about 7.0, 15.8, 17.6, 21.8, or 23.9° 2θ (±0.2° 2θ). In certain embodiments, the solid form has an X-ray powder diffraction pattern comprising at least five characteristic peaks at about 7.0, 15.8, 17.6, 21.8, or 23.9° 2θ (±0.2° 2θ). In certain embodiments, the solid form has an X-ray powder diffraction pattern substantially as shown in FIG. 110. In certain embodiments, the solid form has a DSC thermogram comprising an endotherm between 45° C. and 140° C. with a peak temperature at 106° C.

In another embodiment, provided herein is a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.0, 10.7, 12.2, 17.6, 20.8, 21.0, or 24.0° 2θ (±0.2° 2θ). In certain embodiments, the solid form has an X-ray powder diffraction pattern comprising at least four characteristic peaks at about 7.0, 10.7, 12.2, 17.6, 20.8, 21.0, or 24.0° 2θ (±0.2° 2θ). In certain embodiments, the solid form has an X-ray powder diffraction pattern comprising at least five characteristic peaks at about 7.0, 10.7, 12.2, 17.6, 20.8, 21.0, or 24.0° 2θ (±0.2° 2θ). In certain embodiments, the solid form has an X-ray powder diffraction pattern comprising at least six characteristic peaks at about 7.0, 10.7, 12.2, 17.6, 20.8, 21.0, or 24.0° 2θ (±0.2° 2θ). In certain embodiments, the solid form has an X-ray powder diffraction pattern comprising seven characteristic peaks at about 7.0, 10.7, 12.2, 17.6, 20.8, 21.0, or 24.0° 2θ (±0.2° 2θ). In certain embodiments, the solid form has an X-ray powder diffraction pattern substantially as shown in FIG. 126. In certain embodiments, the solid form has a DSC thermogram comprising multiple endotherms with onset temperatures at 80.4° C. and 149.7° C.

In another embodiment, provided herein is a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 8.0, 11.6, 13.5, 15.8, 17.6, 21.4, or 23.5° 2θ (±0.2° 2θ). In certain embodiments, the solid form has an X-ray powder diffraction pattern comprising at least four characteristic peaks at about 8.0, 11.6, 13.5, 15.8, 17.6, 21.4, or 23.5° 2θ (±0.2° 2θ). In certain embodiments, the solid form has an X-ray powder diffraction pattern comprising at least five characteristic peaks at about 8.0, 11.6, 13.5, 15.8, 17.6, 21.4, or 23.5° 2θ (±0.2° 2θ). In certain embodiments, the solid form has an X-ray powder diffraction pattern comprising at least six characteristic peaks at about 8.0, 11.6, 13.5, 15.8, 17.6, 21.4, or 23.5° 2θ (±0.2° 2θ). In certain embodiments, the solid form has an X-ray powder diffraction pattern comprising seven characteristic peaks at about 8.0, 11.6, 13.5, 15.8, 17.6, 21.4, or 23.5° 2θ (±0.2° 2θ). In certain embodiments, the solid form has an X-ray powder diffraction pattern substantially as shown in FIG. 130. In certain embodiments, the solid form has a DSC thermogram comprising an endotherm with a peak temperature of approximately 140.9° C.

In another embodiment, provided herein is a solid form comprising Compound 7, or tautomer thereof, which is an HBr salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.1, 6.1, 8.2, 20.5 or 22.6° 2θ (±0.2° 2θ). In certain embodiments, the solid form has an X-ray powder diffraction pattern comprising at least four characteristic peaks at about 4.1, 6.1, 8.2, 20.5 or 22.6° 2θ (±0.2° 2θ). In certain embodiments, the solid form has an X-ray powder diffraction pattern comprising five characteristic peaks at about 4.1, 6.1, 8.2, 20.5 or 22.6° 2θ (±0.2° 2θ). In certain embodiments, the solid form has an X-ray powder diffraction pattern substantially as shown in FIG. 48. In certain embodiments, the solid form has a DSC thermogram comprising an endotherm with an onset temperature at 114.7° C. In certain embodiments, the solid form is hydrated.

In another embodiment, provided herein is a solid form comprising Compound 7, or tautomer thereof, which is an HBr salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 2.3, 8.1, 12.2, 15.7 or 18.7° 2θ (±0.2° 2θ). In certain embodiments, the solid form has an X-ray powder diffraction pattern comprising at least four characteristic peaks at about 2.3, 8.1, 12.2, 15.7 or 18.7° 2θ (±0.2° 2θ). In certain embodiments, the solid form has an X-ray powder diffraction pattern comprising five characteristic peaks at about 2.3, 8.1, 12.2, 15.7 or 18.7° 2θ (±0.2° 2θ). In certain embodiments, the solid form has an X-ray powder diffraction pattern substantially as shown in FIG. 52. In certain embodiments, the solid form has a DSC thermogram comprising multiple endotherms with onset temperatures at 46.1° C., 91.1° C., and 125.8° C. In certain embodiments, the solid form is crystalline.

In another embodiment, provided herein is a solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.1, 8.2, 12.9, 20.6, or 24.8° 2θ (±0.2° 2θ). In certain embodiments, the solid form has an X-ray powder diffraction pattern comprising at least four characteristic peaks at about 4.1, 8.2, 12.9, 20.6 or 24.8° 2θ (±0.2° 2θ). In certain embodiments, the solid form has an X-ray powder diffraction pattern comprising five characteristic peaks at about 4.1, 8.2, 12.9, 20.6 or 24.8° 2θ (±0.2° 2θ). In certain embodiments, the solid form has an X-ray powder diffraction pattern substantially as shown in FIG. 56. In certain embodiments, the solid form has a DSC thermogram comprising multiple endotherms with onset temperatures at 39.3° C., 67.6° C., and 100.4° C. In certain embodiments, the solid form is solvated by methyl tert-butyl ether. In certain embodiments, the solid form is hydrated.

In another embodiment, provided herein is a solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 6.9, 10.4, 13.9, 18.9 or 20.9° 2θ (±0.2° 2θ). In certain embodiments, the solid form has an X-ray powder diffraction pattern comprising at least four characteristic peaks at about 6.9, 10.4, 13.9, 18.9 or 20.9° 2θ (±0.2° 2θ). In certain embodiments, the solid form has an X-ray powder diffraction pattern comprising five characteristic peaks at about 6.9, 10.4, 13.9, 18.9 or 20.9° 2θ (±0.2° 2θ). In certain embodiments, the solid form has an X-ray powder diffraction pattern substantially as shown in FIG. 60. In certain embodiments, the solid form has a DSC thermogram comprising an endotherm with an onset temperatures at 91.4° C. In certain embodiments, the solid form is hydrated.

In another embodiment, provided herein is a solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.1, 8.1, 20.3, 24.4, or 27.6° 2θ (±0.2° 2θ). In certain embodiments, the solid form has an X-ray powder diffraction pattern comprising at least four characteristic peaks at about 4.1, 8.1, 20.3, 24.4 or 27.6° 2θ (±0.2° 2θ). In certain embodiments, the solid form has an X-ray powder diffraction pattern comprising five characteristic peaks at about 4.1, 8.1, 20.3, 24.4 or 27.6° 2θ (±0.2° 2θ). In certain embodiments, the solid form has an X-ray powder diffraction pattern substantially as shown in FIG. 64. In certain embodiments, the solid form has a DSC thermogram comprising multiple endotherms with onset temperatures at 68.6° C. and 123.3° C.

In another embodiment, provided herein solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.7, 8.4, 11.0, 16.7 or 22.1° 2θ (±0.2° 2θ). In certain embodiments, the solid form has an X-ray powder diffraction pattern comprising at least four characteristic peaks at about 3.7, 8.4, 11.0, 16.7 or 22.1° 2θ (±0.2° 2θ). In certain embodiments, the solid form has an X-ray powder diffraction pattern comprising five characteristic peaks at about 3.7, 8.4, 11.0, 16.7 or 22.1° 2θ (±0.2° 2θ). In certain embodiments, the solid form has an X-ray powder diffraction pattern substantially as shown in FIG. 68. In certain embodiments, the solid form has a DSC thermogram comprising an endotherm with an onset temperature at 99.3° C. In certain embodiments, the solid form is hydrated.

In another embodiment, provided herein solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.0, 8.1, 15.6, 17.9, 23.0, or 24.3° 2θ (±0.2° 2θ). In certain embodiments, the solid form has an X-ray powder diffraction pattern comprising at least four characteristic peaks at about 4.0, 8.1, 15.6, 17.9, 23.0, or 24.3° 2θ (±0.2° 2θ). In certain embodiments, the solid form has an X-ray powder diffraction pattern comprising five characteristic peaks at about 4.0, 8.1, 15.6, 17.9, 23.0, or 24.3° 2θ (±0.2° 2θ). In certain embodiments, the solid form has an X-ray powder diffraction pattern comprising six characteristic peaks at about 4.0, 8.1, 15.6, 17.9, 23.0, or 24.3° 2θ (±0.2° 2θ). In certain embodiments, the solid form has an X-ray powder diffraction pattern substantially as shown in FIG. 114. In certain embodiments, the solid form has a DSC thermogram comprising an endotherm with an onset temperature at approximately 85° C. In certain embodiments, the solid form is solvated by 1,4-dioxane.

In another embodiment, provided herein solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.3, 8.4, 12.6, 13.2, 14.8, or 25.4° 2θ (±0.2° 2θ). In certain embodiments, the solid form has an X-ray powder diffraction pattern comprising at least four characteristic peaks at about 4.3, 8.4, 12.6, 13.2, 14.8, or 25.4° 2θ (±0.2° 2θ). In certain embodiments, the solid form has an X-ray powder diffraction pattern comprising five characteristic peaks at about 4.3, 8.4, 12.6, 13.2, 14.8, or 25.4° 2θ (±0.2° 2θ). In certain embodiments, the solid form has an X-ray powder diffraction pattern comprising six characteristic peaks at about 4.3, 8.4, 12.6, 13.2, 14.8, or 25.4° 2θ (±0.2° 2θ). In certain embodiments, the solid form has an X-ray powder diffraction pattern substantially as shown in FIG. 118. In certain embodiments, the solid form has a DSC thermogram comprising an endotherm with an onset temperature at approximately 81° C. In certain embodiments, the solid form is non-solvated.

In another embodiment, provided herein solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.1, 8.2, 12.9, 17.9, or 20.6° 2θ (±0.2° 2θ). In certain embodiments, the solid form has an X-ray powder diffraction pattern comprising at least four characteristic peaks at about 4.1, 8.2, 12.9, 17.9, or 20.6° 2θ (±0.2° 2θ). In certain embodiments, the solid form has an X-ray powder diffraction pattern comprising five characteristic peaks at about 4.1, 8.2, 12.9, 17.9, or 20.6° 2θ (±0.2° 2θ). In certain embodiments, the solid form has an X-ray powder diffraction pattern substantially as shown in FIG. 122. In certain embodiments, the solid form has a DSC thermogram comprising an endotherm with an onset temperature at approximately 77° C. In certain embodiments, the solid form is solvated by 1,4-dioxane.

In another embodiment, provided herein is a solid form comprising Compound 9, or tautomer thereof, which is a malonate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.8, 7.6, 11.3, 15.2 or 23.0° 2θ (±0.2° 2θ). In certain embodiments, the solid form has an X-ray powder diffraction pattern comprising at least four characteristic peaks at about 3.8, 7.6, 11.3, 15.2 or 23.0° 2θ (±0.2° 2θ). In certain embodiments, the solid form has an X-ray powder diffraction pattern comprising five characteristic peaks at about 3.8, 7.6, 11.3, 15.2 or 23.0° 2θ (±0.2° 2θ). In certain embodiments, the solid form has an X-ray powder diffraction pattern substantially as shown in FIG. 72. In certain embodiments, the solid form has a DSC thermogram comprising an endotherm with an onset temperature at 63.1° C. In certain embodiments, the solid form is hydrated. In certain embodiments, the solid form is solvated by methyl isobutyl ketone.

In another embodiment, provided herein is a solid form comprising Compound 10, or tautomer thereof, which is an edisylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 6.8, 11.7, 13.5, 20.3 or 23.5° 2θ (±0.2° 2θ). In certain embodiments, the solid form has an X-ray powder diffraction pattern comprising at least four characteristic peaks at about 6.8, 11.7, 13.5, 20.3 or 23.5° 2θ (±0.2° 2θ). In certain embodiments, the solid form has an X-ray powder diffraction pattern comprising five characteristic peaks at about 6.8, 11.7, 13.5, 20.3 or 23.5° 2θ (±0.2° 2θ). In certain embodiments, the solid form has an X-ray powder diffraction pattern substantially as shown in FIG. 76. In certain embodiments, the solid form has a DSC thermogram comprising an endotherm with an onset temperature at 90.2° C. In certain embodiments, the solid form is hydrated.

In another embodiment, provided herein is a solid form comprising Compound 10, or a tautomer thereof, which is an edisylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.3, 9.8, 13.5, 14.6, 22.4 or 26.5° 2θ (±0.2° 2θ). In certain embodiments, the solid form has an X-ray powder diffraction pattern comprising at least four characteristic peaks at about 7.3, 9.8, 13.5, 14.6, 22.4 or 26.5° 2θ (±0.2° 2θ). In certain embodiments, the solid form has an X-ray powder diffraction pattern comprising at least five characteristic peaks at about 7.3, 9.8, 13.5, 14.6, 22.4 or 26.5° 2θ (±0.2° 2θ). In certain embodiments, the solid form has an X-ray powder diffraction pattern substantially as shown in FIG. 80. In certain embodiments, the solid form has a DSC thermogram comprising a broad endotherm between 50° C. and 100° C. with an onset temperature at 59.1° C.

In another embodiment, provided herein is a solid form comprising Compound 10, or tautomer thereof, which is an edisylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.4, 6.8, 13.5, 16.9 or 20.3° 2θ (±0.2° 2θ). In certain embodiments, the solid form has an X-ray powder diffraction pattern comprising at least four characteristic peaks at about 3.4, 6.8, 13.5, 16.9 or 20.3° 2θ (±0.2° 2θ). In certain embodiments, the solid form has an X-ray powder diffraction pattern comprising five characteristic peaks at about 3.4, 6.8, 13.5, 16.9 or 20.3° 2θ (±0.2° 2θ). In certain embodiments, the solid form has an X-ray powder diffraction pattern substantially as shown in FIG. 84. In certain embodiments, the solid form has a DSC thermogram comprising multiple endotherms with onset temperatures at 90.7° C. and 121.7° C.

In another embodiment, provided herein is a solid form comprising Compound 11, or tautomer thereof, which is a tosylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 8.1, 9.9, 13.3, 16.3, 17.5, 19.1 or 21.6° 2θ (±0.2° 2θ). In certain embodiments, the solid form has an X-ray powder diffraction pattern comprising at least four characteristic peaks at about 8.1, 9.9, 13.3, 16.3, 17.5, 19.1 or 21.6° 2θ (±0.2° 2θ). In certain embodiments, the solid form has an X-ray powder diffraction pattern comprising at least five characteristic peaks at about 8.1, 9.9, 13.3, 16.3, 17.5, 19.1 or 21.6° 2θ (±0.2° 2θ). In certain embodiments, the solid form has an X-ray powder diffraction pattern substantially as shown in FIG. 88. In certain embodiments, the solid form has a DSC thermogram comprising multiple endotherms with onset temperatures at 64.3° C. and 149.7° C. In certain embodiments, the solid form is hydrated.

In another embodiment, provided herein is a solid form comprising Compound 11, or tautomer thereof, which is a tosylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 6.8, 8.0, 9.8, 16.2, 17.4, 18.9, 19.1, 20.9 or 21.3° 2θ (±0.2° 2θ). In certain embodiments, the solid form has an X-ray powder diffraction pattern comprising at least four characteristic peaks at about 6.8, 8.0, 9.8, 16.2, 17.4, 18.9, 19.1, 20.9 or 21.3° 2θ (±0.2° 2θ). In certain embodiments, the solid form has an X-ray powder diffraction pattern comprising at least five characteristic peaks at about 6.8, 8.0, 9.8, 16.2, 17.4, 18.9, 19.1, 20.9 or 21.3° 2θ (±0.2° 2θ). In certain embodiments, the solid form has an X-ray powder diffraction pattern substantially as shown in FIG. 91. In certain embodiments, the solid form has a DSC thermogram comprising multiple endotherms with onset temperatures at 64.3° C. and 149.7° C. In certain embodiments, the solid form is hydrated. In certain embodiments, the solid form has a DSC thermogram comprising multiple endotherms with onset temperatures at 68.3° C. and 172.1° C., respectively.

In certain embodiments, provided herein is a solid form comprising an HBr salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a solid form comprising a maleate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a solid form comprising a malonate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a solid form comprising an edisylate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a solid form comprising a tosylate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof.

In certain embodiments, provided herein is an HBr salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a maleate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a malonate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is an edisylate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a tosylate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof.

In another embodiment, provided herein is a pharmaceutical composition comprising a solid form described herein. In another embodiment, the pharmaceutical composition further comprises a second solid form described herein. In certain embodiments, the pharmaceutical composition further comprises an amorphous form of (E)-1-(4-(1-(((4-cyclohexyl-3-(trifluoromethyl)benzyl)oxy)imino)ethyl)-2-ethylbenzyl)azetidine-3-carboxylic acid. In certain embodiments, the pharmaceutical composition further comprises an amorphous form of a salt of (E)-1-(4-(1-(((4-cyclohexyl-3-(trifluoromethyl)benzyl)oxy)imino)ethyl)-2-ethylbenzyl)azetidine-3-carboxylic acid. In certain embodiments, the salt of (E)-1-(4-(1-(((4-cyclohexyl-3-(trifluoromethyl)benzyl)oxy)imino)ethyl)-2-ethylbenzyl)azetidine-3-carboxylic acid is an HCl salt, a L-malate salt, an oxalate salt, a L-tartrate salt, a hemifumarate salt, an HBr salt, a maleate salt, a malonate salt, an edisylate salt or a tosylate salt. In certain embodiments, the pharmaceutical composition further comprises a solid form comprising Compound 2, or tautomer thereof, which is an HCl salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 8.2, 12.3, 18.9, 19.6 or 22.1° 2θ (±0.2° 2θ). In certain embodiments, the pharmaceutical composition further comprises a solid form comprising Compound 3, or tautomer thereof, which is a L-malate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 6.9, 13.6, 18.9, 20.6 or 24.0° 2θ (±0.2° 2θ). In certain embodiments, the pharmaceutical composition further comprises a solid form comprising Compound 4, or tautomer thereof, which is an oxalate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.3, 18.1, 21.4, 22.2 or 28.1° 2θ (±0.2° 2θ). In certain embodiments, the pharmaceutical composition further comprises a solid form comprising Compound 5, or tautomer thereof, which is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.3, 6.6, 13.6, 20.2 or 24.0° 2θ (±0.2° 2θ). In certain embodiments, the pharmaceutical composition further comprises a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.1, 14.2, 17.9, 18.3, 21.4 or 25.4° 2θ (±0.2° 2θ). In certain embodiments, the pharmaceutical composition further comprises a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.0, 12.2, 20.8, 24.0 or 27.4° 2θ (±0.2° 2θ). In certain embodiments, the pharmaceutical composition further comprises a pharmaceutically acceptable excipient or carrier. In certain embodiments, the pharmaceutical composition is a single unit dosage form. In certain embodiments, the pharmaceutical composition is a tablet. In certain embodiments, the pharmaceutical composition is a capsule.

In another embodiment, provided herein is a method of treating multiple sclerosis, wherein the method comprises administering to a patient in need thereof a therapeutically effective amount of a solid form described herein. In another embodiment, provided herein is a method of treating multiple sclerosis, wherein the method comprises administering to a patient in need thereof a therapeutically effective amount of a pharmaceutical composition described herein.

In another embodiment, provided herein is a method of treating psoriasis, wherein the method comprises administering to a patient in need thereof a therapeutically effective amount of a solid form described herein. In another embodiment, provided herein is a method of treating psoriasis, wherein the method comprises administering to a patient in need thereof a therapeutically effective amount of a pharmaceutical formulation described herein.

In another embodiment, provided herein is a method of treating polymyositis, wherein the method comprises administering to a patient in need thereof a therapeutically effective amount of a solid form described herein. In another embodiment, provided herein is a method of treating polymyositis, wherein the method comprises administering to a patient in need thereof a therapeutically effective amount of a pharmaceutical formulation described herein.

In another embodiment, provided herein is a method of making a solid form comprising Compound 2, or tautomer thereof, which is an HCl salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 8.2, 12.3, 15.8 or 20.5° 2θ (±0.2° 2θ), comprising:
  a) adding 1.0 equivalent of a 3 M solution of HCl in water to a solution of (E)-1-(4-(1-(((4-cyclohexyl-3-(trifluoromethyl)benzyl)oxy)imino)ethyl)-2-ethylbenzyl)azetidine-3-carboxylic acid in methyl isobutyl ketone;
b) cycling the temperature between about 5° C. and about 40° C. for about a day;
c) adding hexanes at 40° C.; and
d) cooling the solution to 5° C. for a day.

In another embodiment, provided herein is a method of making a solid form comprising Compound 4, or tautomer thereof, which is an oxalate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.5, 7.0, 16.1, 18.1 or 30.1° 2θ (±0.2° 2θ), comprising:
a) adding 1.0 equivalent of a 0.5 M solution of oxalic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in acetonitrile;
b) cycling the temperature between about 5° C. and about 40° C. for about a day; and
c) cooling the solution to 5° C. for a day.

In another embodiment, provided herein is a method of making a solid form comprising Compound 4, or tautomer thereof, which is an oxalate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 2.4, 4.8, 9.6, 14.3, 21.6 or 24.0° 2θ (±0.2° 2θ), comprising:
a) adding 1.0 equivalent of a 0.5 M solution of oxalic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in an 4:1 mixture of THF/water;
b) cycling the temperature between about 5° C. and about 40° C. for about a day; and
c) cooling the solution to 5° C. for a day.

In another embodiment, provided herein is a method of making a solid form comprising Compound 5, or tautomer thereof, which is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 2.7, 5.2, 6.7, 13.4 or 20.2° 2θ (±0.2° 2θ), comprising:
a) adding 1.0 equivalent of a 0.5 M solution of L-tartaric acid in tetrahydrofuran to a solution of (E)-1-(4-(1-(((4-cyclohexyl-3-(trifluoromethyl)benzyl)oxy)imino)ethyl)-2-ethylbenzyl)azetidine-3-carboxylic acid in an 4:1 mixture of THF/water;
b) cycling the temperature between about 5° C. and about 40° C. for about a day; and
c) cooling the solution to 5° C. for a day.

In another embodiment, provided herein is a method of making a solid form comprising Compound 5, or a tautomer thereof, wherein Compound 5 is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.4, 6.9, 10.5, 13.9, or 20.8° 2θ (±0.2° 2θ), comprising:
a) adding 1.0 equivalent of a 0.5 M solution of L-tartaric acid in tetrahydrofuran to a solution of (E)-1-(4-(1-(((4-cyclohexyl-3-(trifluoromethyl)benzyl)oxy)imino)ethyl)-2-ethylbenzyl)azetidine-3-carboxylic acid in methyl tert-butyl ether;
b) allowing the solution to evaporate;
c) adding a solvent or solvent system to yield a slurry;
d) cycling the temperature of the slurry between about 40° C. and 5° C. for two days;
e) alternatively, heating a slurry to 40° C. and filtering the slurry while hot; and
f) storing the solution at 5° C. for 5 days.

In certain embodiments, the solvent or solvent system is water, a 3:7 mixture of THF and water, a 9:1 mixture of acetonitrile and water, a 1:1 mixture of acetone and water, a 1:9 mixture of acetone and water, or a 9:1 mixture of isopropanol and water.

In another embodiment, provided herein is a method of making a solid form comprising Compound 5, or a tautomer thereof, wherein Compound 5 is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 12.5, 13.8, 14.8, 16.8, 23.8, 25.2, or 33.6° 2θ (±0.2° 2θ), comprising:
a) adding 1.0 equivalent of a 0.5 M solution of L-tartaric acid in tetrahydrofuran to a solution of (E)-1-(4-(1-(((4-cyclohexyl-3-(trifluoromethyl)benzyl)oxy)imino)ethyl)-2-ethylbenzyl)azetidine-3-carboxylic acid in methyl tert-butyl ether;
b) allowing the solution to evaporate;
c) adding a solvent or solvent system to yield a slurry; and
d) cycling the temperature between about 5° C. and about 40° C. for about five days.

In certain embodiments, the solvent or solvent system is water or a 4:1 mixture of isopropanol and water.

In another embodiment, provided herein is a method of making a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 5.4, 7.1, 8.1, 13.5, 15.8, 17.5, 21.4, or 23.5° 2θ (±0.2° 2θ), comprising:
a) adding 1.0 equivalent of a 0.207 M solution of fumaric acid in methanol to a solution of (E)-1-(4-(1-(((4-cyclohexyl-3-(trifluoromethyl)benzyl)oxy)imino)ethyl)-2-ethylbenzyl)azetidine-3-carboxylic acid in acetone in a vial;
b) capping and shaking a vial at ambient temperature for about an hour;
c) uncapping and dying the sample under nitrogen purge;
d) mixing the sample with a solvent; and
e) recapping and stirring the sample for about two days.

In another embodiment, provided herein is a method of making a solid form comprising Compound 6, or tautomer thereof, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 5.4, 7.1, 8.1, 13.5, 15.8, 17.5, 21.4, or 23.5° 2θ (±0.2° 2θ), comprising:
a) adding 0.5 equivalents of a 0.207 M solution of fumaric acid in methanol to a solution of (E)-1-(4-(1-(((4-cyclohexyl-3-(trifluoromethyl)benzyl)oxy)imino)ethyl)-2-ethylbenzyl)azetidine-3-carboxylic acid in acetone in a vial;
b) capping and shaking a vial at ambient temperature for about an hour;
c) uncapping and dying the sample under nitrogen purge;
d) mixing the sample with a solvent; and
e) recapping and stirring the sample for about two days.

In certain embodiments, the solvent is ethyl methyl ketone or dimethyl carbonate. In certain embodiments, the method further comprises stirring the sample in acetonitrile.

In another embodiment, provided herein is a method of making a solid form comprising Compound 6, or a tautomer thereof, wherein Compound 6 is a hemifumarate salt of (E)-1-(4-(1-(((4-cyclohexyl-3-(trifluoromethyl)benzyl)oxy) imino)ethyl)-2-ethylbenzyl)azetidine-3-carboxylic acid, which has an X-ray powder diffraction pattern comprising at least three characteristic peaks at about 2.8, 11.1, 19.4, 20.8, 22.3, or 23.4° 2θ (±0.2° 2θ), comprising:
  a) dispensing Hemifumarate Salt Form B into a vial and adding a solvent or solvent system to create a slurry of Hemifumarate Salt Form B;
  b) cycling the temperature between about 40° C. and 5° C. for about two days.

In certain embodiments, the solvent or solvent system is 1,4-dioxane or a 10% mixture of water in 1,4-dioxane.

In another embodiment, provided herein is a method of making a solid form comprising Compound 6, or a tautomer thereof, wherein Compound 6 is a hemifumarate salt of (E)-1-(4-(1-(((4-cyclohexyl-3-(trifluoromethyl)benzyl)oxy) imino)ethyl)-2-ethylbenzyl)azetidine-3-carboxylic acid, which has an X-ray powder diffraction pattern comprising at least three characteristic peaks at about 7.0, 18.1, 19.5, 19.9, or 21.5° 2θ (±0.2° 2θ), comprising:
  a) dispensing Hemifumarate Salt Form B into a vial and adding a solvent or solvent system to create a slurry of Hemifumarate Salt Form B;
  b) allowing the solvent or solvent system to slowly evaporate through a loosened cap on the vial for 7 days at ambient temperature;
  c) removing the cap and allowing the solvent or solvent system to evaporate for 7 days at ambient temperature;
  d) continuing evaporation of remaining solutions under reduced pressure for 24 hours.

In certain embodiments, the solvent or solvent system is methanol, 5% mixture of water in methanol, or 10% mixture of water in methanol.

In another embodiment, provided herein is a method of making a solid form comprising Compound 6, or a tautomer thereof, wherein Compound 6 is a hemifumarate salt of (E)-1-(4-(1-(((4-cyclohexyl-3-(trifluoromethyl)benzyl)oxy) imino)ethyl)-2-ethylbenzyl)azetidine-3-carboxylic acid, which has an X-ray powder diffraction pattern comprising at least three characteristic peaks at about 7.0, 15.8, 17.6, 21.8, or 23.9° 2θ (±0.2° 2θ), comprising:
  a) dispensing Hemifumarate Salt Form B into a vial and adding a solvent or solvent system to create a slurry of Hemifumarate Salt Form B;
  b) allowing the solvent or solvent system to slowly evaporate through a loosened cap on the vial for 7 days at ambient temperature; and
  c) removing the cap and allowing the solvent or solvent system to evaporate for 7 days at ambient temperature;
  d) continuing evaporation of remaining solutions under reduced pressure for 24 hours.
  f) isolating the solids by vacuum-filtration for 1.5 hours;
  g) drying the solids at 40° C. in a vacuum oven for five hours;
  h) dispensing a portion of the solids into a vial and adding a solvent or solvent system to create a slurry; and
  g) cycling the temperature between about 40° C. and 5° C. for about two days.

In certain embodiments, the solvent or solvent system is a 20% water in isopropanol.

In another embodiment, provided herein is a method of making a solid form comprising Compound 6, or a tautomer thereof, wherein Compound 6 is a hemifumarate salt of (E)-1-(4-(1-(((4-cyclohexyl-3-(trifluoromethyl)benzyl)oxy) imino)ethyl)-2-ethylbenzyl)azetidine-3-carboxylic acid, which has an X-ray powder diffraction pattern comprising at least three characteristic peaks at about 7.0, 10.7, 12.2, 17.6, 20.8, 21.0, or 24.0° 2θ (±0.2° 2θ), comprising:
  a) adding 0.5 equivalents of 99.5+% fumaric acid to a solution of (E)-1-(4-(1-(((4-cyclohexyl-3-(trifluoromethyl)benzyl)oxy)imino)ethyl)-2-ethylbenzyl)azetidine-3-carboxylic acid in methyl tert-butyl ether;
  b) seeding the solution with Hemifumarate Salt form B;
  c) allowing the sample to stir for 2 hours at 40° C.;
  d) slowly cooling the solution to ambient temperature; and
  e) stirring the solution at ambient temperature for 3 days.

In another embodiment, provided herein is a method of making a solid form comprising Compound 6, or a tautomer thereof, wherein Compound 6 is a hemifumarate salt of (E)-1-(4-(1-(((4-cyclohexyl-3-(trifluoromethyl)benzyl)oxy) imino)ethyl)-2-ethylbenzyl)azetidine-3-carboxylic acid, which has an X-ray powder diffraction pattern comprising at least three characteristic peaks at about 8.0, 11.6, 13.5, 15.8, 17.6, 21.4, or 23.5° 2θ (±0.2° 2θ), comprising:
  a) dispensing a solution of (E)-1-(4-(1-(((4-cyclohexyl-3-(trifluoromethyl)benzyl)oxy)imino)ethyl)-2-ethylbenzyl)azetidine-3-carboxylic acid in a 5:8 mixture of acetone and methanol into a vial;
  b) filtering the solution;
  c) adding 0.5 equivalents of fumaric acid;
  d) capping the sample and shaking at 200 RPM at ambient temperature) for 1 hr;
  e) uncapping the vial and drying the sample under nitrogen purge;
  f) mixing the sample with ethyl methyl ketone;
  g) re-capping the sample and stirring at 300 RPM at ambient temperature overnight;
  h) isolating the solids and drying in a vacuum oven at 35° C. for 24 h; and
  i) slurrying the sample in acetonitrile at ambient temperature and stirring for about three days.

In another embodiment, provided herein is a method of making a solid form comprising Compound 7, or tautomer thereof, which is an HBr salt of (E)-1-(4-(1-(((4-cyclohexyl-3-(trifluoromethyl)benzyl)oxy)imino)ethyl)-2-ethylbenzyl) azetidine-3-carboxylic acid, which has an X-ray powder diffraction pattern comprising at least three characteristic peaks at about 4.1, 6.1, 8.2, 20.5 or 22.6° 2θ (±0.2° 2θ), comprising:
  a) adding 1.0 equivalent of a 5 M solution of HBr in water to a solution of (E)-1-(4-(1-(((4-cyclohexyl-3-(trifluoromethyl)benzyl)oxy)imino)ethyl)-2-ethylbenzyl)azetidine-3-carboxylic acid in isopropanol;
  b) cycling the temperature between about 5° C. and about 40° C. for about a day; and
  c) cooling the solution to 5° C. for a day.

In another embodiment, provided herein is a method of making a solid form comprising Compound 7, or tautomer thereof, which is an HBr salt of (E)-1-(4-(1-(((4-cyclohexyl-3-(trifluoromethyl)benzyl)oxy)imino)ethyl)-2-ethylbenzyl) azetidine-3-carboxylic acid, which has an X-ray powder diffraction pattern comprising at least three characteristic peaks at about 2.3, 8.1, 12.2, 15.7 or 18.7° 2θ (±0.2° 2θ), comprising:
  a) adding 1.0 equivalent of a 5 M solution of HBr in water to a solution of (E)-1-(4-(1-(((4-cyclohexyl-3-(trifluoromethyl)benzyl)oxy)imino)ethyl)-2-ethylbenzyl)azetidine-3-carboxylic acid in a solvent;
b) cycling the temperature between about 5° C. and about 40° C. for about a day;
c) adding hexanes at 40° C.; and
d) cooling the solution to 5° C. for a day.

In certain embodiments, the solvent is methyl tert-butyl ether or methyl isobutyl ketone.

In another embodiment, provided herein is a method of making a solid form comprising Compound 8, or tautomer thereof, which is an maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.1, 8.2, 12.9, 20.6 or 24.8° 2θ (±0.2° 2θ), comprising:
a) adding 1.0 equivalent of a 3 M solution of maleic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in methyl tert-butyl ether;
b) cycling the temperature between about 5° C. and about 40° C. for about a day; and
c) cooling the solution to 5° C. for a day.

In another embodiment, provided herein is a method of making a solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 6.9, 10.4, 13.9, 18.9 or 20.9° 2θ (±0.2° 2θ), comprising:
a) adding 1.0 equivalent of a 3 M solution of maleic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in methyl isobutyl ketone;
b) cycling the temperature between about 5° C. and about 40° C. for about a day;
c) adding hexanes at 40° C.; and
c) cooling the solution to 5° C. for a day.

In another embodiment, provided herein is a method of making a solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.1, 8.1, 20.3, 24.4 or 27.6° 2θ (±0.2° 2θ), comprising:
a) adding 1.0 equivalent of a 3 M solution of maleic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in isopropyl acetate;
b) cycling the temperature between about 5° C. and about 40° C. for about a day; and
c) cooling the solution to 5° C. for a day.

In another embodiment, provided herein is a method of making a solid form comprising Compound 8, or tautomer thereof, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.7, 8.4, 11.0, 16.7 or 22.1° 2θ (±0.2° 2θ), comprising:
a) adding 1.0 equivalent of a 3 M solution of maleic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in methyl isobutyl ketone;
b) heating the resulting mixture to 40° C. for one hour;
c) adding seeds of crystalline maleate salt of (E)-1-(4-(1-(((4-cyclohexyl-3-(trifluoromethyl)benzyl)oxy)imino)ethyl)-2-ethylbenzyl)azetidine-3-carboxylic acid; and
d) cycling the temperature between about 5° C. and about 40° C. for about two days.

In another embodiment, provided herein is a method of making a solid form comprising Compound 8, or a tautomer thereof, wherein Compound 8 is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.0, 8.1, 15.6, 17.9, 23.0, or 24.3° 2θ (±0.2° 2θ), comprising:
a) dissolving 1.0 equivalent of maleic acid in a solution of (E)-1-(4-(1-(((4-cyclohexyl-3-(trifluoromethyl)benzyl)oxy)imino)ethyl)-2-ethylbenzyl)azetidine-3-carboxylic acid in methanol;
b) evaporating the solution to dryness under reduced pressure;
c) dissolving the solid in heptane and vortexing;
d) adding 1,4-dioxane and stirring the sample at ambient temperature;
e) cycling the temperature between about 5° C. and about 40° C. for about 21 hours;
f) cooling the sample to 5° C.

A method of making a solid form comprising Compound 8, or a tautomer thereof, wherein Compound 8 is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.3, 8.4, 12.6, 13.2, 14.8, or 25.4° 2θ (±0.2° 2θ), comprising:
a) dissolving 1.0 equivalent of maleic acid in a solution of (E)-1-(4-(1-(((4-cyclohexyl-3-(trifluoromethyl)benzyl)oxy)imino)ethyl)-2-ethylbenzyl)azetidine-3-carboxylic acid in methanol;
b) evaporating the solution to dryness under reduced pressure;
c) dissolving the solid in heptane and vortexing;
d) adding THF and stirring the sample at ambient temperature;
e) cycling the temperature between about 5° C. and about 40° C. for about 21 hours;
f) cooling the sample to 5° C.

A method of making a solid form comprising Compound 8, or a tautomer thereof, wherein Compound 8 is a maleate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 4.1, 8.2, 12.9, 17.9, or 20.6° 2θ (±0.2° 2θ), comprising:
a) dissolving 1.0 equivalent of maleic acid in a solution of (E)-1-(4-(1-(((4-cyclohexyl-3-(trifluoromethyl)benzyl)oxy)imino)ethyl)-2-ethylbenzyl)azetidine-3-carboxylic acid in methanol;
b) evaporating the solution to dryness under reduced pressure;
c) dissolving the solid in heptane and vortexing;
d) adding 1,4-dioxane and stirring the sample at ambient temperature;
e) cycling the temperature between about 5° C. and about 40° C. for about 21 hours;

f) cooling the sample to 5° C. and isolating the solid from the solution through vacuum filtration; and g) drying the sample in a vacuum oven.

In another embodiment, provided herein is a method of making a solid form comprising Compound 9, or tautomer thereof, which is a malonate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.8, 7.6, 11.3, 15.2 or 23.0° 2θ (±0.2° 2θ), comprising:

a) adding 1.0 equivalent of a 3 M solution of malonic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in a solvent;

b) cycling the temperature between about 5° C. and about 40° C. for about a day;

c) adding an anti-solvent at 40° C.; and c) cooling the solution to 5° C. for a day.

In certain embodiments, the solvent is methyl isobutyl ketone or isopropyl acetate. In certain embodiments, the anti-solvent is hexane or diisopropyl ether.

In another embodiment, provided herein is a method of making a solid form comprising Compound 10, or tautomer thereof, which is an edisylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 6.8, 11.7, 13.5, 20.3 or 23.5° 2θ (±0.2° 2θ), comprising:

a) adding 1.0 equivalent of a 3 M solution of ethane-1,2-disulfonic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in acetonitrile;

b) cycling the temperature between about 5° C. and about 40° C. for about a day; and c) cooling the solution to 5° C. for a day.

In another embodiment, provided herein is a method of making a solid form comprising Compound 10, or tautomer thereof, which is an edisylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 7.3, 9.8, 13.5, 14.6, 22.4 or 26.5° 2θ (±0.2° 2θ), comprising:

a) adding 1.0 equivalent of a 3 M solution of ethane-1,2-disulfonic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in methyl isobutyl ketone;

b) cycling the temperature between about 5° C. and about 40° C. for about a day; and c) cooling the solution to 5° C. for a day.

In another embodiment, provided herein is a method of making a solid form comprising Compound 10, or tautomer thereof, which is an edisylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at about 3.4, 6.8, 13.5, 16.9 or 20.3° 2θ (±0.2° 2θ), comprising:

a) adding 1.0 equivalent of a 3 M solution of ethane-1,2-disulfonic acid in water to a solution of (E)-1-(4-(1-(((4-cyclohexyl-3-(trifluoromethyl)benzyl)oxy)imino)ethyl)-2-ethylbenzyl)azetidine-3-carboxylic acid in a solvent;

b) cycling the temperature between about 5° C. and about 40° C. for about a day; and c) cooling the solution to 5° C. for a day.

In certain embodiments, the solvent is methyl tert-butyl ether, isopropyl acetate, or acetonitrile. In certain embodiments, the method further comprises adding an anti-solvent. In certain embodiments, the anti-solvent is diisopropyl ether.

In another embodiment, provided herein is a method of making a solid form comprising Compound 11, or tautomer thereof, which is a tosylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at 8.1, 9.9, 13.3, 16.3, 17.5, or 21.6° 2θ (±0.2° 2θ), comprising:

a) adding 1.0 equivalent of a 0.222M solution of p-toluenesulfonic acid in acetonitrile to a solution of (E)-1-(4-(1-(((4-cyclohexyl-3-(trifluoromethyl)benzyl)oxy)imino)ethyl)-2-ethylbenzyl)azetidine-3-carboxylic acid in acetone in a vial;

b) capping and shaking a vial at ambient temperature for about an hour;

c) uncapping and dying the sample under nitrogen purge;

d) mixing the sample with a solvent; and e) recapping and stirring the sample for about two days.

In certain embodiments, the solvent is 2-propanol or isopropyl acetate

In another embodiment, provided herein is a method of making a solid form comprising Compound 11, or tautomer thereof, which is a tosylate salt of (E)-1-(4-(1-(((4-cyclohexyl-3-(trifluoromethyl)benzyl)oxy)imino)ethyl)-2-ethylbenzyl)azetidine-3-carboxylic acid, which has an X-ray powder diffraction pattern comprising at least three characteristic peaks at 6.8, 8.0, 9.8, 16.2, 17.4, 18.9, 19.1, 20.9 or 21.3° 2θ (±0.2° 2θ), comprising:

a) adding 1.0 equivalent of a 0.222M solution of p-toluenesulfonic acid in acetonitrile to a solution of (E)-1-(4-(1-(((4-cyclohexyl-3-(trifluoromethyl)benzyl)oxy)imino)ethyl)-2-ethylbenzyl)azetidine-3-carboxylic acid in acetone in a vial;

b) capping and shaking a vial at ambient temperature for about an hour;

c) uncapping and dying the sample under nitrogen purge;

d) mixing the sample with a 95:5 v/v mixture of acetone/water; and recapping and stirring the sample for about two days.

4. BRIEF DESCRIPTION OF THE DRAWINGS

5. DETAILED DESCRIPTION

5.1 Definitions

Figure 1:
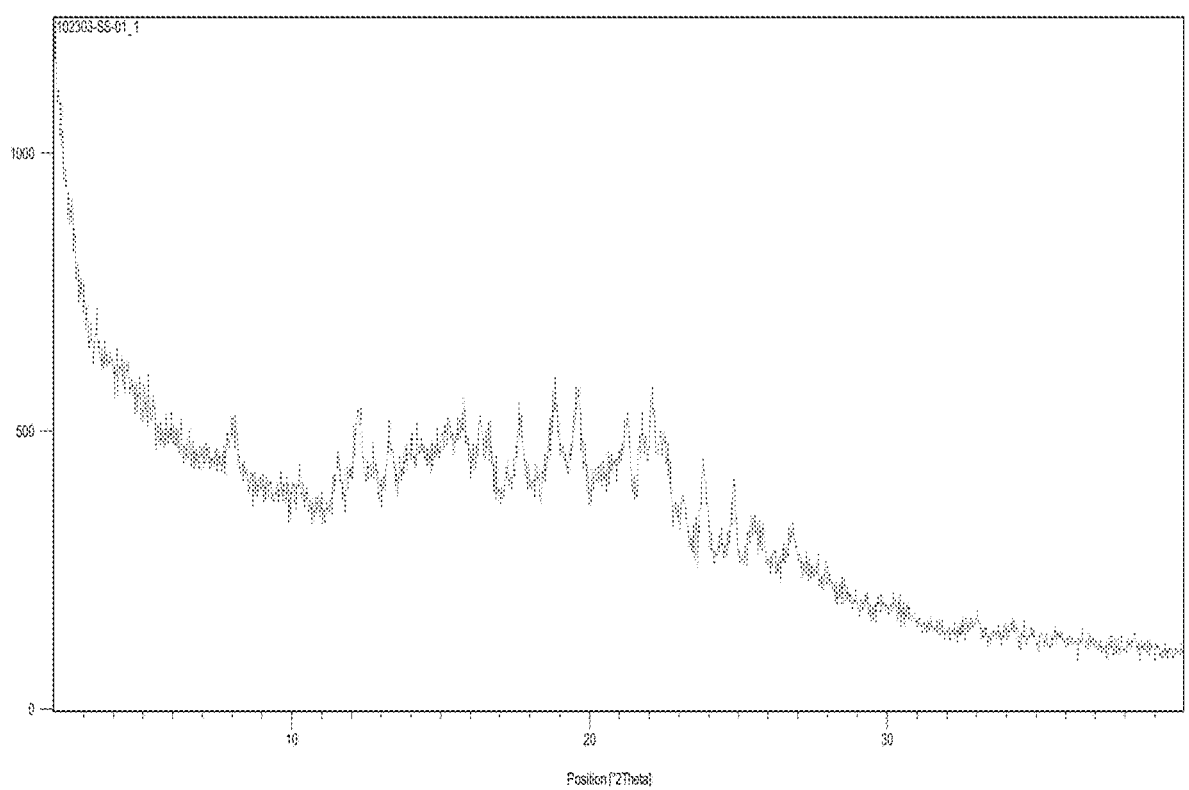
FIG. 1 depicts a PXRD pattern of HCl Salt Form A of Compound 2.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, infrared (IR) or Raman spectroscopy or X-ray powder diffractometry (PXRD); indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), PXRD, single-crystal X-ray diffractometry, vibrational spectroscopy, e.g., IR and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an PXRD peak position may vary by up to ±0.2 degrees two theta while still describing the particular PXRD peak.

As used herein, and unless otherwise specified, a crystalline that is "pure," i.e., substantially free of other crystalline or amorphous solid forms, contains less than about 10% by weight of one or more other crystalline or amorphous solid forms, less than about 5% by weight of one or more other crystalline or amorphous solid forms, less than about 3% by weight of one or more other crystalline or amorphous solid forms, or less than about 1% by weight of one or more other crystalline or amorphous solid forms.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, MD (2005); The United States Pharmacopeia, $23^{rd}$ ed., 1843-1844 (1995).

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 60, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition.

As used herein, and unless otherwise indicated, the term "desolvated solvate" refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

As used herein, and unless otherwise indicated, the term "composition" is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

As used herein, and unless otherwise specified, the term "Compound" means a compound selected from the group consisting of Compound 1, Compound 2, Compound 3, Compound 4, Compound 5, Compound 6, Compound 7, Compound 8, Compound 9, Compound 10 or Compound 11.

As used herein, and unless otherwise indicated, the term "solid form" refers to a physical form which is not predominantly in a liquid or a gaseous state. The terms "solid type" and "type" are used interchangeably herein with "solid form".

As used herein and unless otherwise specified, the term "solid form," refers to Compound 1, Compound 2, Compound 3, Compound 4, Compound 5, Compound 6, Compound 7, Compound 8, Compound 9, Compound 10 or Compound 11, or refers to a physical form comprising Compound 1, Compound 2, Compound 3, Compound 4, Compound 5, Compound 6, Compound 7, Compound 8, Compound 9, Compound 10 or Compound 11, which is not predominantly in a liquid or a gaseous state. A solid form may be a crystalline form or a mixture thereof. In certain embodiments, a solid form may be a liquid crystal.

In certain embodiments, the term "solid forms comprising a Compound" includes solid forms (e.g., crystalline forms, amorphous forms, polymorphs or mixtures thereof) comprising Compound 1, Compound 2, Compound 3, Compound 4, Compound 5, Compound 6, Compound 7, Compound 8, Compound 9, Compound 10 or Compound 11. In certain embodiments, the solid form of Compound 2 is selected from the group consisting of HCl Salt Form A or HCl Salt Form B. In certain embodiments, the solid form of Compound 3 is selected from the group consisting of L-Malate Salt Form A or L-Malate Salt Form B. In certain embodiments, the solid form of Compound 4 is selected from the group consisting of Oxalate Salt Form A, Oxalate Salt Form B, or Oxalate Salt Form C. In certain embodiments, the solid form of Compound 5 is selected from the group consisting of L-Tartrate Salt Form A or L-Tartrate Salt Form B. In certain embodiments, the solid form of Compound 6 is selected from the group consisting of Hemifumarate Salt Form A, Hemifumarate Salt Form B, or Hemifumarate Salt Form C. In certain embodiments, the solid form of Compound 7 is selected from the group consisting of HBr Salt Form A or HBr Salt Form B. In certain embodiments, the solid form of Compound 8 is selected from the group consisting of Maleate Salt Form A, Maleate Salt Form B, Maleate Salt Form C, or Maleate Salt Form D. In certain embodiments, the solid form of Compound 9 is Malonate Salt Form A. In certain embodiments, the solid form of Compound 10 is selected from the group consisting of Edisylate Salt Form A, Edisylate Salt Form B or Edisylate Salt Form C. In certain embodiments, the solid form of Compound 11 is selected from the group consisting of Tosylate Salt Form A or Tosylate Salt Form B.

In certain embodiments, the term "solid forms comprising a Compound" includes solid forms (e.g., crystalline forms, amorphous forms, polymorphs or mixtures thereof) comprising Compound 1, Compound 2, Compound 3, Compound 4, Compound 5, Compound 6, Compound 7, Compound 8, Compound 9, Compound 10 or Compound 11. In certain embodiments, the solid form of Compound 5 is selected from the group consisting of L-Tartrate Salt Form A, L-Tartrate Salt Form B, L-Tartrate Salt Form C, or L-Tartrate Salt Form D. In certain embodiments, the solid form of Compound 6 is selected from the group consisting of Hemifumarate Salt Form A, Hemifumarate Salt Form B, Hemifumarate Salt Form C, Hemifumarate Salt Form D, Hemifumarate Salt Form E, or Hemifumarate Salt Form F, Hemifumarate Salt Form G, or Hemifumarate Salt Form H. In certain embodiments, the solid form of Compound 8 is selected from the group consisting of Maleate Salt Form A, Maleate Salt Form B, Maleate Salt Form C, Maleate Salt Form D, Maleate Salt Form E, Maleate Salt Form F, and Maleate Salt Form G.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, MD (2005); The United States Pharmacopeia, $23^{rd}$ ed., 1843-1844 (1995).

As used herein and unless otherwise specified, the term "crystal form" or "crystalline form" refers to a solid form that is crystalline. In certain embodiments, a crystal form of a substance may be substantially free of amorphous solids and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 900% physically and/or chemically pure.

As used herein and unless otherwise specified, the term "amorphous" or "amorphous solid form" means that the substance, component, or product in question is not substantially crystalline as determined by X-ray diffraction. In particular, the term "amorphous solid" describes a disordered solid form, i.e., a solid form lacking long range crystalline order. In certain embodiments, an amorphous solid form of a substance may be substantially free of other amorphous solid form and/or crystal forms. In certain embodiments, an amorphous solid form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous solid forms and/or crystal forms on a weight basis. In certain embodiments, an amorphous solid form of a substance may be physically and/or chemically pure. In certain embodiments, an amorphous solid form of a substance be about 99%, about 98%, about 97%, about 96%, about 95%, about 94%, about 93%, about 92%, about 91%, or about 90% physically and/or chemically pure.

As used herein, and unless otherwise indicated, the term "tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

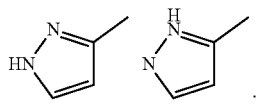

As readily understood by one skilled in the art, a wide variety of functional groups and other structures may exhibit tautomerism and all tautomers of Compound 1, Compound 2, Compound 3, Compound 4, Compound 5, Compound 6, Compound 7, Compound 8, Compound 9, Compound 10 and Compound 11 are within the scope of the present invention.

As used herein, and unless otherwise indicated, the term "treating" means an alleviation, in whole or in part, of the disease or disorder, or symptoms associated with the disease or disorder, or slowing, or halting of further progression or worsening of the disease or disorder, or symptoms associated with the disease or disorder.

As used herein, and unless otherwise indicated, the term "preventing" means prevention of the onset, recurrence, or spread of the disease or disorder, or symptoms associated with the disorder or disease, in a patient at risk for developing the disease or disorder.

As used herein, and unless otherwise specified, the term "therapeutically effective amount" of a compound refers to an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human, in another embodiment a cell from any one of the foregoing animals. In one embodiment, a subject or patient is a non-human animal, in another embodiment a non-human mammal. In another embodiment, a subject or patient is a human having or at risk for having an autoimmune or chronic inflammatory disease. In certain embodiments, the autoimmune or chronic inflammatory disease is polymyositis, dermatomyositis, lupus nephritis, rheumatoid arthritis, inflammatory bowel disease, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease or multiple sclerosis. In certain embodiments, provided herein are methods for treating a subject suffering from or at risk for having relapsing-remitting multiple sclerosis, primary progressive multiple sclerosis, secondary progressive multiple sclerosis, and relapsing secondary progressive multiple sclerosis. In certain embodiments, a subject or patient is a human having or at risk for having a neurological disorder. In certain embodiments, the neurological disorder is Rett Syndrome. In certain embodiments, a subject or patient is a human having or at risk for having renal or hepatic impairment. In certain embodiments, a subject or patient is a human having or at risk for having a disease or disorder associated with sphingosine 1-phosphate, including but not limited to multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, and Graves' disease. In certain embodiments, a subject or patient is a human having or at risk for having a disease or disorder associated with the interferon alpha receptor 1, including but not limited to psoriasis, ulcerative colitis, systemic lupus, multiple sclerosis, and rheumatoid arthritis. In certain embodiments, a subject or patient is a human having a disease or disorder mediated by lymphocyte interactions, such as, for example, in transplantation, such as acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus.

Unless otherwise specified, to the extent that there is a discrepancy between a depicted chemical structure of a compound provided herein and a chemical name of a compound provided herein, the chemical structure shall control.

5.2 Compounds

The solid forms, formulations, and methods of use provided herein relate to solid forms (e.g., crystalline forms, amorphous forms, polymorphs or mixtures thereof) of Compound 1:

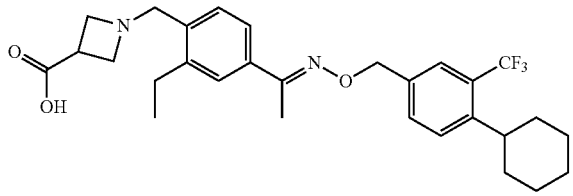

having the name (E)-1-(4-(1-(((4-cyclohexyl-3-(trifluoromethyl)benzyl)oxy)imino)ethyl)-2-ethylbenzyl)azetidine-3-carboxylic acid, including tautomers thereof. Compound 1 can be prepared by methods known in the art. See, e.g., International Patent Application Publication No. WO 2013/113915 A1.

In certain embodiments, provided herein are solid forms, formulations, and methods of use related to solid forms (e.g., crystalline forms, amorphous forms, polymorphs or mixtures thereof) of Compound 2, which is an HCl salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 3, which is a L-malate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 4, which is an oxalate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 5, which is a L-tartrate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 6, which is a hemifumarate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 7, which is an HBr salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 8, which is a maleate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 9, which is a malonate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 10, which is an edisylate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, provided herein are solid forms, formulations, and methods of use related to solid forms (e.g., crystalline forms, amorphous forms, polymorphs or mixtures thereof) of Compound 11, which is a tosylate salt of (E)-1-(4-(1-(((4-cyclohexyl-3-(trifluoromethyl)benzyl)oxy)imino)ethyl)-2-ethylbenzyl)azetidine-3-carboxylic acid, including tautomers thereof.

In certain embodiments, Compound 2, Compound 3, Compound 4, Compound 5, Compound 6, Compound 7, Compound 8, Compound 9, Compound 10 or Compound 11 is the ionized form of (E)-1-(4-(1-(((4-cyclohexyl-3-(trifluoromethyl)benzyl)oxy)imino)ethyl)-2-ethylbenzyl)azetidine-3-carboxylic acid which has undergone salt formation such that the molecule is protonated at one or more basic centers. In certain embodiments, the Compounds are isolated.

In certain embodiments, provided herein is an HBr salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a maleate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a malonate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is an edisylate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof. In certain embodiments, provided herein is a tosylate salt of (E)-1-(4-(1-(((4-cyclohexyl-3-(trifluoromethyl)benzyl)oxy)imino)ethyl)-2-ethylbenzyl)azetidine-3-carboxylic acid, or a tautomer thereof.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Solid Forms

In certain embodiments, provided herein are solid forms comprising Compound 1, a pharmaceutically acceptable salt or a tautomer thereof. In certain embodiments, the solid form is crystalline. In certain embodiments, the solid form is a hydrate. In certain embodiments, the solid form is an anhydrate. In certain embodiments, the solid form is a solvate. In certain embodiments, the solid form is non-solvated. In certain embodiments, the solid form is a pharmaceutically acceptable salt of Compound 1.

In certain embodiments, the solid form comprises Compound 2. In certain embodiments, the solid form comprises Compound 3. In certain embodiments, the solid form comprises Compound 4. In certain embodiments, the solid form comprises Compound 5. In certain embodiments, the solid form comprises Compound 6. In certain embodiments, the solid form comprises Compound 7. In certain embodiments, the solid form comprises Compound 8. In certain embodiments, the solid form comprises Compound 9. In certain embodiments, the solid form comprises Compound 10. In certain embodiments, the solid form comprises Compound 11.

In certain embodiments, the solid form of Compound 2 is selected from the group consisting of: HCl Salt Form A and HCl Salt Form B.

In certain embodiments, the solid form of Compound 3 is selected from the group consisting of: L-Malate Salt Form A and L-Malate Salt Form B.

In certain embodiments, the solid form of Compound 4 is selected from the group consisting of: Oxalate Salt Form A, Oxalate Salt Form B and Oxalate Salt Form C.

In certain embodiments, the solid form of Compound 5 is selected from the group consisting of: L-Tartrate Salt Form A and L-Tartrate Salt Form B.

In certain embodiments, the solid form of Compound 5 is selected from the group consisting of: L-Tartrate Salt Form A, L-Tartrate Salt Form B, L-Tartrate Salt Form C, and L-Tartrate Salt Form D.

In certain embodiments, the solid form of Compound 6 is selected from the group consisting of: Hemifumarate Salt Form A, Hemifumarate Salt Form B, and Hemifumarate Salt Form C.

In certain embodiments, the solid form of Compound 6 is selected from the group consisting of: Hemifumarate Salt Form A, Hemifumarate Salt Form B, Hemifumarate Salt Form C, Hemifumarate Salt Form D, Hemifumarate Salt Form E, and Hemifumarate Salt Form F, Hemifumarate Salt Form G, and Hemifumarate Salt Form H.

In certain embodiments, the solid form of Compound 7 is selected from the group consisting of: HBr Salt Form A and HBr Salt Form B.

In certain embodiments, the solid form of Compound 8 is selected from the group consisting of: Maleate Salt Form A, Maleate Salt Form B, Maleate Salt Form C, or Maleate Salt Form D.

In certain embodiments, the solid form of Compound 8 is selected from the group consisting of: Maleate Salt Form A, Maleate Salt Form B, Maleate Salt Form C, Maleate Salt Form D, Maleate Salt Form E, Maleate Salt Form F, or Maleate Salt Form G.

In certain embodiments, the solid form of Compound 9 is Malonate Salt Form A.

In certain embodiments, the solid form of Compound 10 is selected from the group consisting of: Edisylate Salt Form A, Edisylate Salt Form B, and Edisylate Salt Form C.

In certain embodiments, the solid form of Compound 11 is selected from the group consisting of: Tosylate Salt Form A and Tosylate Salt Form B.

In certain embodiments, the solid form is crystalline. In certain embodiments, the solid form is a hydrate. In certain embodiments, the solid form is an anhydrate. In certain embodiments, the solid form is a solvate. In certain embodiments, the solid form is non-solvated.

In certain embodiments, a solid form provided herein is a cocrystal. In one embodiment, provided herein are solid forms (e.g., crystal forms, amorphous forms, or mixtures thereof) comprising (a) Compound 1; and (b) a coformer. In one embodiment, provided herein are solid forms (e.g., crystal forms, amorphous forms, or mixtures thereof) comprising (a) a salt of Compound 1; and (b) a coformer. In certain embodiments, the solid form comprises (a) any one of Compound 2, Compound 3, Compound 4, Compound 5, Compound 6, Compound 7, Compound 8, Compound 9, Compound 10, or Compound 11; and (b) a coformer. In one embodiment, provided herein is a mixture comprising (a) a cocrystal comprising (i) a salt of Compound 1; and (ii) a coformer; and (b) a solid form of a salt of Compound 1. In one embodiment, provided herein is a mixture comprising (a) a cocrystal comprising (i) a salt of Compound 1; and (ii) a coformer; and (b) a solid form of Compound 1. In one embodiment, provided herein is a mixture comprising (a) a cocrystal comprising (i) a salt of Compound 1; and (ii) a coformer; and (b) an amorphous form of a salt of Compound 1. In certain embodiments, the coformer is fumaric acid. In certain embodiments, the cocrystal is solvated.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (e.g., HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A, and Tosylate Salt Form B) may be characterized using a number of methods known to a person skilled in the art, including, but not limited to, single crystal X-ray diffraction, X-ray powder diffraction (PXRD), microscopy (e.g., scanning electron microscopy (SEM), polarized-light microscopy), thermal analysis (e.g., differential scanning calorimetry (DSC), thermal gravimetric analysis (TGA), and hot-stage microscopy), dynamic vapor sorption (DVS), spectroscopy (e.g., infrared, Raman, and solid-state nuclear magnetic resonance, proton nuclear magnetic resonance ($^1$H NMR) spectrum), and ultra-high performance liquid chromatography (UHPLC). The particle size and size distribution of the solid form provided herein may be determined by conventional methods, such as laser light scattering technique.

The solid forms provided herein (e.g., HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A, and Tosylate Salt Form B) may be characterized using a number of methods known to a person skilled in the art, including, but not limited to, single crystal X-ray diffraction, X-ray powder diffraction (PXRD), microscopy (e.g., scanning electron microscopy (SEM), polarized-light microscopy), thermal analysis (e.g., differential scanning calorimetry (DSC), thermal gravimetric analysis (TGA), and hot-stage microscopy), dynamic vapor sorption (DVS), spectroscopy (e.g., infrared, Raman, and solid-state nuclear magnetic resonance, proton nuclear magnetic resonance ($^1$H NMR) spectrum), and ultra-high performance liquid chromatography (UHPLC). The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, ultra-high performance liquid chromatography (UHPLC), and mass spectrometry.

It should be understood that the numerical values of the peaks of an X-ray powder diffraction pattern may vary slightly from one machine to another or from one sample to another, and so the values quoted are not to be construed as absolute, but with an allowable variability, such as 0.2° 2θ or 0.1° 2θ (see, United State Pharmacopoeia, page 2228 (2003)).

(a) Methods of Preparing Solid Forms

In certain embodiments, provided herein are methods for making a solid form comprising a Compound disclosed herein (e.g., Compound 1, Compound 2, Compound 3, Compound 4, Compound 5, Compound 6, Compound 7, Compound 8, Compound 9, Compound 10, Compound 11), or a tautomer thereof, comprising 1) dispensing a solvent or solvent system (e.g., about 250 μL) into a vial containing an amount of Compound 1 (e.g., about 20 mg); 2) adding a stoichiometric amount (e.g., 1.0 equivalent) of an acid to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent or solvent system used in step 1, followed by temperature cycling (e.g., between about 5° C. and about 40° C.; 1° C. per minute heating/cooling rate with an hour hold between each heating/cooling cycle) of the solution for a period of time (e.g., about a day); 7) optionally adding an anti-solvent (e.g., 1:3 v/v solvent to anti-solvent ratio) at a temperature (e.g., 40° C.) and holding the solution at a temperature (e.g., 40° C.) for a period of time (e.g., three hours); 8) optionally heating the solution to a temperature (e.g., 40° C.) for a period of time (e.g., three hours); 9) optionally cooling the solution to a temperature (e.g., 5° C.) and holding the solution at the temperature for a period of time (e.g., for one day); and 10) optionally equilibrating the solution to a temperature (e.g., 20° C.) and evaporating the solvent slowly at room temperature; 11) isolating solids observed from any step; and 12) air-drying the solids for a period of time (e.g., one hour) followed by drying the solids in a vacuum oven at a temperature (e.g., 40° C.) for a period of time (e.g., 5 hours) to yield a solid form comprising a Compound disclosed herein. In certain embodiments, the solvent or solvent system is acetonitrile, methyl isobutyl ketone, isopropanol, acetone/water (95:5 v/v), ethyl acetate/toluene (1:2 v/v), methyl tert-butyl ether, isopropyl acetate, or tetrahydrofuran/water (4:1 v/v). In certain embodiments, the acid is hydrochloric acid (HCl), L-malic acid, oxalic acid, L-tartaric acid, fumaric acid, hydrobromic acid (HBr), maleic acid, malonic acid, ethane-1,2-disulfonic acid, or p-toluenesulfonic acid. In certain embodiments, the acid is dispensed as a 3 M solution of HCl in water, a 1 M solution of L-malic acid in THF, a 0.5 M solution of oxalic acid in water, a 0.5 M solution of L-tartaric acid in tetrahydrofuran, a 0.2 M solution of fumaric acid in ethanol, a 5 M solution of HBr in water, a 3 M solution of maleic acid in water, a 3 M solution of malonic acid in water, a 3 M solution of ethane-1,2-disulfonic acid in water, or a 0.225 M solution of p-toluenesulfonic acid in acetonitrile. In certain embodiments, the anti-solvent is hexane, cyclohexane, toluene, or diisopropyl ether. In certain embodiments, the solution is evaporated under reduced pressure in a centrifuge evaporator. In certain other embodiments, the solution is evaporated under a slow bleed of inert gas such as nitrogen or argon gas.

In certain embodiments, provided herein are methods for making a solid form comprising a Compound disclosed herein, or a tautomer thereof, comprising 1) combining Compound 1 (e.g., about 100 mg) with a solvent (e.g., about 1.25 mL) and an acid (e.g., about 1.0 equivalent); 2) heating the resulting mixture to a temperature (e.g., about 40° C.) for a period of time (e.g., about one hour); 3) optionally evaporating the mixture to dryness; 4) optionally forming a slurry of the dried solid in a solvent; 5) optionally dissolving the dried solid in a solvent, and adding seeds of a crystalline salt of Compound 1 (e.g., about 1 mg) to the solution; 6) optionally cycling the temperature (e.g., between about 5° C. and about 40° C.; 1° C. per minute heating/cooling rate with an hour hold between each heating/cooling cycle) of the solution for a period of time (e.g., about two days); 7) optionally cooling the solution to 5° C. and holding the solution at 5° C. for a period of time (e.g., three days); 8) isolating solids from the solution; and 9) air-drying the solids for a period of time (e.g., one hour) followed by drying the solids in a vacuum oven at a temperature (e.g., 40° C.) for a period of time (e.g., 5 hours) to yield a crystalline solid form comprising a Compound disclosed herein. In certain embodiments, the solvent or solvent system is acetonitrile, methyl isobutyl ketone, isopropanol, acetone/water (95:5 v/v), ethyl acetate/toluene (1:2 v/v), methyl tert-butyl ether, isopropyl acetate, or tetrahydrofuran/water (8:2 v/v). In certain embodiments, the acid is hydrochloric acid (HCl), L-malic acid, oxalic acid, L-tartaric acid, fumaric acid, hydrobromic acid (HBr), maleic acid, malonic acid, ethane-1,2-disulfonic acid, or p-toluenesulfonic acid. In certain embodiments, the acid is dispensed as a 3 M solution of HCl in water, a 1 M solution of L-malic acid in THF, a 0.5 M solution of oxalic acid in water, a 0.5 M solution of L-tartaric acid in tetrahydrofuran, a 0.2 M solution of fumaric acid in ethanol, a 5 M solution of HBr in water, a 3 M solution of maleic acid in water, a 3 M solution of malonic acid in water, a 3 M solution of ethane-1,2-disulfonic acid in water, or a 0.225 M solution of p-toluenesulfonic acid in acetonitrile. In certain embodiments, the solution is evaporated under reduced pressure in a centrifuge evaporator. In certain other embodiments, the solution is evaporated under a slow bleed of inert gas such as nitrogen or argon gas. In certain embodiments, the acid is hydrochloric acid (HCl), L-malic acid, oxalic acid, L-tartaric acid, fumaric acid, hydrobromic acid (HBr), maleic acid, malonic acid, ethane-1,2-disulfonic acid, or p-toluenesulfonic acid. In certain embodiments, the acid is dispensed as a 3 M solution of HCl in water, a 1 M solution of L-malic acid in THF, a 0.5 M solution of oxalic acid in water, a 0.5 M solution of L-tartaric acid in tetrahydrofuran, a 0.2 M solution of fumaric acid in ethanol, a 5 M solution of HBr in water, a 3 M solution of maleic acid in water, a 3 M solution of malonic acid in water, a 3 M solution of ethane-1,2-disulfonic acid in water, or a 0.225 M solution of p-toluenesulfonic acid in acetonitrile.

In certain embodiments, provided herein are methods for making a solid form comprising a Compound disclosed herein, or a tautomer thereof, comprising 1) dispensing a solution of Compound 1 in a solvent (e.g., a solution of about 126.25 mg/mL of Compound 1 in the solvent) into a vial; 2) adding a stoichiometric amount (e.g., 1.0 equivalent) of an acid in the solvent to the vial; 3) capping and shaking the vials at a frequency (e.g., about 200 rotations per minute) at a temperature (e.g., ambient temperature) for a period of time (e.g., about an hour); 4) uncapping and drying the sample under nitrogen purge; 5) mixing the sample with an amount of a solvent or solvent system (e.g., about 600 µL); 6) recapping and stirring the sample at a temperature (e.g., ambient temperature) for a period of time (e.g., about two days); 7) filtering the sample using Nylon-membrane centrifuge tube filters; 8) recovering the solids and drying in a vacuum oven at a temperature (e.g., 30° C.) overnight to yield a crystalline solid form comprising a Compound disclosed herein. In certain embodiments, the solution is evaporated under reduced pressure in a slow bleed of inert gas such as nitrogen or argon gas. In certain embodiments, the solvent used in step 1 is acetone. In certain embodiments, the solvent or solvent system used in step 5 is acetone/water (95/5 v/v), isopropanol, isopropyl acetate, ethyl methyl ketone, dimethyl carbonate, or acetonitrile. In certain embodiments, the acid is a 0.225 M solution of p-toluenesulfonic acid in acetonitrile or a 0.207 M solution of fumaric acid in methanol.

In certain embodiments, the solvent or solvent system in the preceding methods is water, methanol, 2-methoxyethanol, 1-propanol, nitromethane, acetonitrile, dimethylsulfoxide, acetone, ethyl methyl ketone, dichloromethane, methyl acetate, 4-methyl-2-pentanone, chloroform, ethyl acetate, chlorobenzene, tetrahydrofuran, 1,4-dioxane, isopropyl ether, toluene, cyclohexane, hepatane, 1-butanol, isopranol, trifluroethanol, dimethyl carbonate, methyl tert-butyl ether, isopropyl acetate, ethanol, 1-methoxy-2-propanol, cyclohexanone, dimethylformamide, 2-methoxyethyl ether, 5% water in methanol, 5% water in acetonitrile, 5% water in acetone, 5% water in tetrahydrofuran, 5% water in isopropanol, 10% water in methanol, 10% water in acetonitrile, 10% water in acetone, 10% water in tetrahydrofuran, 10% water in isopropanol, 10% water in 1,4-dioxane, 20% water in acetone, 20% water in isopropanol, 10% dimethylsulfoxide in isopropanol, 10% dimethylsulfoxide in acetonitrile, N-methyl-2-pyrrolidone, or cyclopentyl methyl ether.

(b) Solid Forms of Compound 2

In one embodiment, provided herein is a solid form of Compound 2.

(i) HCl Salt Form A

In one embodiment, the solid form of Compound 2 is HCl Salt Form A. In one embodiment, HCl Salt Form A is crystalline. In one embodiment, HCl Salt Form A is hydrated.

In certain embodiments, provided herein are methods for making HCl Salt Form A, comprising 1) dispensing acetonitrile (e.g., about 250 µL) into a vial containing an amount of Compound 1 (e.g., about 20 mg); 2) adding a stoichiometric amount (e.g., 1.0 equivalent) of a 3 M solution of HCl in water to the vial; 3) cycling the temperature (e.g., between about 5° C. and about 40° C.: 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in acetonitrile, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g. for at least one hour); 7) isolating solids from the solution; and 8) air-drying the solids for a period of time (e.g., one hour) followed by drying the solids in a vacuum oven at a temperature (e.g., 40° C.) for a period of time (e.g., 5 hours) to yield HCl Salt Form A of Compound 2. In certain embodiments, the solution is evaporated under reduced pressure in a centrifuge evaporator. In certain other embodiments, the solution is evaporated under a slow bleed of inert gas such as nitrogen or argon gas.

Figure 2:
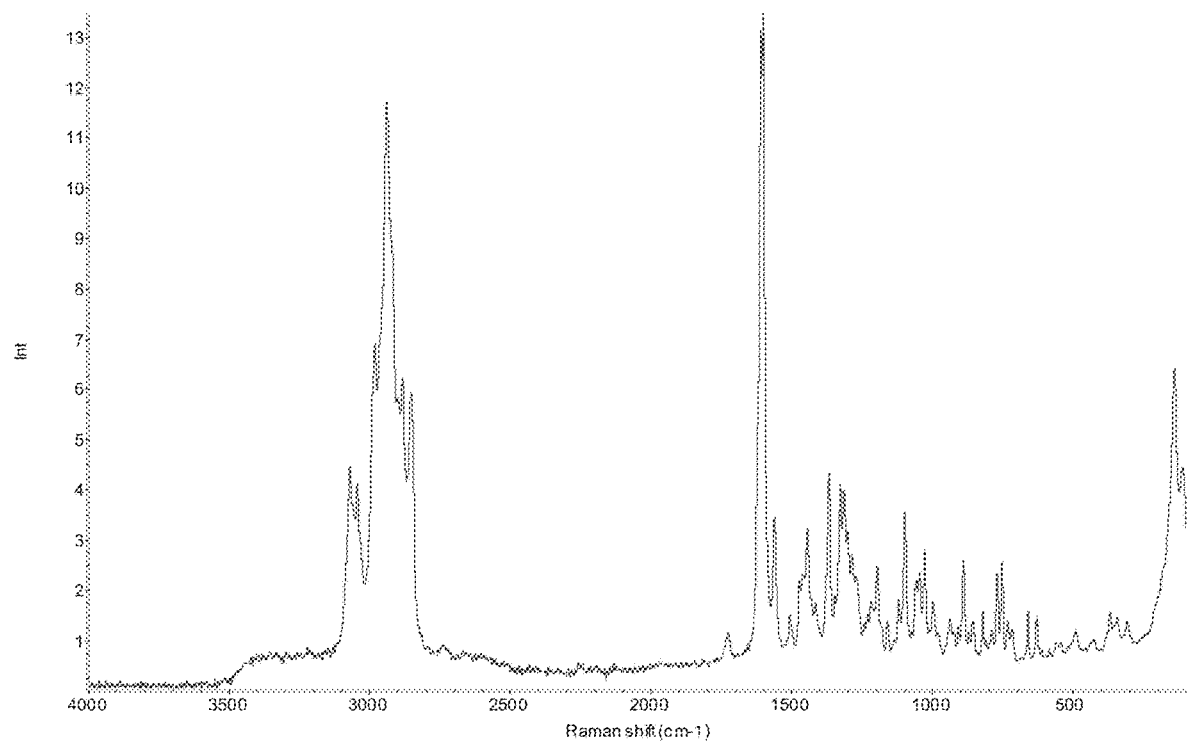
FIG. 2 depicts an FT-Raman spectrum of HCl Salt Form A of Compound 2.

In one embodiment, provided herein is HCl Salt Form A having an FT-Raman Spectrum as depicted in FIG. 2.

Figure 3:
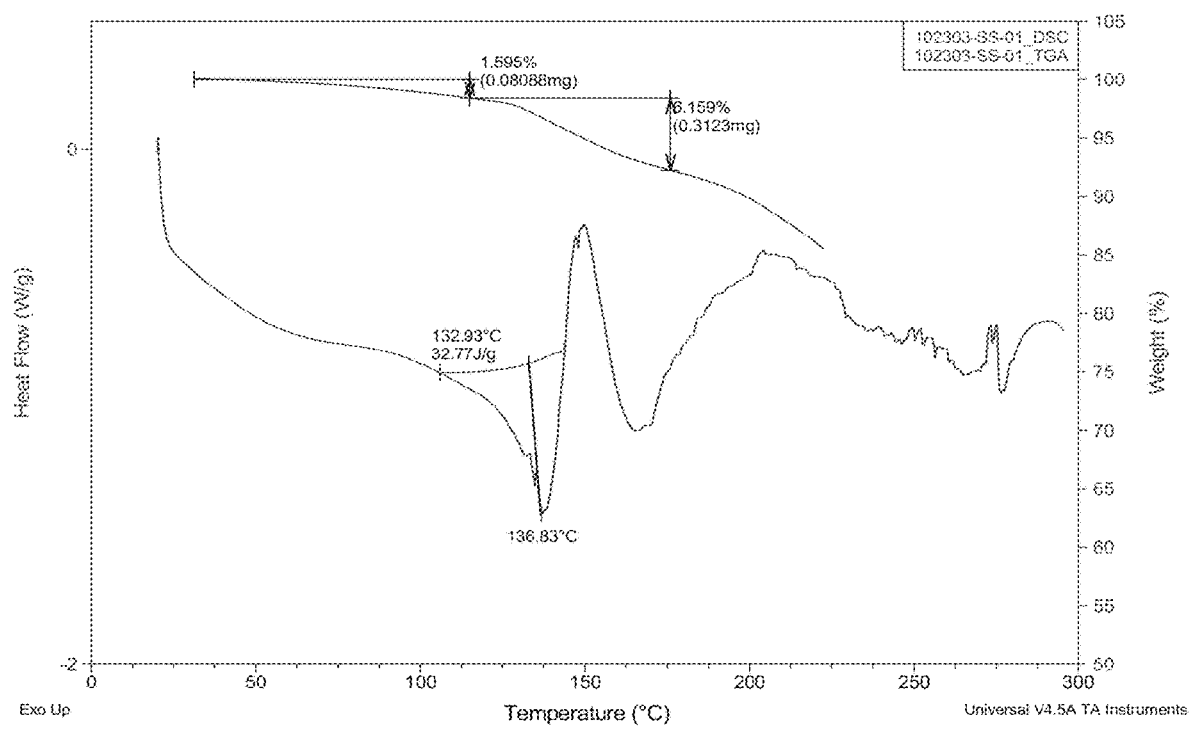
FIG. 3 depicts differential scanning calorimetry/thermal gravimetric analysis of HCl Salt Form A of Compound 2.

In one embodiment, provided herein is a solid form of Compound 2, e.g., HCl Salt Form A of Compound 2, having a DSC thermogram substantially as depicted in FIG. 3 comprising an endotherm with an onset temperature at 132.9° C.

In one embodiment, provided herein is a solid form of Compound 2, e.g., HCl Salt Form A of Compound 2, having a TGA thermogram corresponding substantially to the representative TGA thermogram as depicted in FIG. 3. In certain embodiments, the crystalline form exhibits a TGA thermogram comprising a total mass loss of approximately 1.6% of the total mass of the sample when heated from approximately 25° C. to approximately 115° C.

In certain embodiments, a solid form of Compound 2 provided herein, e.g., HCl Salt Form A, is substantially crystalline, as indicated by, e.g., X-ray powder diffraction measurements. In one embodiment, provided herein is a solid form of Compound 2 having an X-ray powder diffraction pattern (XRPD) substantially as shown in FIG. 1 (e.g., HCl Salt Form A). In one embodiment, a solid form of Compound 2 provided herein, e.g., HCl Salt Form A, has one or more characteristic X-ray powder diffraction peaks at approximately 8.2, 11.5, 12.3, 13.3, 15.8, 16.4, 16.5, 17.7, 18.9, 19.6, 21.3, 22.1, 22.5, 23.1, 23.8, 24.8, 25.5, or 26.8° 2θ (±0.2° 2θ) or (±0.1° 2θ) as depicted in FIG. 1. In a specific embodiment, a solid form of Compound 2 provided herein, e.g., HCl Salt Form A, has one, two, three, four, or five characteristic X-ray powder diffraction peaks at approximately 8.2, 12.3, 18.9, 19.6, or 22.1° 2θ (±0.2° 2θ).

In certain embodiments, HCl Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, HCl Salt Form A is mixed with at least one of HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, HCl Salt Form A is mixed with at least one of HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, HCl Salt Form A is substantially pure. In certain embodiments, the substantially pure HCl Salt Form A is substantially free of other solid forms, including but not limited to amorphous solid. In certain embodiments, the purity of the substantially pure HCl Salt Form A is no less than about 95%, no less than about 96%, no less than about 97%, no less than about 98%, no less than about 98.5%, no less than about 99%, no less than about 99.5%, or no less than about 99.8%.

(ii) HCl Salt Form B

In one embodiment, the solid form of Compound 2 is HCl Salt Form B. In one embodiment, HCl Salt Form B is crystalline. In one embodiment, HCl Salt Form B is hydrated.

In certain embodiments, provided herein are methods for making HCl Salt Form B, comprising 1) dispensing methyl isobutyl ketone (e.g., about 250 µL) into a vial containing an amount of Compound 1 (e.g., about 20 mg); 2) adding a stoichiometric amount (e.g., 1.0 equivalent) of a 3 M solution of HCl in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in methyl isobutyl ketone, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g. for at least one hour); 7) adding hexane (e.g., 1:3 v/v methyl isobutyl ketone to hexane ratio) at a temperature (e.g., 40° C.) and holding the solution at a temperature (e.g., 40° C.) for a period of time (e.g., three hours); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) equilibrating the solution to a temperature (e.g., 20° C.) and evaporating the solvent slowly at room temperature to yield HCl Salt Form B of Compound 2. In certain embodiments, the solution is evaporated under reduced pressure in a centrifuge evaporator. In certain other embodiments, the solution is evaporated under a slow bleed of inert gas such as nitrogen or argon gas.

In certain embodiments, provided herein are methods for making HCl Salt Form B comprising 1) combining Compound 1 (e.g., about 101.9 mg) with methyl isobutyl ketone (e.g., about 1.25 mL) and HCl (e.g., about 1.0 equivalent of a 3 M solution in water); 2) heating the resulting mixture to a temperature (e.g., about 40° C.) for a period of time (e.g., about one hour); 3) evaporating the solution to dryness and dissolving the dried sample in methyl isobutyl ketone; 4) adding seeds of a crystalline HCl salt of Compound 2 (e.g., about 1 mg) to the solution; 5) cycling the temperature (e.g., between about 5° C. and about 40° C.; 1° C. per minute heating/cooling rate with an hour hold between each heating/cooling cycle) of the solution for a period of time (e.g., about two days); 6) isolating solids from the solution; and 7) air-drying the solids for a period of time (e.g., one hour) followed by drying the solids in a vacuum oven at a temperature (e.g., 40° C.) for a period of time (e.g., 5 hours) to yield HCl Salt Form B of Compound 2. In certain embodiments, the solution is evaporated under reduced pressure in a centrifuge evaporator. In certain other embodiments, the solution is evaporated under a slow bleed of inert gas such as nitrogen or argon gas.

Figure 6:
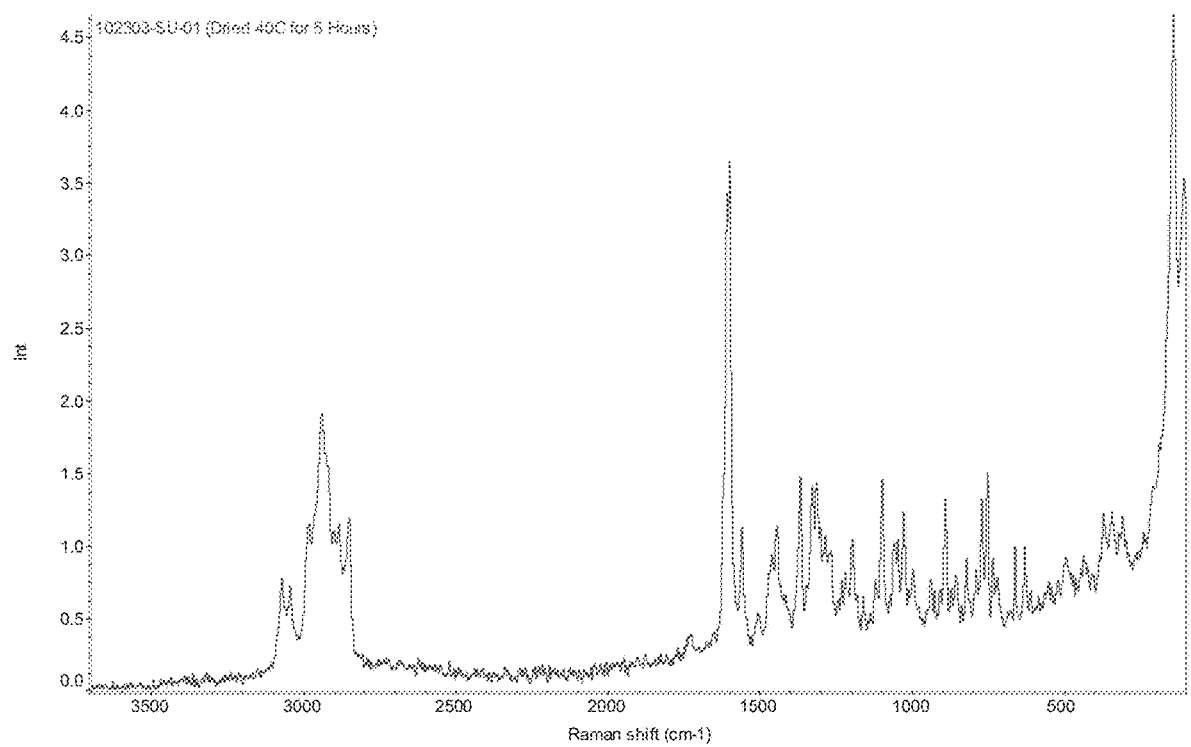
FIG. 6 depicts an FT-Raman spectrum of HCl Salt Form B of Compound 2.

In one embodiment, provided herein is HCl Salt Form B having an FT-Raman Spectrum as depicted in FIG. 6.

Figure 7:
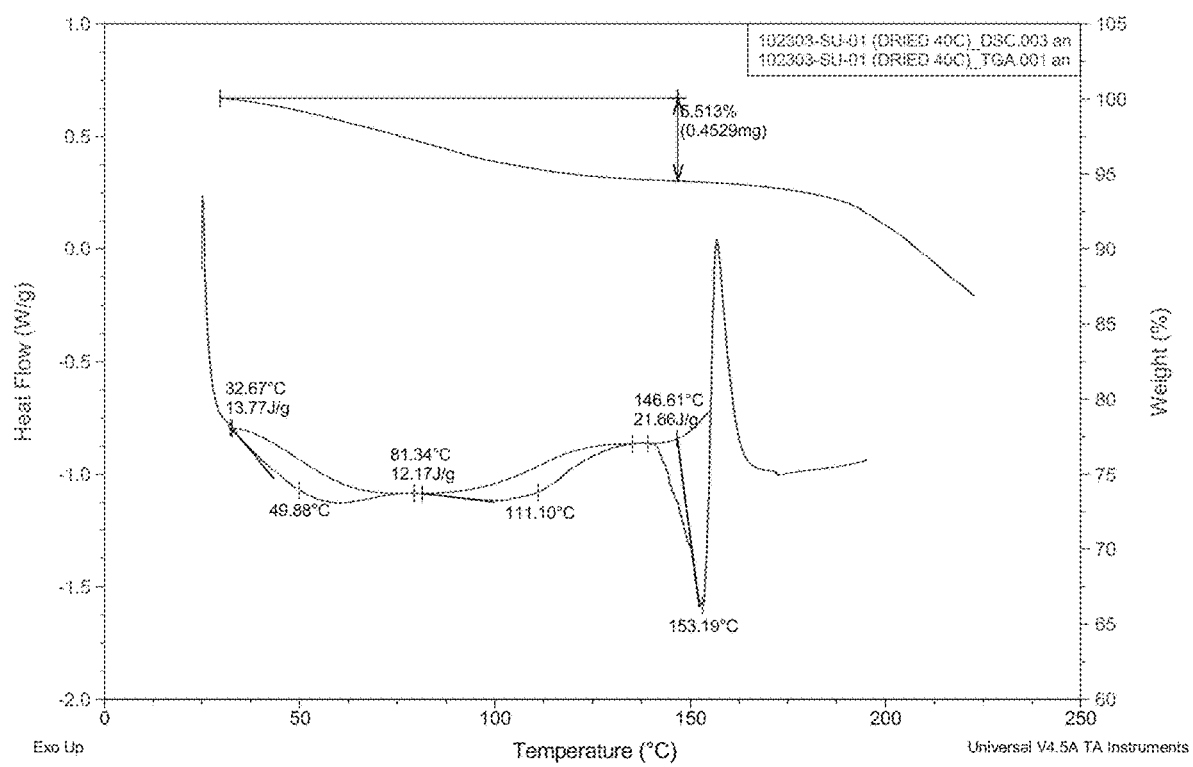
FIG. 7 depicts differential scanning calorimetry/thermal gravimetric analysis of HCl Salt Form B of Compound 2.

In one embodiment, provided herein is a solid form of Compound 2, e.g., HCl Salt Form B of Compound 2, having a DSC thermogram substantially as depicted in FIG. 7 comprising multiple endotherms with onset temperatures at 32.7° C., 81.3° C., and 146.6° C.

In one embodiment, provided herein is a solid form of Compound 2, e.g., HCl Salt Form B of Compound 2, having a TGA thermogram corresponding substantially to the representative TGA thermogram as depicted in FIG. 7. In certain embodiments, the crystalline form exhibits a TGA thermogram comprising a total mass loss of approximately 5.5% of the total mass of the sample when heated from approximately 25° C. to approximately 147° C. In certain embodiments, the crystalline form exhibits a TGA thermogram comprising a total mass loss of approximately 6.5% of the total mass of the sample when heated from approximately 25° C. to approximately 147° C.

Figure 5:
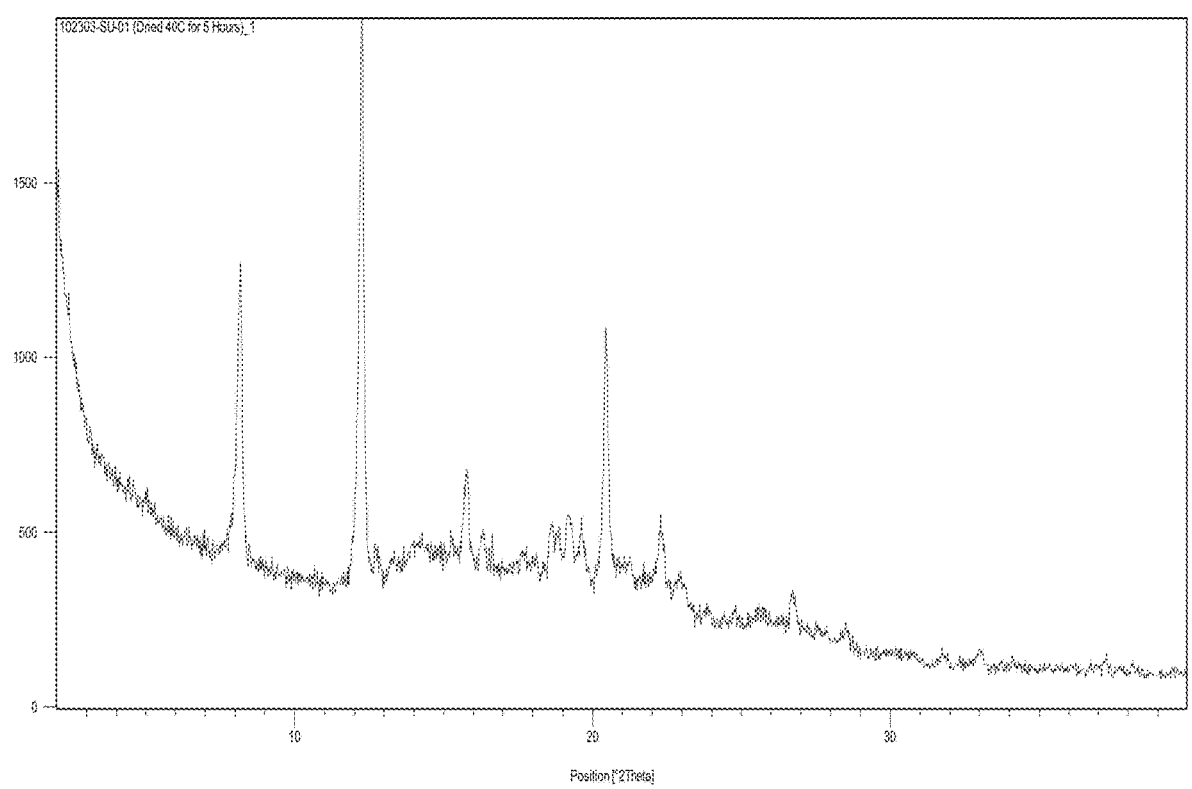
FIG. 5 depicts a PXRD pattern of HCl Salt Form B of Compound 2.

In certain embodiments, a solid form of Compound 2 provided herein, e.g., HCl Salt Form B, is substantially crystalline, as indicated by, e.g., X-ray powder diffraction measurements. In one embodiment, provided herein is a solid form of Compound 2 having an X-ray powder diffraction pattern (XRPD) substantially as shown in FIG. 5 (e.g., HCl Salt Form B). In one embodiment, a solid form of Compound 2 provided herein, e.g., HCl Salt Form B, has one or more characteristic X-ray powder diffraction peaks at approximately 8.2, 12.3, 15.8, 16.3, 18.6, 19.2, 19.6, 20.5, 22.3, 22.9, or 26.7° 2θ (±0.2° 2θ) or (±0.1° 2θ) as depicted in FIG. 5. In a specific embodiment, a solid form of Compound 2 provided herein, e.g., HCl Salt Form B, has one, two, three, or four characteristic X-ray powder diffraction peaks at approximately 8.2, 12.3, 15.8, or 20.5° 2θ (±0.2° 2θ).

In certain embodiments, HCl Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, HCl Salt Form B is mixed with at least one of HCl Salt Form A, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, HCl Salt Form B is mixed with at least one of HCl Salt Form A, L-Malate Salt Form A, L-Malate Salt Form B, Oxalate Salt Form A, Oxalate Salt Form B, Oxalate Salt Form C, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, HCl Salt Form B is substantially pure. In certain embodiments, the substantially pure HCl Salt Form B is substantially free of other solid forms, including but not limited to amorphous solid. In certain embodiments, the purity of the substantially pure HCl Salt Form B is no less than about 95%, no less than about 96%, no less than about 97%, no less than about 98%, no less than about 98.5%, no less than about 99%, no less than about 99.5%, or no less than about 99.8%.

(c) Solid Forms of Compound 3

In one embodiment, provided herein is a solid form of Compound 3.

(i) L-Malate Salt Form A

In one embodiment, the solid form of Compound 3 is L-Malate Salt Form A. In one embodiment, Malate Salt Form A is crystalline.

In certain embodiments, provided herein are methods for making L-Malate Salt Form A, comprising 1) dispensing a solvent or solvent system (e.g., about 250 µL) into a vial containing an amount of Compound 1 (e.g., about 20 mg); 2) adding a stoichiometric amount (e.g., 1.0 equivalent) a 1 M solution of L-malic acid in THF to the vial, 3) cycling the temperature (e.g., between about 5° C. and about 40° C.; 1° C. per minute heating/cooling rate with an hour hold between each heating/cooling cycle) of the solution for a period of time (e.g., about a day): 4) equilibrating the solution to a temperature (e.g., 20° C.) for a period of time (e.g., about one hour); 5) evaporating the solution to dryness; 6) suspending the dried sample in the solvent or solvent system, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g., for at least one hour); 7) optionally adding an anti-solvent (e.g., 1:3 v/v solvent to anti-solvent ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) equilibrating the solution to a temperature (e.g., 20° C.) and evaporating the solvent slowly at room temperature to yield L-Malate Salt Form A of Compound 3. In certain embodiments, the solvent or solvent system is acetonitrile, methyl tert-butyl ether, isopropanol, or a 2:1 v/v mixture of toluene/ethyl acetate. In certain embodiments, the anti-solvent is cyclohexane. In certain embodiments, the solution is evaporated under reduced pressure in a centrifuge evaporator. In certain other embodiments, the solution is evaporated under a slow bleed of inert gas such as nitrogen or argon gas.

In certain embodiments, provided herein are methods for making L-Malate Salt Form A comprising 1) combining Compound 1 (e.g., about 97.9 mg) with isopropyl acetate (e.g., about 1.25 mL) and L-malic acid (e.g., about 1.0 equivalent of a 1 M solution in THF); 2) heating the resulting mixture to a temperature (e.g., about 40° C.) for a period of time (e.g., about one hour); 3) evaporating the solution to dryness and dissolving the dried sample in isopropyl acetate; 4) adding seeds of a crystalline L-malate salt of Compound 1 (e.g., about 1 mg) to the solution; 5) cycling the temperature (e.g., between about 5° C. and about 40° C. 1° C. per minute heating/cooling rate with an hour hold between each heating/cooling cycle) of the solution for a period of time (e.g., about two days); 6) isolating solids from the solution; and 7) air-drying the solids for a period of time (e.g., one hour) followed by drying the solids in a vacuum oven at a temperature (e.g., 40° C.) for a period of time (e.g., 5 hours) to yield Malate Salt Form A of Compound 3. In certain embodiments, the solution is evaporated under reduced pressure in a centrifuge evaporator. In certain other embodiments, the solution is evaporated under a slow bleed of inert gas such as nitrogen or argon gas.

Figure 10:
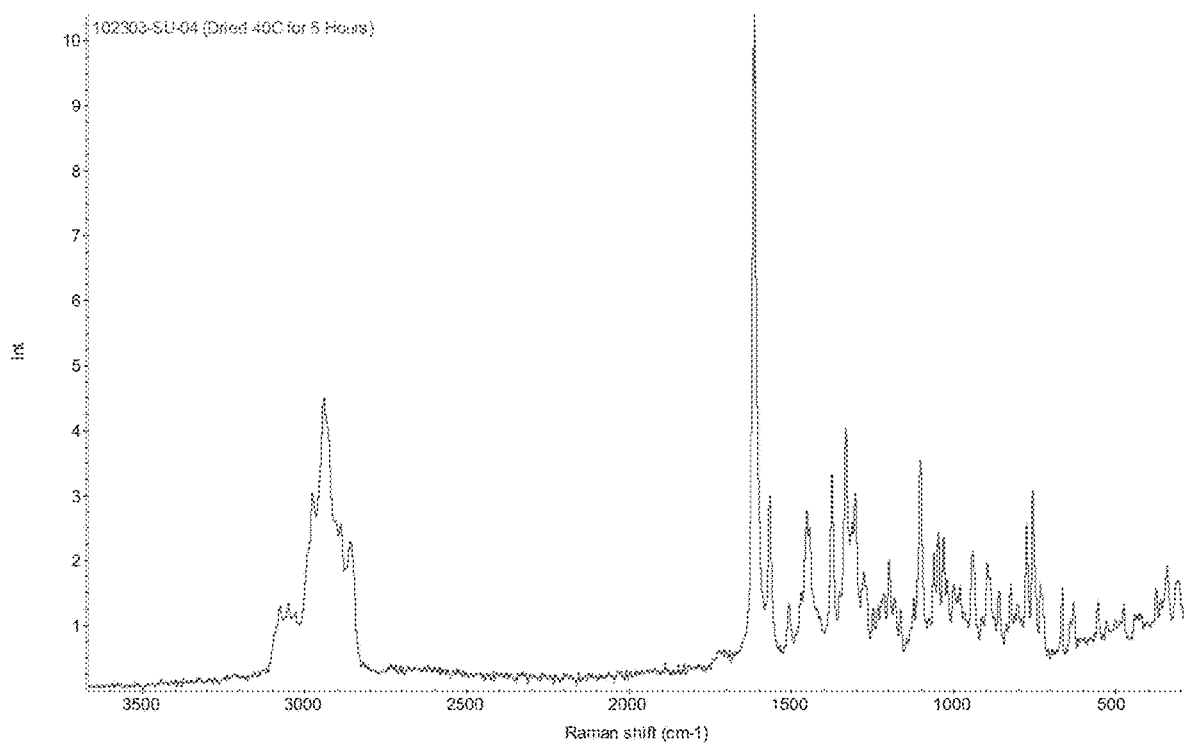
FIG. 10 depicts an FT-Raman spectrum of L-Malate Salt Form A of Compound 3.

In one embodiment, provided herein is L-Malate Salt Form A having an FT-Raman Spectrum as depicted in FIG. 10.

Figure 11:
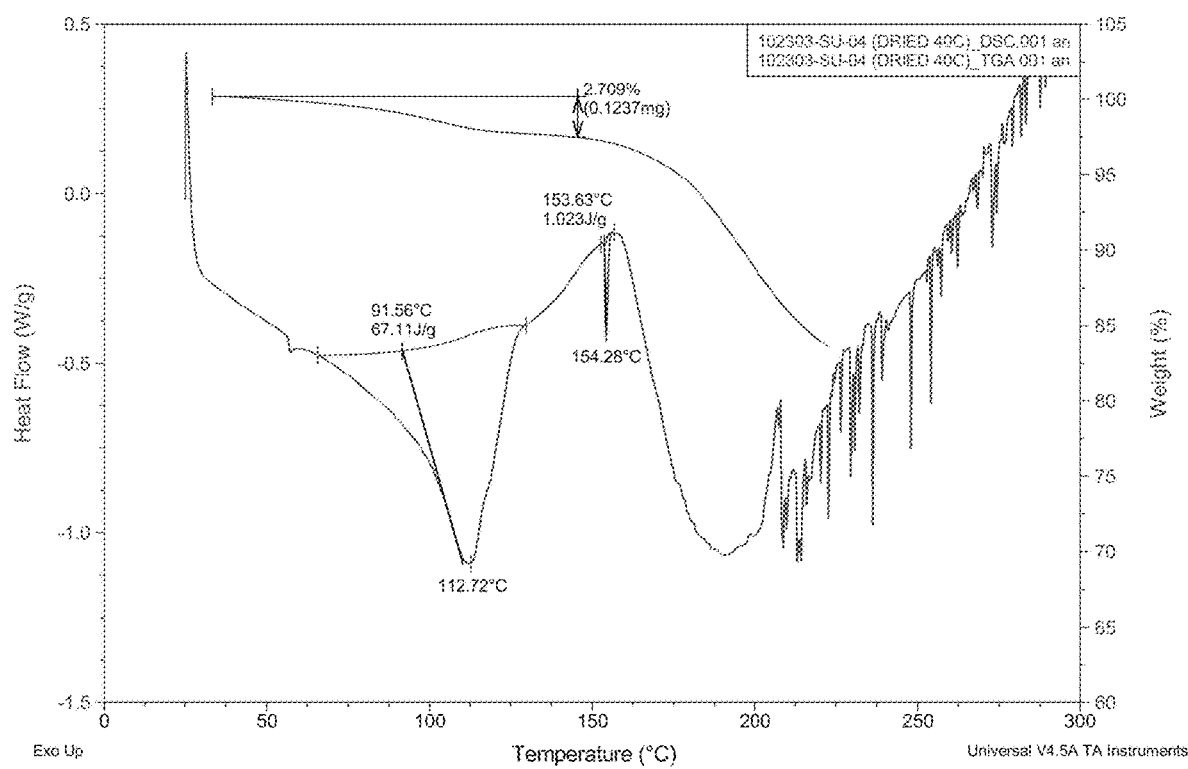
FIG. 11 depicts differential scanning calorimetry/thermal gravimetric analysis of L-Malate Salt Form A of Compound 3.

In one embodiment, provided herein is a solid form of Compound 3, e.g., L-Malate Salt Form A of Compound 3, having a DSC thermogram substantially as depicted in FIG. 11 comprising an endotherm with onset temperature at 91.6° C., followed by a small endotherm with an onset temperature at 153.6° C.

In one embodiment, provided herein is a solid form of Compound 3, e.g., L-Malate Salt Form A of Compound 3, having a TGA thermogram corresponding substantially to the representative TGA thermogram as depicted in FIG. 11. In certain embodiments, the crystalline form exhibits a TGA thermogram comprising a total mass loss of approximately 2.7% of the total mass of the sample when heated from approximately 25° C. to approximately 145° C.

Figure 9:
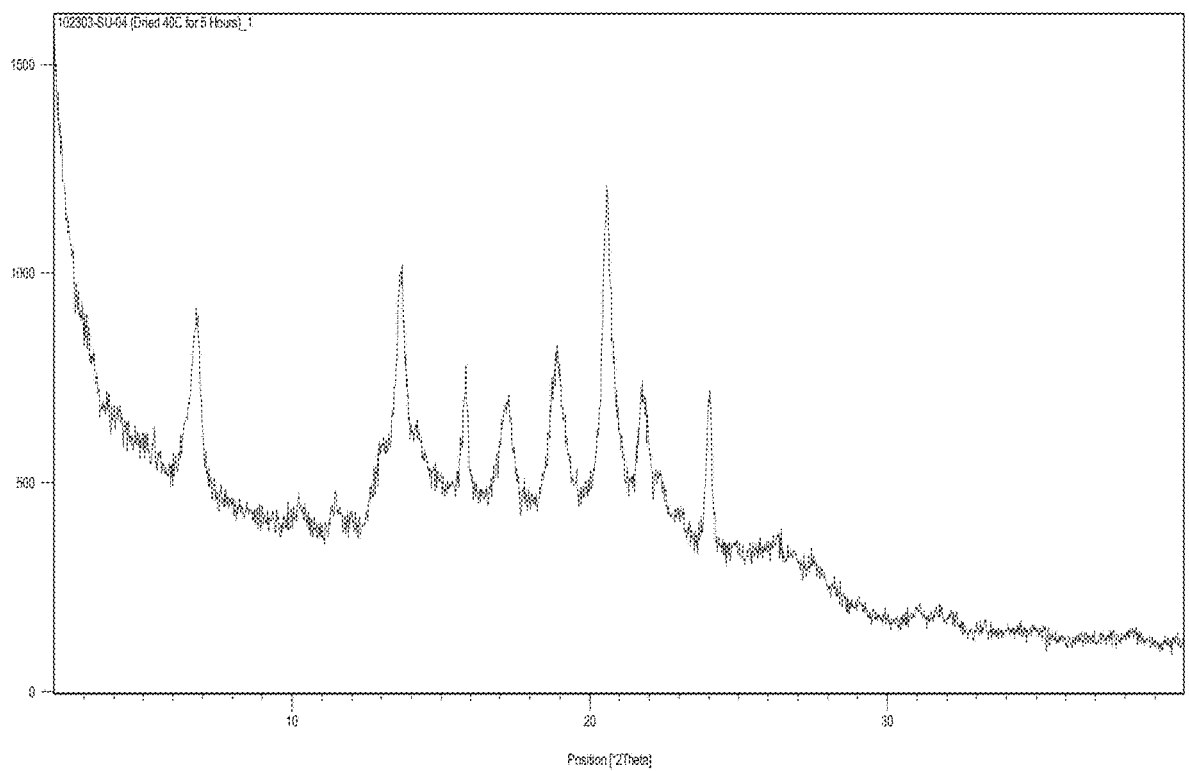
FIG. 9 depicts a PXRD pattern of L-Malate Salt Form A of Compound 3.

In certain embodiments, a solid form of Compound 3 provided herein, e.g., L-Malate Salt Form A, is substantially crystalline, as indicated by, e.g., X-ray powder diffraction measurements. In one embodiment, provided herein is a solid form of Compound 3 having an X-ray powder diffraction pattern (XRPD) substantially as shown in FIG. 9 (e.g., L-Malate Salt Form A). In one embodiment, a solid form of Compound 3 provided herein, e.g., L-Malate Salt Form A, has one or more characteristic X-ray powder diffraction peaks at approximately 6.9, 10.3, 11.4, 13.6, 15.9, 17.2, 18.9, 20.6, 21.7, 24.0, 26.3° 2θ (±0.2° 2θ) or (±0.1° 2θ) as depicted in FIG. 9. In a specific embodiment, a solid form of Compound 3 provided herein, e.g., L-Malate Salt Form A, has one, two, three, four, or five characteristic X-ray powder diffraction peaks at approximately 6.9, 13.6, 18.9, 20.6, or 24.0° 2θ (±0.2° 2θ).

In certain embodiments, L-Malate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, L-Malate Salt Form A is mixed with at least one of HCl Salt Form A, HCl Salt Form B, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, L-Malate Salt Form A is mixed with at least one of HCl Salt Form A, HCl Salt Form B, L-Malate Salt Form B, Oxalate Salt Form A, Oxalate Salt Form B, Oxalate Salt Form C, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, L-Malate Salt Form A is substantially pure. In certain embodiments, the substantially pure L-Malate Salt Form A is substantially free of other solid forms, including but not limited to amorphous solid. In certain embodiments, the purity of the substantially pure L-Malate Salt Form A is no less than about 95%, no less than about 96%, no less than about 97%, no less than about 98%, no less than about 98.5%, no less than about 99%, no less than about 99.5%, or no less than about 99.8%.

(ii) L-Malate Salt Form B

In one embodiment, the solid form of Compound 3 is Malate Salt Form B. In one embodiment, Malate Salt Form B is crystalline.

In certain embodiments, provided herein are methods for making L-Malate Salt Form B, comprising 1) dispensing a solvent (e.g., about 250 μL) into a vial containing an amount of Compound 1 (e.g., about 20 mg); 2) adding a stoichiometric amount (e.g., 1.0 equivalent) a 1 M solution of L-malic acid in THF to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent or solvent system, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g. for at least one hour); 7) optionally adding an anti-solvent (e.g., 1:3 v/v solvent to anti-solvent ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) isolating the solids from solution; 11) air-drying the solids to yield L-Malate Salt Form B of Compound 3. In certain embodiments, the solvent is isopropyl acetate. In certain embodiments, the anti-solvent is diisopropyl ether. In certain embodiments, the solution is evaporated under reduced pressure in a centrifuge evaporator. In certain other embodiments, the solution is evaporated under a slow bleed of inert gas such as nitrogen or argon gas.

Figure 14:
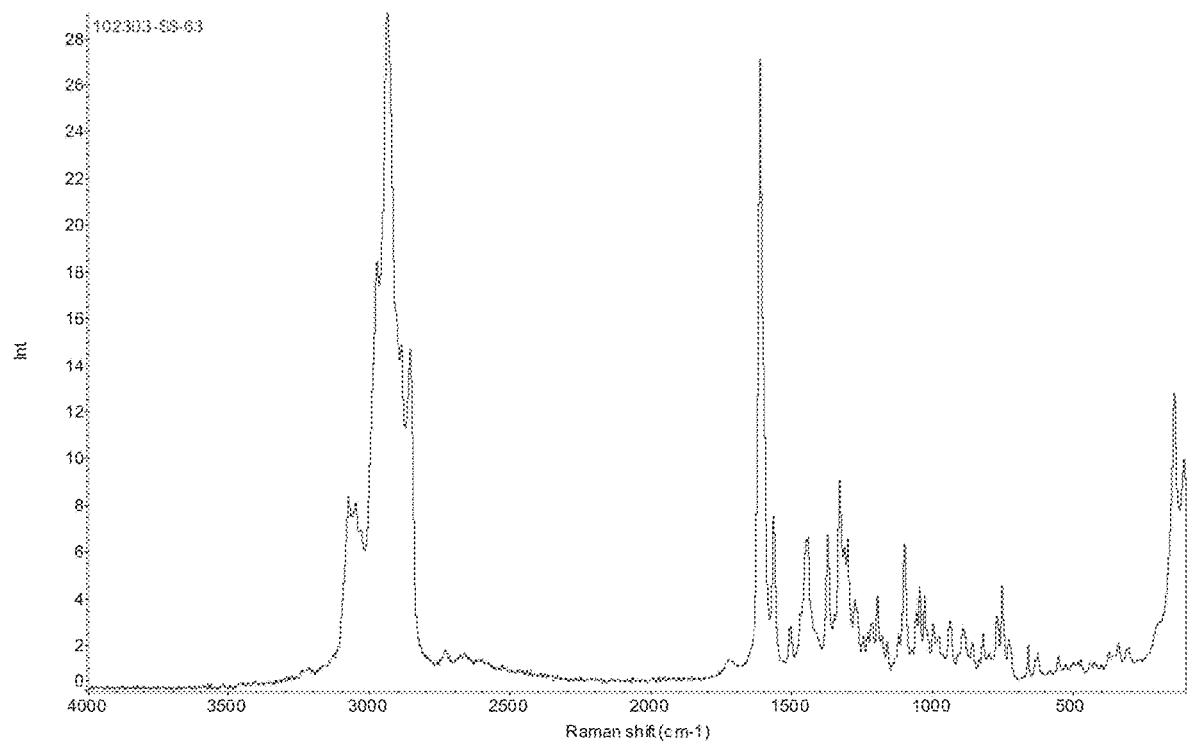
FIG. 14 depicts an FT-Raman spectrum of L-Malate Salt Form B of Compound 3.

In one embodiment, provided herein is L-Malate Salt Form B having an FT-Raman Spectrum as depicted in FIG. 14.

Figure 15:
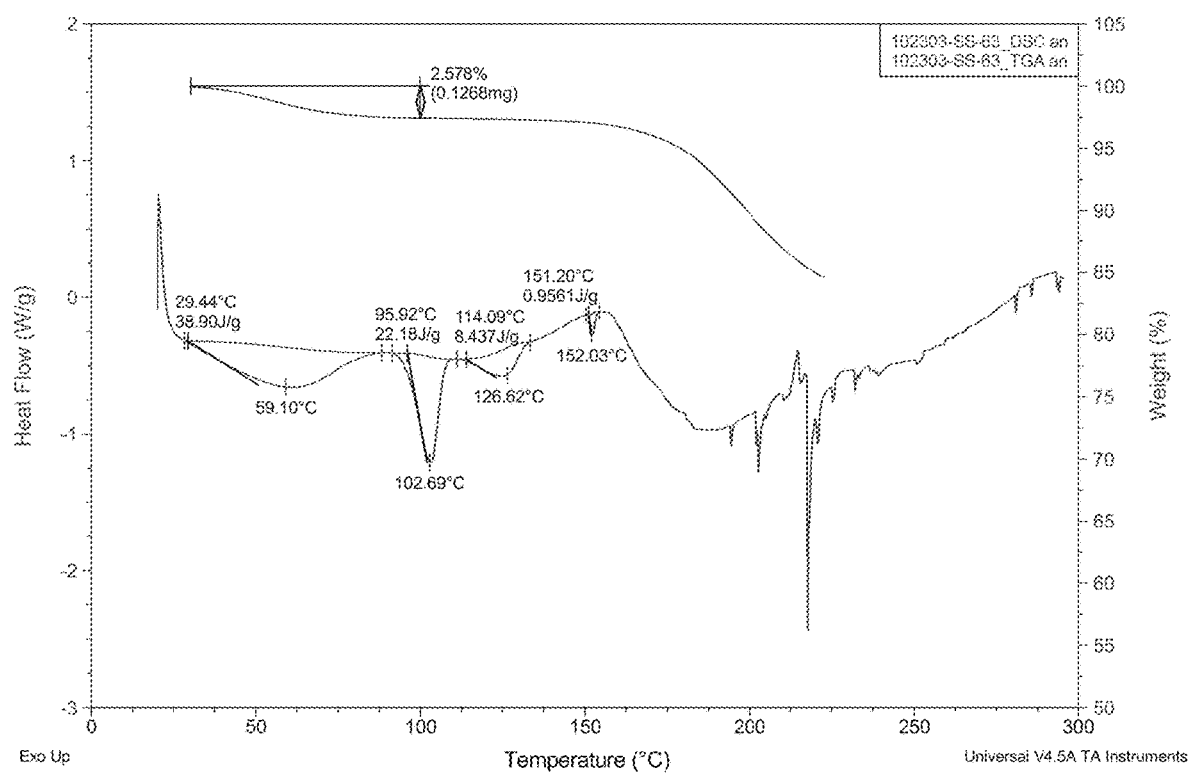
FIG. 15 depicts differential scanning calorimetry/thermal gravimetric analysis of L-Malate Salt Form B of Compound 3.

In one embodiment, provided herein is a solid form of Compound 3, e.g., L-Malate Salt Form B of Compound 3, having a DSC thermogram substantially as depicted in FIG. 15 comprising multiple endotherms with onset temperatures at 29.4° C., 95.9° C., 114.1° C., and 151.2° C.

In one embodiment, provided herein is a solid form of Compound 3, e.g., L-Malate Salt Form B of Compound 3, having a TGA thermogram corresponding substantially to the representative TGA thermogram as depicted in FIG. 15. In certain embodiments, the crystalline form exhibits a TGA thermogram comprising a total mass loss of approximately 2.6% of the total mass of the sample when heated from approximately 30° C. to approximately 100° C.

Figure 13:
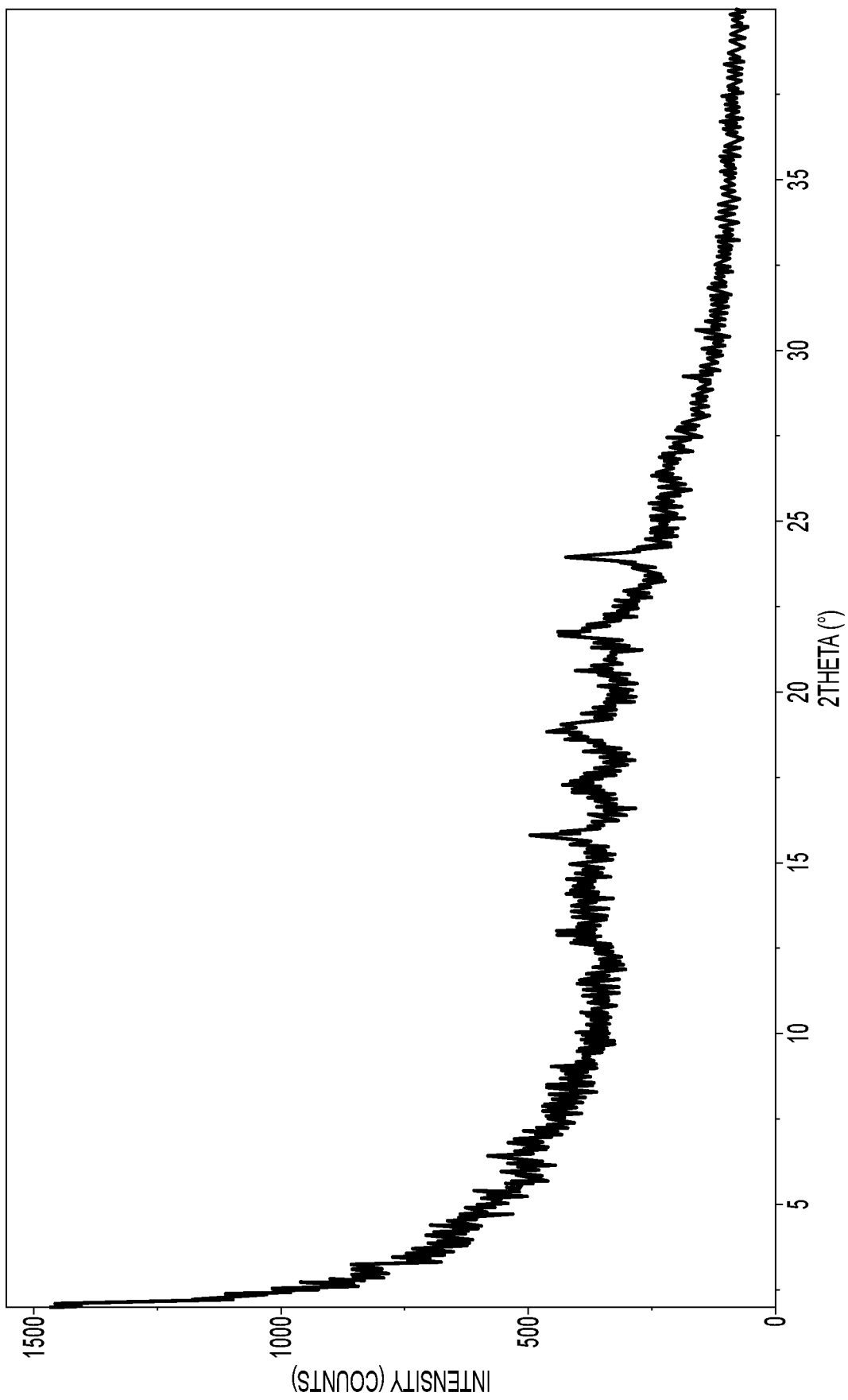
FIG. 13 depicts a PXRD pattern of L-Malate Salt Form B of Compound 3.

In certain embodiments, a solid form of Compound 3 provided herein, e.g., L-Malate Salt Form B, is substantially crystalline, as indicated by, e.g., X-ray powder diffraction measurements. In one embodiment, provided herein is a solid form of Compound 3 having an X-ray powder diffraction pattern (XRPD) substantially as shown in FIG. 13 (e.g., L-Malate Salt Form B). In one embodiment, a solid form of Compound 3 provided herein, e.g., L-Malate Salt Form B, has one or more characteristic X-ray powder diffraction peaks at approximately 6.4, 12.9, 15.8, 17.4, 18.9, 20.7, 21.7, or 24.0° 2θ (±0.2° 2θ) or (±0.1° 2θ) as depicted in FIG. 13. In a specific embodiment, a solid form of Compound 3 provided herein, e.g., L-Malate Salt Form B, has one, two, three, four, or five characteristic X-ray powder diffraction peaks at approximately 15.8, 17.4, 18.9, 21.7, or 24.0° 2θ (±0.2° 2θ).

In certain embodiments, L-Malate Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, L-Malate Salt Form B is mixed with at least one of HCl Salt Form A, HCl Salt Form B, L-Malate Salt Form A, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, L-Malate Salt Form B is mixed with at least one of HCl Salt Form A, HC Salt Form B, L-Malate Salt Form A, Oxalate Salt Form A, Oxalate Salt Form B, Oxalate Salt Form C, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, L-Malate Salt Form B is substantially pure. In certain embodiments, the substantially pure L-Malate Salt Form B is substantially free of other solid forms, including but not limited to amorphous solid. In certain embodiments, the purity of the substantially pure L-Malate Salt Form B is no less than about 95%, no less than about 96%, no less than about 97%, no less than about 98%, no less than about 98.5%, no less than about 99%, no less than about 99.5%, or no less than about 99.8%.

(d) Solid Forms of Compound 4

In one embodiment, provided herein is a solid form of Compound 4.

(i) Oxalate Salt Form A

In one embodiment, the solid form of Compound 4 is Oxalate Salt Form A. In one embodiment, Oxalate Salt Form A is crystalline. In one embodiment, Oxalate Salt Form A is non-solvated.

In certain embodiments, provided herein are methods for making Oxalate Salt Form A, comprising 1) dispensing a solvent or solvent system (e.g., about 250 µL) into a vial containing an amount of Compound 1 (e.g., about 20 mg); 2) adding a stoichiometric amount (e.g., 1.0 equivalent) a 0.5 M solution of oxalic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent, followed by temperature cycling (e.g., between about 5° C. and about 40° C.; 1° C. per minute heating/cooling rate with an hour hold between each heating/cooling cycle) of the solution for a period of time (e.g., about a day); 7) equilibrating the solution to a temperature (e.g., 20° C.) for a period of time (e.g., for at least one hour); and 8) isolating solids from the solution; and 9) air-drying the solids for a period of time (e.g., one hour) followed by drying the solids in a vacuum oven at a temperature (e.g., 40° C.) for a period of time (e.g., 5 hours) to yield Oxalate Salt Form A of Compound 4. In certain embodiments, the solvent or solvent system is methyl tert-butyl ether, 2-propanol, a 95:5 v/v mixture of acetone/water, a 1:2 v/v mixture of ethyl acetate/toluene, methy isobutyl ketone, or isopropyl acetate. In certain embodiments, the solution is evaporated under reduced pressure in a centrifuge evaporator. In certain other embodiments, the solution is evaporated under a slow bleed of inert gas such as nitrogen or argon gas.

Figure 18:
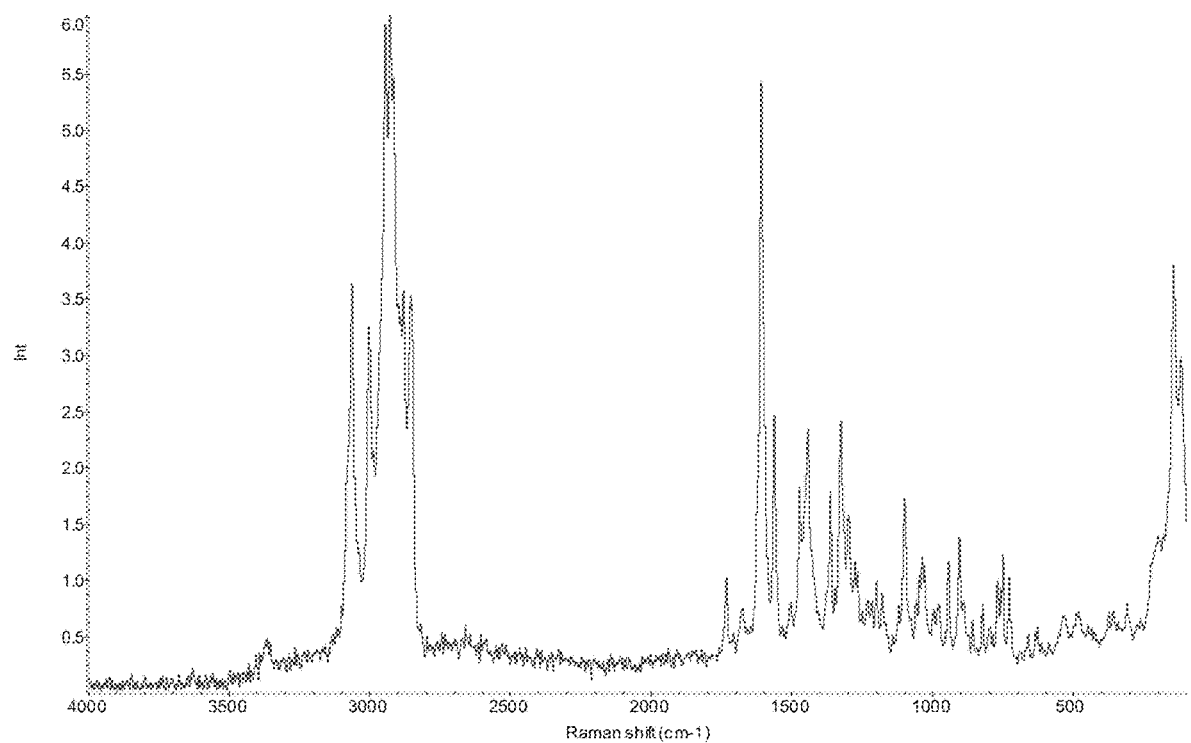
FIG. 18 depicts an FT-Raman spectrum of Oxalate Salt Form A of Compound 4.

In one embodiment, provided herein is Oxalate Salt Form A having an FT-Raman Spectrum as depicted in FIG. 18.

Figure 19:
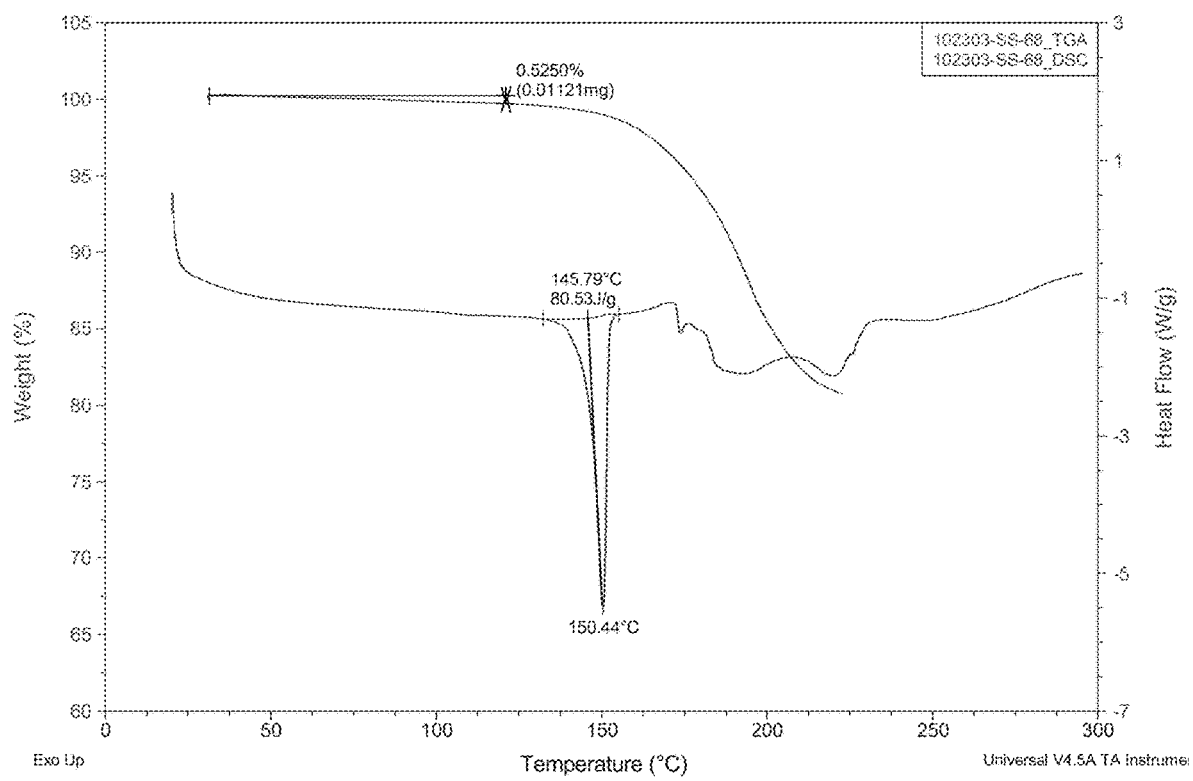
FIG. 19 depicts differential scanning calorimetry/thermal gravimetric analysis of Oxalate Salt Form A of Compound 4.

In one embodiment, provided herein is a solid form of Compound 4, e.g., Oxalate Salt Form A of Compound 4, having a DSC thermogram substantially as depicted in FIG. 19 comprising an endotherm with an onset temperature at 145.8° C.

In one embodiment, provided herein is a solid form of Compound 4, e.g., Oxalate Salt Form A of Compound 4, having a TGA thermogram corresponding substantially to the representative TGA thermogram as depicted in FIG. 19. In certain embodiments, the crystalline form exhibits a TGA thermogram comprising a total mass loss of approximately 0.5% of the total mass of the sample when heated from approximately 30° C. to approximately 120° C.

Figure 17:
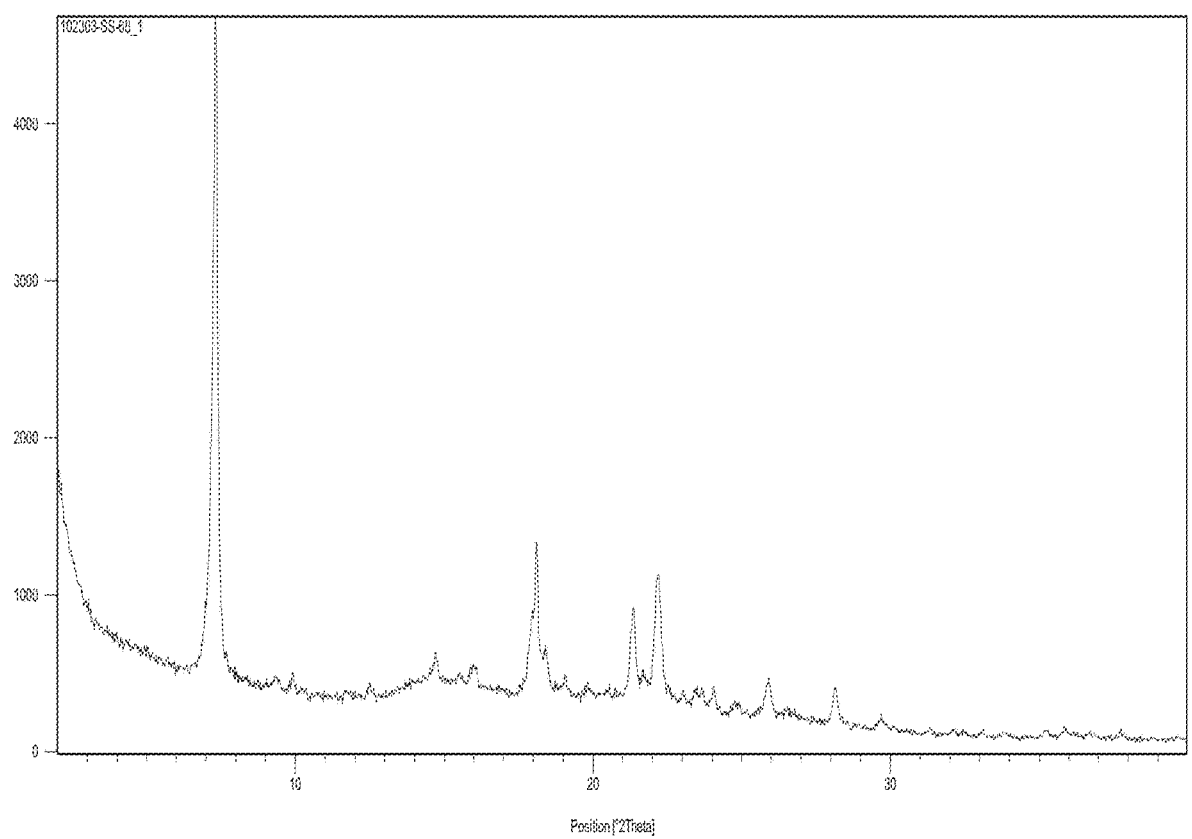
FIG. 17 depicts a PXRD pattern of Oxalate Salt Form A of Compound 4.

In certain embodiments, a solid form of Compound 4 provided herein, e.g., Oxalate Salt Form A, is substantially crystalline, as indicated by, e.g., X-ray powder diffraction measurements. In one embodiment, provided herein is a solid form of Compound 4 having an X-ray powder diffraction pattern (XRPD) substantially as shown in FIG. 17 (e.g., Oxalate Salt Form A). In one embodiment, a solid form of Compound 4 provided herein, e.g., Oxalate Salt Form A, has one or more characteristic X-ray powder diffraction peaks at approximately 7.3, 9.3, 9.9, 12.5, 14.7, 15.5, 16.1, 18.1, 18.4, 19.1, 19.8, 21.4, 22.2, 23.0, 23.4, 24.0, 24.8, 25.9, 28.1, or 29.7° 2θ (±0.2° 2θ) or (±0.1° 2θ) as depicted in FIG. 17. In a specific embodiment, a solid form of Compound 4 provided herein, e.g., Oxalate Salt Form A, has one, two, three, four, or five characteristic X-ray powder diffraction peaks at approximately 7.3, 18.1, 21.4, 22.2, or 28.1° 2θ (±0.2° 2θ).

In certain embodiments, Oxalate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Oxalate Salt Form A is mixed with at least one of HCl Salt Form A, HCl Salt Form B, L-Malate Salt Form A, L-Malate Salt Form B, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Oxalate Salt Form A is mixed with at least one of HCl Salt Form A, HCl Salt Form B, L-Malate Salt Form A, L-Malate Salt Form B, Oxalate Salt Form B, Oxalate Salt Form C, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Oxalate Salt Form A is substantially pure. In certain embodiments, the substantially pure Oxalate Salt Form A is substantially free of other solid forms, including but not limited to amorphous solid. In certain embodiments, the purity of the substantially pure Oxalate Salt Form A is no less than about 95%, no less than about 96%, no less than about 97%, no less than about 98%, no less than about 98.5%, no less than about 99%, no less than about 99.5%, or no less than about 99.8%.

(ii) Oxalate Salt Form B

In one embodiment, the solid form of Compound 4 is Oxalate Salt Form B. In one embodiment, Oxalate Salt Form B is crystalline. In one embodiment, Oxalate Salt Form B is non-solvated.

In certain embodiments, provided herein are methods for making Oxalate Salt Form B, comprising 1) dispensing acetonitrile (e.g., about 250 µL) into a vial containing an amount of Compound 1 (e.g., about 20 mg); 2) adding a stoichiometric amount (e.g., 1.0 equivalent) of a 0.5 M solution of oxalic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in acetonitrile, followed by temperature cycling (e.g., between about 5° C. and about 40° C.; 1° C. per minute heating/cooling rate with an hour hold between each heating/cooling cycle) of the solution for a period of time (e.g., about a day); 7) equilibrating the solution to a temperature (e.g., 20° C.) for a period of time (e.g., for at least one hour); and 8) isolating solids from the solution; and 9) air-drying the solids for a period of time (e.g., one hour) followed by drying the solids in a vacuum oven at a temperature (e.g., 40° C.) for a period of time (e.g., 5 hours) to yield Oxalate Salt Form B of Compound 4. In certain embodiments, the solution is evaporated under reduced pressure in a centrifuge evaporator. In certain other embodiments, the solution is evaporated under a slow bleed of inert gas such as nitrogen or argon gas.

In certain embodiments, provided herein are methods for making Oxalate Salt Form B comprising 1) combining Compound 1 (e.g., about 101.8 mg) with acetonitrile (e.g., about 1.25 mL) and oxalic acid (e.g., about 1.0 equivalent of a 0.5 M solution in water); 2) heating the resulting mixture to a temperature (e.g., about 40° C.) for a period of time (e.g., about one hour); 3) evaporating the solution to dryness and dissolving the dried sample in acetonitrile (e.g., about 1.25 mL); 4) adding seeds of a crystalline oxalate salt of Compound 1 (e.g., about 1 mg) to the solution; 5) cycling the temperature (e.g., between about 5° C. and about 40° C.: 1° C. per minute heating/cooling rate with an hour hold between each heating/cooling cycle) of the solution for a period of time (e.g., about two days); 6) adding acetonitrile (e.g., about 1.0 mL) to enable proper stirring; 6) isolating solids from the sample through vacuum filtration; and 7) air-drying the solids for a period of time (e.g., one hour) followed by drying the solids in a vacuum oven at a temperature (e.g., 40° C.) for a period of time (e.g., 5 hours) to yield Oxalate Salt Form B of Compound 4. In certain embodiments, the solution is evaporated under reduced pressure in a centrifuge evaporator. In certain other embodiments, the solution is evaporated under a slow bleed of inert gas such as nitrogen or argon gas.

Figure 22:
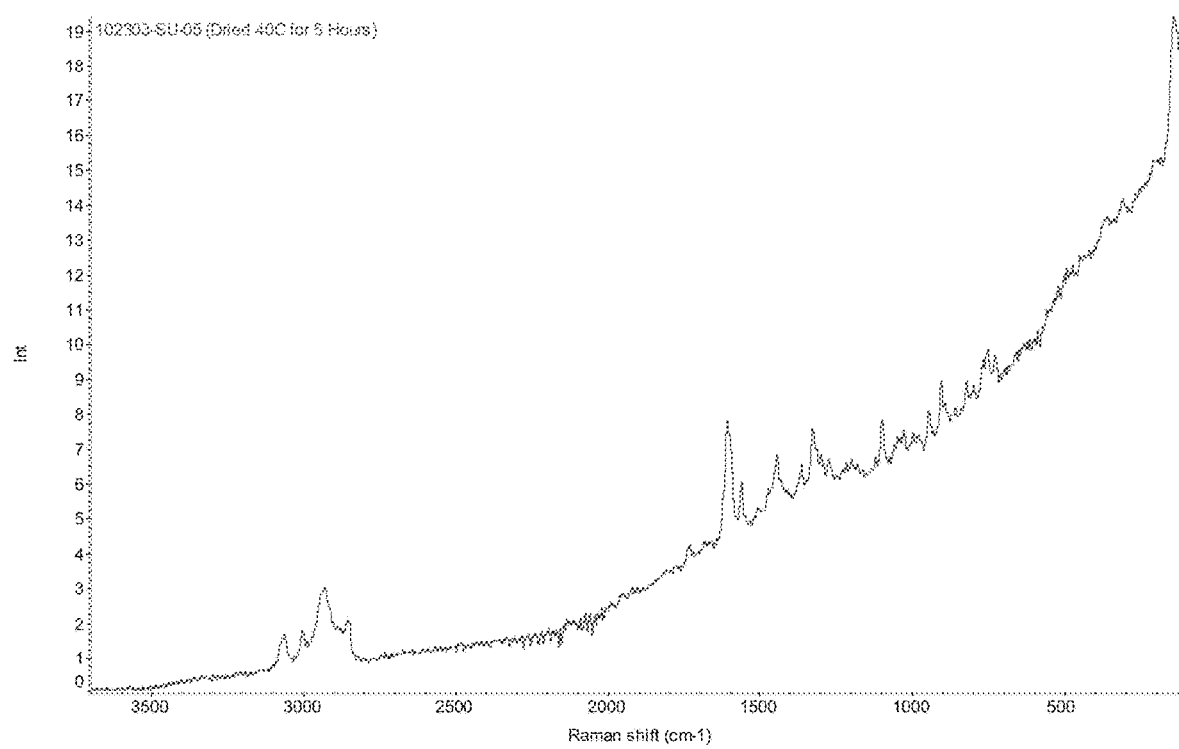
FIG. 22 depicts an FT-Raman spectrum of Oxalate Salt Form B of Compound 4.

In one embodiment, provided herein is Oxalate Salt Form B having an FT-Raman Spectrum as depicted in FIG. 22.

Figure 23:
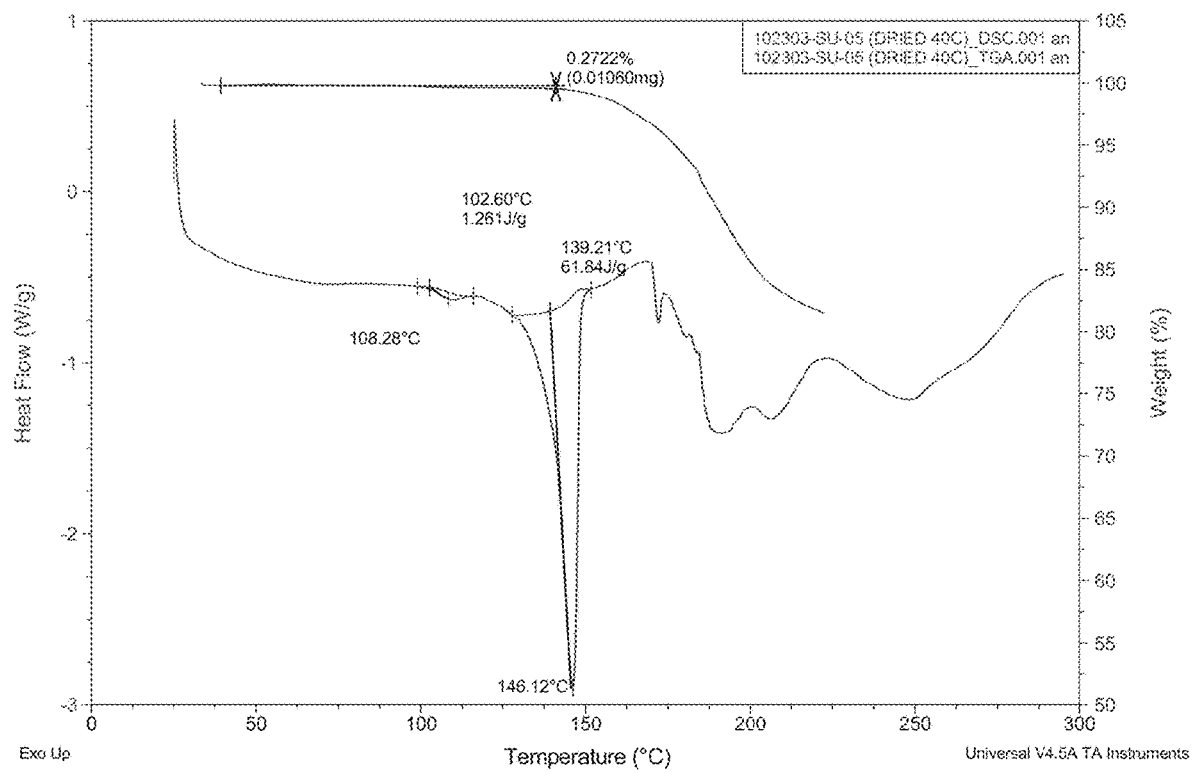
FIG. 23 depicts differential scanning calorimetry/thermal gravimetric analysis of Oxalate Salt Form B of Compound 4.

In one embodiment, provided herein is a solid form of Compound 4, e.g., Oxalate Salt Form B of Compound 4, having a DSC thermogram substantially as depicted in FIG. 23 comprising multiple endotherms with onset temperatures at 102.6° C. and 139.2° C., respectively.

In one embodiment, provided herein is a solid form of Compound 4, e.g., Oxalate Salt Form B of Compound 4, having a TGA thermogram corresponding substantially to the representative TGA thermogram as depicted in FIG. 23. In certain embodiments, the crystalline form exhibits a TGA thermogram comprising a total mass loss of approximately 0.3% of the total mass of the sample when heated from approximately 30° C. to approximately 140° C.

Figure 21:
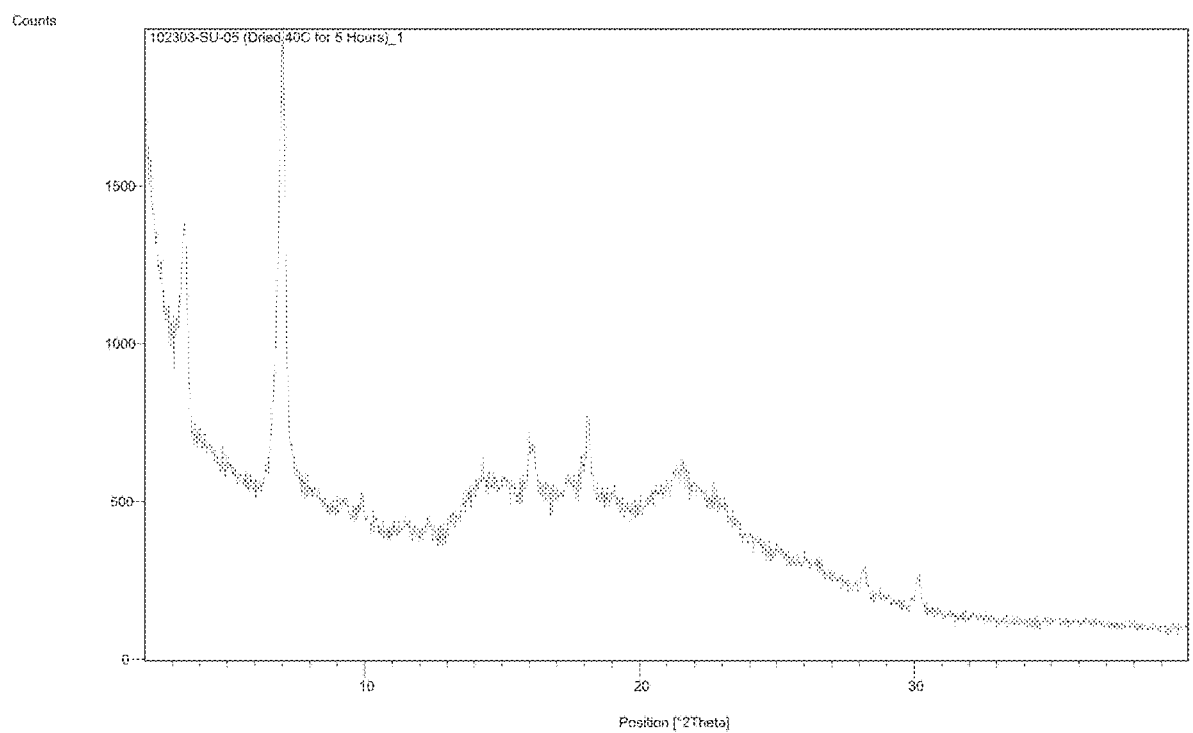
FIG. 21 depicts a PXRD pattern of Oxalate Salt Form B of Compound 4.

In certain embodiments, a solid form of Compound 4 provided herein, e.g., Oxalate Salt Form B, is substantially crystalline, as indicated by, e.g., X-ray powder diffraction measurements. In one embodiment, provided herein is a solid form of Compound 4 having an X-ray powder diffraction pattern (XRPD) substantially as shown in FIG. 21 (e.g., Oxalate Salt Form B). In one embodiment, a solid form of Compound 4 provided herein, e.g., Oxalate Salt Form B, has one or more characteristic X-ray powder diffraction peaks at approximately 3.5, 7.0, 9.9, 16.1, 18.1, 28.2, or 30.1° 2θ (±0.2° 2θ) or (±0.1° 2θ) as depicted in FIG. 21. In a specific embodiment, a solid form of Compound 4 provided herein, e.g., Oxalate Salt Form B, has one, two, three, four, or five characteristic X-ray powder diffraction peaks at approximately 3.5, 7.0, 16.1, 18.1, or 30.1° 2θ (±0.2° 2θ).

In certain embodiments, Oxalate Salt Form B is mixed with other solid forms, including but not limited to the amorphous solid of Compound 1, Compound 2, Compound 3, Compound 4, Compound 5, Compound 6, Compound 7, Compound 8, Compound 9, Compound 10, or Compound 11. In certain embodiments, Oxalate Salt Form B is mixed with at least one of HCl Salt Form A, HCl Salt Form B, L-Malate Salt Form A, L-Malate Salt Form B, Oxalate Salt Form A, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Oxalate Salt Form B is mixed with at least one of HCl Salt Form A, HCl Salt Form B, L-Malate Salt Form A, L-Malate Salt Form B, Oxalate Salt Form A, Oxalate Salt Form C, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Oxalate Salt Form B is substantially pure. In certain embodiments, the substantially pure Oxalate Salt Form B is substantially free of other solid forms, including but not limited to amorphous solid. In certain embodiments, the purity of the substantially pure Oxalate Salt Form B is no less than about 95%, no less than about 96%, no less than about 97%, no less than about 98%, no less than about 98.5%, no less than about 99%, no less than about 99.5%, or no less than about 99.8%.

(iii) Oxalate Salt Form C

In one embodiment, the solid form of Compound 4 is Oxalate Salt Form C. In one embodiment, Oxalate Salt Form C is crystalline. In one embodiment, Oxalate Salt Form C is hydrated and solvated by tetrahydrofuran.

In certain embodiments, provided herein are methods for making Oxalate Salt Form C, comprising 1) dispensing an 4:1 v/v mixture of THF/water (e.g., about 250 μL) into a vial containing an amount of Compound 1 (e.g., about 20 mg); 2) adding a stoichiometric amount (e.g., 1.0 equivalent) a 0.5 M solution of oxalic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in an 4:1 v/v mixture of THF/water, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g. for at least one hour); 7) heating the solution to a temperature (e.g., 40° C.) for a period of time (e.g., three hours); 8) cooling the solution to a temperature (e.g., 5° C.) and holding the solution at the temperature for a period of time (e.g., for one day); and 9) equilibrating the solution to a temperature (e.g., 20° C.) and evaporating the solvent slowly at room temperature to yield Oxalate Salt Form C of Compound 4. In certain embodiments, the solution is evaporated under reduced pressure in a centrifuge evaporator. In certain other embodiments, the solution is evaporated under a slow bleed of inert gas such as nitrogen or argon gas.

Figure 26:
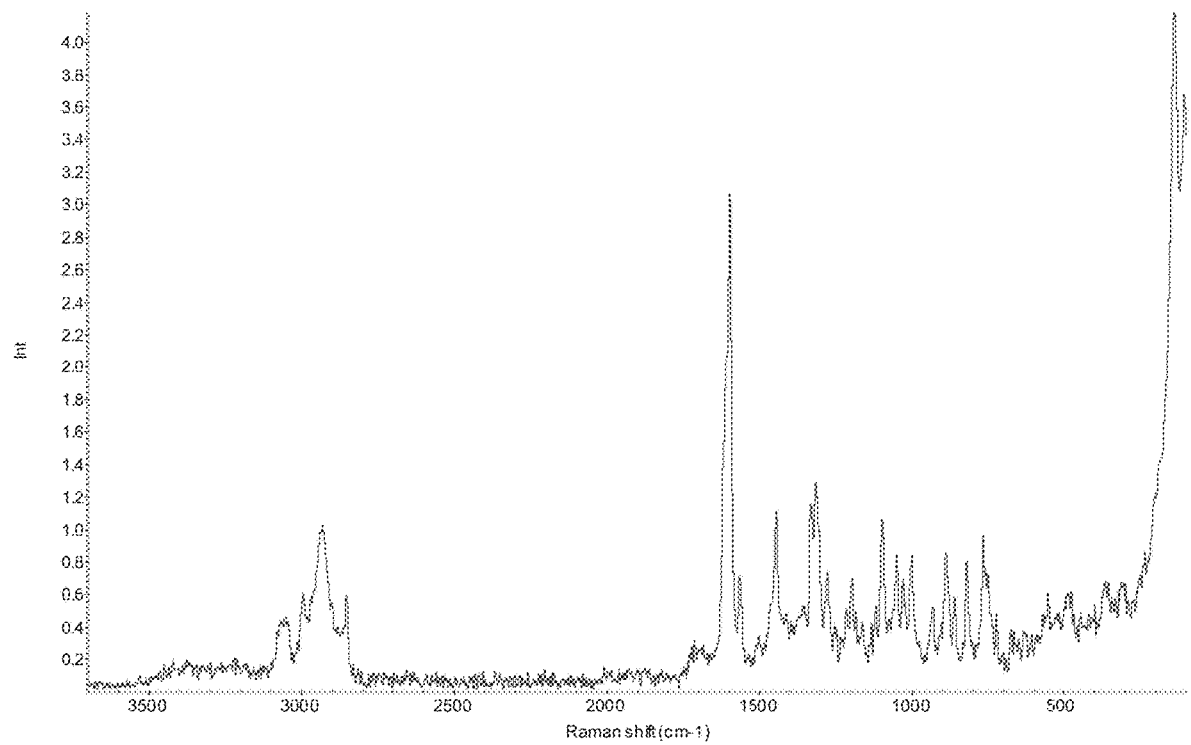
FIG. 26 depicts an FT-Raman spectrum of Oxalate Salt Form C of Compound 4.

In one embodiment, provided herein is Oxalate Salt Form C having an FT-Raman Spectrum as depicted in FIG. 26.

Figure 27:
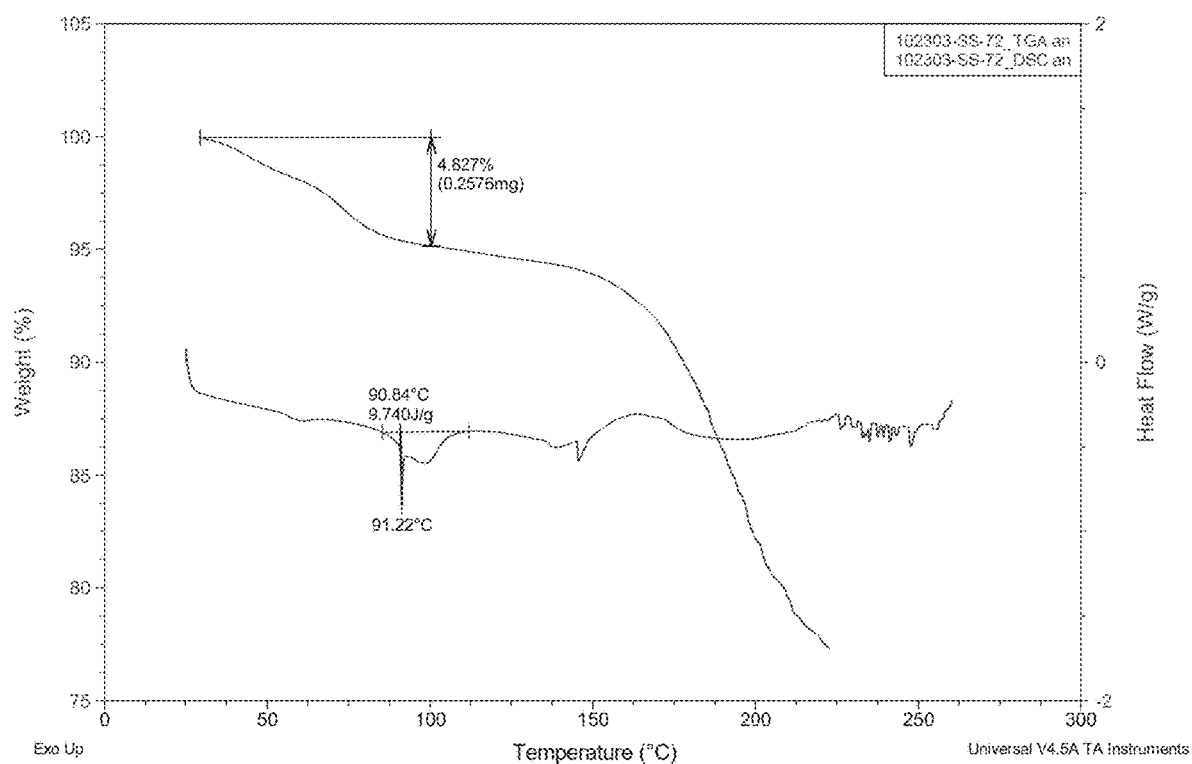
FIG. 27 depicts differential scanning calorimetry/thermal gravimetric analysis of Oxalate Salt Form C of Compound 4.

In one embodiment, provided herein is a solid form of Compound 4, e.g., Oxalate Salt Form C of Compound 4, having a DSC thermogram substantially as depicted in FIG. 27 comprising an endotherm with an onset temperature at 90.8° C.

In one embodiment, provided herein is a solid form of Compound 4, e.g., Oxalate Salt Form C of Compound 4, having a TGA thermogram corresponding substantially to the representative TGA thermogram as depicted in FIG. 27. In certain embodiments, the crystalline form exhibits a TGA thermogram comprising a total mass loss of approximately 4.8% of the total mass of the sample when heated from approximately 25° C. to approximately 100° C.

Figure 25:
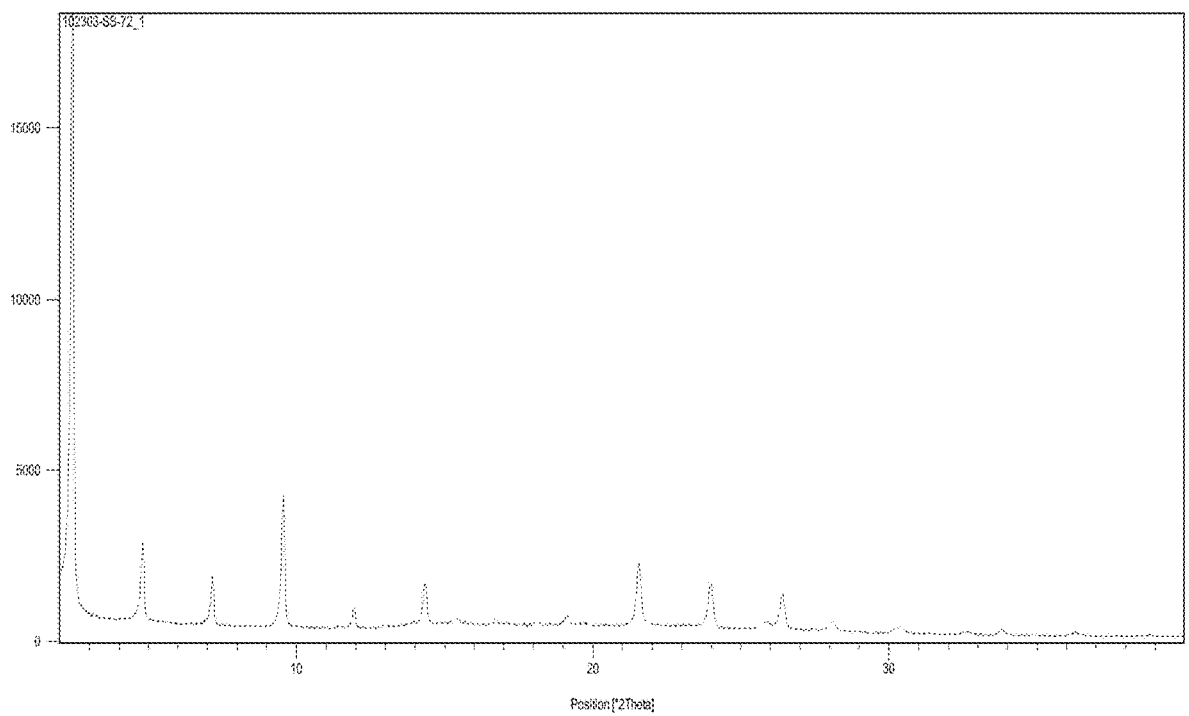
FIG. 25 depicts a PXRD pattern of Oxalate Salt Form C of Compound 4.

In certain embodiments, a solid form of Compound 4 provided herein, e.g., Oxalate Salt Form C, is substantially crystalline, as indicated by, e.g., X-ray powder diffraction measurements. In one embodiment, provided herein is a solid form of Compound 4 having an X-ray powder diffraction pattern (XRPD) substantially as shown in FIG. 25 (e.g., Oxalate Salt Form C). In one embodiment, a solid form of Compound 4 provided herein, e.g., Oxalate Salt Form C, has one or more characteristic X-ray powder diffraction peaks at approximately 2.4, 4.8, 7.2, 9.6, 11.9, 13.0, 14.3, 15.4, 16.7, 18.1, 19.2, 21.6, 24.0, 25.9, 26.4, 28.1, 30.4, 32.7, 33.8, or 36.3° 2θ (±0.2° 2θ) or (±0.1° 2θ) as depicted in FIG. 25. In a specific embodiment, a solid form of Compound 4 provided herein, e.g., Oxalate Salt Form C, has one, two, three, four, five, or six characteristic X-ray powder diffraction peaks at approximately 2.4, 4.8, 9.6, 14.3, 21.6, or 24.0° 2θ (±0.2° 2θ).

In certain embodiments, Oxalate Salt Form C is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Oxalate Salt Form C is mixed with at least one of HCl Salt Form A, HCl Salt Form B, L-Malate Salt Form A, L-Malate Salt Form B, Oxalate Salt Form A, Oxalate Salt Form B, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Oxalate Salt Form C is mixed with at least one of HCl Salt Form A, HCl Salt Form B, L-Malate Salt Form A, L-Malate Salt Form B, Oxalate Salt Form A, Oxalate Salt Form B, L-Tartrate Salt Form A, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Oxalate Salt Form C is substantially pure. In certain embodiments, the substantially pure Oxalate Salt Form C is substantially free of other solid forms, including but not limited to amorphous solid. In certain embodiments, the purity of the substantially pure Oxalate Salt Form C is no less than about 95%, no less than about 96%, no less than about 97%, no less than about 98%, no less than about 98.5%, no less than about 99%, no less than about 99.5%, or no less than about 99.8%.

(e) Solid Forms of Compound 5

In one embodiment, provided herein is a solid form of Compound 5.

(i) L-Tartrate Salt Form A

In one embodiment, the solid form of Compound 5 is L-Tartrate Salt Form A. In one embodiment, L-Tartrate Salt Form A is crystalline. In one embodiment, L-Tartrate Salt Form A is solvated by diisopropyl ether.

In one embodiment, L-Tartrate Salt Form A is a mono-tartrate salt.

In certain embodiments, provided herein are methods for making L-Tartrate Salt Form A, comprising 1) dispensing a solvent (e.g., about 250 µL) into a vial containing an amount of Compound 1 (e.g., about 20 mg); 2) adding a stoichiometric amount (e.g., 1.0 equivalent) of a 0.5 M solution of L-tartaric acid in THF to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent or solvent system, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g. for at least one hour); 7) isolating solids from the sample through vacuum filtration; and 8) air-drying the solids for a period of time (e.g., one hour) followed by drying the solids in a vacuum oven at a temperature (e.g., 40° C.) for a period of time (e.g., 5 hours) to yield L-Tartrate Salt Form A of Compound 5. In certain embodiments, the solvent is methyl tert-butyl ether. In certain embodiments, the solution is evaporated under reduced pressure in a centrifuge evaporator. In certain other embodiments, the solution is evaporated under a slow bleed of inert gas such as nitrogen or argon gas. In certain embodiments, the solvent or solvent system is a 1:4 mixture of acetone and diisopropyl ether. In certain embodiments, the solvent or solvent system is a 30% mixture of heptane in methyl ethyl ketone. In certain embodiments, the solvent or solvent system is a 1:9 mixture of 1,4-dioxane and heptane. In certain embodiments, the solvent or solvent system is heptane. In certain embodiments, the solvent or solvent system is a 70% mixture of heptane in ethyl methyl ketone. In certain embodiments, the solvent or solvent system is a 1:9 mixture of ethyl acetate and heptane.

In certain embodiments, provided herein are methods for making L-Tartrate Salt Form A, comprising 1) dispensing a solvent (e.g., about 250 µL) into a vial containing an amount of Compound 1 (e.g., about 20 mg); 2) adding a stoichiometric amount (e.g., 1.0 equivalent) of a 0.5 M solution of L-tartaric acid in THF to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent solvent system, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g. for at least one hour); 7) optionally adding an anti-solvent (e.g., 1:3 v/v solvent to anti-solvent ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) equilibrating the solution to a temperature (e.g., 20° C.) and evaporating the solvent slowly at room temperature to yield L-Tartrate Salt Form A of Compound 5. In certain embodiments, the solvent is acetonitrile. In certain embodiments, the anti-solvent is diisopropyl ether. In certain embodiments, the solution is evaporated under reduced pressure in a centrifuge evaporator. In certain other embodiments, the solution is evaporated under a slow bleed of inert gas such as nitrogen or argon gas.

Figure 30:
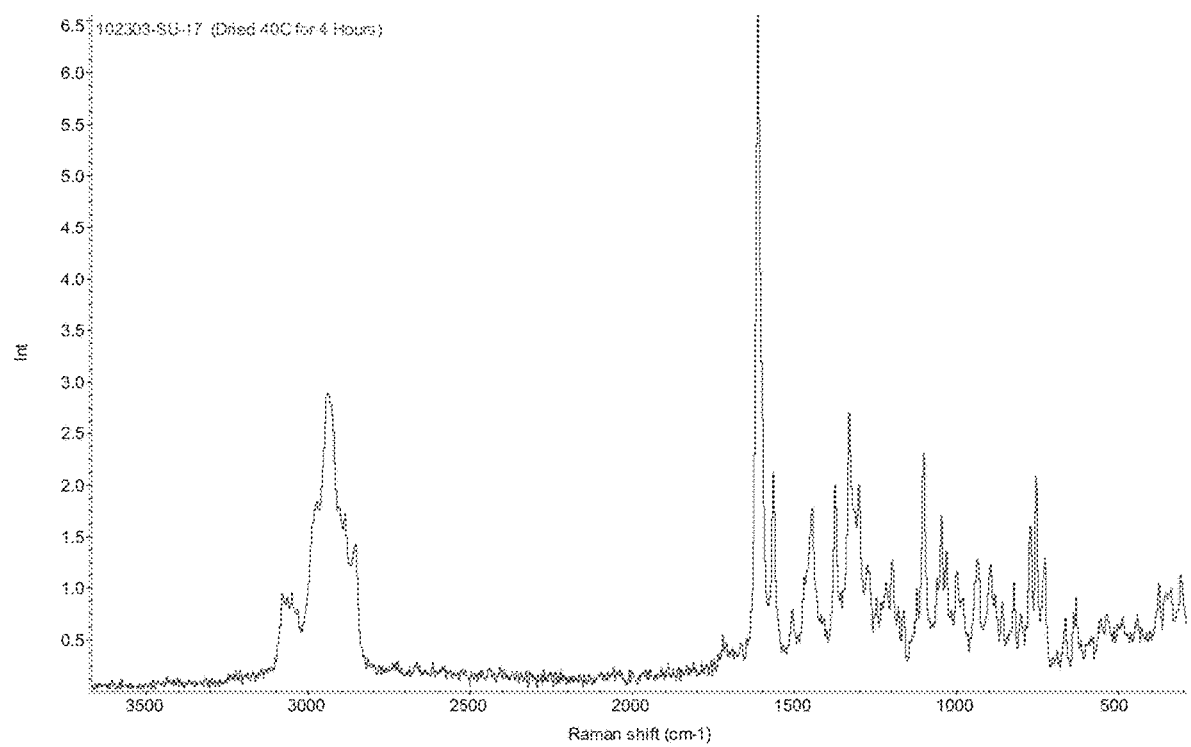
FIG. 30 depicts an FT-Raman spectrum of L-Tartrate Salt Form A of Compound 5.

In certain embodiments, provided herein are methods for making L-Tartrate Salt Form A comprising 1) combining Compound 1 (e.g., about 95.9 mg) with methyl tert-butyl ether (e.g., about 1.25 mL) and L-tartaric acid (0.5M solution in THF, 1 equivalent); 2) stirring the resulting mixture at ambient temperature for a period of time (e.g., about one hour); 3) evaporating the solution to dryness; 4) adding methyl tert-butyl ether (e.g., about 1 mL) to the dried sample; 5) adding seeds of a crystalline L-tartrate salt of Compound 1 (e.g., about 1 mg) to the sample; 6) cycling the temperature (e.g., between about 5° C. and about 40° C.; 1° C. per minute heating/cooling rate with an hour hold between each heating/cooling cycle) of the solution for a period of time (e.g., about one day); 7) stirring the sample at 5° C. for a period of time (e.g., about two days); 8) isolating solids from the sample; and 9) air-drying the solids for a period of time (e.g., one hour) followed by drying the solids in a vacuum oven at a temperature (e.g., 40° C.) for a period of time (e.g., 4 hours) to yield L-Tartrate Salt Form A of Compound 5. In certain embodiments, the solution is evaporated under reduced pressure in a centrifuge evaporator. In certain other embodiments, the solution is evaporated under a slow bleed of inert gas such as nitrogen or argon gas In one embodiment, provided herein is L-Tartrate Salt Form A having an FT-Raman Spectrum as depicted in FIG. 30.

Figure 31:
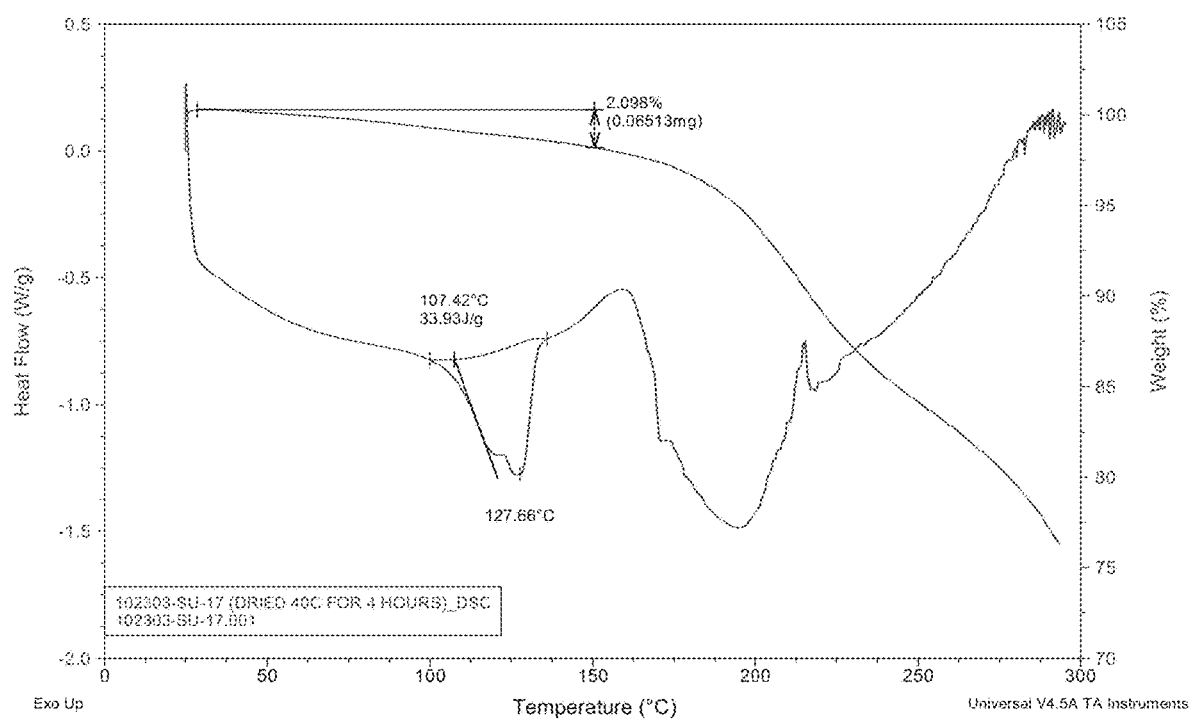
FIG. 31 depicts differential scanning calorimetry/thermal gravimetric analysis of L-Tartrate Salt Form A of Compound 5.

In one embodiment, provided herein is a solid form of Compound 5, e.g., L-Tartrate Salt Form A of Compound 5, having a DSC thermogram substantially as depicted in FIG. 31 comprising an endotherm with an onset temperature at 107.4° C.

In one embodiment, provided herein is a solid form of Compound 5, e.g., L-Tartrate Salt Form A of Compound 5, having a TGA thermogram corresponding substantially to the representative TGA thermogram as depicted in FIG. 31. In certain embodiments, the crystalline form exhibits a TGA thermogram comprising a total mass loss of approximately 2% of the total mass of the sample when heated from approximately 28° C. to approximately 150° C.

Figure 29:
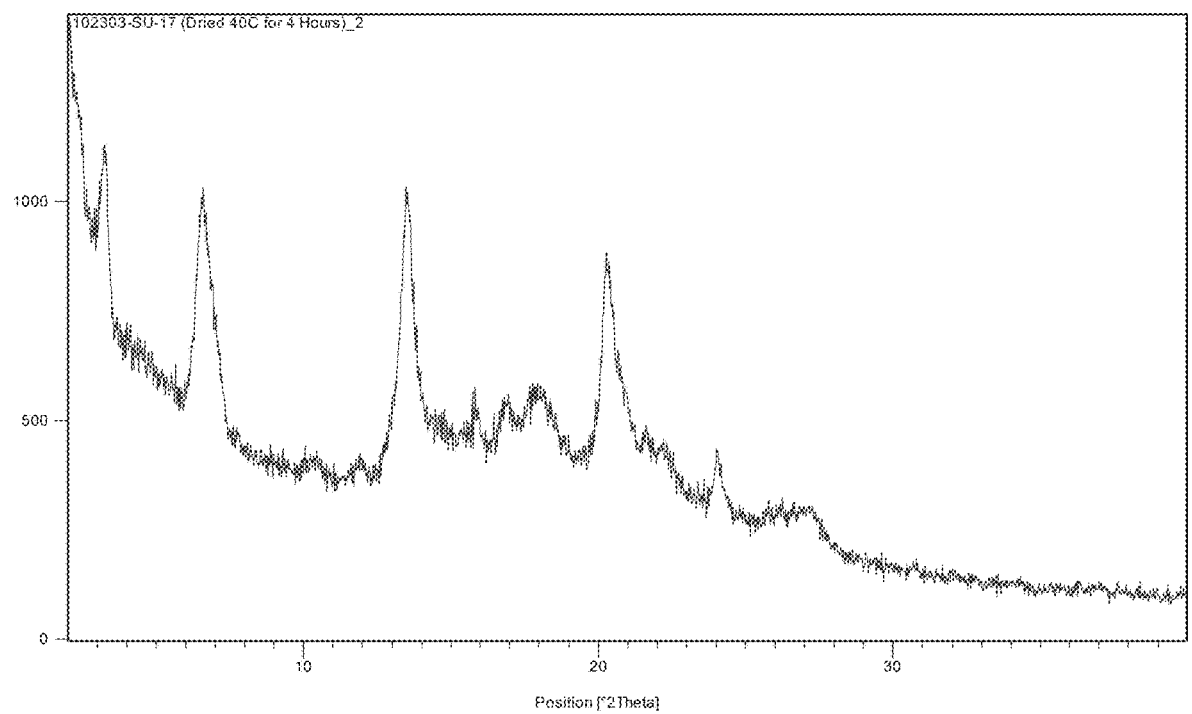
FIG. 29 depicts a PXRD pattern of L-Tartrate Salt Form A of Compound 5.

In certain embodiments, a solid form of Compound 5 provided herein, e.g., L-Tartrate Salt Form A, is substantially crystalline, as indicated by, e.g., X-ray powder diffraction measurements. In one embodiment, provided herein is a solid form of Compound 5 having an X-ray powder diffraction pattern (XRPD) substantially as shown in FIG. 29 (e.g., L-Tartrate Salt Form A). In one embodiment, a solid form of Compound 5 provided herein, e.g., L-Tartrate Salt Form A, has one or more characteristic X-ray powder diffraction peaks at approximately 3.3, 6.6, 10.3, 11.9, 13.6, 15.9, 16.9, 17.9, 20.2, 21.6, 22.3, 24.0, or 27.2° 2θ (±0.2° 2θ) or (±0.1° 2θ) as depicted in FIG. 29. In a specific embodiment, a solid form of Compound 5 provided herein, e.g., L-Tartrate Salt Form A, has one, two, three, four, or five characteristic X-ray powder diffraction peaks at approximately 3.3, 6.6, 13.6, 20.2, or 24.0° 2θ (±0.2° 2θ).

In certain embodiments, L-Tartrate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, L-Tartrate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, L-Tartrate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, L-Tartrate Salt Form A is substantially pure. In certain embodiments, the substantially pure L-Tartrate Salt Form A is substantially free of other solid forms, including but not limited to amorphous solid. In certain embodiments, the purity of the substantially pure L-Tartrate Salt Form A is no less than about 95%, no less than about 96%, no less than about 97%, no less than about 98%, no less than about 98.5%, no less than about 99%, no less than about 99.5%, or no less than about 99.8%.

(ii) L-Tartrate Salt Form B

In one embodiment, the solid form of Compound 5 is L-Tartrate Salt Form B. In one embodiment, L-Tartrate Salt Form B is crystalline. In one embodiment, L-Tartrate Salt Form B is hydrated.

In one embodiment, L-Tartrate Salt Form B is a monotartrate salt.

In certain embodiments, provided herein are methods for making L-Tartrate Salt Form B, comprising 1) dispensing an 4:1 v/v mixture of THF/water (e.g., about 250 µL) into a vial containing an amount of Compound 1 (e.g., about 20 mg); 2) adding a stoichiometric amount (e.g., 1.0 equivalent) a 0.5 M solution of L-tartaric acid in THF to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in an 4:1 v/v mixture of THF/water, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g., for at least one hour); 7) optionally heating the solution to a temperature (e.g., 40° C.) for a period of time (e.g., three hours); 8) cooling the solution to a temperature (e.g., 5° C.) and holding the solution at the temperature for a period of time (e.g., for one day); and 9) equilibrating the solution to a temperature (e.g., 20° C.) and evaporating the solvent slowly at room temperature to yield L-Tartrate Salt Form B of Compound 5. In certain embodiments, the solution is evaporated under reduced pressure in a centrifuge evaporator. In certain other embodiments, the solution is evaporated under a slow bleed of inert gas such as nitrogen or argon gas.

Figure 34:
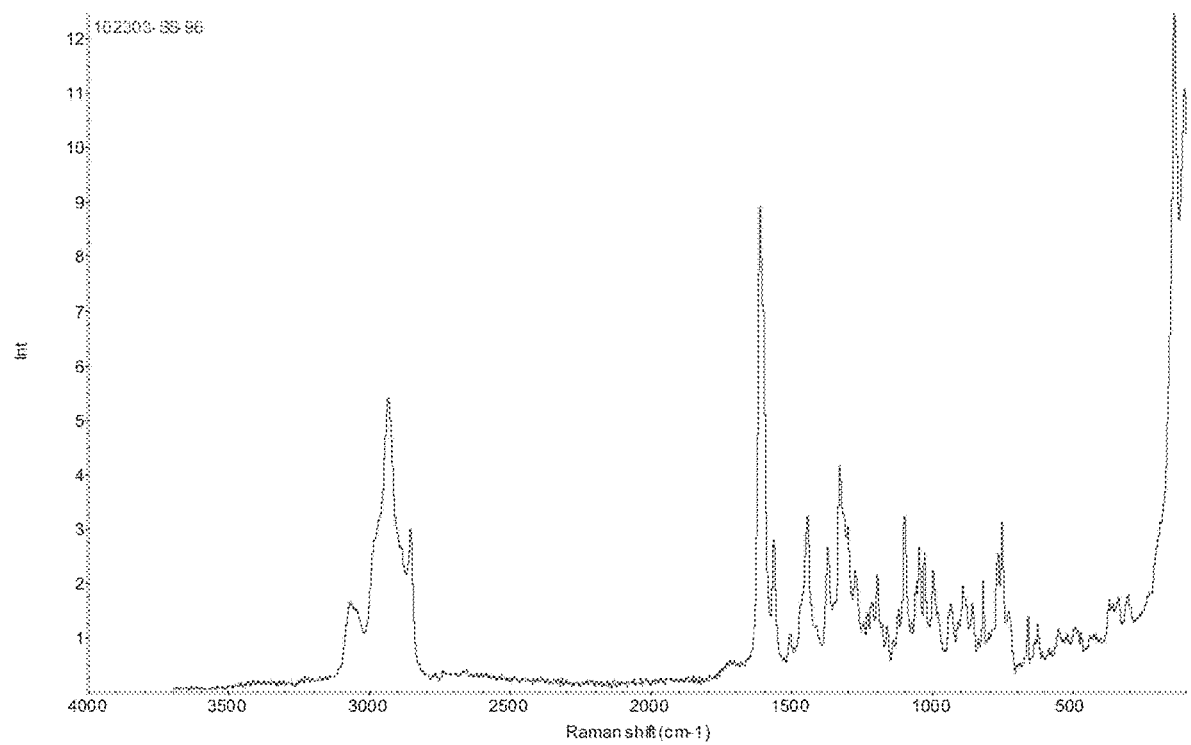
FIG. 34 depicts an FT-Raman spectrum of L-Tartrate Salt Form B of Compound 5.

In one embodiment, provided herein is L-Tartrate Salt Form B having an FT-Raman Spectrum as depicted in FIG. 34.

Figure 35:
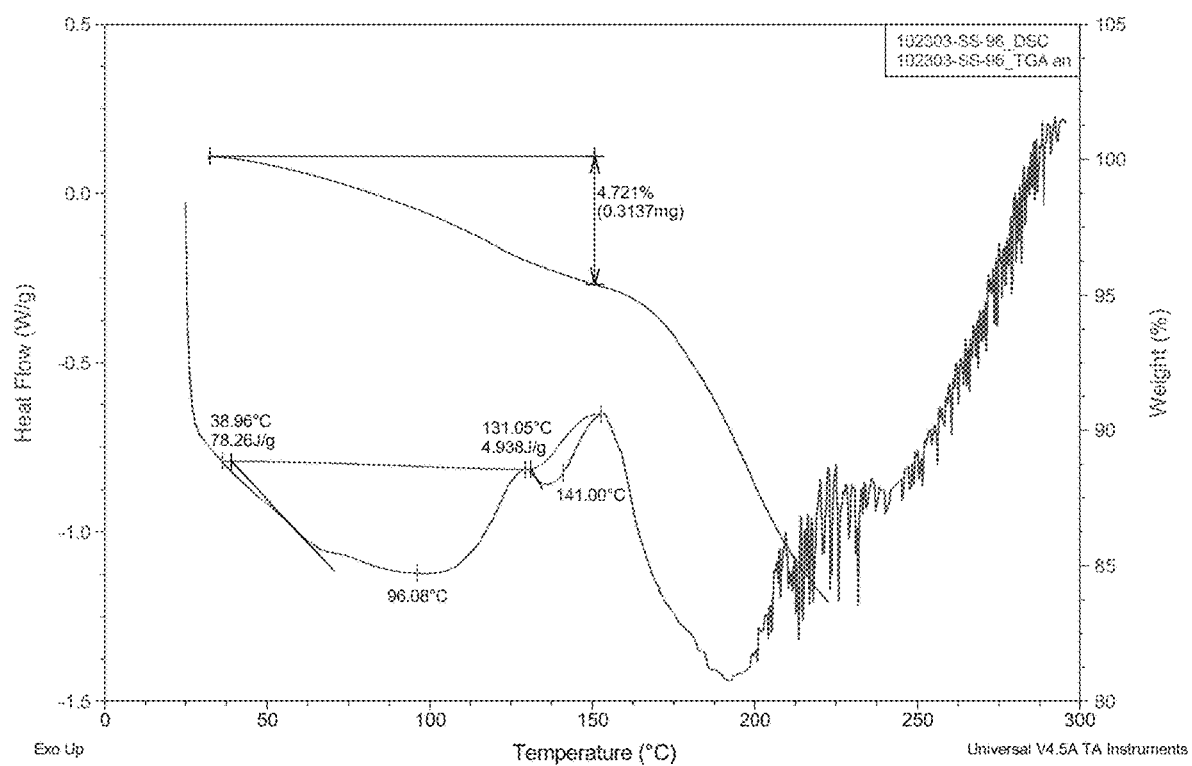
FIG. 35 depicts differential scanning calorimetry/thermal gravimetric analysis of L-Tartrate Salt Form B of Compound 5.

In one embodiment, provided herein is a solid form of Compound 5, e.g., L-Tartrate Salt Form B of Compound 5, having a DSC thermogram substantially as depicted in FIG. 35 comprising multiple endotherms with onset temperatures at 39° C. and 131° C., respectively.

In one embodiment, provided herein is a solid form of Compound 5, e.g., L-Tartrate Salt Form B of Compound 5, having a TGA thermogram corresponding substantially to the representative TGA thermogram as depicted in FIG. 35. In certain embodiments, the crystalline form exhibits a TGA thermogram comprising a total mass loss of approximately 4.7% of the total mass of the sample when heated from approximately 25° C. to approximately 150° C.

Figure 33:
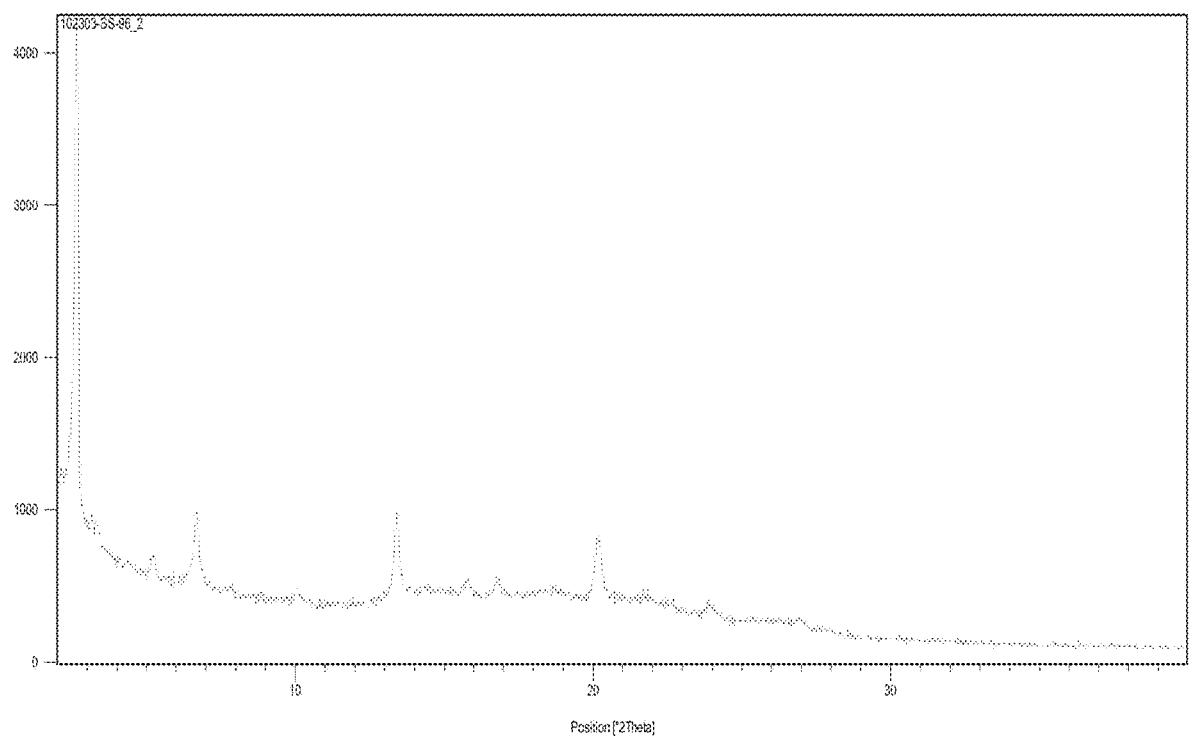
FIG. 33 depicts a PXRD pattern of L-Tartrate Salt Form B of Compound 5.

In certain embodiments, a solid form of Compound 5 provided herein, e.g., L-Tartrate Salt Form B, is substantially crystalline, as indicated by, e.g., X-ray powder diffraction measurements. In one embodiment, provided herein is a solid form of Compound 5 having an X-ray powder diffraction pattern (XRPD) substantially as shown in FIG. 33 (e.g., L-Tartrate Salt Form B). In one embodiment, a solid form of Compound 5 provided herein, e.g., L-Tartrate Salt Form B, has one or more characteristic X-ray powder diffraction peaks at approximately 2.7, 3.3, 5.2, 6.7, 10.1, 13.4, 15.8, 16.8, 20.2, or 23.9° 2θ (±0.2° 2θ) or (±0.1° 2θ) as depicted in FIG. 33. In a specific embodiment, a solid form of Compound 5 provided herein, e.g., L-Tartrate Salt Form B, has one, two, three, four, or five characteristic X-ray powder diffraction peaks at approximately 2.7, 5.2, 6.7, 13.4, or 20.2° 2θ (±0.2° 2θ).

In certain embodiments, L-Tartrate Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, L-Tartrate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, L-Tartrate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, L-Tartrate Salt Form B is substantially pure. In certain embodiments, the substantially pure L-Tartrate Salt Form B is substantially free of other solid forms, including but not limited to amorphous solid. In certain embodiments, the purity of the substantially pure L-Tartrate Salt Form B is no less than about 95%, no less than about 96%, no less than about 97%, no less than about 98%, no less than about 98.5%, no less than about 99%, no less than about 99.5%, or no less than about 99.8%.

(iii) L-Tartrate Salt Form C

In one embodiment, the solid form of Compound 5 is L-Tartrate Salt Form C. In one embodiment, L-Tartrate Salt Form C is crystalline. In one embodiment, L-Tartrate Salt Form C is hydrated.

In one embodiment, L-Tartrate Salt Form C is a hemitartrate salt.

In certain embodiments, provided herein are methods for making L-Tartrate Salt Form C, comprising 1) dispensing methyl tert-butyl ether (e.g., about 25 mL) into a vial containing an amount of Compound 1 (e.g., about 2.5 g); 2) adding a stoichiometric amount (e.g., 1.0 equivalent) of a 0.5 M solution of L-tartaric acid in THF to the vial; 3) dispensing an aliquot of the solution into a vial and allowing the solution to evaporate; 4) adding a solvent or solvent system to yield a slurry; 5) cycling the temperature (e.g., between about 5° C. and about 40° C.; 1° C. per minute heating/cooling rate with an hour hold between each heating/cooling cycle) of the solution for a period of time (e.g., about two days); and 6) isolating solids from the solution by vacuum filtration under nitrogen to yield L-Tartrate Salt Form C of Compound 5. In certain embodiments, the solvent is water. In certain embodiments, the solvent or solvent system is a 1:9 mixture of 1,4-dioxane and water. In certain embodiments, the solvent or solvent system is a 1:4 mixture of dimethylsulfoxide and water. In certain embodiments, the solvent or solvent system is a 1:1 mixture of acetone and water. In certain embodiments, the solvent or solvent system is a 1:9 mixture of acetone and water.

In certain embodiments, provided herein are methods for making L-Tartrate Salt Form C, comprising 1) dispensing methyl tert-butyl ether (e.g., about 25 mL) into a vial containing an amount of Compound 1 (e.g., about 2.5 g); 2) adding a stoichiometric amount (e.g., 1.0 equivalent) of a 0.5

M solution of L-tartaric acid in THF to the vial; 3) dispensing an aliquot of the solution into a vial and allowing the solution to evaporate; 4) adding a solvent or solvent system to yield a slurry; 5) heating the slurry at a temperature (e.g., about 40° C.) and filtering the slurry while hot; 6) storing the solution at a temperature (e.g., 5° C.) for a period of time (e.g., about 5 days); and 7) isolating solids from the sample through vacuum filtration under nitrogen to yield L-Tartrate Salt Form C of Compound 5. In certain embodiments, the solvent or solvent system is a 3:7 mixture of THF and water. In certain embodiments, the solvent or solvent system is a 9:1 mixture of acetonitrile and water. In certain embodiments, the solvent or solvent system is a 3:7 mixture of acetone and water. In certain embodiments, the solvent or solvent system is a 9:1 mixture of isopropanol and water.

Figure 95:
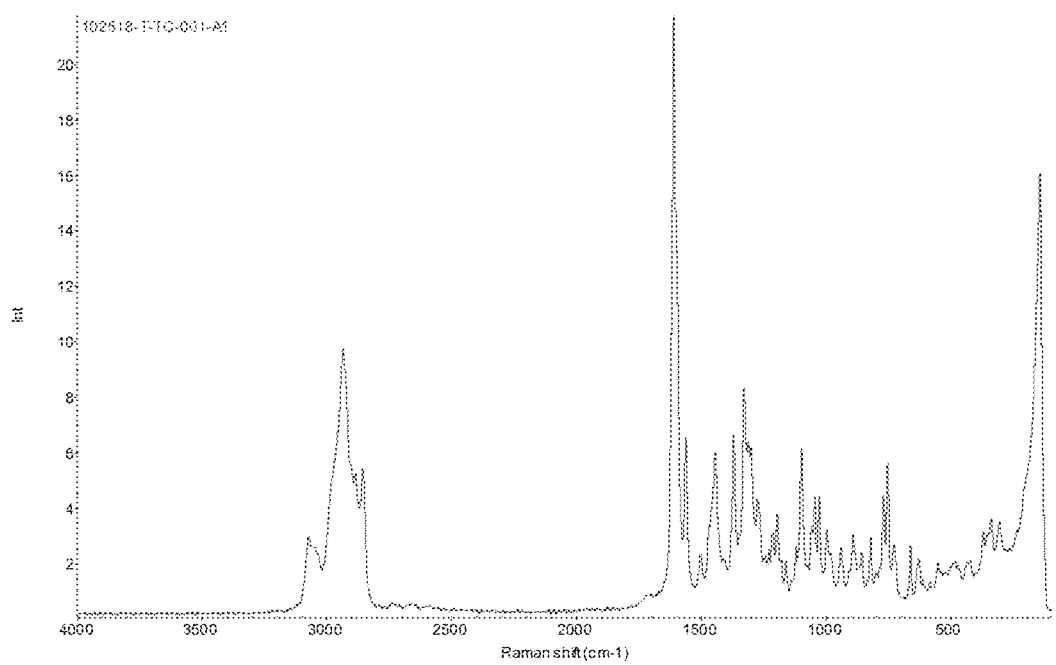
FIG. 95 depicts an FT-Raman spectrum of L-Tartrate Salt Form C of Compound 5.

In one embodiment, provided herein is L-Tartrate Salt Form C having an FT-Raman Spectrum as depicted in FIG. 95.

Figure 96:
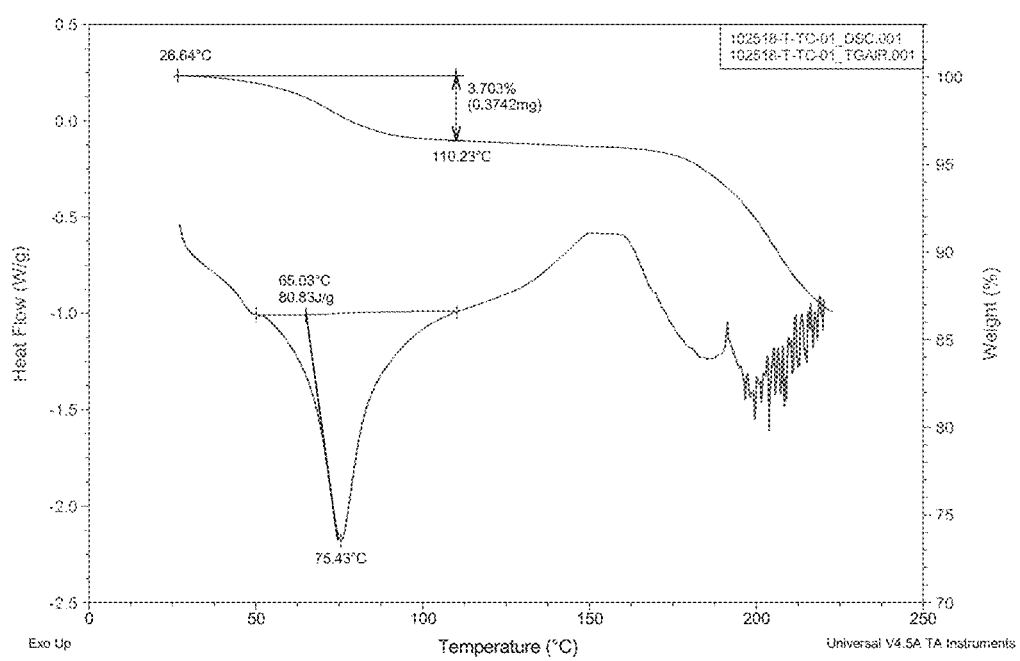
FIG. 96 depicts differential scanning calorimetry/thermal gravimetric analysis of L-Tartrate Salt Form C of Compound 5.

In one embodiment, provided herein is a solid form of Compound 5, e.g., L-Tartrate Salt Form C of Compound 5, having a DSC thermogram substantially as depicted in FIG. 96 comprising an endotherm with an onset temperature at 65° C.

In one embodiment, provided herein is a solid form of Compound 5, e.g., L-Tartrate Salt Form C of Compound 5, having a TGA thermogram corresponding substantially to the representative TGA thermogram as depicted in FIG. 96. In certain embodiments, the crystalline form exhibits a TGA thermogram comprising a total mass loss of approximately 3.7% of the total mass of the sample when heated from approximately 26.6° C. to approximately 110.2° C.

Figure 94:
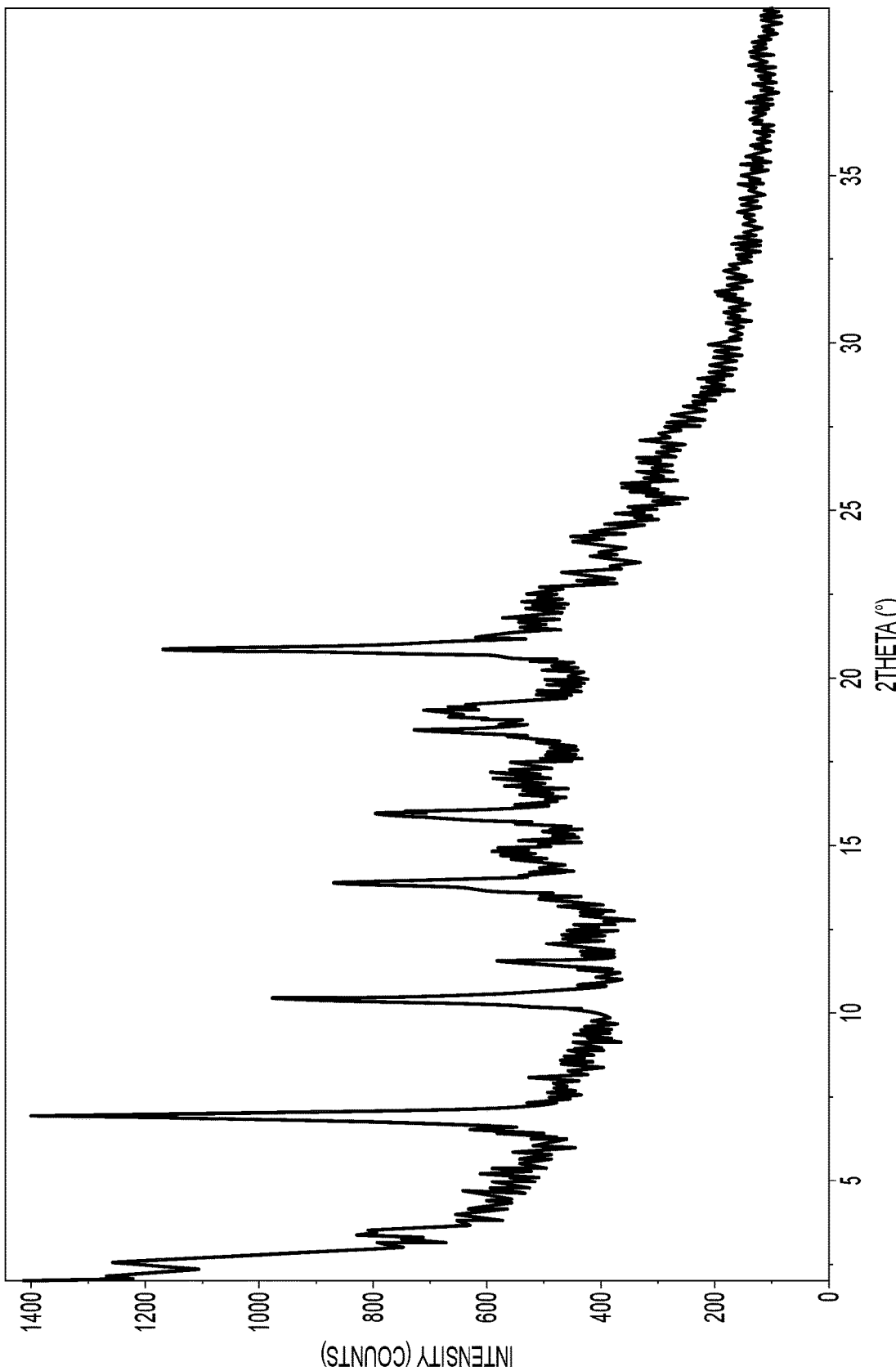
FIG. 94 depicts a PXRD pattern of L-Tartrate Salt Form C of Compound 5.

In certain embodiments, a solid form of Compound 5 provided herein, e.g., L-Tartrate Salt Form C, is substantially crystalline, as indicated by, e.g., X-ray powder diffraction measurements. In one embodiment, provided herein is a solid form of Compound 5 having an X-ray powder diffraction pattern (XRPD) substantially as shown in FIG. 94 (e.g., L-Tartrate Salt Form C). In one embodiment, a solid form of Compound 5 provided herein, e.g., L-Tartrate Salt Form C, has one or more characteristic X-ray powder diffraction peaks at approximately 2.6, 3.4, 6.9, 10.5, 11.5, 13.9, 14.8, 16.0, 18.4, 19.2, or 20.8° 2θ (±0.2° 2θ) or (±0.1° 2θ) as depicted in FIG. 94. In a specific embodiment, a solid form of Compound 5 provided herein, e.g., L-Tartrate Salt Form C, has one, two, three, four, or five characteristic X-ray powder diffraction peaks at approximately 3.4, 6.9, 10.5, 13.9, or 20.8° 2θ (±0.2° 2θ).

In certain embodiments, L-Tartrate Salt Form C is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, L-Tartrate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, L-Tartrate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, L-Tartrate Salt Form C is substantially pure. In certain embodiments, the substantially pure L-Tartrate Salt Form C is substantially free of other solid forms, including but not limited to amorphous solid. In certain embodiments, the purity of the substantially pure L-Tartrate Salt Form C is no less than about 95%, no less than about 96%, no less than about 97%, no less than about 98%, no less than about 98.5%, no less than about 99%, no less than about 99.5%, or no less than about 99.8%.

(iv) L-Tartrate Salt Form D

In one embodiment, the solid form of Compound 5 is L-Tartrate Salt Form D. In one embodiment, L-Tartrate Salt Form D is crystalline. In one embodiment, L-Tartrate Salt Form D is hydrated.

In one embodiment, L-Tartrate Salt Form D is a di-tartrate salt.

In certain embodiments, provided herein are methods for making L-Tartrate Salt Form D, comprising 1) dispensing methyl tert-butyl ether (e.g., about 25 mL) into a vial containing an amount of Compound 1 (e.g., about 2.5 g); 2) adding a stoichiometric amount (e.g., 1.0 equivalent) of a 0.5 M solution of L-tartaric acid in THF to the vial; 3) dispensing an aliquot of the solution into a vial and allowing the solution to evaporate; 4) adding a solvent or solvent system to yield a slurry; 5) optionally adding seeds of L-Tartrate Salt Form D and mixing at a temperature (e.g., 40° C.) for a period of time (e.g., 30 minutes); 6) cycling the temperature (e.g., between about 5° C. and about 40° C.; 1° C. per minute heating/cooling rate with an hour hold between each heating/cooling cycle) of the solution for a period of time (e.g., about five days); and 7) isolating solids from the sample through vacuum filtration under nitrogen to yield L-Tartrate Salt Form D of Compound 5. In certain embodiments, the solvent or solvent system is a 4:1 mixture of isopropanol and water.

Figure 99:
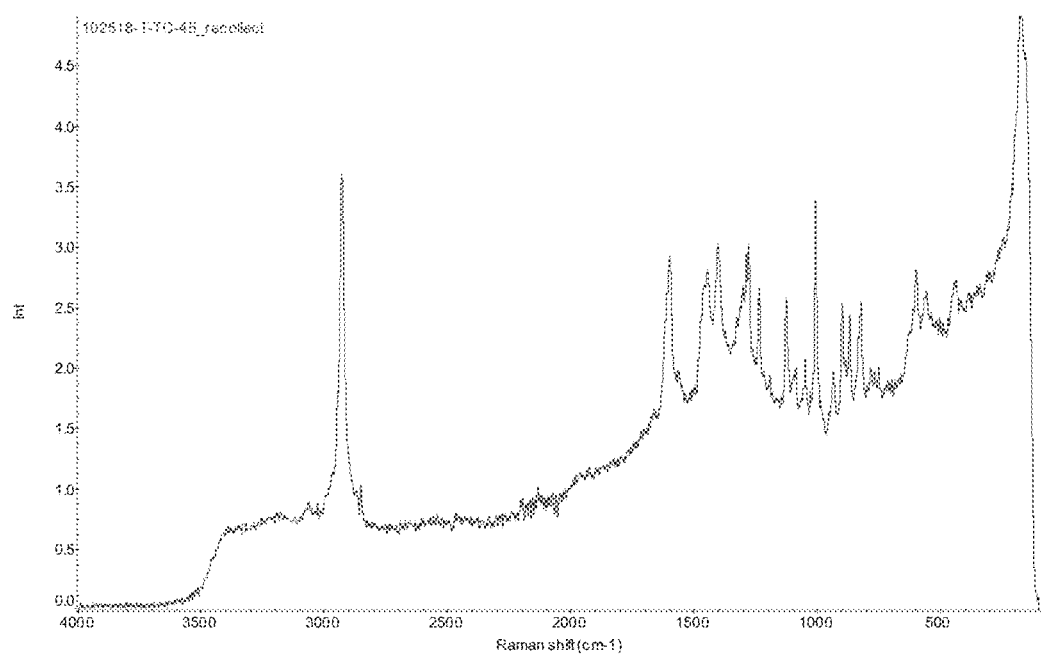
FIG. 99 depicts an FT-Raman spectrum of L-Tartrate Salt Form D of Compound 5.

In one embodiment, provided herein is L-Tartrate Salt Form D having an FT-Raman Spectrum as depicted in FIG. 99.

Figure 100:
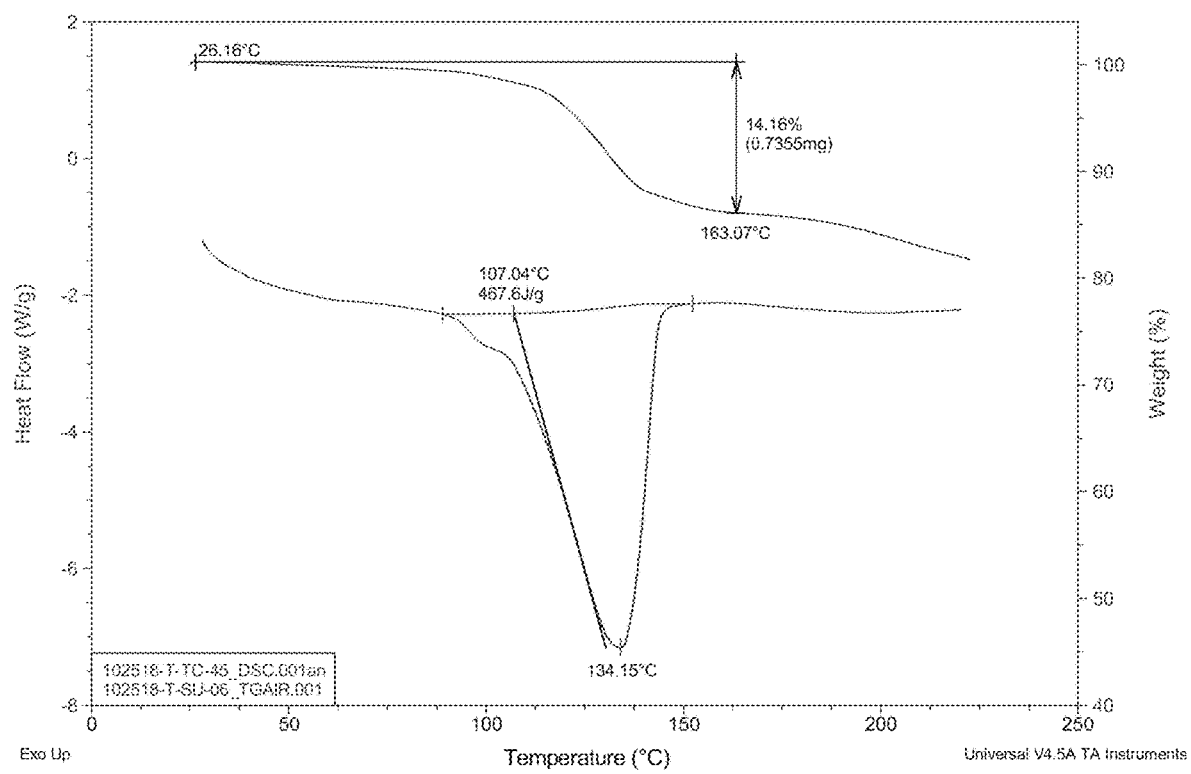
FIG. 100 depicts differential scanning calorimetry/thermal gravimetric analysis of L-Tartrate Salt Form D of Compound 5.

In one embodiment, provided herein is a solid form of Compound 5, e.g., L-Tartrate Salt Form D of Compound 5, having a DSC thermogram substantially as depicted in FIG. 100 comprising an endotherm with an onset temperature at 107° C.

In one embodiment, provided herein is a solid form of Compound 5, e.g., L-Tartrate Salt Form D of Compound 5, having a TGA thermogram corresponding substantially to the representative TGA thermogram as depicted in FIG. 100. In certain embodiments, the crystalline form exhibits a TGA thermogram comprising a total mass loss of approximately 14% of the total mass of the sample when heated.

Figure 98:
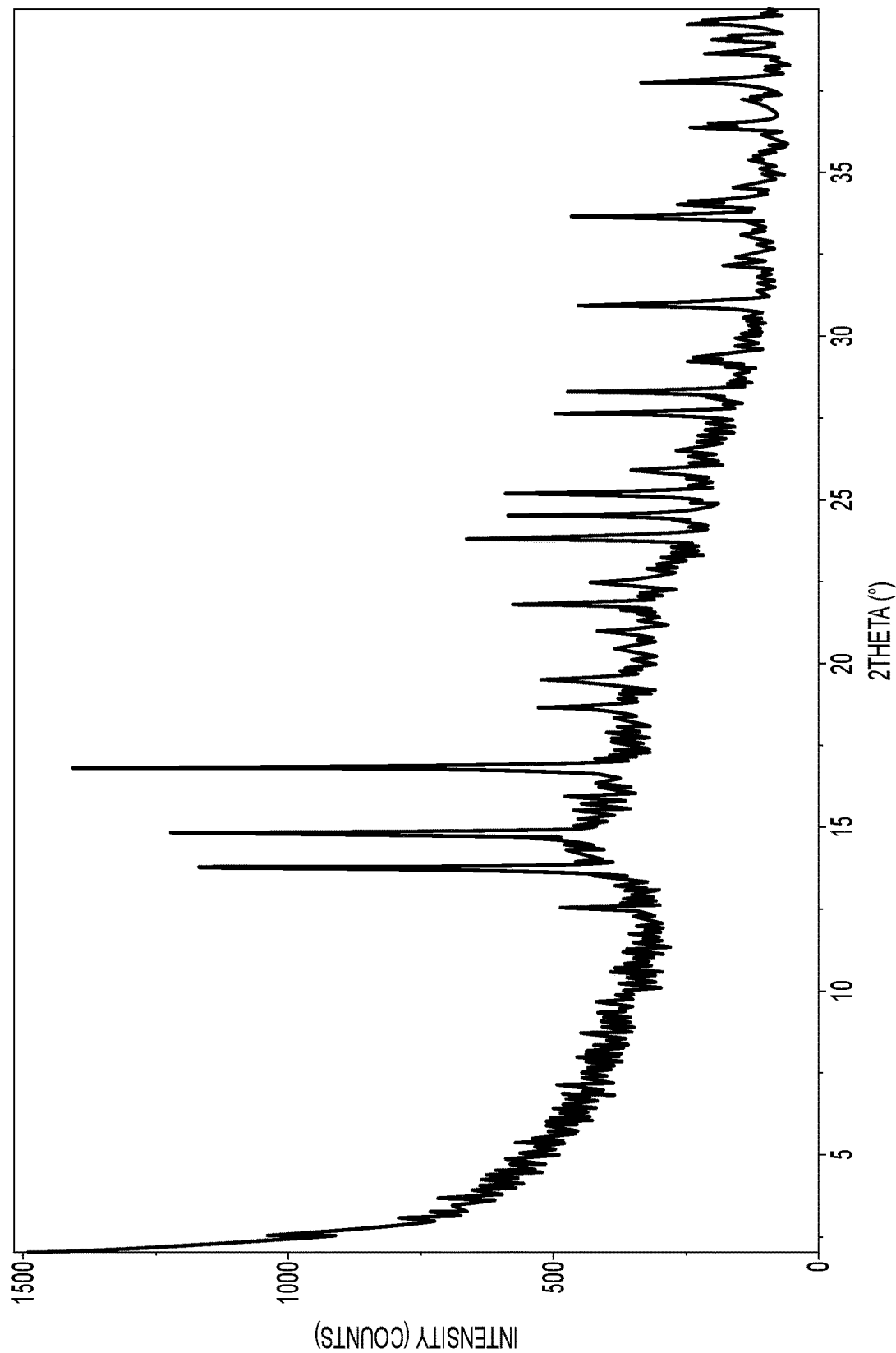
FIG. 98 depicts a PXRD pattern of L-Tartrate Salt Form D of Compound 5.

In certain embodiments, a solid form of Compound 5 provided herein, e.g., L-Tartrate Salt Form D, is substantially crystalline, as indicated by, e.g., X-ray powder diffraction measurements. In one embodiment, provided herein is a solid form of Compound 5 having an X-ray powder diffraction pattern (XRPD) substantially as shown in FIG. 98

(e.g., L-Tartrate Salt Form D). In one embodiment, a solid form of Compound 5 provided herein, e.g., L-Tartrate Salt Form D, has one or more characteristic X-ray powder diffraction peaks at approximately 12.5, 13.8, 14.8, 16.8, 18.7, 19.5, 21.8, 23.8, 24.5, 25.2, 27.6, 28.3, 30.9, 31.0, 33.6, 34.0, 36.4, or 37.7° 2θ (±0.2° 2θ) or (±0.1° 2θ) as depicted in FIG. 98. In a specific embodiment, a solid form of Compound 5 provided herein, e.g., L-Tartrate Salt Form D, has one, two, three, four, or five characteristic X-ray powder diffraction peaks at approximately 12.5, 13.8, 14.8, 16.8, 23.8, 25.2, or 33.6° 2θ (±0.2° 2θ).

In certain embodiments, L-Tartrate Salt Form D is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, L-Tartrate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, L-Tartrate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, L-Tartrate Salt Form D is substantially pure. In certain embodiments, the substantially pure L-Tartrate Salt Form D is substantially free of other solid forms, including but not limited to amorphous solid. In certain embodiments, the purity of the substantially pure L-Tartrate Salt Form D is no less than about 95%, no less than about 96%, no less than about 97%, no less than about 98%, no less than about 98.5%, no less than about 99%, no less than about 99.5%, or no less than about 99.8%.

(f) Solid Forms of Compound 6

In one embodiment, provided herein is a solid form of Compound 6.

(i) Hemifumarate Salt Form A

In one embodiment, the solid form of Compound 6 is Hemifumarate Salt Form A. In one embodiment, Hemifumarate Salt Form A is crystalline. In one embodiment, Hemifumarate Salt Form A is hydrated.

In certain embodiments, provided herein are methods for making Hemifumarate Salt Form A, comprising 1) dispensing a solvent or solvent system (e.g., about 250 µL) into a vial containing an amount of Compound 1 (e.g., about 20 mg); 2) adding a stoichiometric amount (e.g., 1.0 equivalent) a 0.2 M solution of fumaric acid in ethanol to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent or solvent system, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g., for at least one hour); 7) isolating solids from the sample through vacuum filtration; and 8) air-drying the solids for a period of time (e.g., one hour) followed by drying the solids in a vacuum oven at a temperature (e.g., 40° C.) for a period of time (e.g., 5 hours) to yield Hemifumarate Salt Form A of Compound 6. In certain embodiments, the solvent or solvent system is acetonitrile, methyl isobutyl ketone, isopropyl acetate. In certain embodiments, the solution is evaporated under reduced pressure in a centrifuge evaporator. In certain other embodiments, the solution is evaporated under a slow bleed of inert gas such as nitrogen or argon gas.

In certain embodiments, provided herein are methods for making Hemifumarate Salt Form A, comprising 1) dispensing a solvent or solvent system (e.g., about 250 µL) into a vial containing an amount of Compound 1 (e.g., about 20 mg); 2) adding a stoichiometric amount (e.g., 1.0 equivalent) a 0.2 M solution of fumaric acid in ethanol to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent or solvent system, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g., for at least one hour); 7) optionally adding an anti-solvent (e.g., 1:3 v/v solvent to anti-solvent ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) equilibrating the solution to a temperature (e.g., 20° C.) and evaporating the solvent slowly at room temperature to yield Hemifumarate Salt Form A of Compound 6. In certain embodiments, the solvent or solvent system is isopropanol, or a 4:1 v/v mixture of THF/water. In certain embodiments, the anti-solvent is cyclohexane. In certain embodiments, the solution is evaporated under reduced pressure in a centrifuge evaporator. In certain other embodiments, the solution is evaporated under a slow bleed of inert gas such as nitrogen or argon gas.

Figure 38:
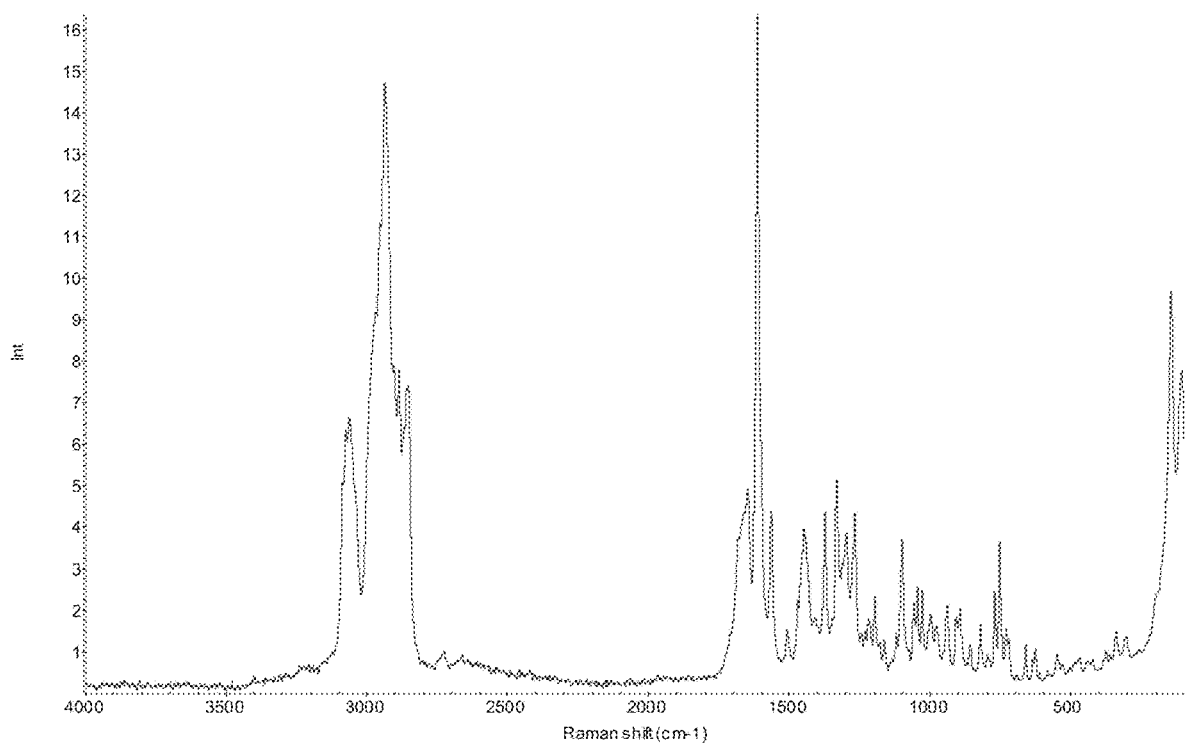
FIG. 38 depicts an FT-Raman spectrum of Hemifumarate Salt Form A of Compound 6.

In one embodiment, provided herein is Hemifumarate Salt Form A having an FT-Raman Spectrum as depicted in FIG. 38.

Figure 39:
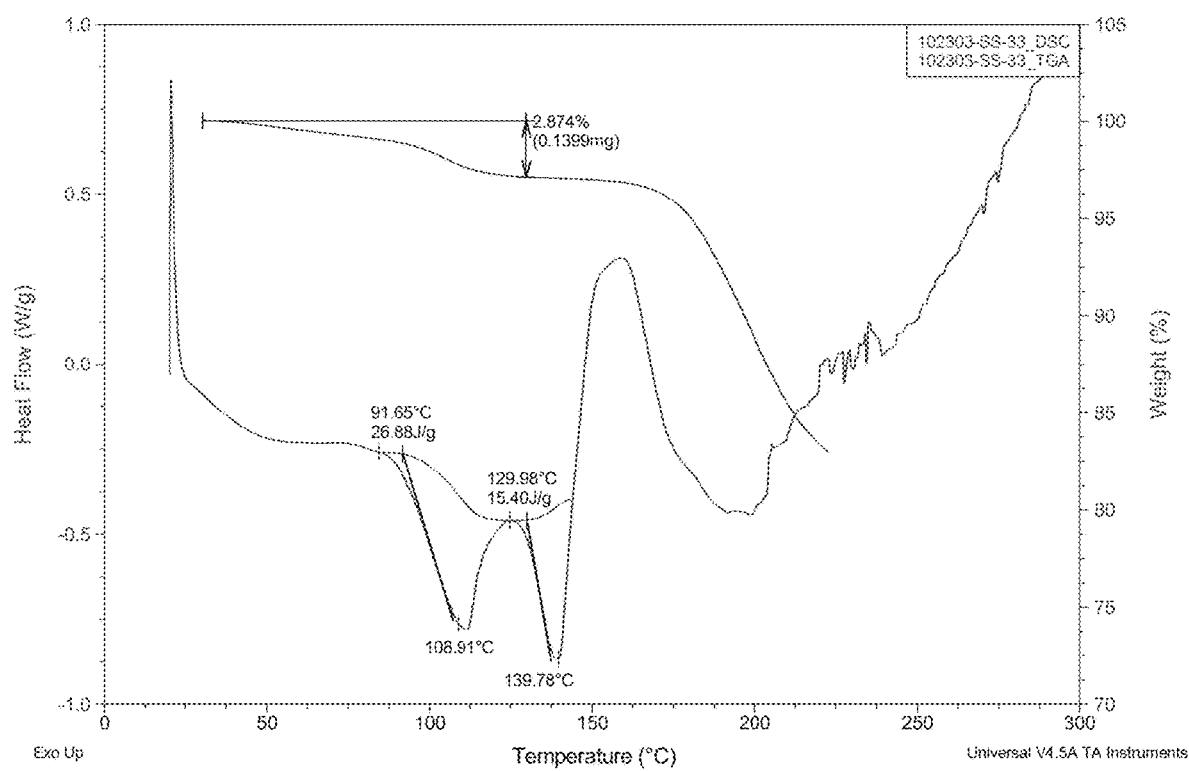
FIG. 39 depicts differential scanning calorimetry/thermal gravimetric analysis of Hemifumarate Salt Form A of Compound 6.

In one embodiment, provided herein is a solid form of Compound 6, e.g., Hemifumarate Salt Form A of Compound 6, having a DSC thermogram substantially as depicted in FIG. 39 comprising multiple endotherms with onset temperatures at 91.7° C. and 130° C.

In one embodiment, provided herein is a solid form of Compound 6, e.g., Hemifumarate Salt Form A of Compound 6, having a TGA thermogram corresponding substantially to the representative TGA thermogram as depicted in FIG. 39. In certain embodiments, the crystalline form exhibits a TGA thermogram comprising a total mass loss of approximately 2.9% of the total mass of the sample when heated from approximately 25° C. to approximately 130° C.

Figure 37:
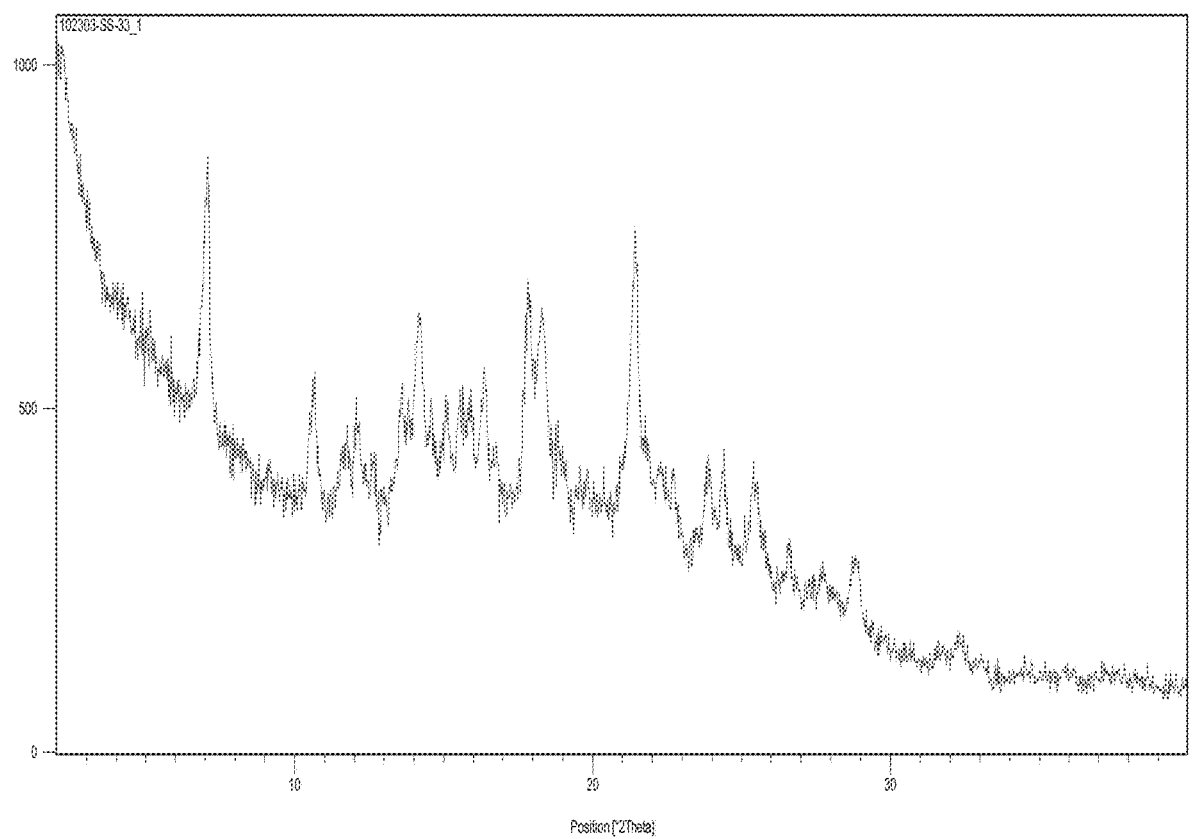
FIG. 37 depicts a PXRD pattern of Hemifumarate Salt Form A of Compound 6.

In certain embodiments, a solid form of Compound 6 provided herein, e.g., Hemifumarate Salt Form A, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 37 (e.g., Hemifumarate Salt Form A). In one embodiment, a solid form of Compound 6 provided herein, e.g., Hemifumarate Salt Form A, has one or more characteristic X-ray powder diffraction peaks at approximately 7.1, 10.7, 11.7, 12.1, 13.6, 14.2, 15.1, 16.4, 17.9, 18.3, 21.4, 23.9, 24.4, 25.4, 26.6, or 28.9° 2θ (±0.2° 2θ) or (±0.1° 2θ) as depicted in FIG. 37. In a specific embodiment, a solid form of Compound 6 provided herein, e.g., Hemifumarate Salt Form A, has one, two, three, four, five, or six characteristic X-ray powder diffraction peaks at approximately 7.1, 14.2, 17.9, 18.3, 21.4, or 25.4° 2θ (±0.2° 2θ).

In certain embodiments, Hemifumarate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Hemifumarate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Hemifumarate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form A is substantially pure. In certain embodiments, the substantially pure Hemifumarate Salt Form A is substantially free of other solid forms, including but not limited to amorphous solid. In certain embodiments, the purity of the substantially pure Hemifumarate Salt Form A is no less than about 95%, no less than about 96%, no less than about 97%, no less than about 98%, no less than about 98.5%, no less than about 99%, no less than about 99.5%, or no less than about 99.8%.

(ii) Hemifumarate Salt Form B

In one embodiment, the solid form of Compound 6 is Hemifumarate Salt Form B. In one embodiment, Hemifumarate Salt Form B is crystalline.

In certain embodiments, provided herein are methods for making Hemifumarate Salt Form B, comprising 1) dispensing a solvent or solvent system (e.g., about 250 μL) into a vial containing an amount of Compound 1 (e.g., about 20 mg); 2) adding a stoichiometric amount (e.g., 1.0 equivalent) a 0.2 M solution of fumaric acid in ethanol to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent or solvent system, followed by temperature cycling (e.g., between about 5° C. and about 40° C.; 1° C. per minute heating/cooling rate with an hour hold between each heating/cooling cycle) of the solution for a period of time (e.g., about a day), and equilibrating at 20° C. at the end of temperature cycling for a period of time (e.g., for at least one hour); 7) isolating solids from the sample through vacuum filtration; and 8) air-drying the solids for a period of time (e.g., one hour) followed by drying the solids in a vacuum oven at a temperature (e.g., 40° C.) for a period of time (e.g., 5 hours) to yield Hemifumarate Salt Form B of Compound 6. In certain embodiments, the solvent or solvent system is methyl tert-butyl ether or a 2:1 v/v mixture toluene/ethyl acetate. In certain embodiments, the solution is evaporated under reduced pressure in a centrifuge evaporator. In certain other embodiments, the solution is evaporated under a slow bleed of inert gas such as nitrogen or argon gas.

In certain embodiments, provided herein are methods for making Hemifumarate Salt Form B comprising 1) combining Compound 1 (e.g., about 102.5 mg) with methyl tert-butyl ether (e.g., about 1.25 mL) and fumaric acid (e.g., about 1.0 equivalent of a 0.2 M solution in ethanol); 2) heating the resulting mixture to a temperature (e.g., about 40° C.) for a period of time (e.g., about one hour): 3) evaporating the solution to dryness and adding methyl t-butyl ether (e.g., about 1.25 mL); 4) adding seeds of a crystalline fumarate salt of Compound 1 (e.g., about 1 mg) to the sample; 5) cycling the temperature (e.g., between about 5° C. and about 40° C.; 1° C. per minute heating/ cooling rate with an hour hold between each heating/cooling cycle) of the solution for a period of time (e.g., about two days); 6) isolating solids from the sample through vacuum filtration; and 7) air-drying the solids for a period of time (e.g., one hour) followed by drying the solids in a vacuum oven at a temperature (e.g., 40° C.) for a period of time (e.g., 5 hours) to yield Hemifumarate Salt Form B of Compound 6. In certain embodiments, the solution is evaporated under reduced pressure in a centrifuge evaporator. In certain other embodiments, the solution is evaporated under a slow bleed of inert gas such as nitrogen or argon gas.

Figure 42:
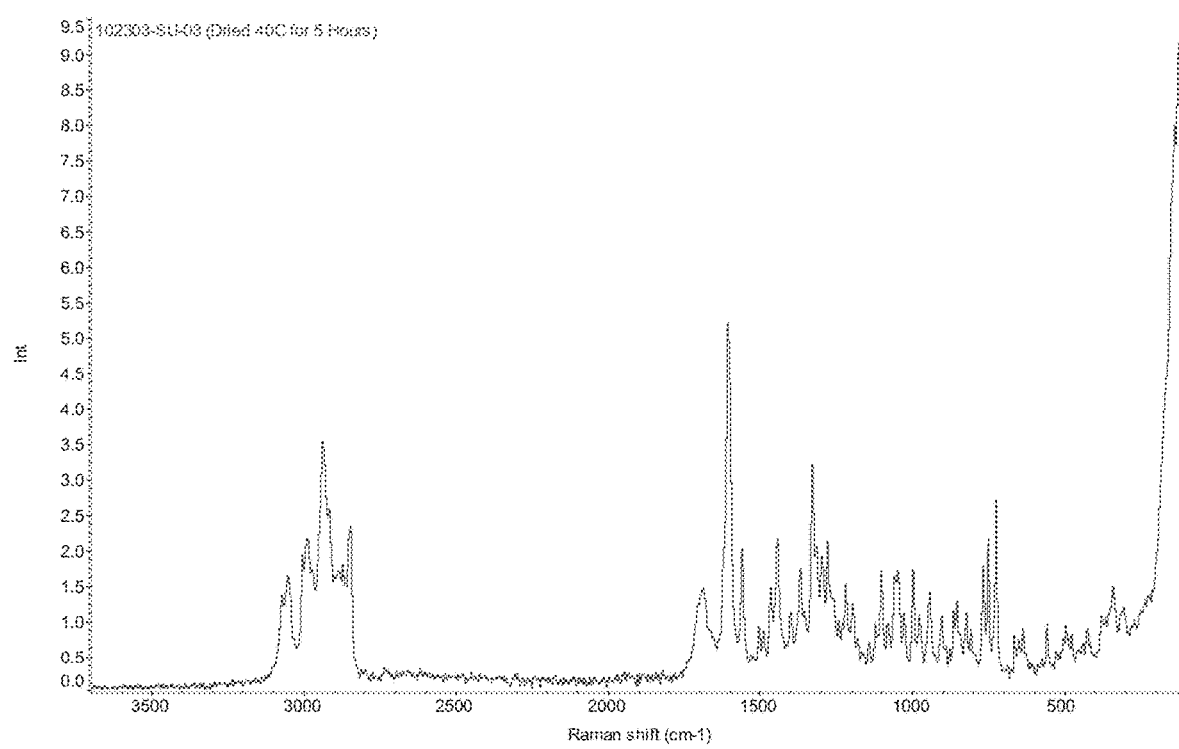
FIG. 42 depicts an FT-Raman spectrum of Hemifumarate Salt Form B of Compound 6.

In one embodiment, provided herein is Hemifumarate Salt Form B having an FT-Raman Spectrum as depicted in FIG. 42.

Figure 43:
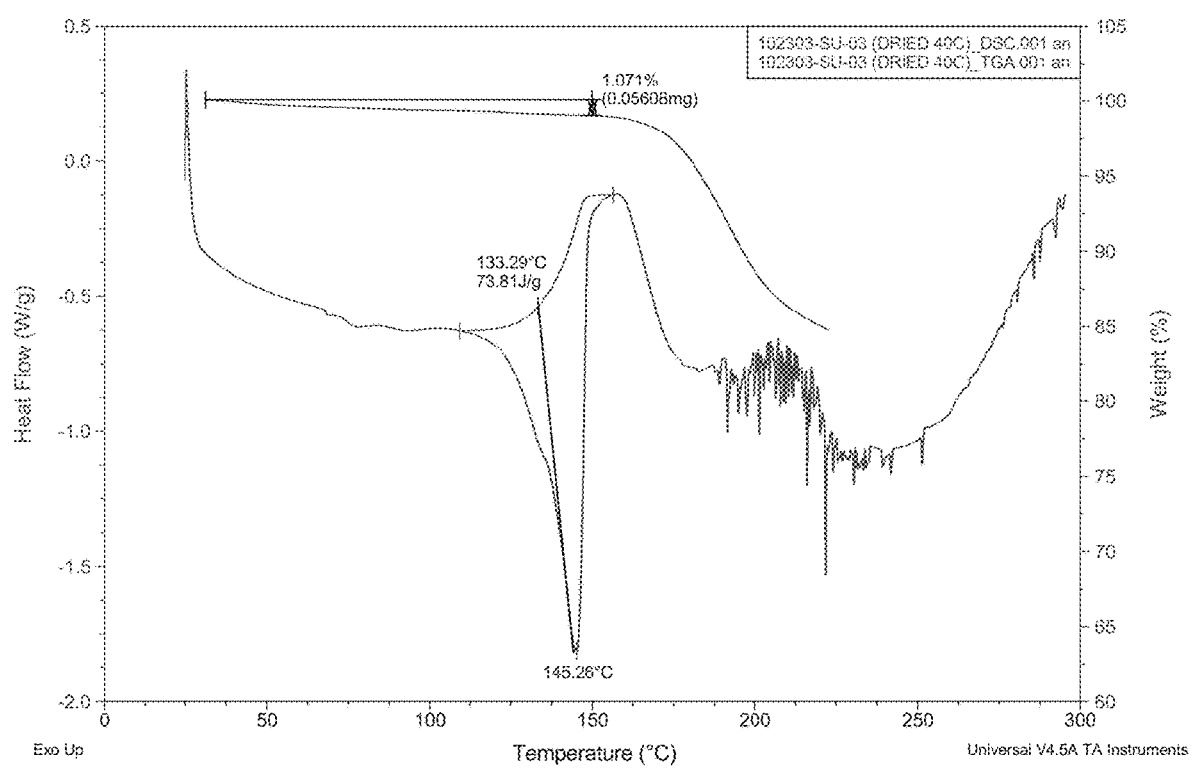
FIG. 43 depicts differential scanning calorimetry/thermal gravimetric analysis of Hemifumarate Salt Form B of Compound 6.

In one embodiment, provided herein is a solid form of Compound 6, e.g., Hemifumarate Salt Form B of Compound 6, having a DSC thermogram substantially as depicted in FIG. 43 comprising an endotherm with an onset temperature at 133.3° C.

In one embodiment, provided herein is a solid form of Compound 6, e.g., Hemifumarate Salt Form B of Compound 6, having a TGA thermogram corresponding substantially to the representative TGA thermogram as depicted in FIG. 43. In certain embodiments, the crystalline form exhibits a TGA thermogram comprising a total mass loss of approximately 1.1% of the total mass of the sample when heated from approximately 25° C. to approximately 150° C.

Figure 41:
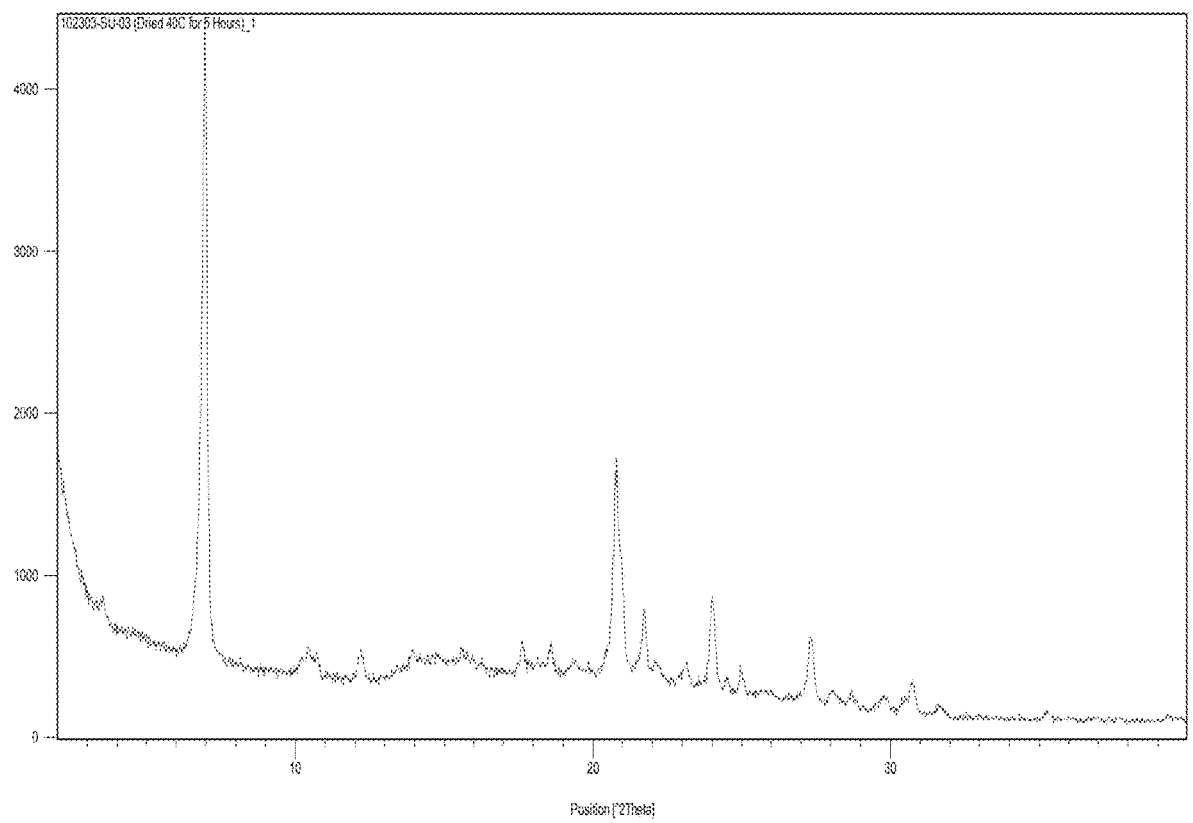
FIG. 41 depicts a PXRD pattern of Hemifumarate Salt Form B of Compound 6.

In certain embodiments, a solid form of Compound 6 provided herein, e.g., Hemifumarate Salt Form B, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 41 (e.g., Hemifumarate Salt Form B). In one embodiment, a solid form of Compound 6 provided herein, e.g., Hemifumarate Salt Form B, has one or more characteristic X-ray powder diffraction peaks at approximately 3.5, 7.0, 10.4, 10.8, 12.2, 13.9, 15.6, 17.6, 18.6, 19.3, 20.8, 21.7, 22.2, 23.1, 24.0, 24.5, 25.0, 27.4, 28.0, 28.7, 29.9, 30.7, or 31.7° 2θ (±0.2° 2θ) or (±0.1° 2θ) as depicted in FIG. 41. In a specific embodiment, a solid form of Compound 6 provided herein, e.g., Hemifumarate Salt Form B, has one, two, three, four, or five characteristic X-ray powder diffraction peaks at approximately 7.0, 12.2, 20.8, 24.0, or 27.4° 2θ (±0.2° 2θ).

In certain embodiments, Hemifumarate Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Hemifumarate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Hemifumarate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form B is substantially pure. In certain embodiments, the substantially pure Hemifumarate Salt Form B is substantially free of other solid forms, including but not limited to amorphous solid. In certain embodiments, the purity of the substantially pure Hemifumarate Salt Form B is no less than about 95%, no less than about 96%, no less than about 97%, no less than about 98%, no less than about 98.5%, no less than about 99%, no less than about 99.5%, or no less than about 99.8%.

(iii) Hemifumarate Salt Form C

In one embodiment, the solid form of Compound 6 is Hemifumarate Salt Form C. In one embodiment, Hemifumarate Salt Form C is crystalline.

In certain embodiments, Hemifumarate Salt Form C is moderately crystalline.

In certain embodiments, provided herein are methods for making Hemifumarate Salt Form C, comprising 1) dispensing a solution of Compound 1 in a solvent (e.g., a solution of about 0.244 mmol/mL of Compound 1 in the solvent) into a vial; 2) adding a stoichiometric amount (e.g., 1.0 equivalent) of a 0.207 M solution of fumaric acid in methanol to the vial; 3) capping and shaking the vials at a frequency (e.g., about 200 rotations per minute) at a temperature (e.g., ambient temperature) for a period of time (e.g., about an hour); 4) uncapping and drying the sample under nitrogen purge; 5) mixing the sample with an amount of the solvent (e.g., about 600 µL); 6) recapping and stirring the sample at a temperature (e.g., ambient temperature) for a period of time (e.g., about two days); 7) filtering the sample using Nylon-membrane centrifuge tube filters; 8) recovering the solids and drying in a vacuum oven at a temperature (e.g., 30° C.) overnight to yield Hemifumarate Salt Form C of Compound 11. In certain embodiments, the solution is evaporated under reduced pressure in a centrifuge evaporator. In certain embodiments, the solvent used in step 1 is acetone. In certain embodiments, the solvent used in step 5 is ethyl methyl ketone, dimethyl carbonate, or acetonitrile. In certain embodiments, the solids recovered after step 8 were suspended in acetonitrile, allowed to stir at ambient temperature overnight, filtered, and dried in a vacuum oven at a temperature (e.g., 30° C.) overnight to yield Hemifumarate Salt Form C of Compound 11.

In certain embodiments, provided herein are methods for making Hemifumarate Salt Form C, comprising 1) dispensing a solution of Compound 1 in a solvent (e.g., a solution of about 0.244 mmol/mL of Compound 1 in the solvent) into a vial; 2) adding an amount (e.g., 0.5 equivalents) of a 0.207 M solution of fumaric acid in methanol to the vial; 3) capping and shaking the vials at a frequency (e.g., about 200 rotations per minute) at a temperature (e.g., ambient temperature) for a period of time (e.g., about an hour); 4) uncapping and drying the sample under nitrogen purge; 5) mixing the sample with an amount of the solvent (e.g., about 600 µL); 6) recapping and stirring the sample at a temperature (e.g., ambient temperature) for a period of time (e.g., about two days); 7) filtering the sample using Nylon-membrane centrifuge tube filters: 8) recovering the solids and drying in a vacuum oven at a temperature (e.g., 30° C.) overnight to yield Hemifumarate Salt Form C of Compound 11. In certain embodiments, the solution is evaporated under reduced pressure in a centrifuge evaporator. In certain embodiments, the solvent used in step 1 is acetone. In certain embodiments, the solvent used in step 5 is ethyl methyl ketone, dimethyl carbonate, or acetonitrile. In certain embodiments, the solids recovered after step 8 were suspended in acetonitrile, allowed to stir at ambient temperature overnight, filtered, and dried in a vacuum oven at a temperature (e.g., 30° C.) overnight to yield Hemifumarate Salt Form C of Compound 11.

Figure 46:
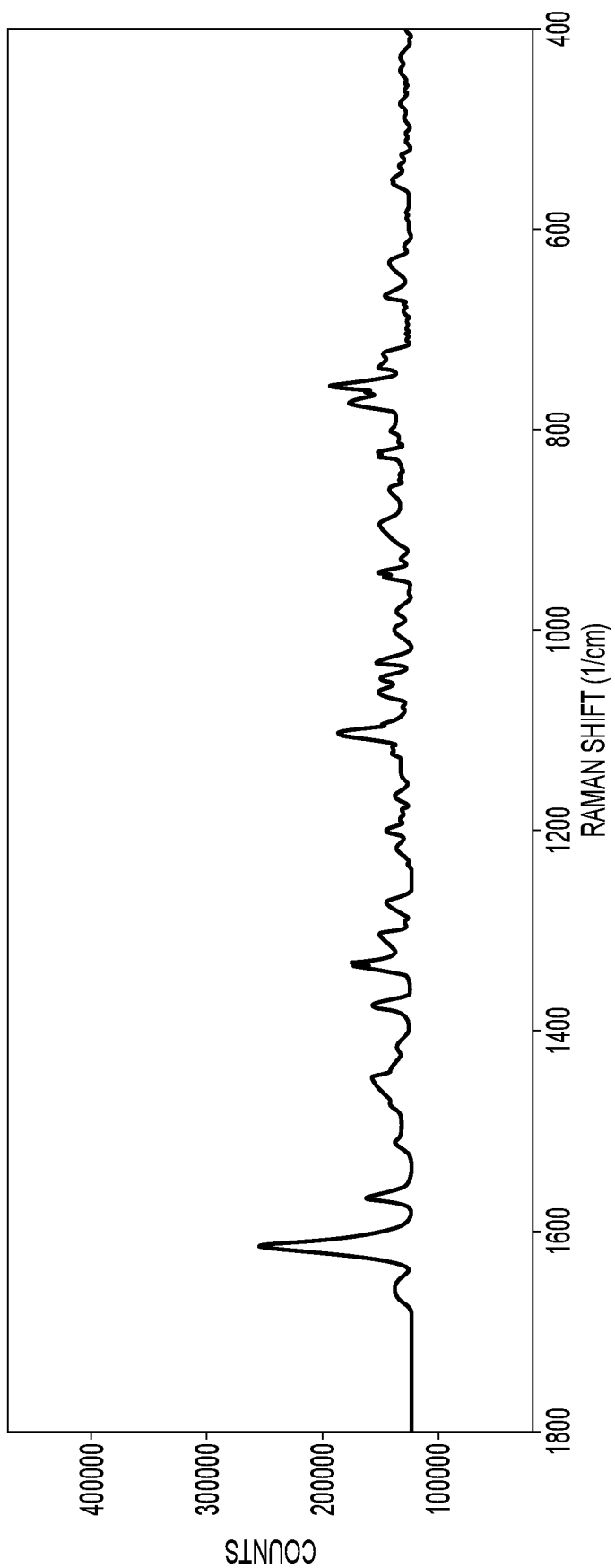
FIG. 46 depicts a Raman spectrum of Hemifumarate Salt Form C of Compound 6.

In one embodiment, provided herein is Hemifumarate Salt Form C having a Raman Spectrum as depicted in FIG. 46.

Figure 47:
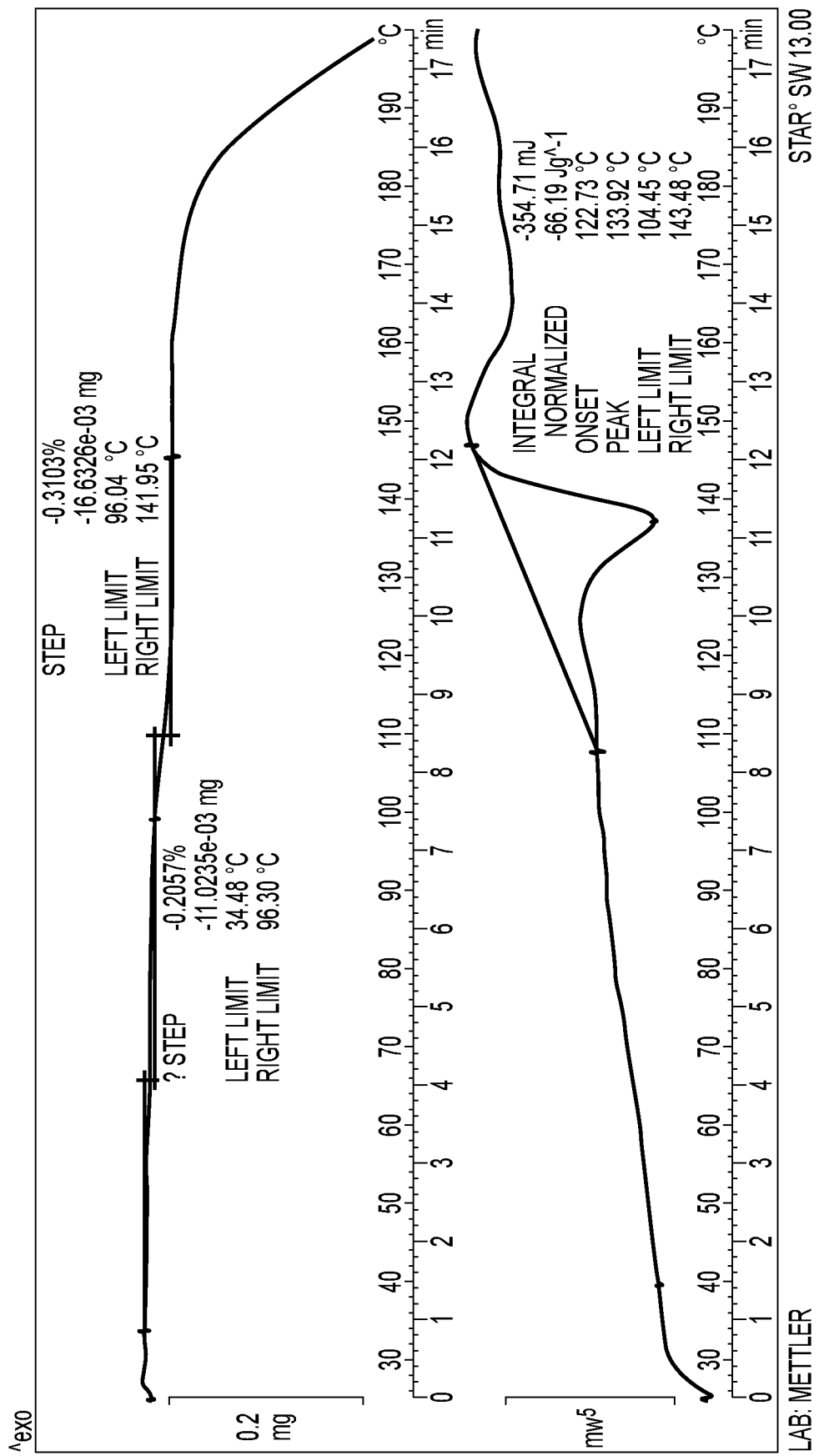
FIG. 47 depicts differential scanning calorimetry/thermal gravimetric analysis of Hemifumarate Salt Form C of Compound 6.

In one embodiment, provided herein is a solid form of Compound 6, e.g., Hemifumarate Salt Form C of Compound 6, having a DSC thermogram substantially as depicted in FIG. 47 comprising an endotherm with an onset temperature at 122.7° C.

In one embodiment, provided herein is a solid form of Compound 6, e.g., Hemifumarate Salt Form C of Compound 6, having a TGA thermogram corresponding substantially to the representative TGA thermogram as depicted in FIG. 47. In certain embodiments, the crystalline form exhibits a TGA thermogram comprising a total mass loss of approximately 0.2% of the total mass of the sample when heated from approximately 34.5° C. to approximately 96.3° C.

Figure 45:
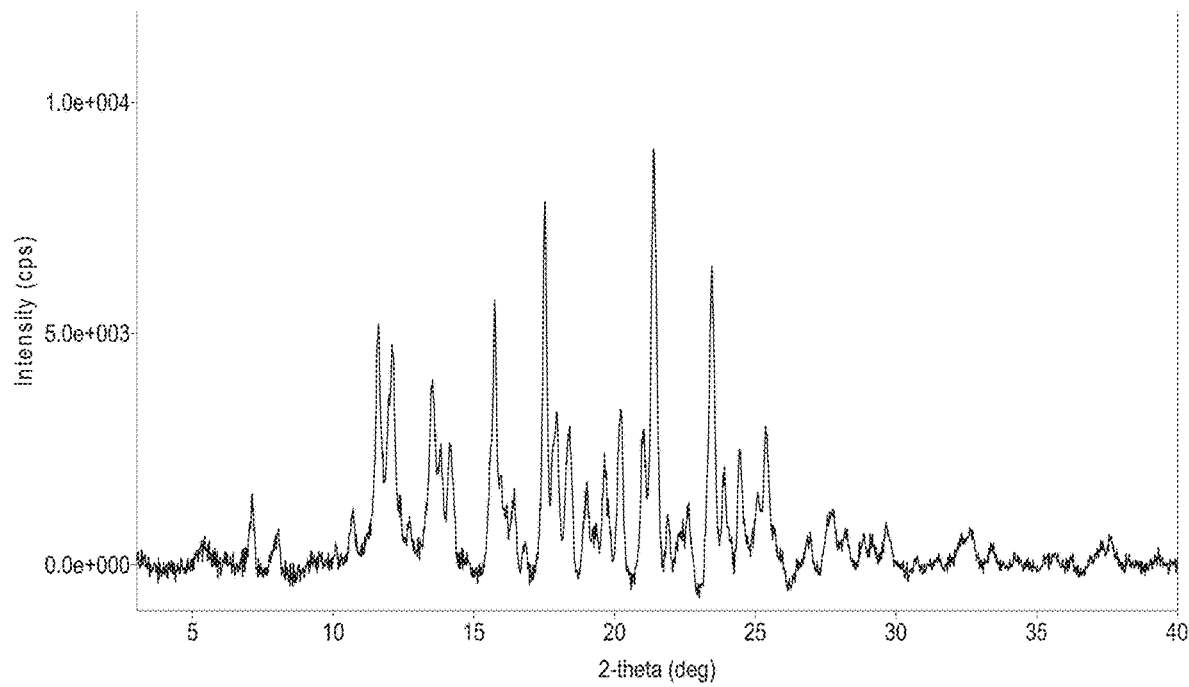
FIG. 45 depicts a PXRD pattern of Hemifumarate Salt Form C of Compound 6.

In certain embodiments, a solid form of Compound 6 provided herein, e.g., Hemifumarate Salt Form C, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 45 (e.g., Hemifumarate Salt Form C). In one embodiment, a solid form of Compound 6 provided herein, e.g., Hemifumarate Salt Form C, has one or more characteristic X-ray powder diffraction peaks at approximately 5.4, 7.1, 8.1, 10.7, 11.6, 12.1, 12.7, 13.5, 13.8, 14.1, 15.8, 16.0, 16.4, 16.8, 17.5, 17.9, 18.4, 19.0, 19.6, 20.2, 21.0, 21.4, 21.9, 22.6, 23.5, 23.9, 24.4, 24.9, 25.1, 25.4, 26.9, 27.7, 28.3, 29.1, 29.6, or 32.6° 2θ (±0.2° 2θ) or (±0.1° 2θ) as depicted in FIG. 45. In a specific embodiment, a solid form of Compound 6 provided herein, e.g., Hemifumarate Salt Form C, has one, two, three, four, or five characteristic X-ray powder diffraction peaks at approximately 5.4, 7.1, 8.1, 13.5, 15.8, 17.5, 21.4, or 23.5° 2θ (±0.2° 2θ).

In certain embodiments, Hemifumarate Salt Form C is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Hemifumarate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Hemifumarate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form C is substantially pure. In certain embodiments, the substantially pure Hemifumarate Salt Form C is substantially free of other solid forms, including but not limited to amorphous solid. In certain embodiments, the purity of the substantially pure Hemifumarate Salt Form C is no less than about 95%, no less than about 96%, no less than about 97%, no less than about 98%, no less than about 98.5%, no less than about 99%, no less than about 99.5%, or no less than about 99.8%.

(iv) Hemifumarate Salt Form D

In one embodiment, the solid form of Compound 6 is Hemifumarate Salt Form D. In one embodiment, Hemifumarate Salt Form D is crystalline. In one embodiment, Hemifumarate Salt Form D is solvated by 1,4-dioxane.

In certain embodiments, provided herein are methods for making Hemifumarate Salt Form D, comprising 1) dispensing Hemifumarate Salt Form B into a vial; 2) adding a solvent or solvent system to create a slurry of Hemifumarate Salt Form B in the solvent or solvent system; 3) cycling the temperature (e.g., between about 5° C. and about 40° C.: 1° C. per minute heating/cooling rate with an hour hold between each heating/cooling cycle) of the slurry for a period of time (e.g., about two days); 4) isolating solids from the sample through vacuum filtration; and 5) air-drying the solids for a period of time (e.g., one hour) to yield Hemifumarate Salt Form D. In some embodiments, the solvent or solvent system is 1,4-dioxane. In some embodiments, the solvent or solvent system is a 10% mixture of water in 1,4-dioxane.

Figure 103:
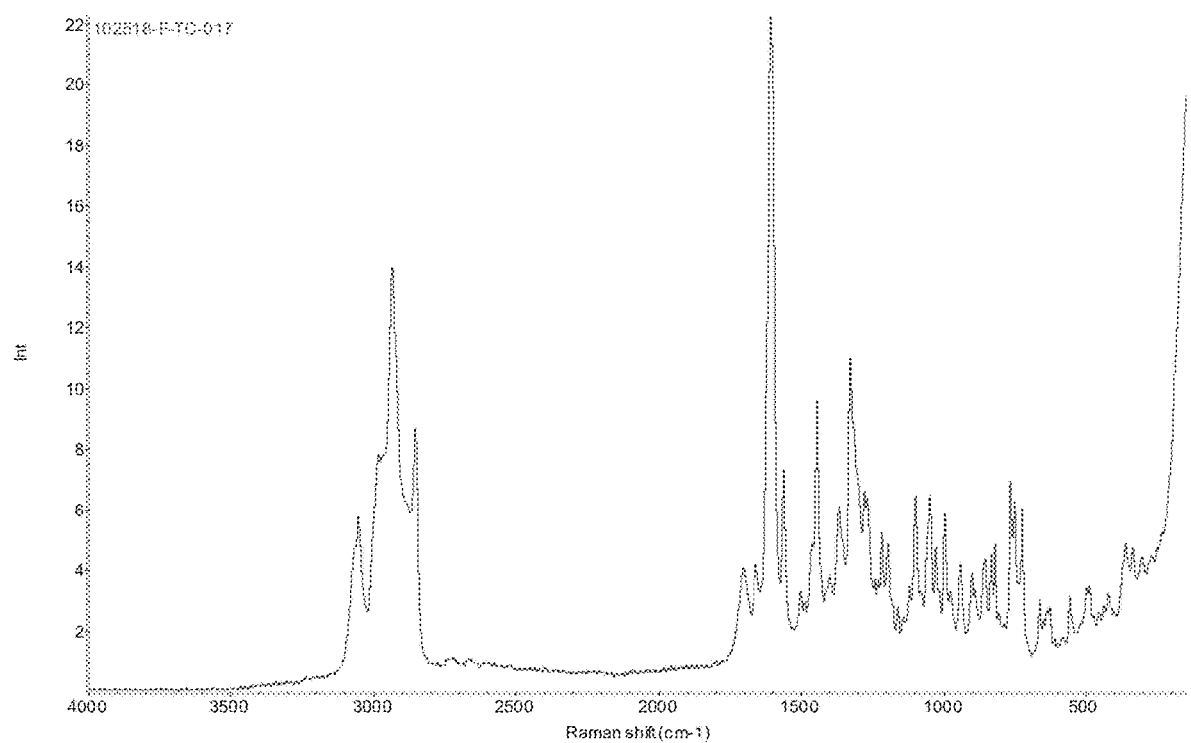
FIG. 103 depicts an FT-Raman spectrum of Hemifumarate Salt Form D of Compound 6.

In one embodiment, provided herein is Hemifumarate Salt Form D having an FT-Raman Spectrum as depicted in FIG. 103.

Figure 104:
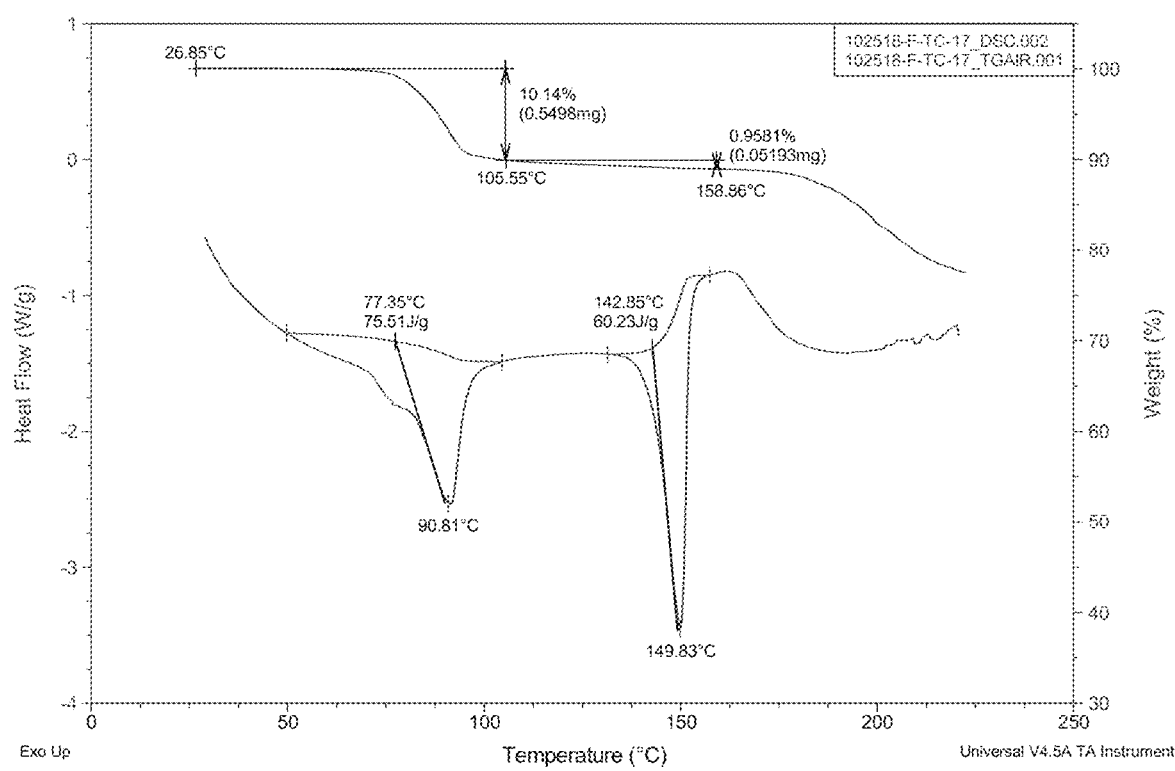
FIG. 104 depicts differential scanning calorimetry/thermal gravimetric analysis of Hemifumarate Salt Form D of Compound 6.

In one embodiment, provided herein is a solid form of Compound 6, e.g., Hemifumarate Salt Form D of Compound 6, having a DSC thermogram substantially as depicted in FIG. 104 comprising an endotherm between 50 and 110° C. with a peak temperature at 91° C., and a large endotherm with an onset temperature at 143° C.

In one embodiment, provided herein is a solid form of Compound 6, e.g., Hemifumarate Salt Form D of Compound 6, having a TGA thermogram corresponding substantially to the representative TGA thermogram as depicted in FIG. 104. In certain embodiments, the crystalline form exhibits a TGA thermogram comprising a total mass loss of approximately 10.1% of the total mass of the sample when heated from approximately 27° C. to approximately 106° C.

Figure 102:
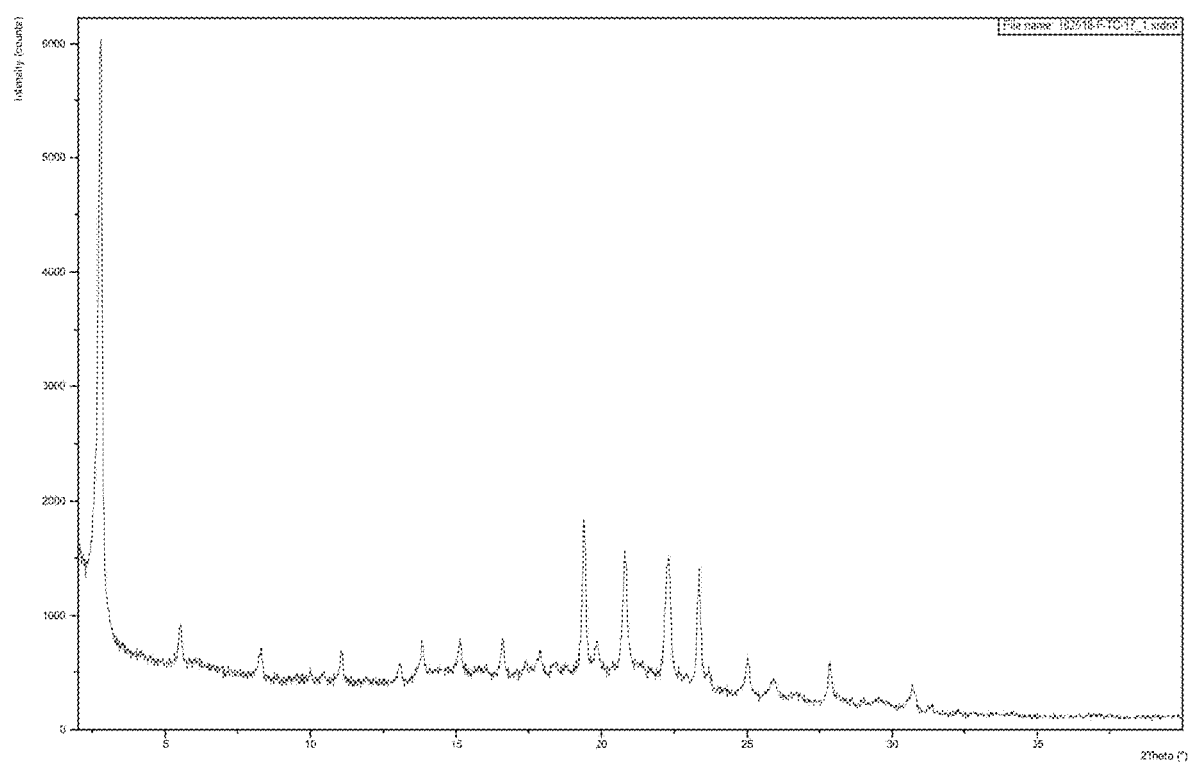
FIG. 102 depicts a PXRD pattern of Hemifumarate Salt Form D of Compound 6.

In certain embodiments, a solid form of Compound 6 provided herein, e.g., Hemifumarate Salt Form D, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 102 (e.g., Hemifumarate Salt Form D). In one embodiment, a solid form of Compound 6 provided herein, e.g., Hemifumarate Salt Form D, has one or more characteristic X-ray powder diffraction peaks at approximately 2.8, 5.6, 8.3, 11.1, 13.1, 13.8, 15.1, 16.6, 19.4, 19.9, 20.8, 22.3, 23.4, 25.0, 26.0, 27.9, or 30.7° 2θ (±0.2° 2θ) or (±0.1° 2θ) as depicted in FIG. 102. In a specific embodiment, a solid form of Compound 6 provided herein, e.g., Hemifumarate Salt Form D, has one, two, three, four, or five characteristic X-ray powder diffraction peaks at approximately 2.8, 11.1, 19.4, 20.8, 22.3, or 23.4° 2θ (±0.2° 2θ).

In certain embodiments, Hemifumarate Salt Form D is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Hemifumarate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Hemifumarate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form D is substantially pure. In certain embodiments, the substantially pure Hemifumarate Salt Form D is substantially free of other solid forms, including but not limited to amorphous solid. In certain embodiments, the purity of the substantially pure Hemifumarate Salt Form D is no less than about 95%, no less than about 96%, no less than about 97%, no less than about 98%, no less than about 98.5%, no less than about 99%, no less than about 99.5%, or no less than about 99.8%.

(v) Hemifumarate Salt Form E

In one embodiment, the solid form of Compound 6 is Hemifumarate Salt Form E. In one embodiment, Hemifumarate Salt Form E is crystalline. In one embodiment, Hemifumarate Salt Form E is non-solvated.

In certain embodiments, provided herein are methods for making Hemifumarate Salt Form E, comprising 1) dispensing Hemifumarate Salt Form B into a vial; 2) adding a solvent or solvent system to create a slurry of Hemifumarate Salt Form B; 3) optionally adding seeds of Hemifumarate Salt Form E to the slurry; 4) allowing the solvent or solvent system to slowly evaporate through a loosened cap on the vial for a period of time (e.g., 7 days) at a temperature (e.g., ambient temperature); 5) removing the cap and allowing the solvent or solvent system to evaporate for a period of time (e.g., 7 days) at a temperature (e.g., ambient temperature); and 6) evaporating the remaining solution under reduced pressure for a period of time (e.g., 24 hours) to yield Hemifumarate Salt Form E. In some embodiments, the solvent or solvent system is methanol. In some embodiments, the solvent or solvent system is a 5% mixture of water in methanol. In some embodiments, the solvent or solvent system is a 10% mixture of water in methanol.

Figure 107:
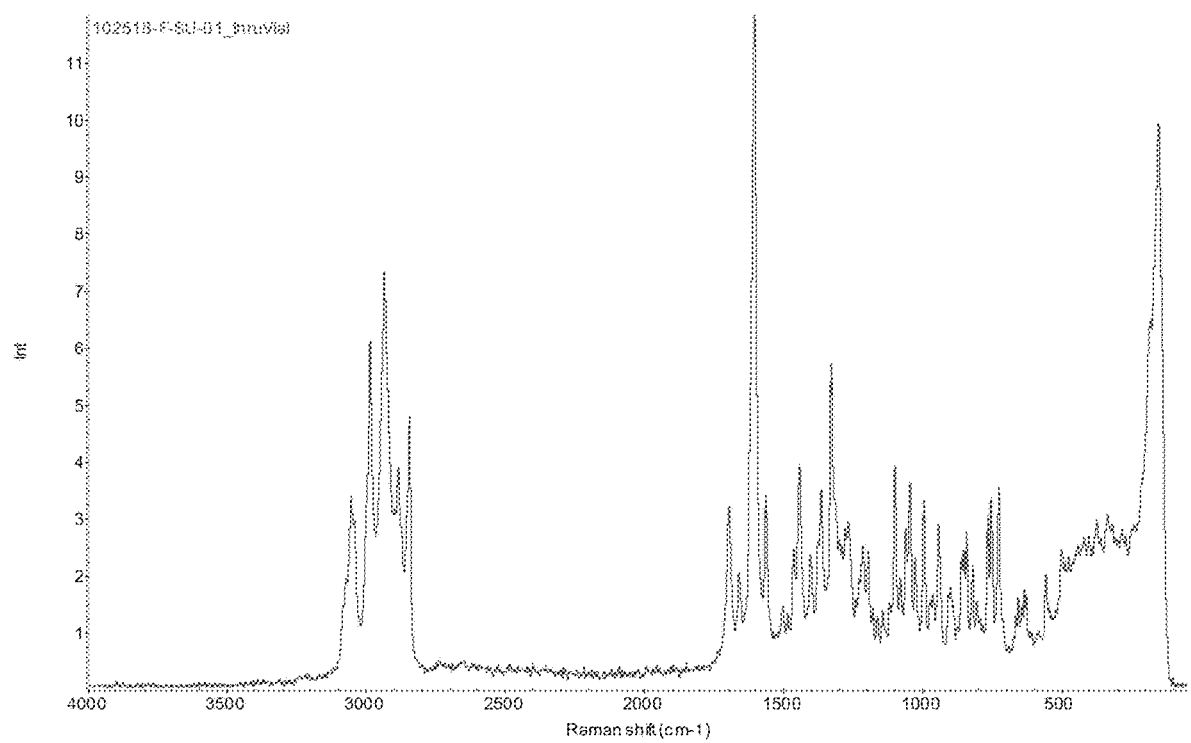
FIG. 107 depicts an FT-Raman spectrum of Hemifumarate Salt Form E of Compound 6.

In one embodiment, provided herein is Hemifumarate Salt Form E having an FT-Raman Spectrum as depicted in FIG. 107.

Figure 108:
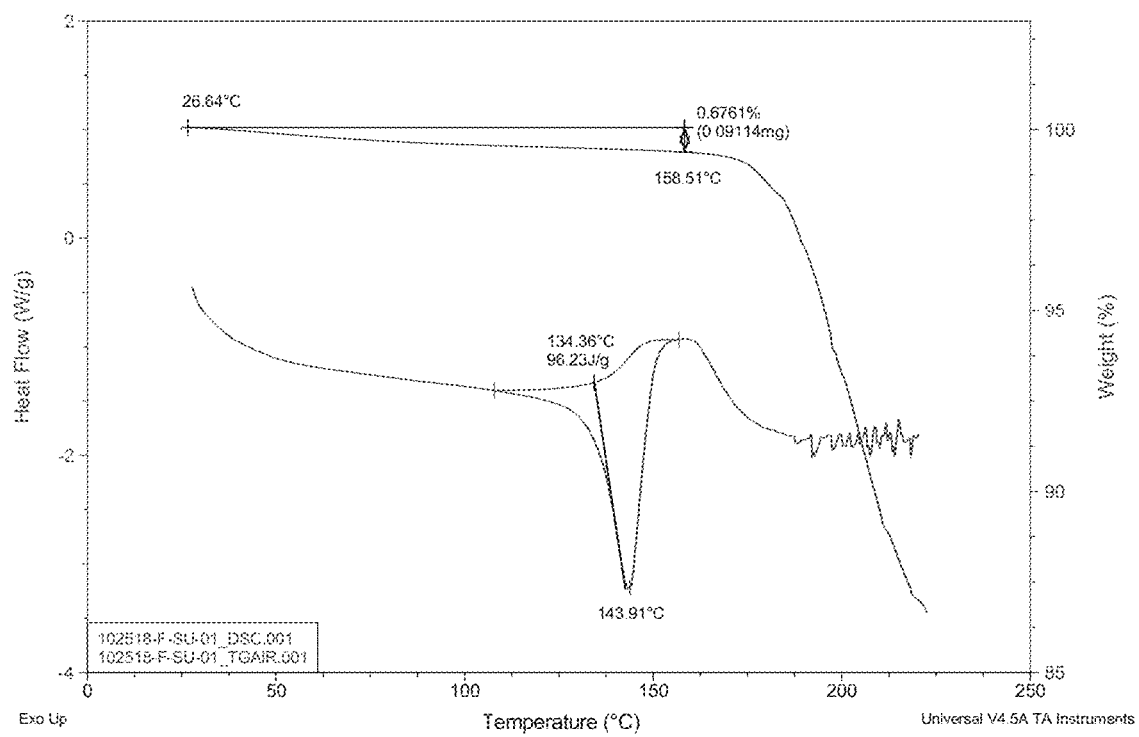
FIG. 108 depicts differential scanning calorimetry/thermal gravimetric analysis of Hemifumarate Salt Form E of Compound 6.

In one embodiment, provided herein is a solid form of Compound 6, e.g., Hemifumarate Salt Form E of Compound 6, having a DSC thermogram substantially as depicted in FIG. 108 comprising an endotherm with an onset temperature at 134° C.

In one embodiment, provided herein is a solid form of Compound 6, e.g., Hemifumarate Salt Form E of Compound 6, having a TGA thermogram corresponding substantially to the representative TGA thermogram as depicted in FIG. 108. In certain embodiments, the crystalline form exhibits a TGA thermogram comprising a total mass loss of approximately 0.7% of the total mass of the sample when heated from approximately 27° C. to approximately 159° C.

Figure 106:
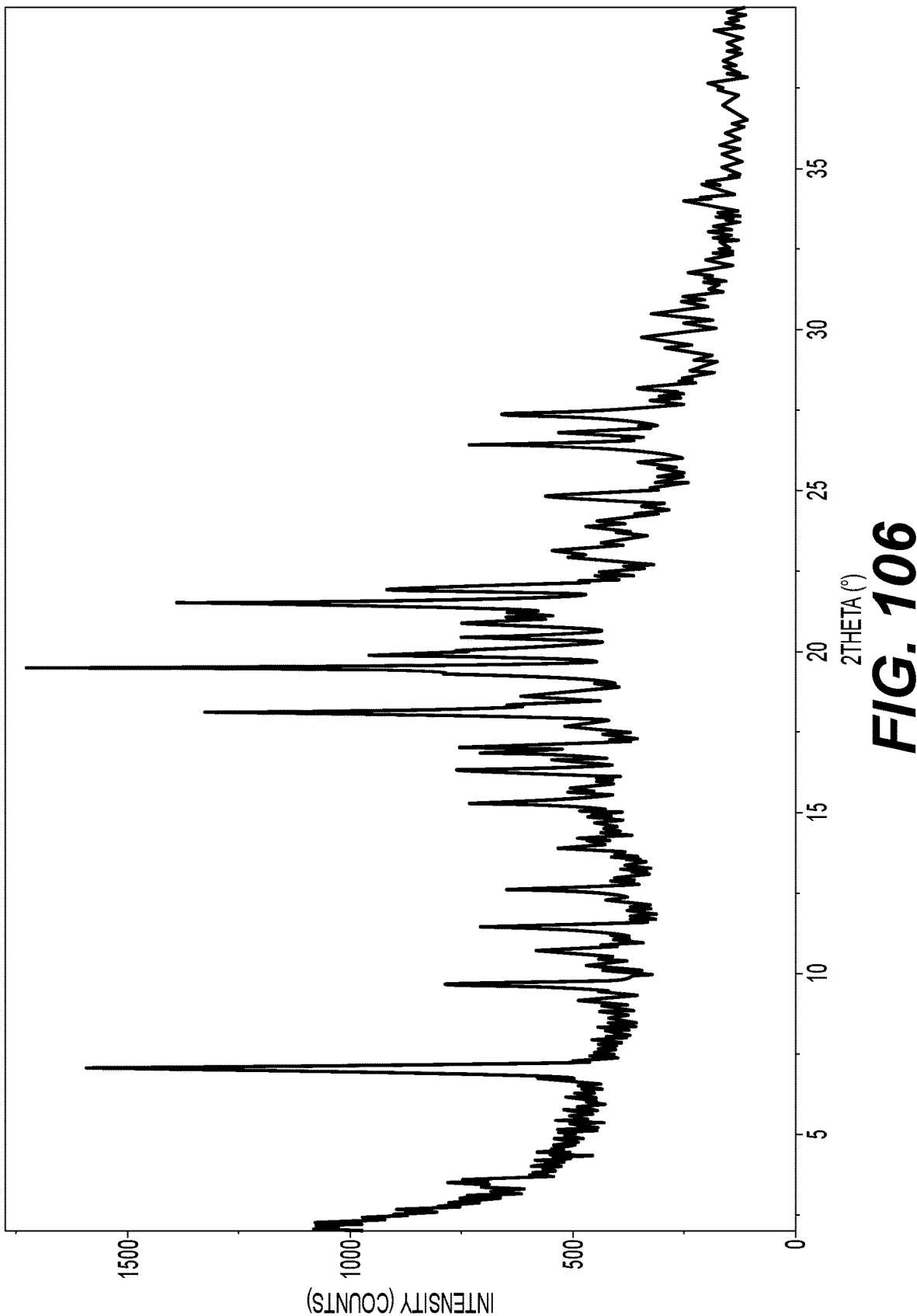
FIG. 106 depicts a PXRD pattern of Hemifumarate Salt Form E of Compound 6.

In certain embodiments, a solid form of Compound 6 provided herein, e.g., Hemifumarate Salt Form E, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 106 (e.g., Hemifumarate Salt Form E). In one embodiment, a solid form of Compound 6 provided herein, e.g., Hemifumarate Salt Form E, has one or more characteristic X-ray powder diffraction peaks at approximately 3.6, 7.0, 9.7, 10.7, 11.4, 12.6, 13.9, 15.3, 16.3, 16.8, 17.0, 17.7, 18.1, 18.6, 19.5, 19.9, 20.1, 20.5, 20.9, 21.5, 22.0, 23.1, 23.8, 24.8, 26.4, 26.8, 27.3, 28.2, 29.8, or 30.5° 2θ (±0.2° 2θ) or (±0.1° 2θ) as depicted in FIG. 106. In a specific embodiment, a solid form of Compound 6 provided herein, e.g., Hemifumarate Salt Form E, has one, two, three, four, or five characteristic X-ray powder diffraction peaks at approximately 7.0, 18.1, 19.5, 19.9, or 21.5° 2θ (±0.2° 2θ).

In certain embodiments, Hemifumarate Salt Form E is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Hemifumarate Salt Form E is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Hemifumarate Salt Form E is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form E is substantially pure. In certain embodiments, the substantially pure Hemifumarate Salt Form E is substantially free of other solid forms, including but not limited to amorphous solid. In certain embodiments, the purity of the substantially pure Hemifumarate Salt Form E is no less than about 95%, no less than about 96%, no less than about 97%, no less than about 98%, no less than about 98.5%, no less than about 99%, no less than about 99.5%, or no less than about 99.8%.

(vi) Hemifumarate Salt Form F

In one embodiment, the solid form of Compound 6 is Hemifumarate Salt Form F. In one embodiment, Hemifumarate Salt Form F is crystalline. In one embodiment, Hemifumarate Salt Form F is poorly crystalline. In one embodiment, Hemifumarate Salt Form F is hydrated.

In certain embodiments, provided herein are methods for making Hemifumarate Salt Form F, comprising 1) dispensing Hemifumarate Salt Form B into a vial; 2) adding a solvent or solvent system to create a slurry of Hemifumarate Salt Form B; 3) allowing the solvent or solvent system to slowly evaporate through a loosened cap on the vial for a period of time (e.g., 7 days) at a temperature (e.g., ambient temperature); 4) removing the cap and allowing the solvent or solvent system to evaporate for a period of time (e.g., 7 days) at a temperature (e.g., ambient temperature); and 5) evaporating the remaining solvent or solvent system under reduced pressure for a period of time (e.g., 24 hours) to yield Hemifumarate Salt Form F. In some embodiments, the solvent or solvent system is a 20% mixture of water in acetone.

Figure 111:
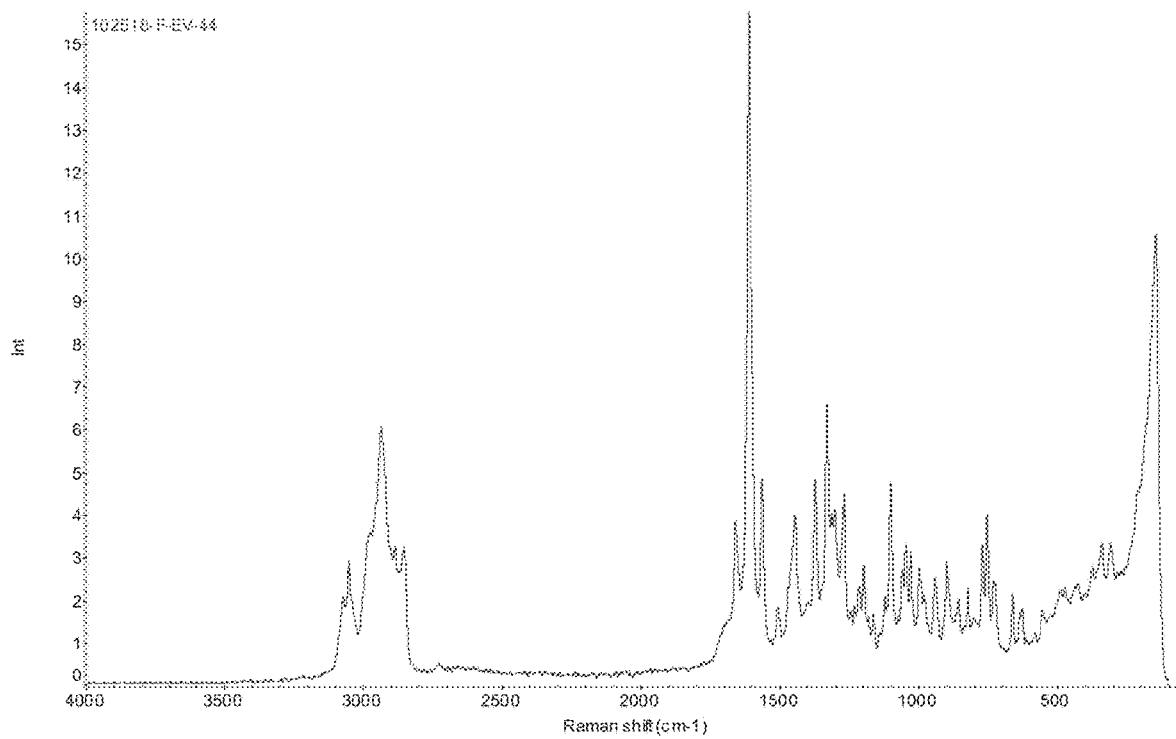
FIG. 111 depicts an FT-Raman spectrum of Hemifumarate Salt Form F of Compound 6.

In one embodiment, provided herein is Hemifumarate Salt Form F having an FT-Raman Spectrum as depicted in FIG. 111.

Figure 112:
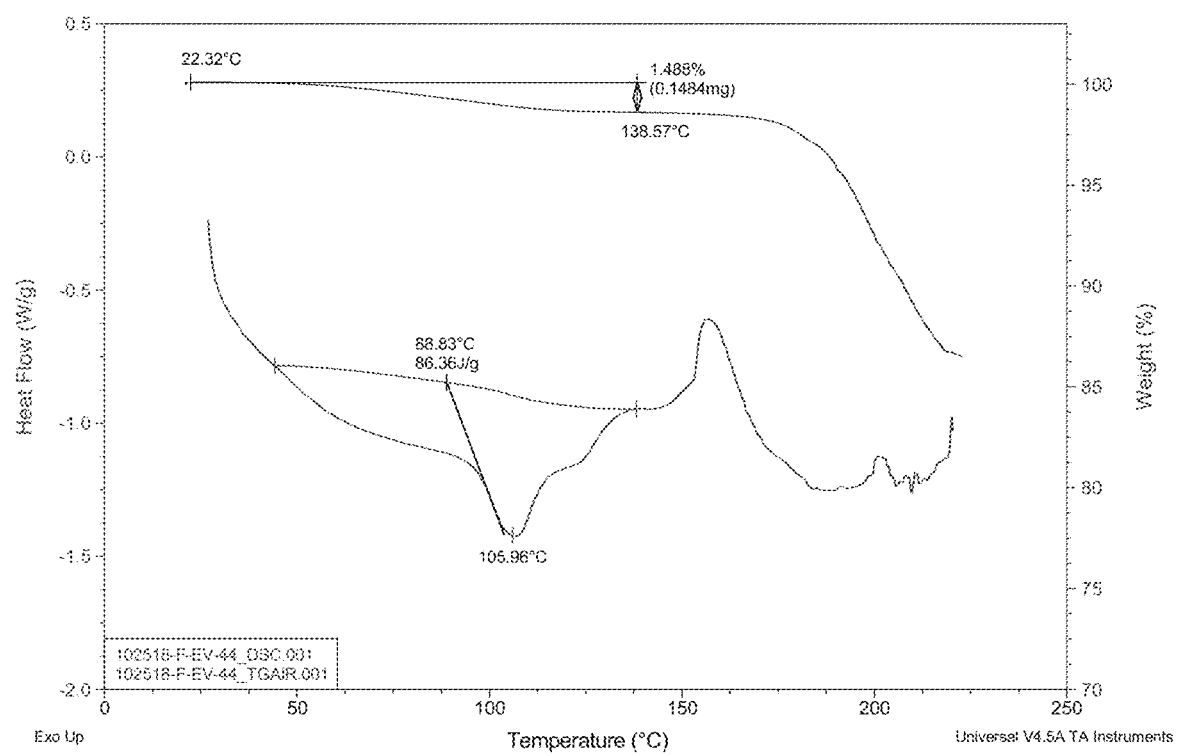
FIG. 112 depicts differential scanning calorimetry/thermal gravimetric analysis of Hemifumarate Salt Form F of Compound 6.

In one embodiment, provided herein is a solid form of Compound 6, e.g., Hemifumarate Salt Form F of Compound 6, having a DSC thermogram substantially as depicted in FIG. 112 comprising an endotherm between 45° C. and 140° C. with a peak temperature at 106° C.

In one embodiment, provided herein is a solid form of Compound 6, e.g., Hemifumarate Salt Form F of Compound 6, having a TGA thermogram corresponding substantially to the representative TGA thermogram as depicted in FIG. 112. In certain embodiments, the crystalline form exhibits a TGA thermogram comprising a total mass loss of approximately 1.5% of the total mass of the sample when heated from approximately 22° C. to approximately 139° C.

Figure 110:
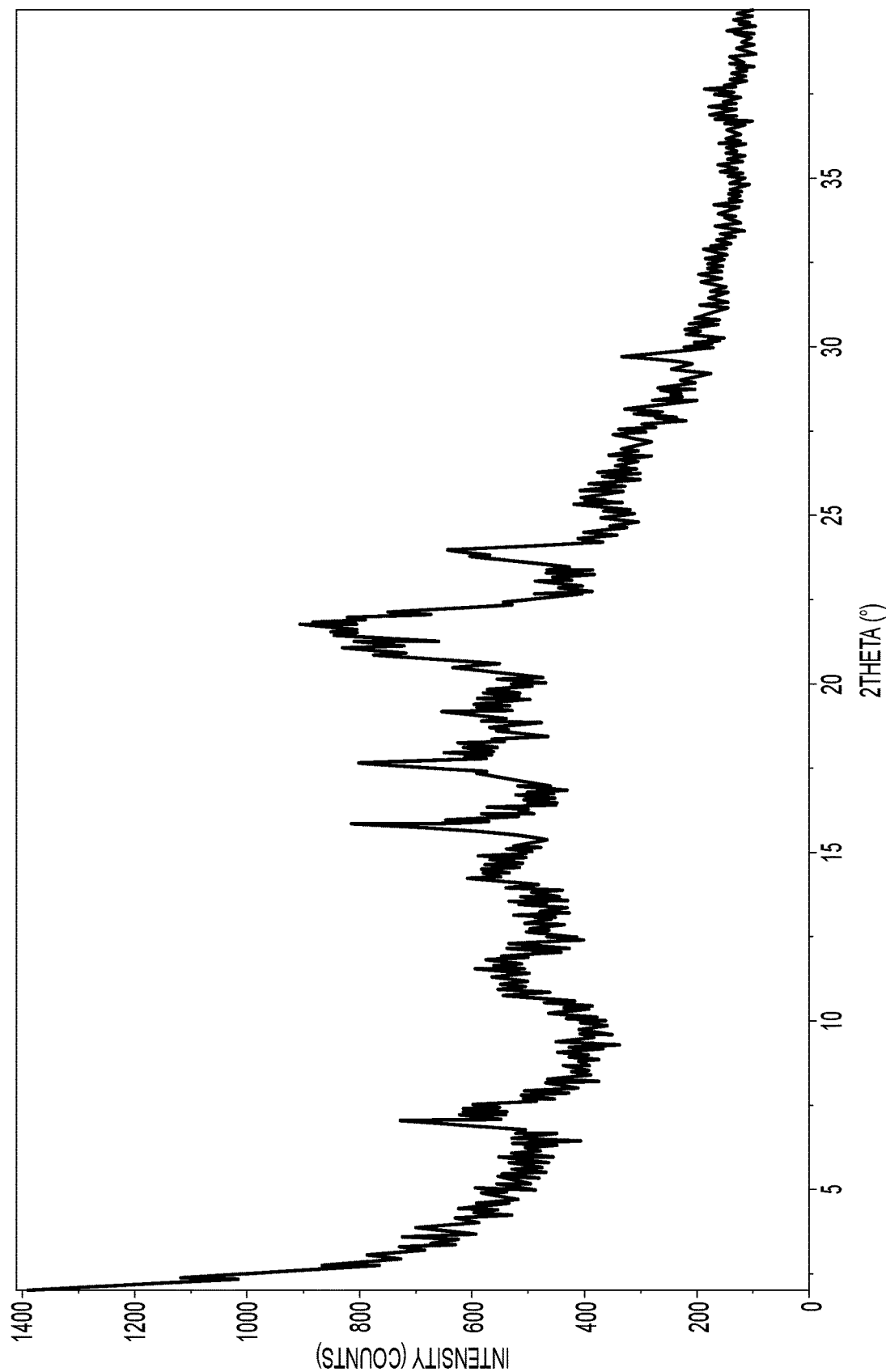
FIG. 110 depicts a PXRD pattern of Hemifumarate Salt Form F of Compound 6.

In certain embodiments, a solid form of Compound 6 provided herein, e.g., Hemifumarate Salt Form F, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 110 (e.g., Hemifumarate Salt Form F). In one embodiment, a solid form of Compound 6 provided herein, e.g., Hemifumarate Salt Form F, has one or more characteristic X-ray powder diffraction peaks at approximately 7.0, 15.8, 17.6, 21.8, 23.9, or 29.7° 2θ (±0.2° 2θ) or (±0.1° 2θ) as depicted in FIG. 110. In a specific embodiment, a solid form of Compound 6 provided herein, e.g., Hemifumarate Salt Form F, has one, two, three, four, or five characteristic X-ray powder diffraction peaks at approximately 7.0, 15.8, 17.6, 21.8, or 23.9° 2θ (±0.2° 2θ).

In certain embodiments, Hemifumarate Salt Form F is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Hemifumarate Salt Form F is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Hemifumarate Salt Form F is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form F is substantially pure. In certain embodiments, the substantially pure Hemifumarate Salt Form F is substantially free of other solid forms, including but not limited to amorphous solid. In certain embodiments, the purity of the substantially pure Hemifumarate Salt Form F is no less than about 95%, no less than about 96%, no less than about 97%, no less than about 98%, no less than about 98.5%, no less than about 99%, no less than about 99.5%, or no less than about 99.8%.

(vii) Hemifumarate Salt Form G

In one embodiment, the solid form of Compound 6 is Hemifumarate Salt Form G. In one embodiment, Hemifumarate Salt Form G is crystalline.

In certain embodiments, provided herein are methods for making Hemifumarate Salt Form G comprising 1) combining Compound 1 (e.g., about 5 g) with methyl tert-butyl ether (e.g., about 62.5 mL) and mixing at a temperature (e.g., about 40° C.) for a period of time (e.g., 30 minutes); 2) adding 99.5+% fumaric acid (e.g., about 0.5 equivalents) at a temperature (e.g., about 40° C.) and seeding the solution with Hemifumarate Salt Form B; 3) allowing the sample to stir for a period of time (e.g., 2 hours) at a temperature (e.g., 40° C.); 4) slowly cooling the solution to ambient temperature; 5) stirring the solution at a temperature (e.g., ambient temperature) for a period of time (e.g., 3 days); 6) isolating solids from the solution by vacuum filtration for a period of time (e.g., 1.5 hours); 7) drying the solids at a temperature (e.g., 40° C.) in a vacuum oven for a period of time (e.g., five hours); 8) mixing a portion of the solids with 20% water in isopropanol to create a slurry; 9) cycling the temperature between about 5° C. and about 40° C. (1° C. per minute heating/cooling rate with an hour hold between each heating/cooling cycle) for a period of time (e.g., 2 days); and 10) isolating the solids via vacuum filtration to yield Hemifumarate Salt Form G of Compound 6.

Figure 127:
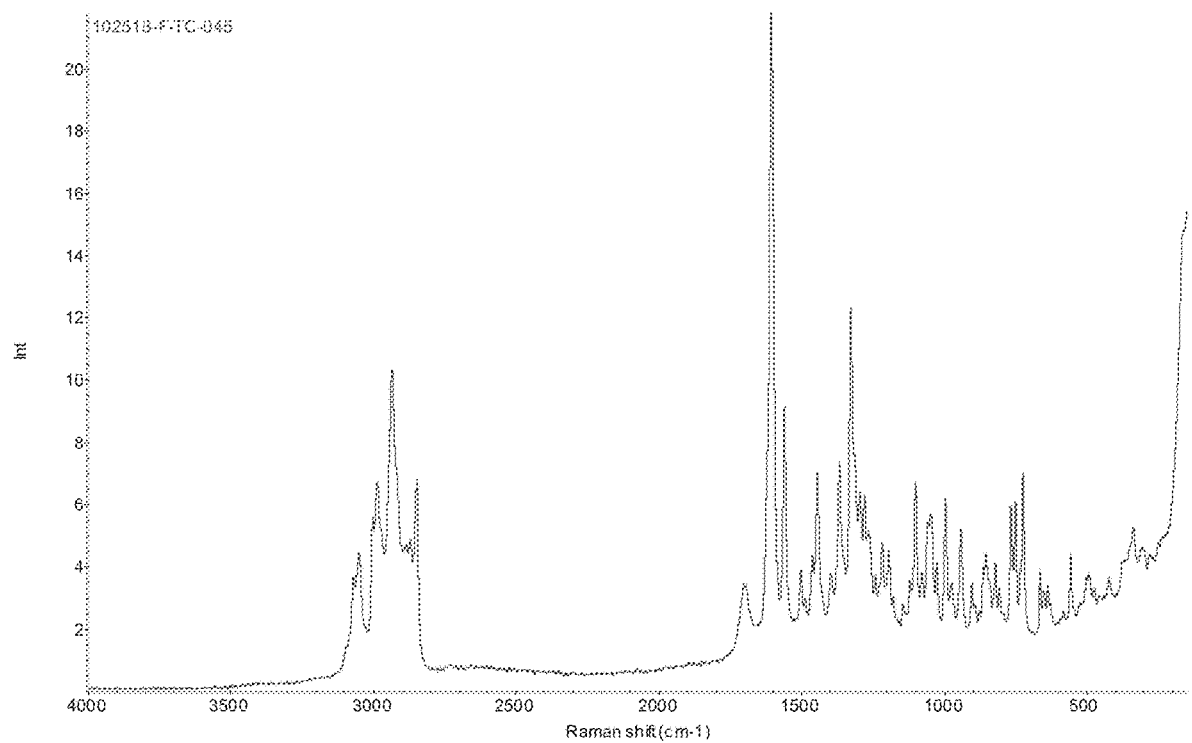
FIG. 127 depicts an FT-Raman spectrum of Hemifumarate Salt Form G of Compound 6.

In one embodiment, provided herein is Hemifumarate Salt Form G having an FT-Raman Spectrum as depicted in FIG. 127.

Figure 128:
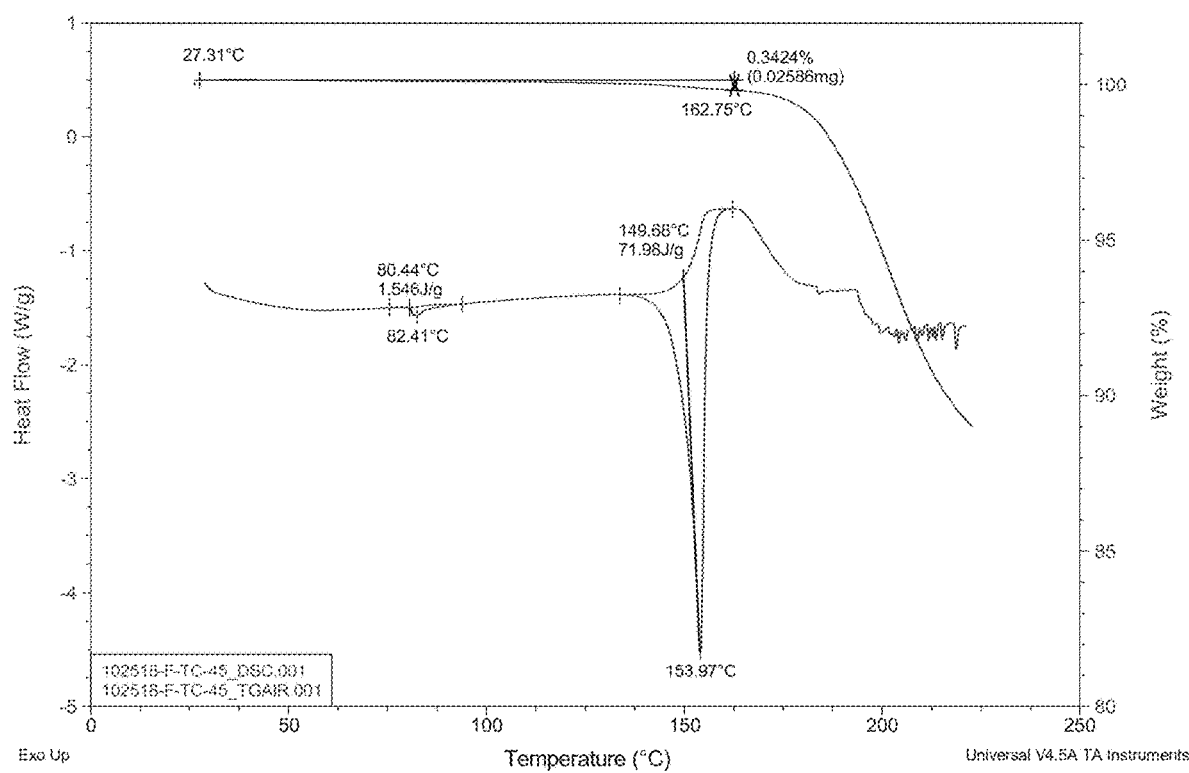
FIG. 128 depicts differential scanning calorimetry/thermal gravimetric analysis of Hemifumarate Salt Form G of Compound 6.

In one embodiment, provided herein is a solid form of Compound 6, e.g., Hemifumarate Salt Form G of Compound 6, having a DSC thermogram substantially as depicted in FIG. 128 comprising multiple endotherms with onset temperatures at 80.4° C. and 149.7° C.

In one embodiment, provided herein is a solid form of Compound 6, e.g., Hemifumarate Salt Form G of Compound 6, having a TGA thermogram corresponding substantially to the representative TGA thermogram as depicted in FIG. 128. In certain embodiments, the crystalline form exhibits a TGA thermogram comprising a total mass loss of approximately 0.3% of the total mass of the sample when heated from approximately 27° C. to approximately 163° C.

Figure 126:
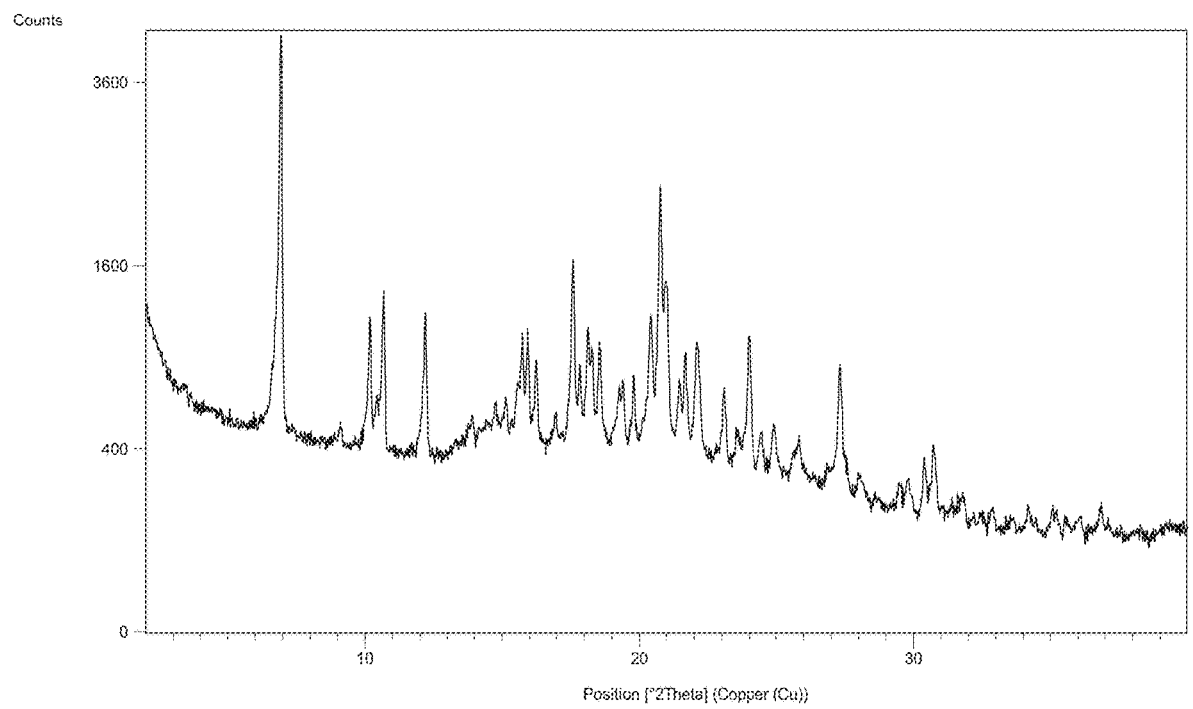
FIG. 126 depicts a PXRD pattern of Hemifumarate Salt Form G of Compound 6.

In certain embodiments, a solid form of Compound 6 provided herein, e.g., Hemifumarate Salt Form G, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 126 (e.g., Hemifumarate Salt Form G). In one embodiment, a solid form of Compound 6 provided herein, e.g., Hemifumarate Salt Form G, has one or more characteristic X-ray powder diffraction peaks at approximately 7.0, 9.1, 10.2, 10.7, 12.2, 15.7, 15.9, 16.3, 17.0, 17.6, 17.8, 1801, 18.3, 18.6, 19.3, 19.4, 19.8, 20.4, 20.8, 21.0, 21.5, 21.7, 22.1, 23.1, 23.6, 24.0, 24.5, 24.9, 25.8, 27.3, 29.8, 30.4, or 30.7° 2θ (±0.2° 2θ) or (±0.1° 2θ) as depicted in FIG. 126. In a specific embodiment, a solid form of Compound 6 provided herein, e.g., Hemifumarate Salt Form G, has one, two, three, four, or five characteristic X-ray powder diffraction peaks at approximately 7.0, 10.7, 12.2, 17.6, 20.8, 21.0, or 24.0° 2θ (±0.2° 2θ).

In certain embodiments, Hemifumarate Salt Form G is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In further embodiments, Hemifumarate Salt Form G is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form G is substantially pure. In certain embodiments, the substantially pure Hemifumarate Salt Form G is substantially free of other solid forms, including but not limited to amorphous solid. In certain embodiments, the purity of the substantially pure Hemifumarate Salt Form G is no less than about 95%, no less than about 96%, no less than about 97%, no less than about 98%, no less than about 98.5%, no less than about 99%, no less than about 99.5%, or no less than about 99.8%.

(viii) Hemifumarate Salt Form H

In one embodiment, the solid form of Compound 6 is Hemifumarate Salt Form H. In one embodiment, Hemifumarate Salt Form H is crystalline. In certain embodiments, Hemifumarate Salt Form H is moderately crystalline.

In certain embodiments, provided herein are methods for making a Hemifumarate Salt Form H, comprising 1) dispensing a solution of Compound 1 in a solvent or solvent system (e.g., 100 mg of Compound 1 dissolved in 1.3 mL of a 5:8 mixture of acetone and methanol) into a vial; 2) filtering the solution through a PTFE-membraned syringe filer; 3) adding an amount (e.g., 0.5 equivalents) of fumaric acid (e.g., a 0.084 M solution in methanol); 4) capping the sample and shaking at 200 RPM at a temperature (e.g., ambient temperature) for a period of time (e.g., 1 hr); 5) uncapping the vial and drying the sample under nitrogen purge; 6) mixing the sample with an amount (e.g., 300 uL) of ethyl methyl ketone; 7) re-capping the sample and stirring at 300 RPM at a temperature (e.g., ambient temperature) for a period of time (e.g., overnight); 8) filtering the sample using Nylon-membraned centrifuge tube filter; 9) isolating the solids and drying in a vacuum oven at a temperature (e.g., 35° C.) for a period of time (e.g., about 24 h); 10) slurrying the sample in acetonitrile at a temperature (e.g., ambient temperature) and stirring for a period of time (e.g., about three days); 11) filtering the sample using Nylon-membraned centrifuge tube filter; and 12) isolating the solids and drying in a vacuum oven at a temperature (e.g., 35° C.) for a period of time (e.g., about 24 h) to yield Hemifumarate Salt Form H.

Figure 131:
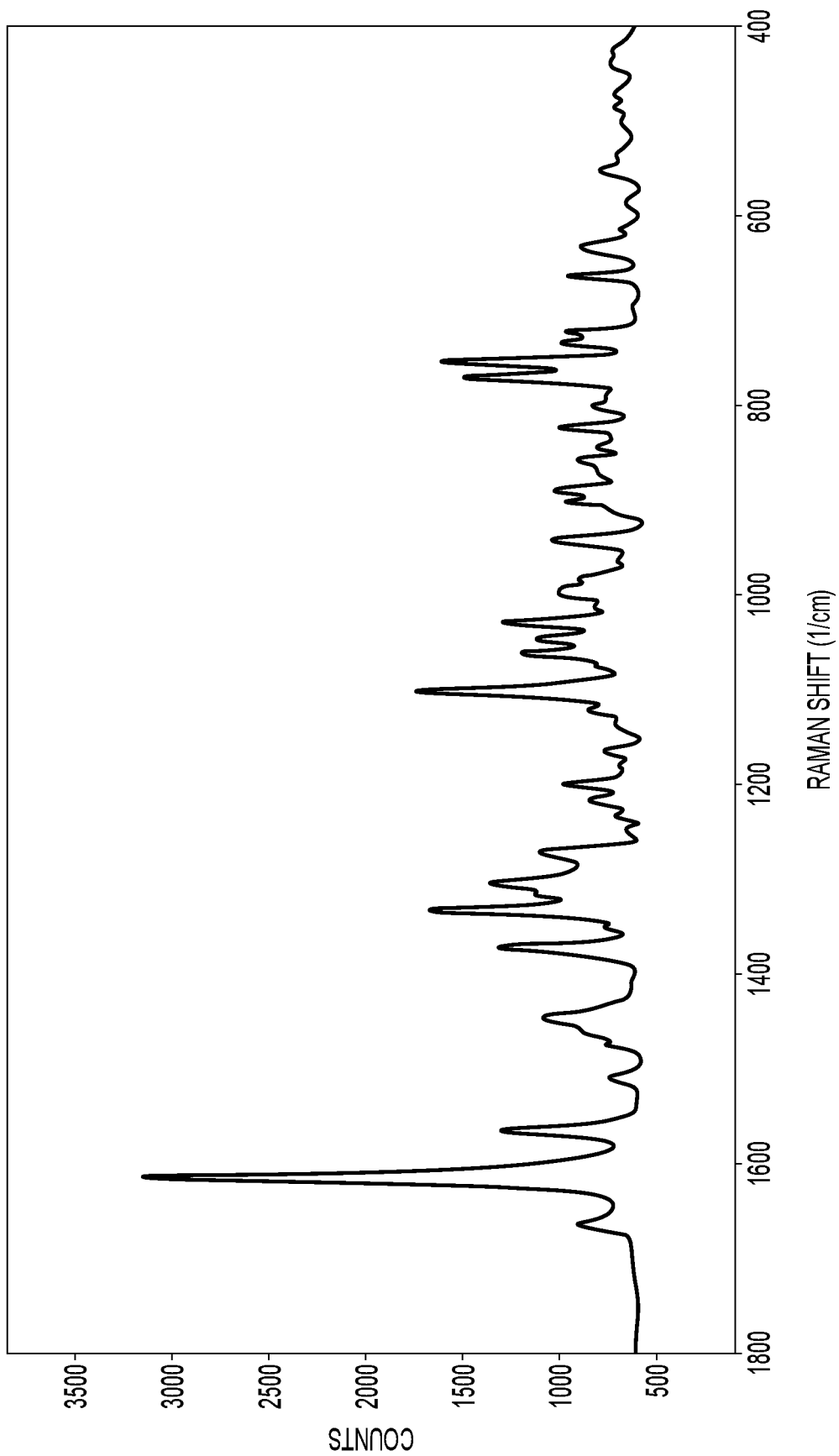
FIG. 131 depicts a Raman spectrum of Hemifumarate Salt Form H of Compound 6.

In another embodiment, Hemifumarate Salt Form H has a Raman Spectrum as depicted in FIG. 131.

Figure 132:
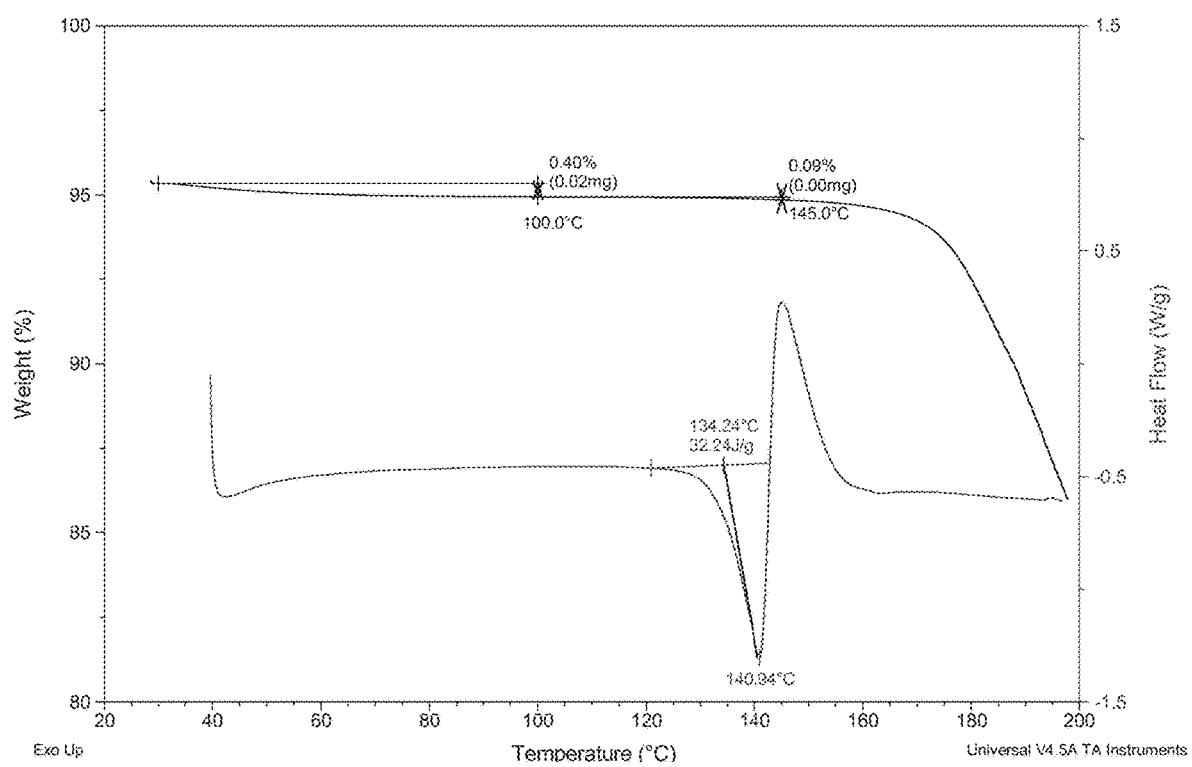
FIG. 132 depicts differential scanning calorimetry/thermal gravimetric analysis of Hemifumarate Salt Form H of Compound 6.

In one embodiment, provided herein is a solid form of Compound 6, e.g., Hemifumarate Salt Form H of Compound 6, having a DSC thermogram substantially as depicted in FIG. 132 comprising an endotherm with a peak temperature of approximately 140.9° C.

In one embodiment, provided herein is a solid form of Compound 6, e.g., Hemifumarate Salt Form H of Compound 6, having a TGA thermogram corresponding substantially to the representative TGA thermogram as depicted in FIG. 132. In certain embodiments, the crystalline form exhibits a TGA thermogram comprising a total mass loss of approximately 0.4% of the total mass of the sample when heated to approximately 100° C.

Figure 130:
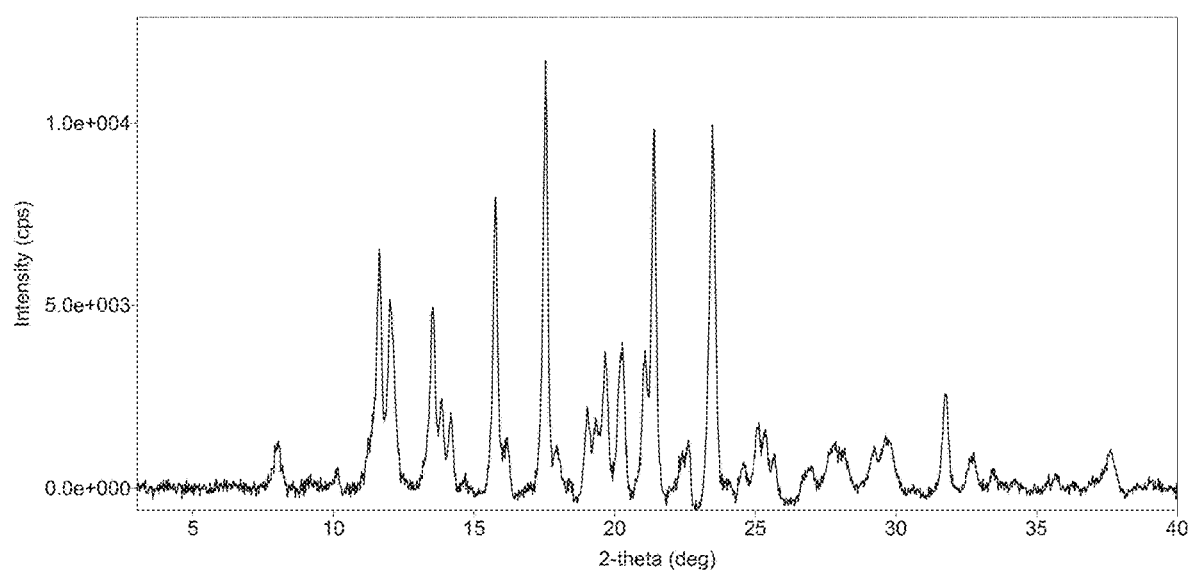
FIG. 130 depicts a PXRD pattern of Hemifumarate Salt Form H of Compound 6.

In certain embodiments, a solid form of Compound 6 provided herein, e.g., Hemifumarate Salt Form H, is substantially crystalline, as indicated by, e.g., X-ray powder diffraction measurements. In one embodiment, provided herein is a solid form of Compound 6 having an X-ray powder diffraction pattern (XRPD) substantially as shown in FIG. 130 (e.g., Hemifumarate Salt Form H). In one embodiment, a solid form of Compound 6 provided herein, e.g., Hemifumarate Salt Form H, has one or more characteristic X-ray powder diffraction peaks at approximately 8.0, 11.6, 12.0, 13.5, 13.8, 14.1, 15.8, 16.2, 17.6, 19.0, 19.3, 19.7, 20.2, 21.0, 21.4, 22.5, 23.5, 25.1, 27.8, or 29.60° 2θ (±0.2° 2θ) or (±0.1° 2θ) as depicted in FIG. 130. In a specific embodiment, a solid form of Compound 6 provided herein, e.g., Hemifumarate Salt Form H, has one, two, three, four, or five characteristic X-ray powder diffraction peaks at approximately 8.0, 11.6, 13.5, 15.8, 17.6, 21.4, or 23.5° 2θ (±0.2° 2θ).

In certain embodiments, Hemifumarate Salt Form H is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In further embodiments, Hemifumarate Salt Form H is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Hemifumarate Salt Form H is substantially pure. In certain embodiments, the substantially pure Hemifumarate Salt Form H is substantially free of other solid forms, including but not limited to amorphous solid. In certain embodiments, the purity of the substantially pure Hemifumarate Salt Form H is no less than about 95%, no less than about 96%, no less than about 97%, no less than about 98%, no less than about 98.5%, no less than about 99%, no less than about 99.5%, or no less than about 99.8%.

(g) Solid Forms of Compound 7

In one embodiment, provided herein is a solid form of Compound 7.

(i) HBr Salt Form A

In one embodiment, the solid form of Compound 7 is HBr Salt Form A. In one embodiment, HBr Salt Form A is crystalline. In one embodiment, HBr Salt Form A is hydrated.

In certain embodiments, provided herein are methods for making HBr Salt Form A, comprising 1) dispensing isopropanol (e.g., about 250 μL) into a vial containing an amount of Compound 1 (e.g., about 20 mg); 2) adding a stoichiometric amount (e.g., 1.0 equivalent) a 5 M solution of HBr in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in isopropanol, followed by temperature cycling (e.g., between about 5° C. and about 40° C.; 1° C. per minute heating/cooling rate with an hour hold between each heating/cooling cycle) of the solution for a period of time (e.g., about a day); and 7) equilibrating the solution to a temperature (e.g., 20° C.) for a period of time (e.g., for at least one hour); and 8) isolating solids from the solution; and 9) air-drying the solids for a period of time (e.g., one hour) followed by drying the solids in a vacuum oven at a temperature (e.g., 40° C.) for a period of time (e.g., 5 hours) to yield HBr Salt Form A of Compound 7. In certain embodiments, the solution is evaporated under reduced pressure in a centrifuge evaporator. In certain other embodiments, the solution is evaporated under a slow bleed of inert gas such as nitrogen or argon gas.

In certain embodiments, provided herein are methods for making HBr Salt Form A comprising 1) combining Compound 1 (e.g., about 101.5 mg) with isopropanol (e.g., about 1.25 mL) and HBr (e.g., about 1.0 equivalent of a 5 M solution in water); 2) heating the resulting mixture to a temperature (e.g., about 40° C.) for a period of time (e.g., about one hour); 3) adding seeds of crystalline HBr salt of Compound 1 (e.g., about 1 mg) to the solution; 4) cycling the temperature (e.g., between about 5° C. and about 40° C.; 1° C. per minute heating/cooling rate with an hour hold between each heating/cooling cycle) of the solution for a period of time (e.g., about two days); 5) isolating solids from the solution through vacuum filtration; 6) air-drying the solids for a period of time (e.g., 90 minutes) followed by drying the solids in a vacuum oven at a temperature (e.g., 40° C.) for a period of time (e.g., 5 hours) to yield HBr Salt Form A of Compound 7.

Figure 49:
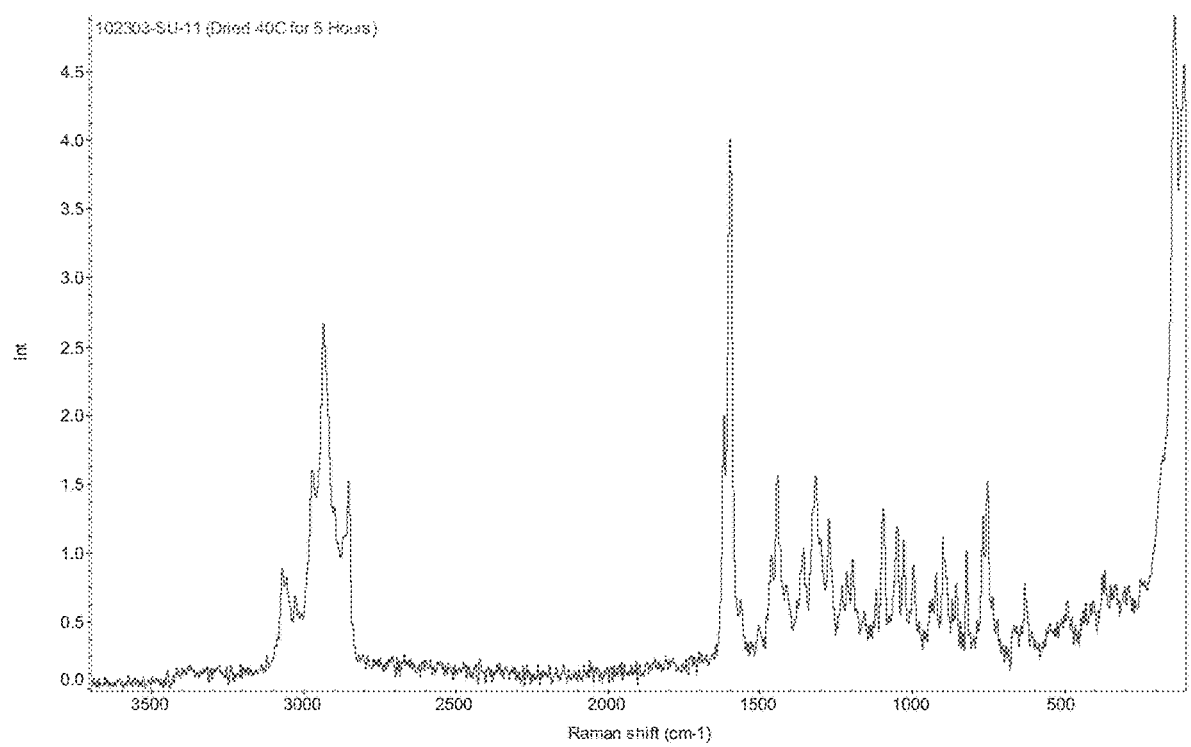
FIG. 49 depicts an FT-Raman spectrum of HBr Salt Form A of Compound 7.

In one embodiment, provided herein is HBr Salt Form A having an FT-Raman Spectrum as depicted in FIG. 49.

Figure 50:
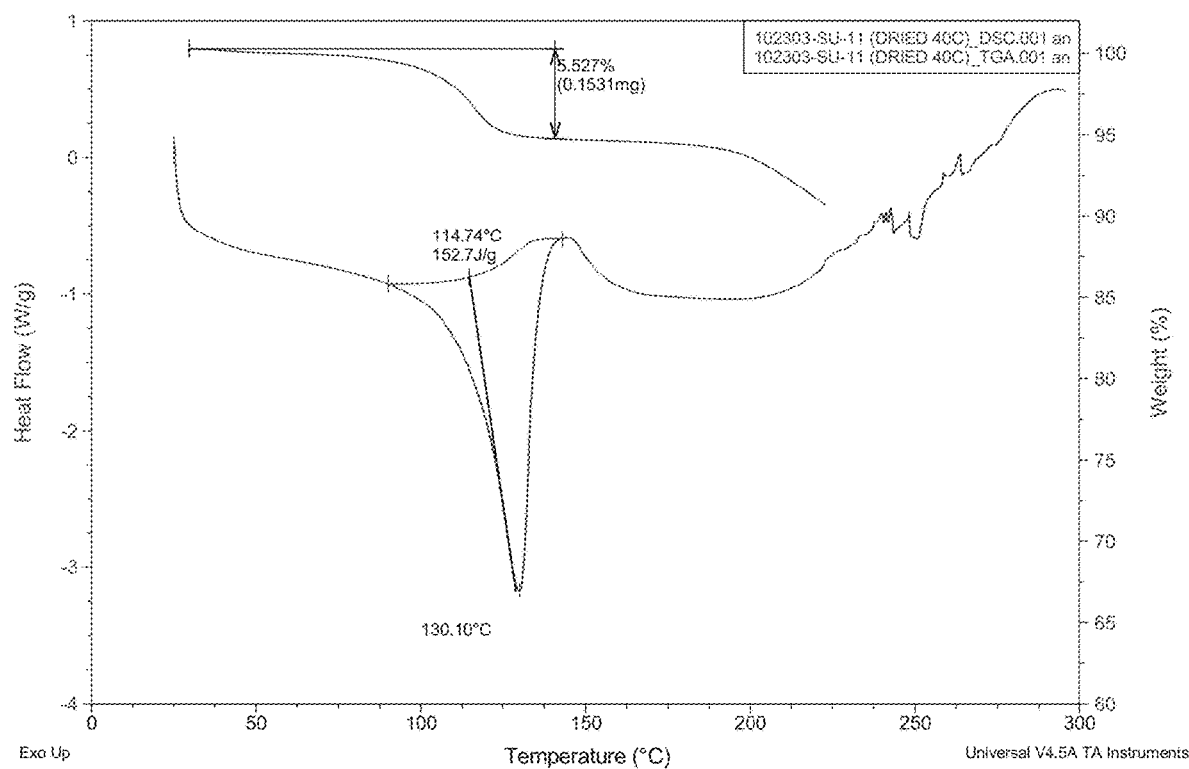
FIG. 50 depicts differential scanning calorimetry/thermal gravimetric analysis of HBr Salt Form A of Compound 7.

In one embodiment, provided herein is a solid form of Compound 7, e.g., HBr Salt Form A of Compound 7, having a DSC thermogram substantially as depicted in FIG. 50 comprising an endotherm with an onset temperature at 114.7° C.

In one embodiment, provided herein is a solid form of Compound 7, e.g., HBr Salt Form A of Compound 7, having a TGA thermogram corresponding substantially to the representative TGA thermogram as depicted in FIG. 50. In certain embodiments, the crystalline form exhibits a TGA thermogram comprising a total mass loss of approximately 5.5% of the total mass of the sample when heated from approximately 25° C. to approximately 141° C.

Figure 48:
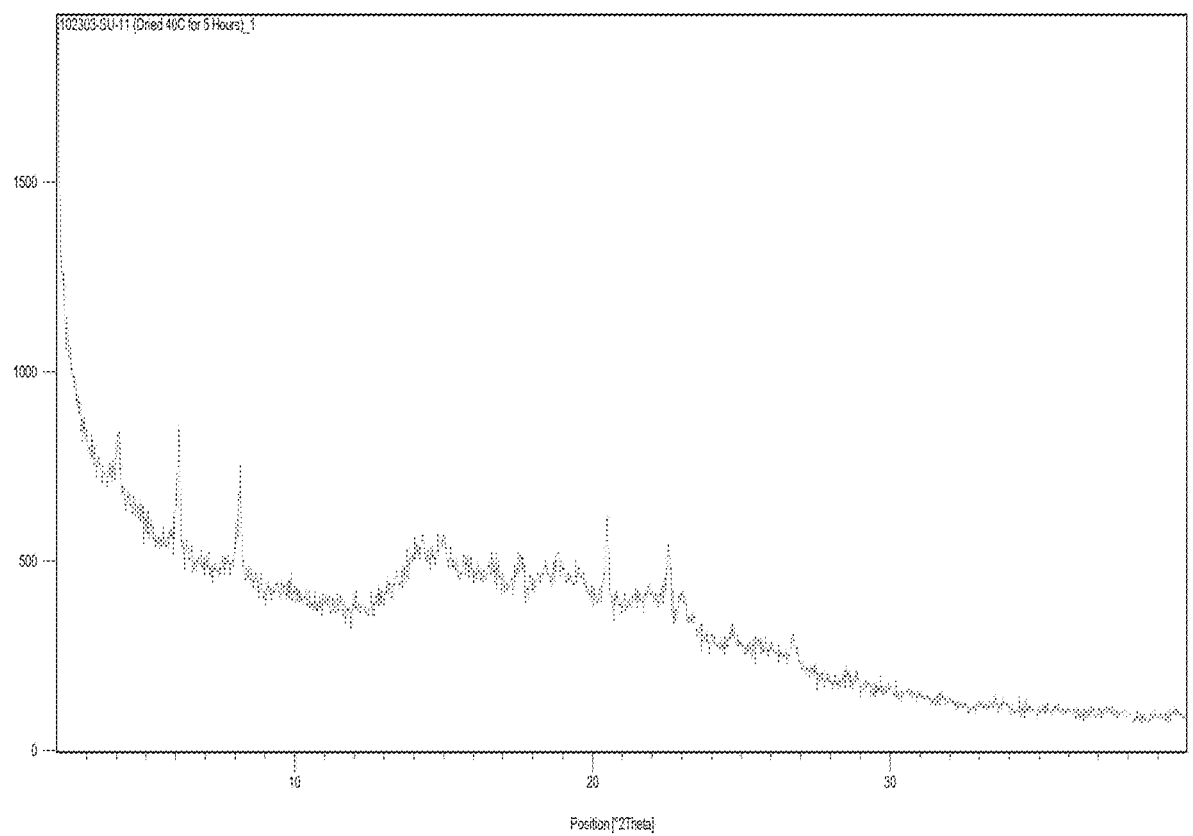
FIG. 48 depicts a PXRD pattern of HBr Salt Form A of Compound 7.

In certain embodiments, a solid form of Compound 7 provided herein, e.g., HBr Salt Form A, is substantially crystalline, as indicated by, e.g., X-ray powder diffraction measurements. In one embodiment, provided herein is a solid form of Compound 7 having an X-ray powder diffraction pattern (XRPD) substantially as shown in FIG. 48 (e.g., HBr Salt Form A). In one embodiment, a solid form of Compound 7 provided herein, e.g., HBr Salt Form A, has one or more characteristic X-ray powder diffraction peaks at approximately 4.1, 6.1, 8.2, 20.5, 22.6, or 26.8° 2θ (±0.2° 2θ) or (±0.1° 2θ) as depicted in FIG. 48. In a specific embodiment, a solid form of Compound 7 provided herein, e.g., HBr Salt Form A, has one, two, three, four, or five characteristic X-ray powder diffraction peaks at approximately 4.1, 6.1, 8.2, 20.5, or 22.6° 2θ (±0.2° 2θ). In certain embodiments, the solid form of Compound 7 is HBr Salt Form A.

In certain embodiments, HBr Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, HBr Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A, or Tosylate Salt Form B. In further embodiments, HBr Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, HBr Salt Form A is substantially pure. In certain embodiments, the substantially pure HBr Salt Form A is substantially free of other solid forms, including but not limited to amorphous solid. In certain embodiments, the purity of the substantially pure HBr Salt Form A is no less than about 95%, no less than about 96%, no less than about 97%, no less than about 98%, no less than about 98.5%, no less than about 99%, no less than about 99.5%, or no less than about 99.8%.

(ii) HBr Salt Form B

In one embodiment, provided herein is a solid form of Compound 7. In one embodiment, the solid form of Compound 7 is HBr Salt Form B. In one embodiment, HBr Salt Form B is crystalline. In one embodiment, HBr Salt Form B is poorly crystalline. In one embodiment, HBr Salt Form B is hydrated.

In certain embodiments, provided herein are methods for making HBr Salt Form B, comprising 1) dispensing a solvent (e.g., about 250 μL) into a vial containing an amount of Compound 1 (e.g., about 20 mg); 2) adding a stoichiometric amount (e.g., 1.0 equivalent) a 5 M solution of HBr in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent, followed by temperature cycling (e.g., between about 5° C. and about 40° C.; 1° C. per minute heating/cooling rate with an hour hold between each heating/cooling cycle) of the solution for a period of time (e.g., about a day); 7) adding hexanes (e.g., 1:3 v/v solvent to hexanes ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) equilibrating the solution to a temperature (e.g., 20° C.) and evaporating the solvent slowly at room temperature to yield HBr Salt Form B of Compound 7. In certain embodiments, the solvent is methyl tert-butyl ether or methyl isobutyl ketone. In certain embodiments, the solution is evaporated under reduced pressure in a centrifuge evaporator. In certain other embodiments, the solution is evaporated under a slow bleed of inert gas such as nitrogen or argon gas.

Figure 53:
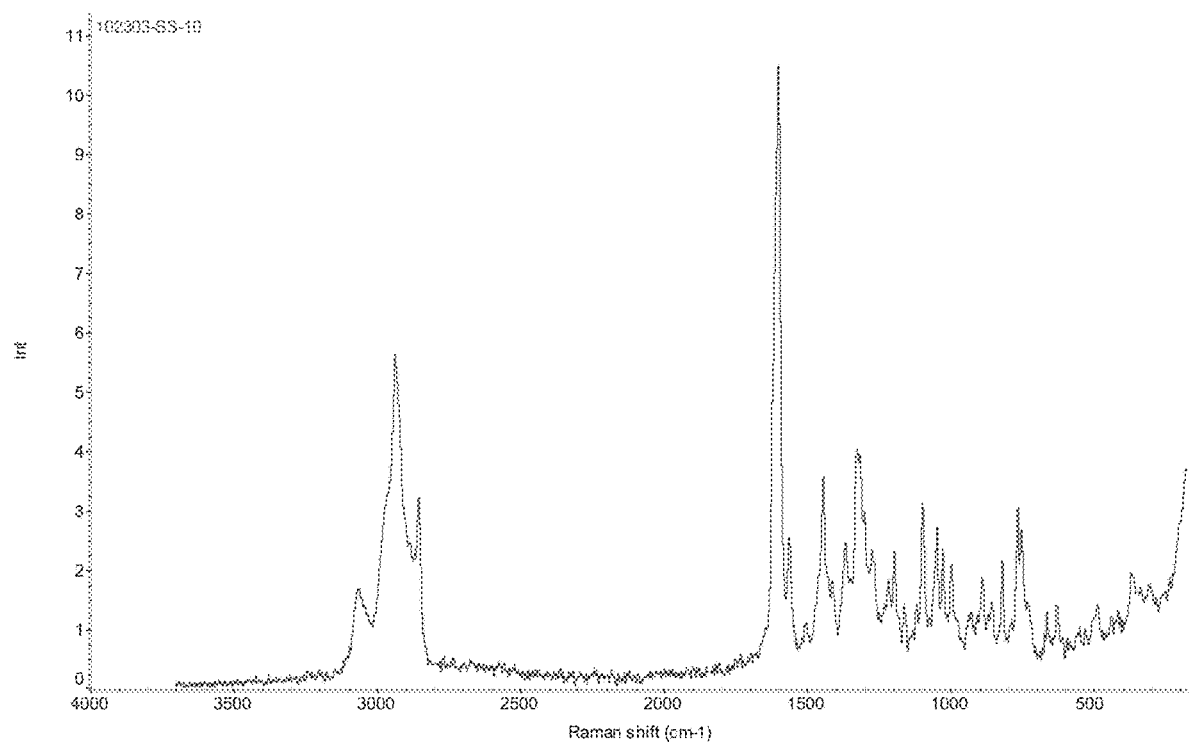
FIG. 53 depicts an FT-Raman spectrum of HBr Salt Form B of Compound 7.

In one embodiment, provided herein is HBr Salt Form B having an FT-Raman Spectrum as depicted in FIG. 53

Figure 54:
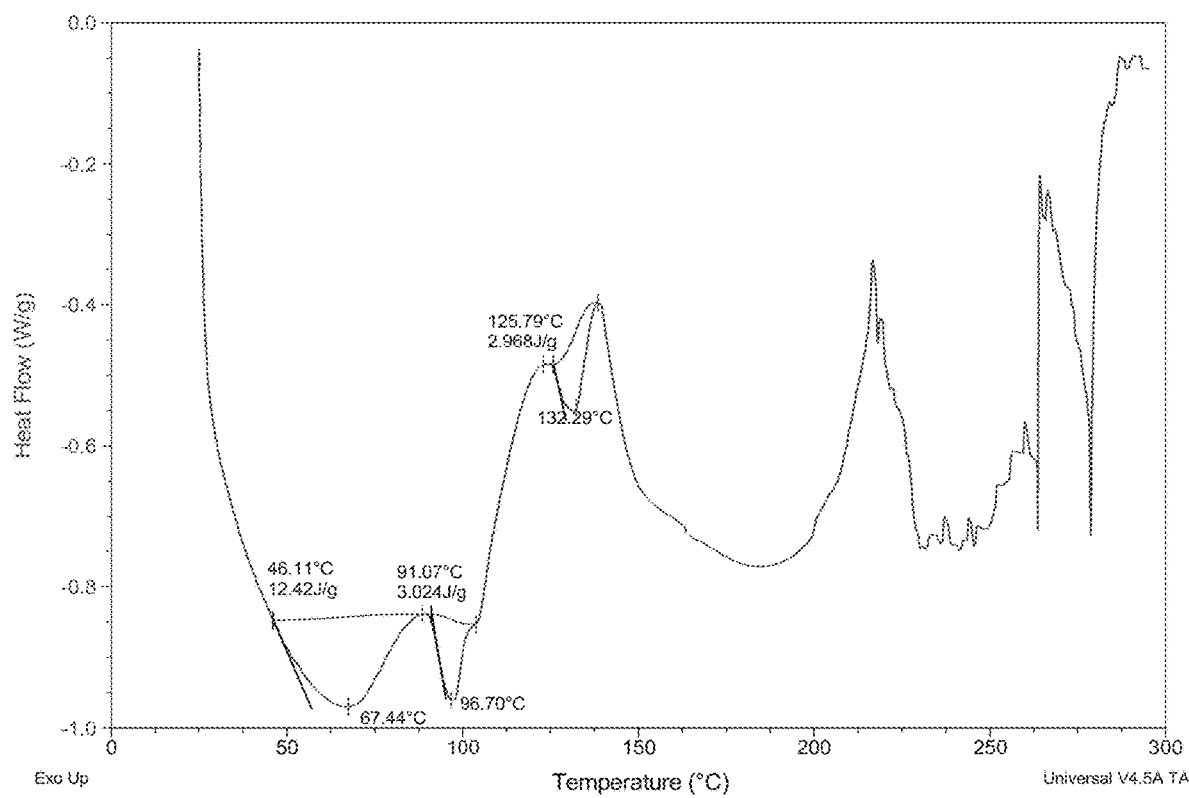
FIG. 54 depicts differential scanning calorimetry of HBr Salt Form B of Compound 7.

In one embodiment, provided herein is a solid form of Compound 7, e.g., HBr Salt Form B of Compound 7, having a DSC thermogram substantially as depicted in FIG. 54 comprising multiple endotherms with onset temperatures at 46.1° C., 91.1° C., and 125.8° C.

Figure 52:
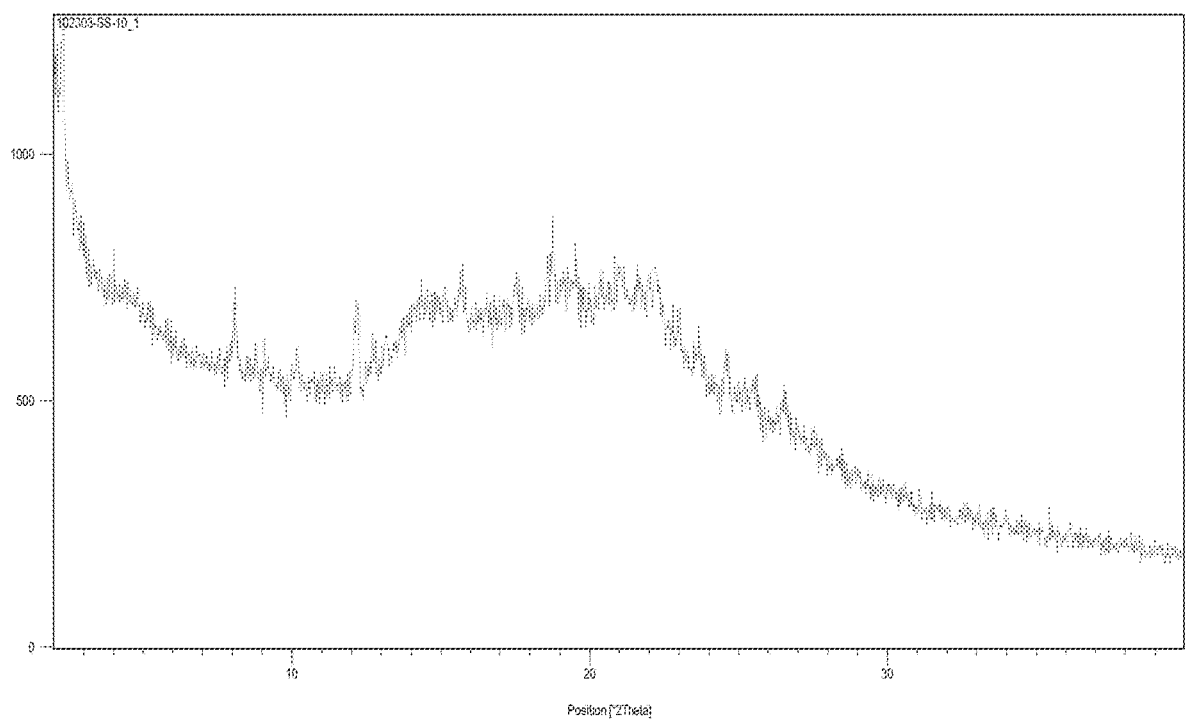
FIG. 52 depicts a PXRD pattern of HBr Salt Form B of Compound 7.

In certain embodiments, a solid form of Compound 7 provided herein, e.g., HBr Salt Form B, is substantially crystalline, as indicated by, e.g., X-ray powder diffraction measurements. In one embodiment, provided herein is a solid form of Compound 7 having an X-ray powder diffraction pattern (XRPD) substantially as shown in FIG. 52 (e.g., HBr Salt Form B). In one embodiment, a solid form of Compound 7 provided herein, e.g., HBr Salt Form B, has one or more characteristic X-ray powder diffraction peaks at approximately 2.3, 8.1, 10.2, 12.2, 15.7, 17.5, 18.7, 19.5, 23.6, or 24.6° 2θ (±0.2° 2θ) or (±0.1° 2θ) as depicted in FIG. 52. In a specific embodiment, a solid form of Compound 7 provided herein, e.g., HBr Salt Form B, has one, two, three, four, or five characteristic X-ray powder diffraction peaks at approximately 2.3, 8.1, 12.2, 15.7, or 18.7° 2θ (±0.2° 2θ). In certain embodiments, the solid form of Compound 7 is HBr Salt Form B.

In certain embodiments, HBr Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, HBr Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A, or Tosylate Salt Form B. In further embodiments, HBr Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, HBr Salt Form B is substantially pure. In certain embodiments, the substantially pure HBr Salt Form B is substantially free of other solid forms, including but not limited to amorphous solid. In certain embodiments, the purity of the substantially pure HBr Salt Form B is no less than about 95%, no less than about 96%, no less than about 97%, no less than about 98%, no less than about 98.5%, no less than about 99%, no less than about 99.5%, or no less than about 99.8%.

(h) Solid Forms of Compound 8

In certain embodiments, provided herein is Compound 8.

(i) Maleate Salt Form A

In one embodiment, provided herein is a solid form of Compound 8. In one embodiment, the solid form of Compound 8 is Maleate Salt Form A. In one embodiment, Maleate Salt Form A is crystalline. In one embodiment, Maleate Salt Form A is hydrated and solvated by methyl tert-butyl ether.

In certain embodiments, provided herein are methods for making Maleate Salt Form A, comprising 1) dispensing methyl tert-butyl ether (e.g., about 250 µL) into a vial containing an amount of Compound 1 (e.g., about 20 mg); 2) adding a stoichiometric amount (e.g., 1.0 equivalent) a 3 M solution of maleic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in methyl tert-butyl ether, followed by temperature cycling (e.g., between about 5° C. and about 40° C.; 1° C. per minute heating/cooling rate with an hour hold between each heating/cooling cycle) of the solution for a period of time (e.g., about a day); 7) equilibrating the solution to a temperature (e.g., 20° C.) for a period of time (e.g., for at least one hour); 8) isolating solids from the solution; and 9) air-drying the solids for a period of time (e.g., one hour) followed by drying the solids in a vacuum oven at a temperature (e.g., 40° C.) for a period of time (e.g., 5 hours) to yield Maleate Salt Form A of Compound 8. In certain embodiments, the solution is evaporated under reduced pressure in a centrifuge evaporator. In certain other embodiments, the solution is evaporated under a slow bleed of inert gas such as nitrogen or argon gas.

Figure 57:
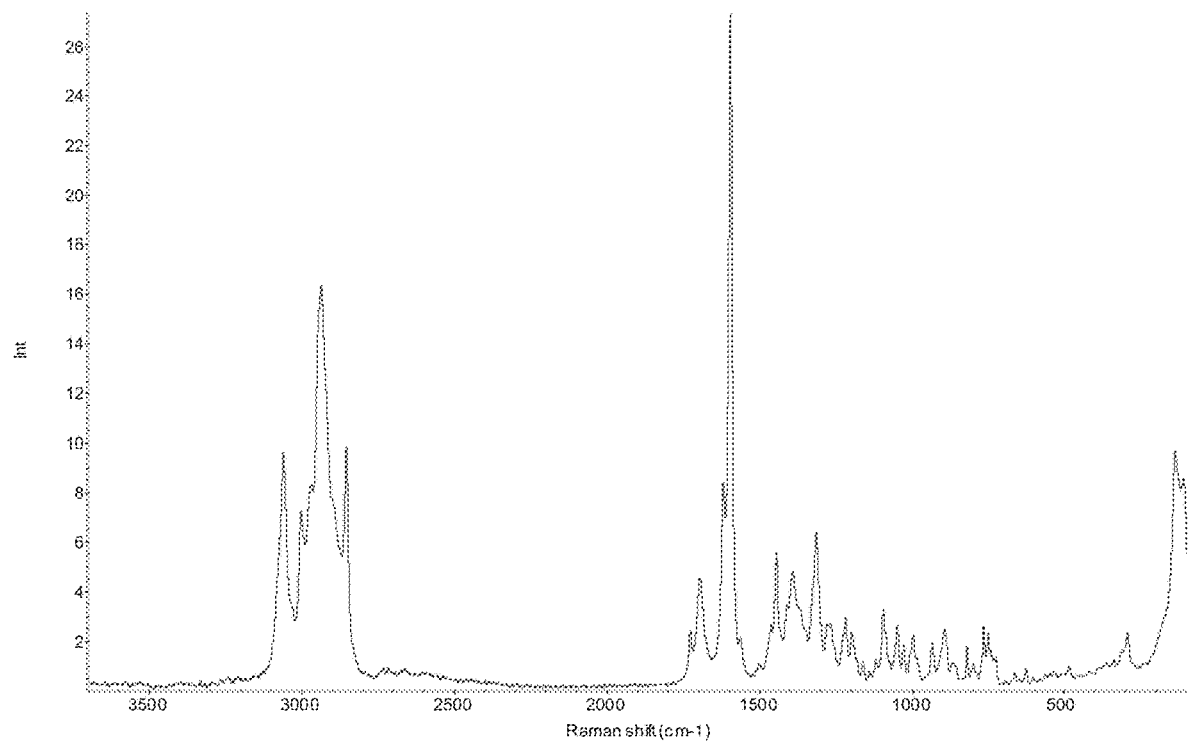
FIG. 57 depicts an FT-Raman spectrum of Maleate Salt Form A of Compound 8.

In one embodiment, provided herein is Maleate Salt Form A having an FT-Raman Spectra as depicted in FIG. 57.

Figure 58:
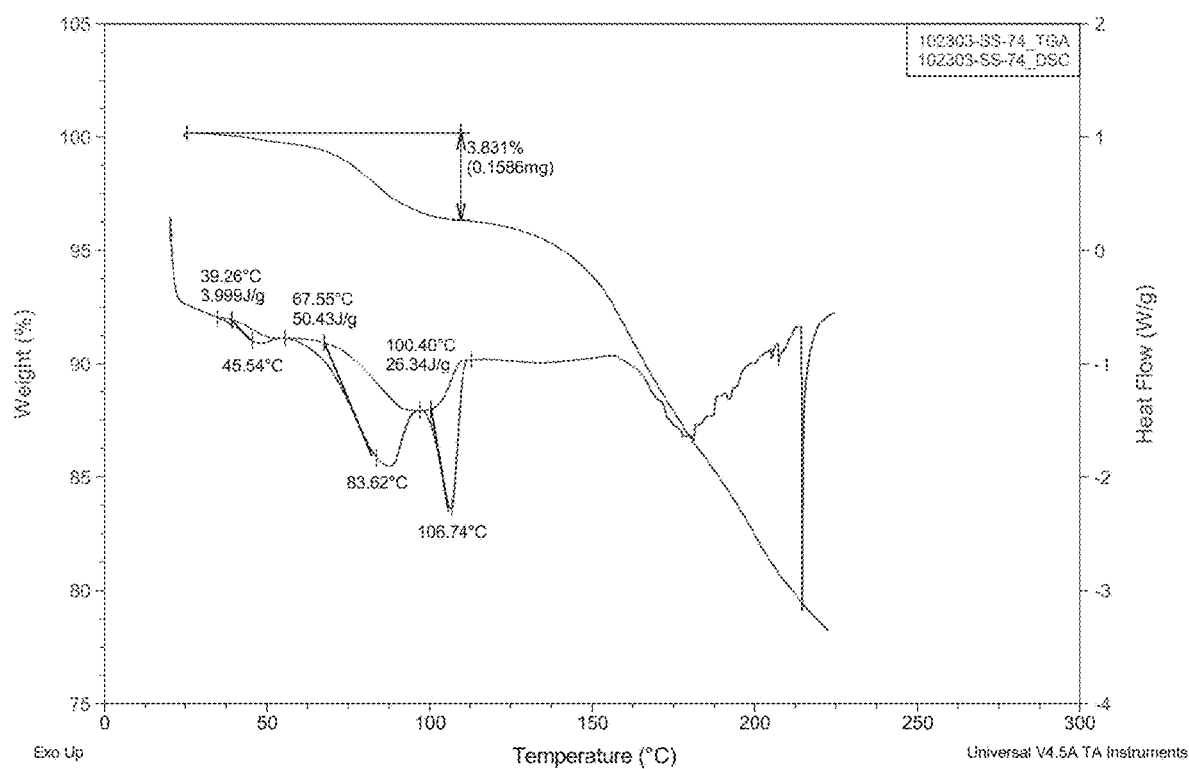
FIG. 58 depicts differential scanning calorimetry/thermal gravimetric analysis of Maleate Salt Form A of Compound 8.

In one embodiment, provided herein is a solid form of Compound 8, e.g., Maleate Salt Form A of Compound 8, having a DSC thermogram substantially as depicted in FIG. 58 comprising multiple endotherms with onset temperatures at 39.3° C., 67.6° C., and 100.4° C.

In one embodiment, provided herein is a solid form of Compound 8, e.g., Maleate Salt Form A of Compound 8, having a TGA thermogram corresponding substantially to the representative TGA thermogram as depicted in FIG. 58. In certain embodiments, the crystalline form exhibits a TGA thermogram comprising a total mass loss of approximately 3.8% of the total mass of the sample when heated from approximately 25° C. to approximately 110° C.

Figure 56:
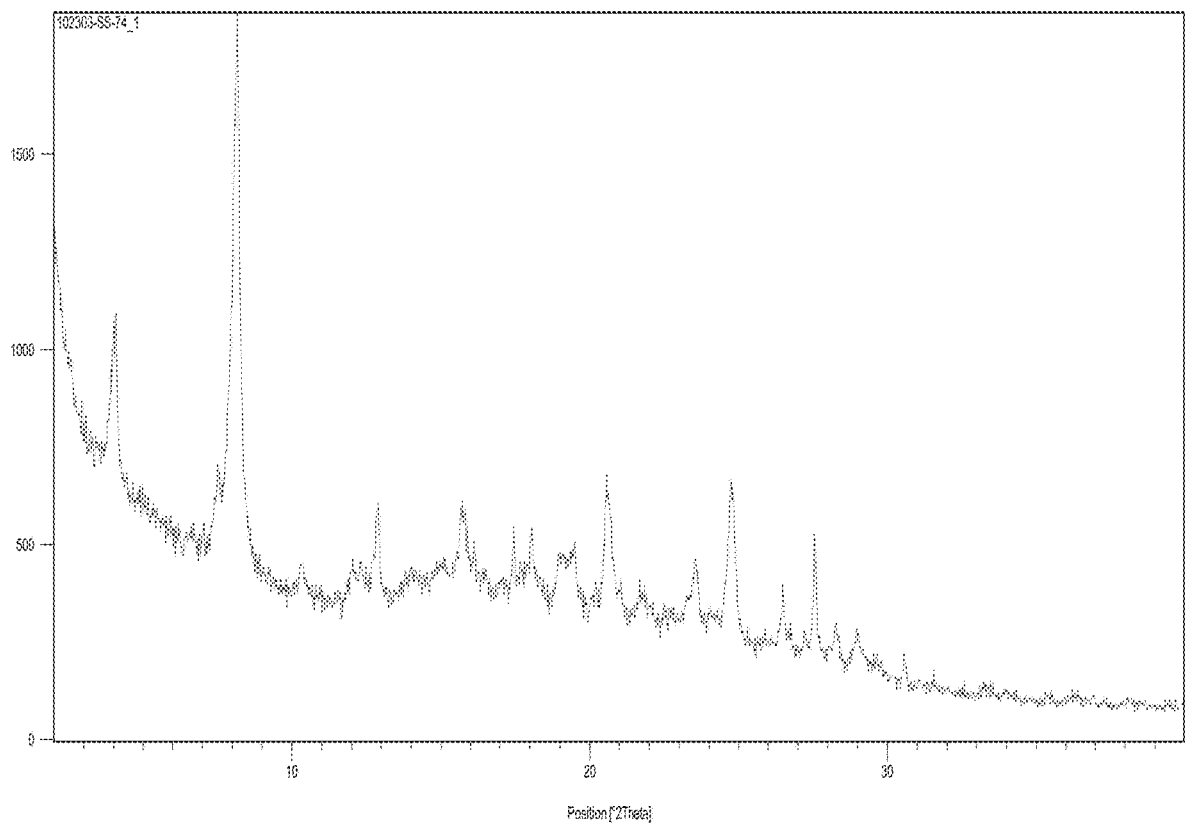
FIG. 56 depicts a PXRD pattern of Maleate Salt Form A of Compound 8.

In certain embodiments, a solid form of Compound 8 provided herein, e.g., Maleate Salt Form A, is substantially crystalline, as indicated by, e.g., X-ray powder diffraction measurements. In one embodiment, provided herein is a solid form of Compound 8 having an X-ray powder diffraction pattern (XRPD) substantially as shown in FIG. 56 (e.g., Maleate Salt Form A). In one embodiment, a solid form of Compound 8 provided herein, e.g., Maleate Salt Form A, has one or more characteristic X-ray powder diffraction peaks at approximately 4.1, 7.5, 8.2, 10.4, 12.0, 12.9, 15.7, 17.5, 18.1, 19.0, 19.5, 20.6, 21.7, 23.6, 24.8, 26.5, 27.6, 28.3, 29.0, or 30.6° 2θ (±0.2° 2θ) or (±0.1° 2θ) as depicted in FIG. 56. In a specific embodiment, a solid form of Compound 8 provided herein, e.g., Maleate Salt Form A, has one, two, three, four, or five characteristic X-ray powder diffraction peaks at approximately 4.1, 8.2, 12.9, 20.6, or 24.8° 2θ (±0.2° 2θ).

In certain embodiments, Maleate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Maleate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Maleate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Maleate Salt Form A is substantially pure. In certain embodiments, the substantially pure Maleate Salt Form A is substantially free of other solid forms, including but not limited to amorphous solid. In certain embodiments, the purity of the substantially pure Maleate Salt Form A is no less than about 95%, no less than about 96%, no less than about 97%, no less than about 98%, no less than about 98.5%, no less than about 99%, no less than about 99.5%, or no less than about 99.8%.

(ii) Maleate Salt Form B

In one embodiment, the solid form of Compound 8 is Maleate Salt Form B. In one embodiment, Maleate Salt Form B is crystalline. In one embodiment, Maleate Salt Form B is hydrated.

In certain embodiments, provided herein are methods for making Maleate Salt Form B, comprising 1) dispensing methyl isobutyl ketone (e.g., about 250 µL) into a vial containing an amount of Compound 1 (e.g., about 20 mg); 2) adding a stoichiometric amount (e.g., 1.0 equivalent) a 3 M solution of maleic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in methyl isobutyl ketone, followed by temperature cycling (e.g., between about 5° C. and about 40° C.; 1° C. per minute heating/ cooling rate with an hour hold between each heating/cooling cycle) of the solution for a period of time (e.g., about a day), and equilibrating at 20° C. at the end of temperature cycling for a period of time (e.g., for at least one hour) 7) adding hexane (e.g., 1:3 v/v methyl isobutyl ketone to hexanes ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) isolating solids from the solution; and 11) air-drying the solids for a period of time (e.g., one hour) followed by drying the solids in a vacuum oven at a temperature (e.g., 40° C.) for a period of time (e.g., 5 hours) to yield Maleate Salt Form B of Compound 8. In certain embodiments, the solution is evaporated under reduced pressure in a centrifuge evaporator. In certain other embodiments, the solution is evaporated under a slow bleed of inert gas such as nitrogen or argon gas.

Figure 61:
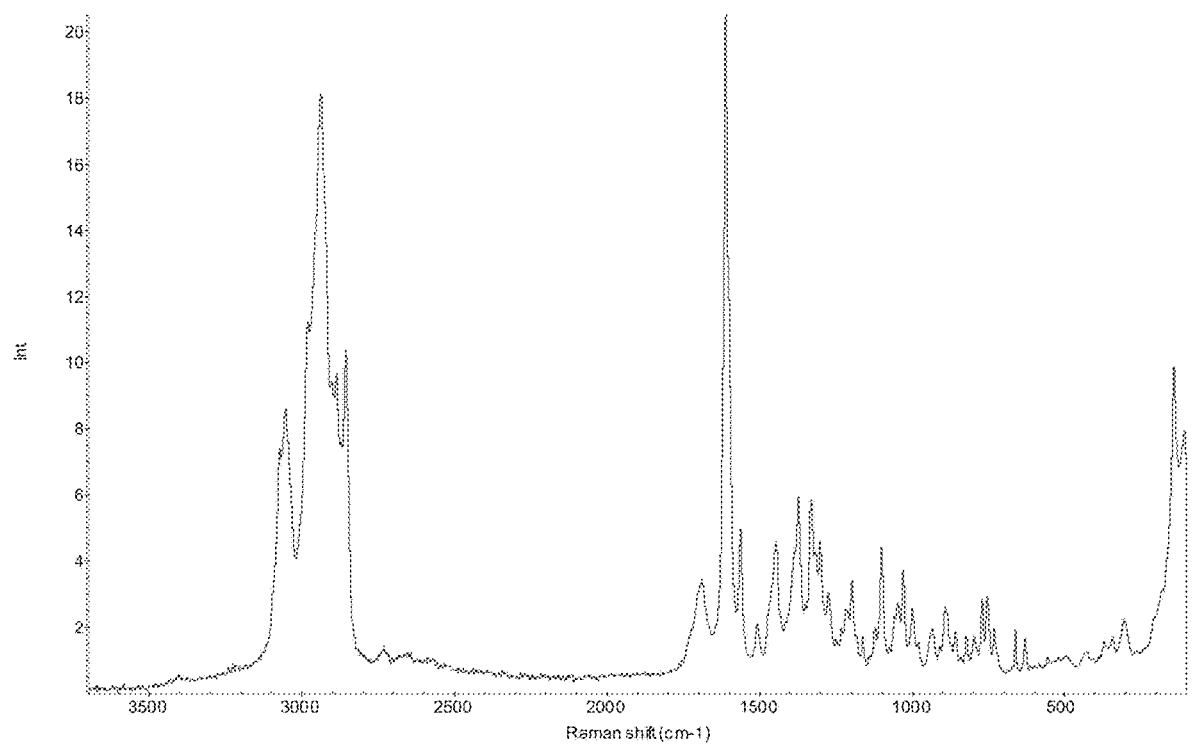
FIG. 61 depicts an FT-Raman spectrum of Maleate Salt Form B of Compound 8.

In one embodiment, provided herein is Maleate Salt Form B having an FT-Raman Spectrum as depicted in FIG. 61.

Figure 62:
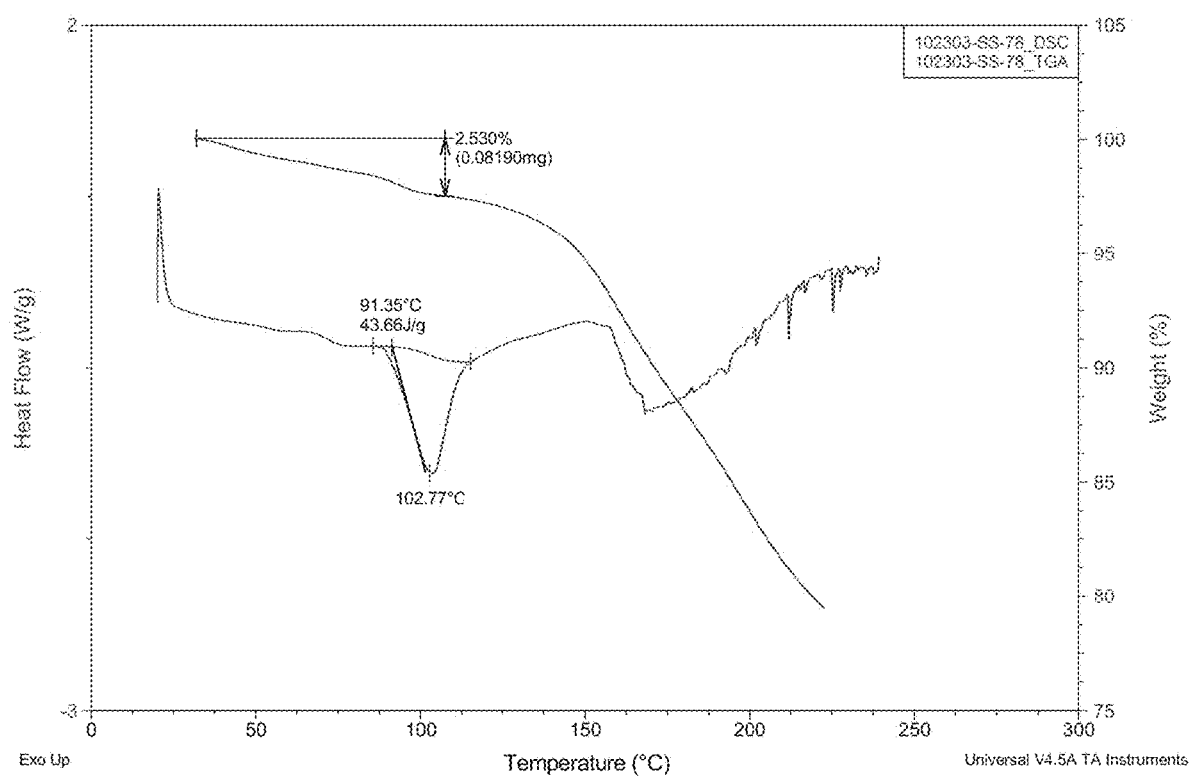
FIG. 62 depicts differential scanning calorimetry/thermal gravimetric analysis of Maleate Salt Form B of Compound 8.

In one embodiment, provided herein is a solid form of Compound 8, e.g., Maleate Salt Form B of Compound 8, having a DSC thermogram substantially as depicted in FIG. 62 comprising an endotherm with an onset temperature at 91.4° C.

In one embodiment, provided herein is a solid form of Compound 8, e.g., Maleate Salt Form B of Compound 8, having a TGA thermogram corresponding substantially to the representative TGA thermogram as depicted in FIG. 62. In certain embodiments, the crystalline form exhibits a TGA thermogram comprising a total mass loss of approximately 2.5% of the total mass of the sample when heated from approximately 30° C. to approximately 110° C.

Figure 60:
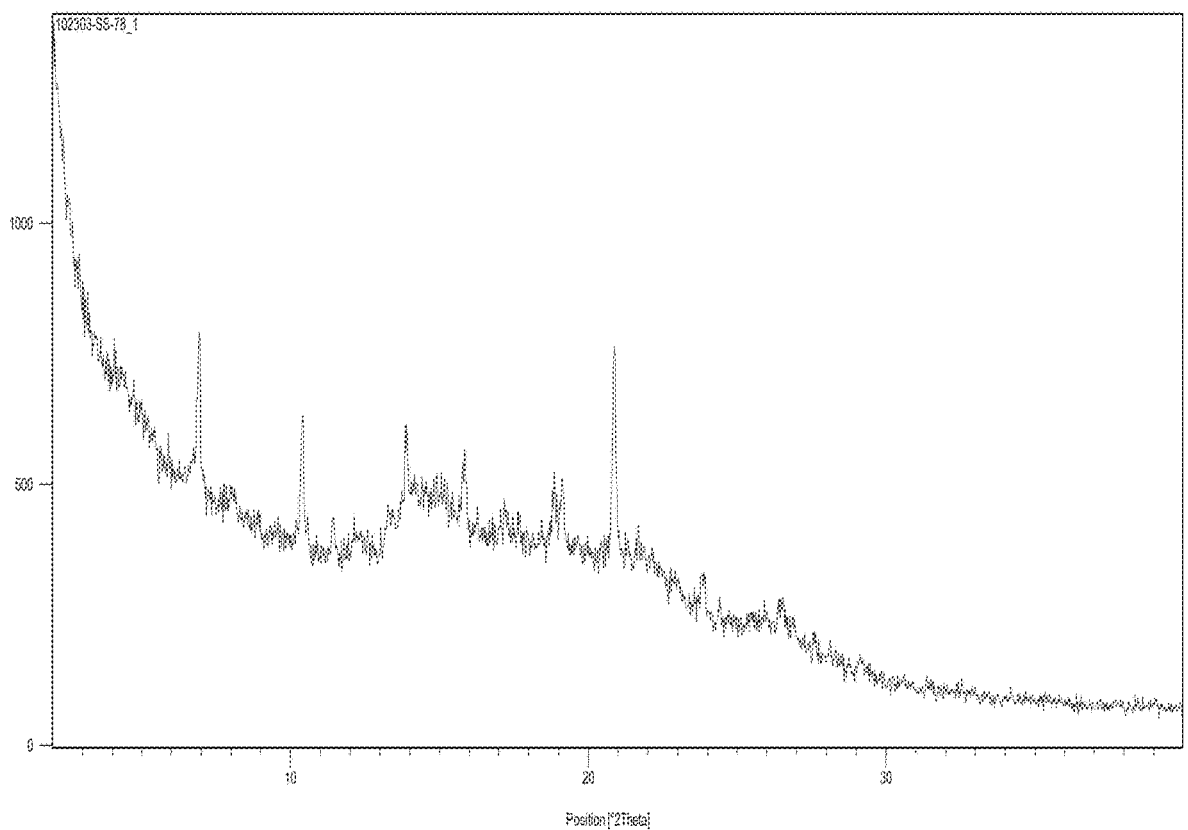
FIG. 60 depicts a PXRD pattern of Maleate Salt Form B of Compound 8.

In certain embodiments, a solid form of Compound 8 provided herein, e.g., Maleate Salt Form B, is substantially crystalline, as indicated by, e.g., X-ray powder diffraction measurements. In one embodiment, provided herein is a solid form of Compound 8 having an X-ray powder diffraction pattern (XRPD) substantially as shown in FIG. 60 (e.g., Maleate Salt Form B). In one embodiment, a solid form of Compound 8 provided herein, e.g., Maleate Salt Form B, has one or more characteristic X-ray powder diffraction peaks at approximately 6.9, 10.4, 11.4, 13.9, 15.8, 18.9, 19.1, 20.9, or 23.9° 2θ (±0.2° 2θ) or (±0.1° 2θ) as depicted in FIG. 60. In a specific embodiment, a solid form of Compound 8 provided herein, e.g., Maleate Salt Form B, has one, two, three, four, or five characteristic X-ray powder diffraction peaks at approximately 6.9, 10.4, 13.9, 18.9 or 20.9° 2θ (±0.2° 2θ).

In certain embodiments, Maleate Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Maleate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Maleate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Maleate Salt Form B is substantially pure. In certain embodiments, the substantially pure Maleate Salt Form B is substantially free of other solid forms, including but not limited to amorphous solid. In certain embodiments, the purity of the substantially pure Maleate Salt Form B is no less than about 95%, no less than about 96%, no less than about 97%, no less than about 98%, no less than about 98.5%, no less than about 99%, no less than about 99.5%, or no less than about 99.8%.

(iii) Maleate Salt Form C

In one embodiment, the solid form of Compound 8 is Maleate Salt Form C. In one embodiment, Maleate Salt Form C is crystalline.

In certain embodiments, provided herein are methods for making Maleate Salt Form C, comprising 1) dispensing isopropyl acetate (e.g., about 250 µL) into a vial containing an amount of Compound 1 (e.g., about 20 mg); 2) adding a stoichiometric amount (e.g., 1.0 equivalent) a 3 M solution of maleic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in isopropyl acetate, followed by temperature cycling (e.g., between about 5° C. and about 40° C.; 1° C. per minute heating/cooling rate with an hour hold between each heating/cooling cycle) of the solution for a period of time (e.g., about a day), and equilibrating the solution to a temperature (e.g., 20° C.) for a period of time (e.g., about one hour) at the end of temperature cycling; 7) isolating solids from the solution; and 8) air-drying the solids for a period of time (e.g., one hour) followed by drying the solids in a vacuum oven at a temperature (e.g., 40° C.) for a period of time (e.g., 5 hours) to yield Maleate Salt Form C of Compound 8. In certain embodiments, the solution is evaporated under reduced pressure in a centrifuge evaporator. In certain other embodiments, the solution is evaporated under a slow bleed of inert gas such as nitrogen or argon gas.

Figure 65:
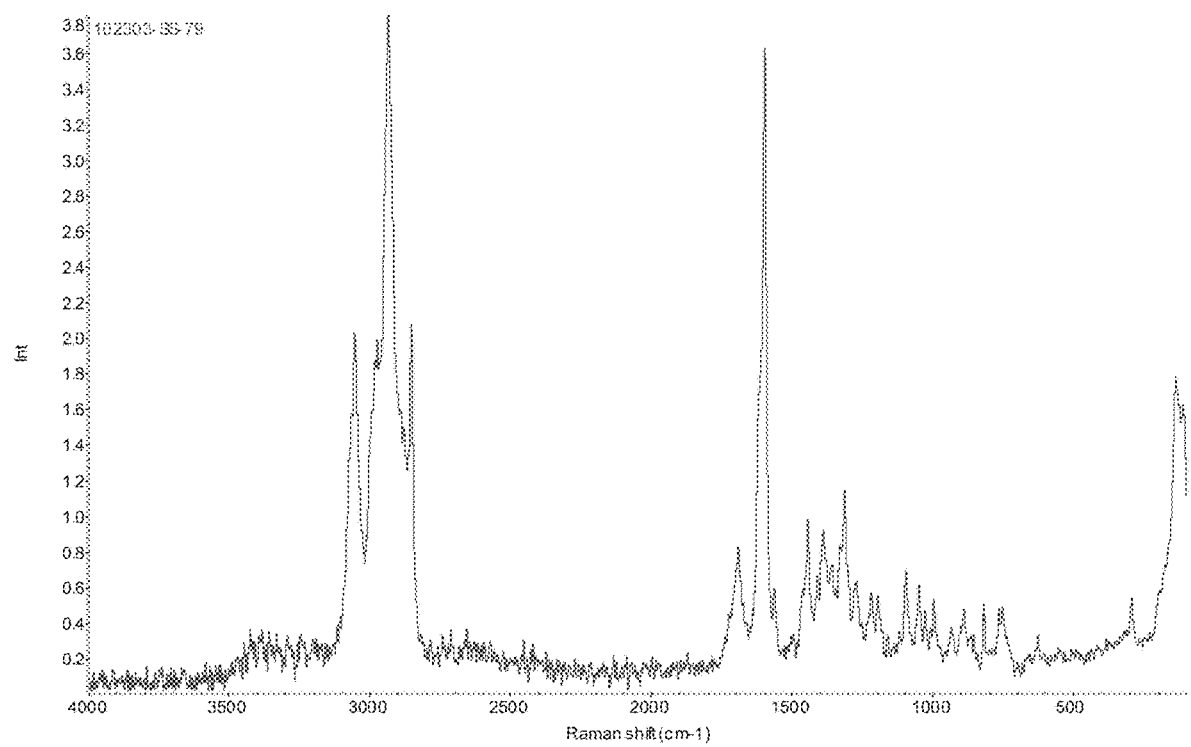
FIG. 65 depicts an FT-Raman spectrum of Maleate Salt Form C of Compound 8.

In one embodiment, provided herein is Maleate Salt Form C having an FT-Raman Spectrum as depicted in FIG. 65.

Figure 66:
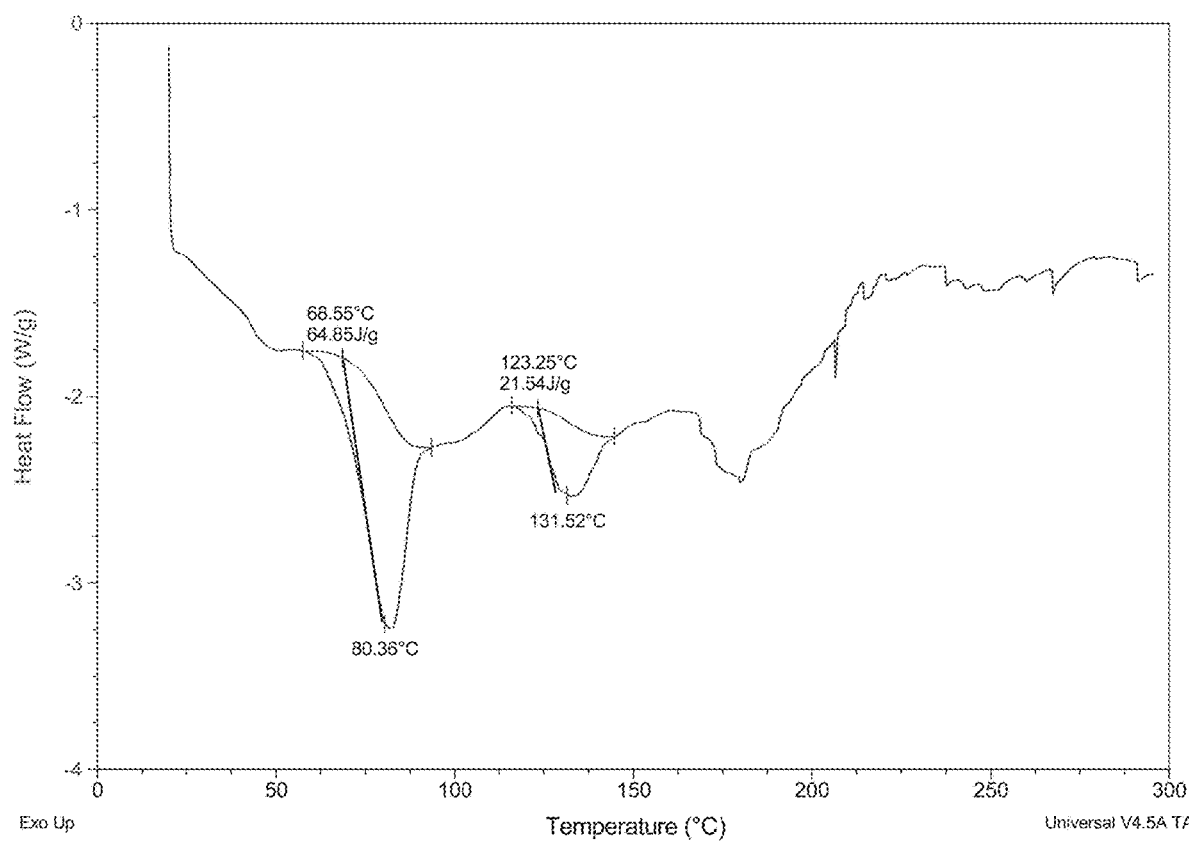
FIG. 66 depicts differential scanning calorimetry/thermal gravimetric analysis of Maleate Salt Form C of Compound 8.

In one embodiment, provided herein is a solid form of Compound 8, e.g., Maleate Salt Form C of Compound 8, having a DSC thermogram substantially as depicted in FIG. 66 comprising multiple endotherms with onset temperatures at 68.6° C. and 123.3° C., respectively.

Figure 64:
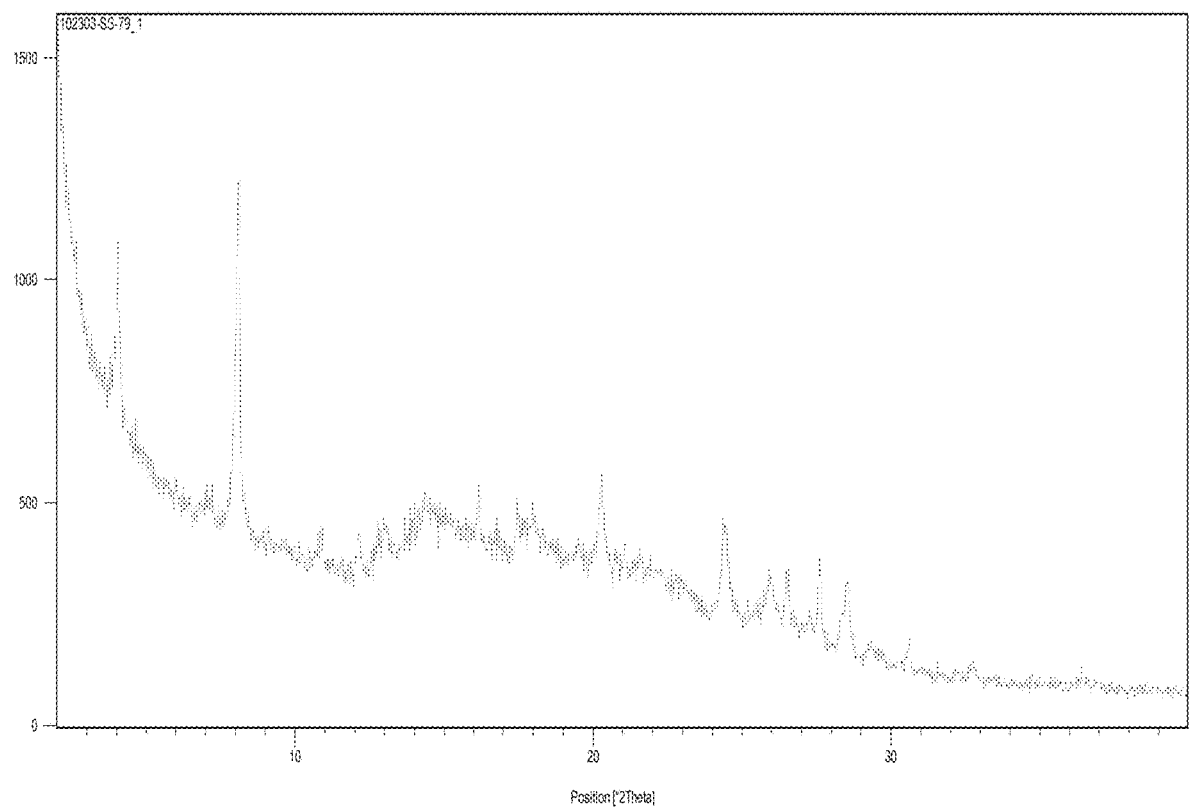
FIG. 64 depicts a PXRD pattern of Maleate Salt Form C of Compound 8.

In certain embodiments, a solid form of Compound 8 provided herein, e.g., Maleate Salt Form C, is substantially crystalline, as indicated by, e.g., X-ray powder diffraction measurements. In one embodiment, provided herein is a solid form of Compound 8 having an X-ray powder diffraction pattern (XRPD) substantially as shown in FIG. 64 (e.g., Maleate Salt Form C). In one embodiment, a solid form of Compound 8 provided herein, e.g., Maleate Salt Form C, has one or more characteristic X-ray powder diffraction peaks at approximately 4.1, 8.1, 10.9, 12.1, 16.2, 20.3, 24.4, 26.0, 26.5, 27.6, 28.6, or 30.6° 2θ (±0.2° 2θ) or (±0.1° 2θ) as depicted in FIG. 64. In a specific embodiment, a solid form of Compound 8 provided herein, e.g., Maleate Salt Form C, has one, two, three, four, or five characteristic X-ray powder diffraction peaks at approximately 4.1, 8.1, 20.3, 24.4, or 27.6° 2θ (±0.2° 2θ).

In certain embodiments, Maleate Salt Form C is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Maleate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Maleate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Maleate Salt Form C is substantially pure. In certain embodiments, the substantially pure Maleate Salt Form C is substantially free of other solid forms, including but not limited to amorphous solid. In certain embodiments, the purity of the substantially pure Maleate Salt Form C is no less than about 95%, no less than about 96%, no less than about 97%, no less than about 98%, no less than about 98.5%, no less than about 99%, no less than about 99.5%, or no less than about 99.8%.

(iv) Maleate Salt Form D

In one embodiment, the solid form of Compound 8 is Maleate Salt Form D. In one embodiment, Maleate Salt Form D is crystalline.

In one embodiment, Maleate Salt Form D is a hydrate.

In certain embodiments, provided herein are methods for making Maleate Salt Form D comprising 1) combining Compound 1 (e.g., about 100 mg) with methyl isobutyl ketone (e.g., about 1.25 mL) and maleic acid (e.g., about 1.0 equivalent of a 3 M solution in water); 2) heating the resulting mixture to a temperature (e.g., about 40° C.) for a period of time (e.g., about one hour); 3) evaporating the solution to dryness under reduced pressure and dissolving the solid in methyl isobutyl ketone (e.g., about 1.25 mL); 4) adding seeds of crystalline maleate salt of Compound 1 (e.g., about 1 mg) to the solution; 5) cycling the temperature (e.g., between about 5° C. and about 40° C.; 1° C. per minute heating/cooling rate with an hour hold between each heating/cooling cycle) of the solution for a period of time (e.g., about two days); 5) isolating solids from the solution through vacuum filtration; 6) air-drying the solids for one hour and drying in a vacuum oven at a temperature (e.g., 40° C.) for a period of time (e.g., 5 hours) to isolate Maleate Salt Form D of Compound 8. In certain embodiments, the solution is evaporated under reduced pressure in a centrifuge evaporator.

In certain embodiments, provided herein are methods for making Maleate Salt Form D comprising 1) combining Compound 1 (e.g., about 1.7 g) with methanol (e.g., about 11 mL) and maleic acid (e.g., about 380.36 mg); 2) heating the resulting mixture to a temperature (e.g., about 40° C.) for a period of time (e.g., about one hour); 3) dispensing an aliquot (e.g., about 0.21 mL) to a vial and evaporating the solution to dryness under reduced pressure; 4) dissolving the sample in a solvent or solvent system; 5) cycling the temperature (e.g., between about 5° C. and about 40° C.; 1° C. per minute heating/cooling rate with an hour hold between each heating/cooling cycle) of the solution for a period of time (e.g., overnight); 6) isolating solids from the solution through vacuum filtration to isolate Maleate Salt Form D of Compound 8. In certain embodiments, the solution is evaporated under reduced pressure in a centrifuge evaporator. In certain embodiments, the solvent or solvent system is a 1:9 mixture of 1-propanol alcohol and isopropyl ether. In certain embodiments, the solvent or solvent system is a 1:9 mixture of nitromethane and isopropyl ether. In certain embodiments, the solvent or solvent system is a 1:9 mixture of acetonitrile and isopropyl ether. In certain embodiments, the solvent or solvent system is toluene. In certain embodiments, the solvent or solvent system is dimethyl carbonate. In certain embodiments, the solvent or solvent system is methyl tert-butyl ether. In certain embodiments, the solvent or solvent system is isopropyl acetate. In certain embodiments, the solvent or solvent system is a 1:9 mixture of ethanol and isopropyl ether. In certain embodiments, the solvent or solvent system is a 1:2 mixture of ethyl acetate and cyclohexane. In certain embodiments, the solvent or solvent system is a 1:2 mixture of methyl isobutyl ketone and heptane.

Figure 69:
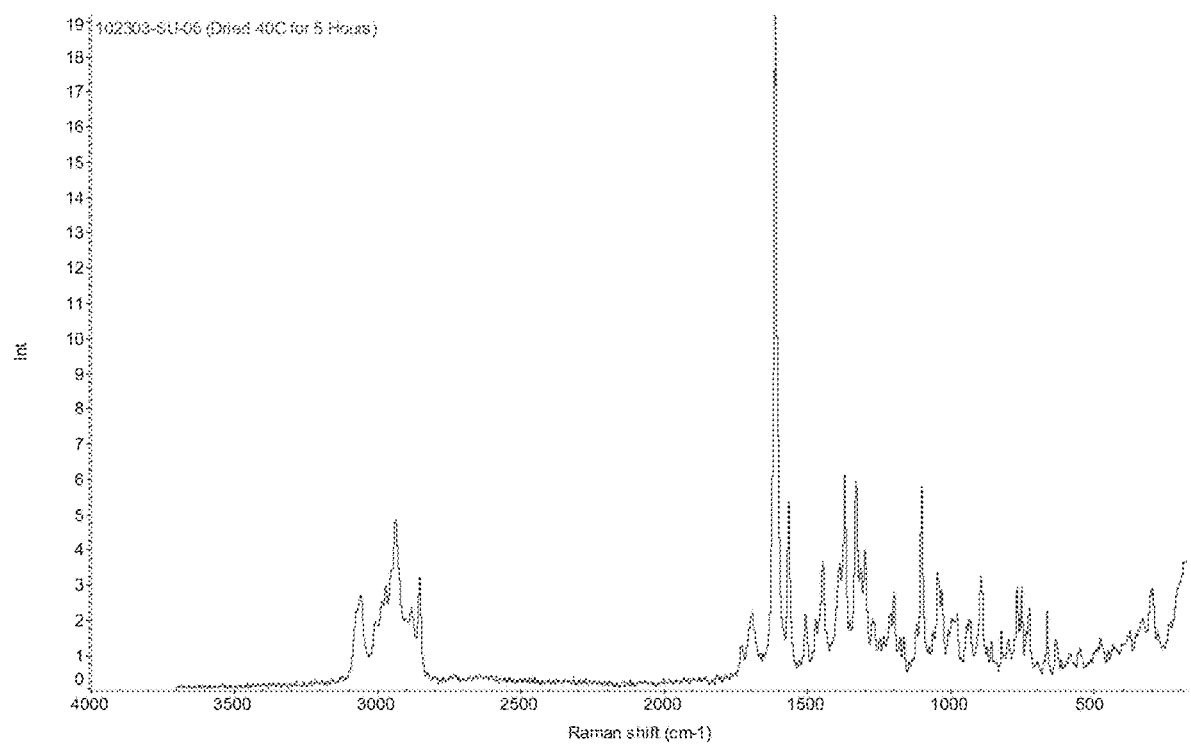
FIG. 69 depicts an FT-Raman spectrum of Maleate Salt Form D of Compound 8.

In one embodiment, provided herein is Maleate Salt Form D having an FT-Raman Spectrum as depicted in FIG. 69.

Figure 70:
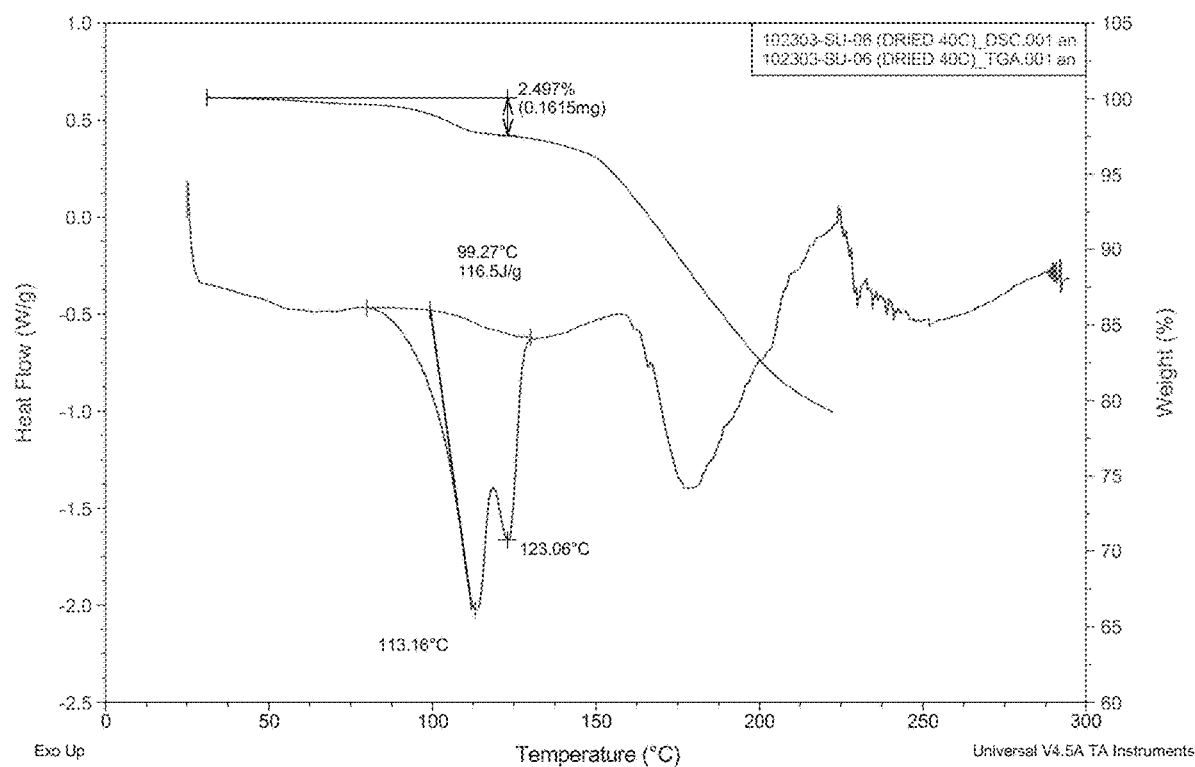
FIG. 70 depicts differential scanning calorimetry/thermal gravimetric analysis of Maleate Salt Form D of Compound 8.

In one embodiment, provided herein is a solid form of Compound 8, e.g., Maleate Salt Form D of Compound 8, having a DSC thermogram substantially as depicted in FIG. 70 comprising endotherms with peak maximum temperatures at approximately 113.2° C. and 123.1° C., respectively.

In one embodiment, provided herein is a solid form of Compound 8, e.g., Maleate Salt Form D of Compound 8, having a TGA thermogram corresponding substantially to the representative TGA thermogram as depicted in FIG. 70. In certain embodiments, the crystalline form exhibits a TGA thermogram comprising a total mass loss of approximately 2.5% of the total mass of the sample when heated from approximately 25° C. to approximately 123° C.

Figure 68:
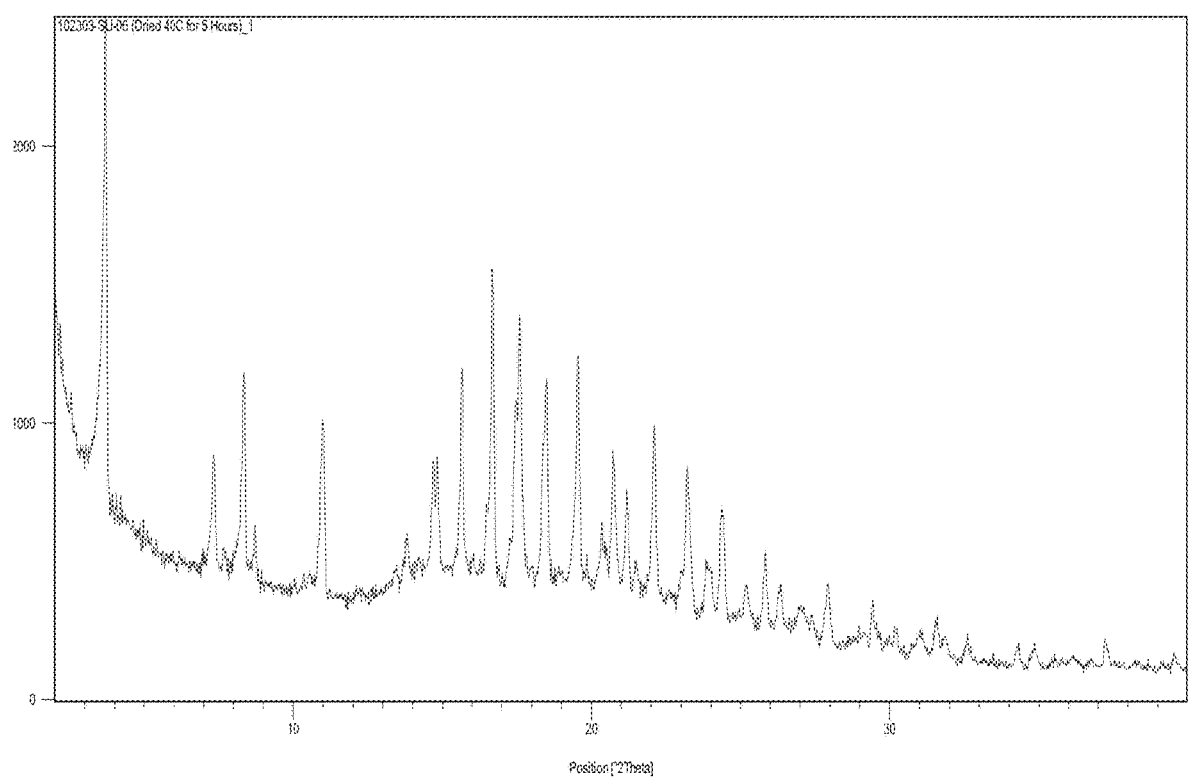
FIG. 68 depicts a PXRD pattern of Maleate Salt Form D of Compound 8.

In certain embodiments, a solid form of Compound 8 provided herein, e.g., Maleate Salt Form D, is substantially crystalline, as indicated by, e.g., X-ray powder diffraction measurements. In one embodiment, provided herein is a solid form of Compound 8 having an X-ray powder diffraction pattern (XRPD) substantially as shown in FIG. 68 (e.g., Maleate Salt Form D). In one embodiment, a solid form of Compound 8 provided herein, e.g., Maleate Salt Form D, has one or more characteristic X-ray powder diffraction peaks at approximately 3.7, 7.4, 8.4, 8.7, 11.0, 13.8, 14.7, 14.8, 15.7, 16.7, 17.5, 17.6, 18.5, 19.5, 20.3, 20.7, 21.2, 22.1, 23.2, 23.8, 24.3, 25.2, 25.9, 26.3, 27.0, 27.9 29.4, 30.2, 31.0 31.6, 32.6, 34.3, 34.8, or 37.2° 2θ (±0.2° 2θ) or (±0.1° 2θ) as depicted in FIG. 68. In a specific embodiment, a solid form of Compound 8 provided herein, e.g., Maleate Salt Form D, has one, two, three, four, or five characteristic X-ray powder diffraction peaks at approximately 3.7, 8.4, 11.0, 16.7, or 22.1° 2θ (±0.2° 2θ).

In certain embodiments, Maleate Salt Form D is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Maleate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Malonate Salt Form A, Edisylate Salt Form A, Edisylate Salt Form B, Edisylate Salt Form C, Tosylate Salt Form A or Tosylate Salt Form B. In further embodiments, Maleate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Maleate Salt Form D is substantially pure. In certain embodiments, the substantially pure Maleate Salt Form D is substantially free of other solid forms, including but not limited to amorphous solid. In certain embodiments, the purity of the substantially pure Maleate Salt Form D is no less than about 95%, no less than about 96%, no less than about 97%, no less than about 98%, no less than about 98.5%, no less than about 99%, no less than about 99.5%, or no less than about 99.8%.

(v) Maleate Salt Form E

In one embodiment, the solid form of Compound 8 is Maleate Salt Form E. In one embodiment, Maleate Salt Form E is crystalline. In another embodiment, Maleate Salt Form E is moderately crystalline. In one embodiment, Maleate Salt Form E is solvated by 1,4-dioxane.

In certain embodiments, provided herein are methods for making Maleate Salt Form E comprising 1) combining Compound 1 with methanol and maleic acid (e.g., about 1.0 equivalent); 2) evaporating the solution to dryness under reduced pressure; 3) adding heptane (e.g., about 0.2 mL) to the solid and vortexing the sample; 4) adding 1,4-dioxane (e.g., about 0.2 mL) and stirring the solution at a temperature (e.g., ambient temperature); 5) cycling the temperature (e.g., between about 5° C. and about 40° C.; 1° C. per minute heating/cooling rate with an hour hold between each heating/cooling cycle) of the solution for a period of time (e.g., about 21 hours); 6) cooling the sample to 5° C. and isolating solids from the solution through vacuum filtration; 7) air-drying the solids for a period of time (e.g., one hour) to isolate Maleate Salt Form E of Compound 8.

In certain embodiments, provided herein are methods for making Maleate Salt Form E comprising 1) combining Compound 1 with methanol and maleic acid (e.g., about 1.0 equivalent); 2) evaporating the solution to dryness under reduced pressure; 3) adding 1,4-dioxane (e.g., about 0.2 mL) and stirring the solution at a temperature (e.g., ambient temperature); 4) cycling the temperature (e.g., between about 5° C. and about 40° C.; 1° C. per minute heating/cooling rate with an hour hold between each heating/cooling cycle) of the solution for a period of time (e.g., about 21 hours); 5) cooling the sample to 5° C. and isolating solids from the solution through vacuum filtration; 6) air-drying the solids for a period of time (e.g., one hour) to isolate Maleate Salt Form E of Compound 8.

Figure 115:
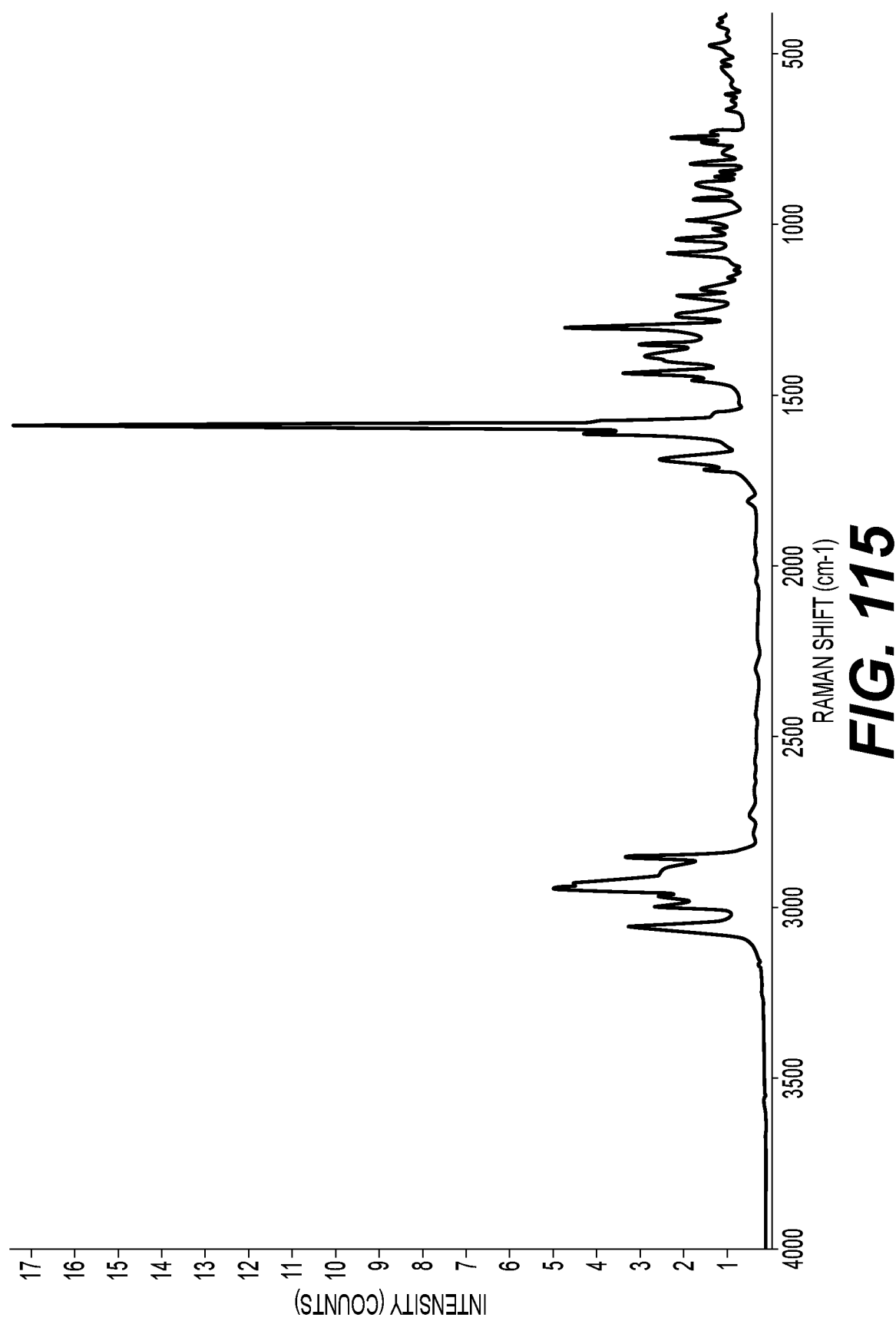
FIG. 115 depicts an FT-Raman spectrum of Maleate Salt Form E of Compound 8.

In one embodiment, provided herein is Maleate Salt Form E having an FT-Raman Spectrum as depicted in FIG. 115.

In one embodiment, provided herein is a solid form of Compound 8, e.g., Maleate Salt Form E of Compound 8, having a DSC thermogram substantially as depicted in 116 comprising an endotherm with an onset temperature at approximately 85° C.

Figure 116:
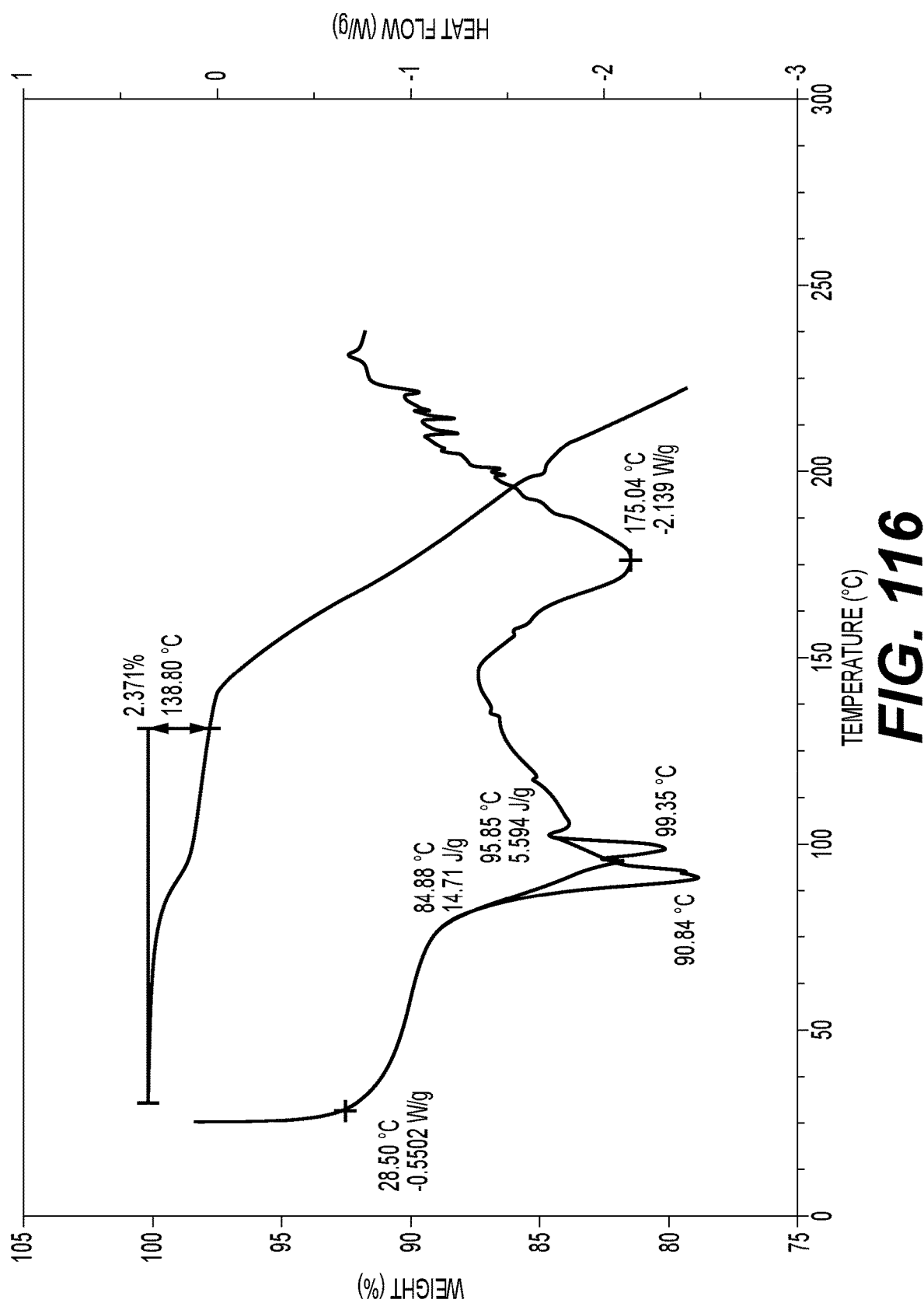
FIG. 116 depicts differential scanning calorimetry/thermal gravimetric analysis of Maleate Salt Form E of Compound 8.

In one embodiment, provided herein is a solid form of Compound 8, e.g., Maleate Salt Form E of Compound 8, having a TGA thermogram corresponding substantially to the representative TGA thermogram as depicted in FIG. 116. In certain embodiments, the crystalline form exhibits a TGA thermogram comprising a total mass loss of approximately 2.4% of the total mass of the sample when heated from approximately 25° C. to approximately 131° C.

Figure 114:
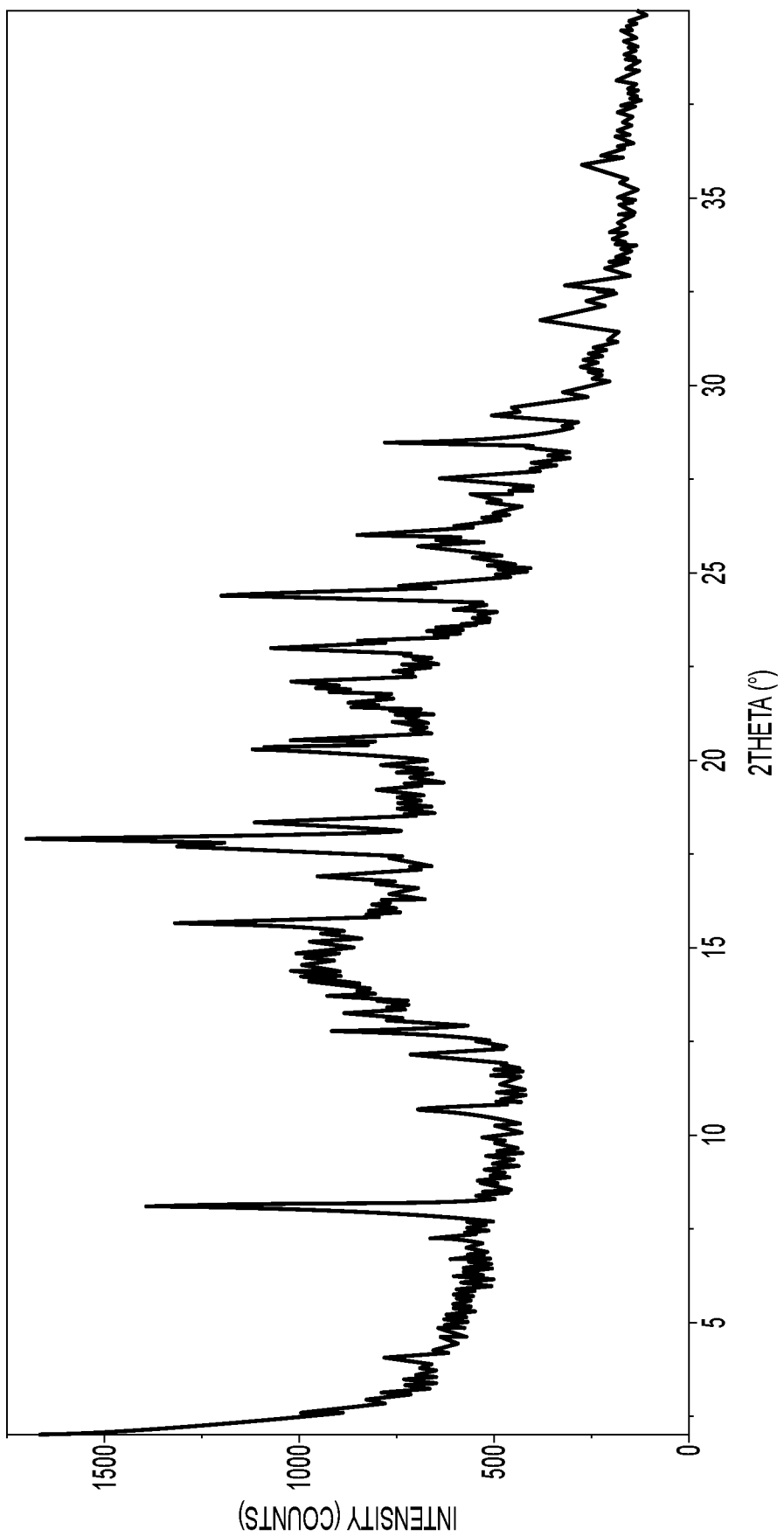
FIG. 114 depicts a PXRD pattern of Maleate Salt Form E of Compound 8.

In certain embodiments, a solid form of Compound 8 provided herein, e.g., Maleate Salt Form E, is substantially crystalline, as indicated by, e.g., X-ray powder diffraction measurements. In one embodiment, provided herein is a solid form of Compound 8 having an X-ray powder diffraction pattern (XRPD) substantially as shown in FIG. 114 (e.g., Maleate Salt Form E). In one embodiment, a solid form of Compound 8 provided herein, e.g., Maleate Salt Form E, has one or more characteristic X-ray powder diffraction peaks at approximately 4.0, 7.2, 8.1, 10.7, 12.1, 12.8, 13.2, 15.6, 16.9, 17.7, 17.9, 18.3, 20.3, 20.5, 22.1, 23.0, 24.3, 25.7, 26.0, 27.5, 28.5, 29.2, 31.8, 32.7, or 35.8° 2θ (±0.2° 2θ) or (±0.1° 2θ) as depicted in FIG. 114. In a specific embodiment, a solid form of Compound 8 provided herein, e.g., Maleate Salt Form E, has one, two, three, four, or five characteristic X-ray powder diffraction peaks at approximately 4.0, 8.1, 15.6, 17.9, 23.0, or 24.3° 2θ (±0.2° 2θ).

In certain embodiments, Maleate Salt Form E is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Maleate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Malonate Salt Form A, Edisylate Salt Form A, Edisylate Salt Form B, Edisylate Salt Form C, Tosylate Salt Form A or Tosylate Salt Form B. In further embodiments, Maleate Salt Form D is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Maleate Salt Form E is substantially pure. In certain embodiments, the substantially pure Maleate Salt Form E is substantially free of other solid forms, including but not limited to amorphous solid. In certain embodiments, the purity of the substantially pure Maleate Salt Form E is no less than about 95%, no less than about 96%, no less than about 97%, no less than about 98%, no less than about 98.5%, no less than about 99%, no less than about 99.5%, or no less than about 99.8%.

(vi) Maleate Salt Form F

In one embodiment, the solid form of Compound 8 is Maleate Salt Form F. In one embodiment, Maleate Salt Form F is crystalline. In another embodiment, Maleate Salt Form F is moderately crystalline. In one embodiment, Maleate Salt Form F is non-solvated.

In certain embodiments, provided herein are methods for making Maleate Salt Form F comprising 1) combining Compound 1 with methanol and maleic acid (e.g., about 1.0 equivalent); 2) evaporating the solution to dryness under reduced pressure; 3) adding heptane (e.g., about 0.2 mL) to the solid and vortexing the sample; 4) adding THF (e.g., about 0.2 mL) and stirring the solution at a temperature (e.g., ambient temperature); 5) cycling the temperature (e.g., between about 5° C. and about 40° C.; 1° C. per minute heating/cooling rate with an hour hold between each heating/cooling cycle) of the solution for a period of time (e.g., about 21 hours); 6) cooling the sample to 5° C. and isolating solids from the solution through vacuum filtration; 7) air-drying the solids for a period of time (e.g., one hour) to isolate Maleate Salt Form F of Compound 8.

Figure 119:
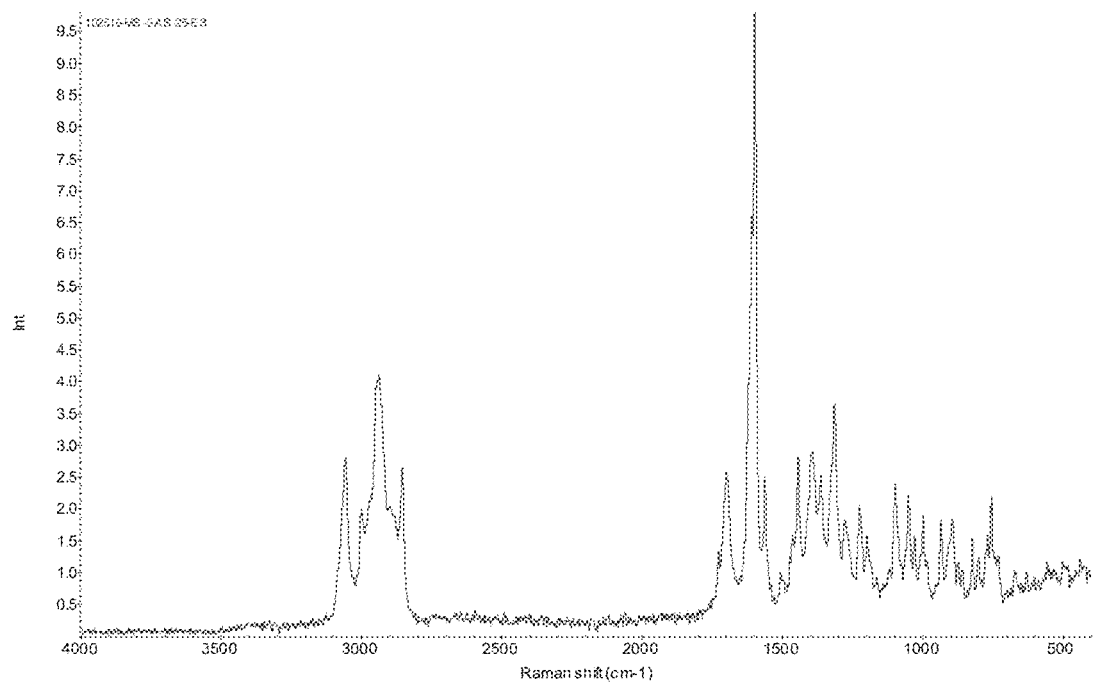
FIG. 119 depicts an FT-Raman spectrum of Maleate Salt Form F of Compound 8.

In one embodiment, provided herein is Maleate Salt Form F having an FT-Raman Spectrum as depicted in FIG. 119.

Figure 120:
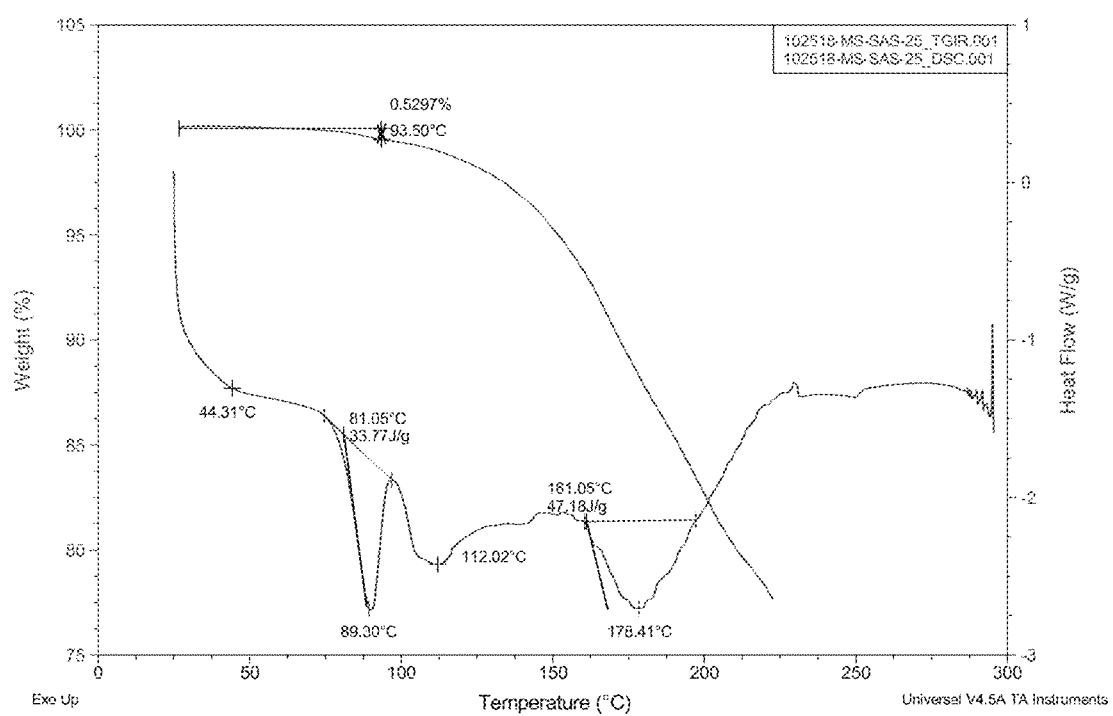
FIG. 120 depicts differential scanning calorimetry/thermal gravimetric analysis of Maleate Salt Form F of Compound 8.

In one embodiment, provided herein is a solid form of Compound 8, e.g., Maleate Salt Form F of Compound 8, having a DSC thermogram substantially as depicted in FIG. 120 comprising an endotherm with an onset temperature at approximately 81° C.

In one embodiment, provided herein is a solid form of Compound 8, e.g., Maleate Salt Form F of Compound 8, having a TGA thermogram corresponding substantially to the representative TGA thermogram as depicted in FIG. 120. In certain embodiments, the crystalline form exhibits a TGA thermogram comprising a total mass loss of approximately 0.5% of the total mass of the sample when heated from approximately 25° C. to approximately 94° C.

Figure 118:
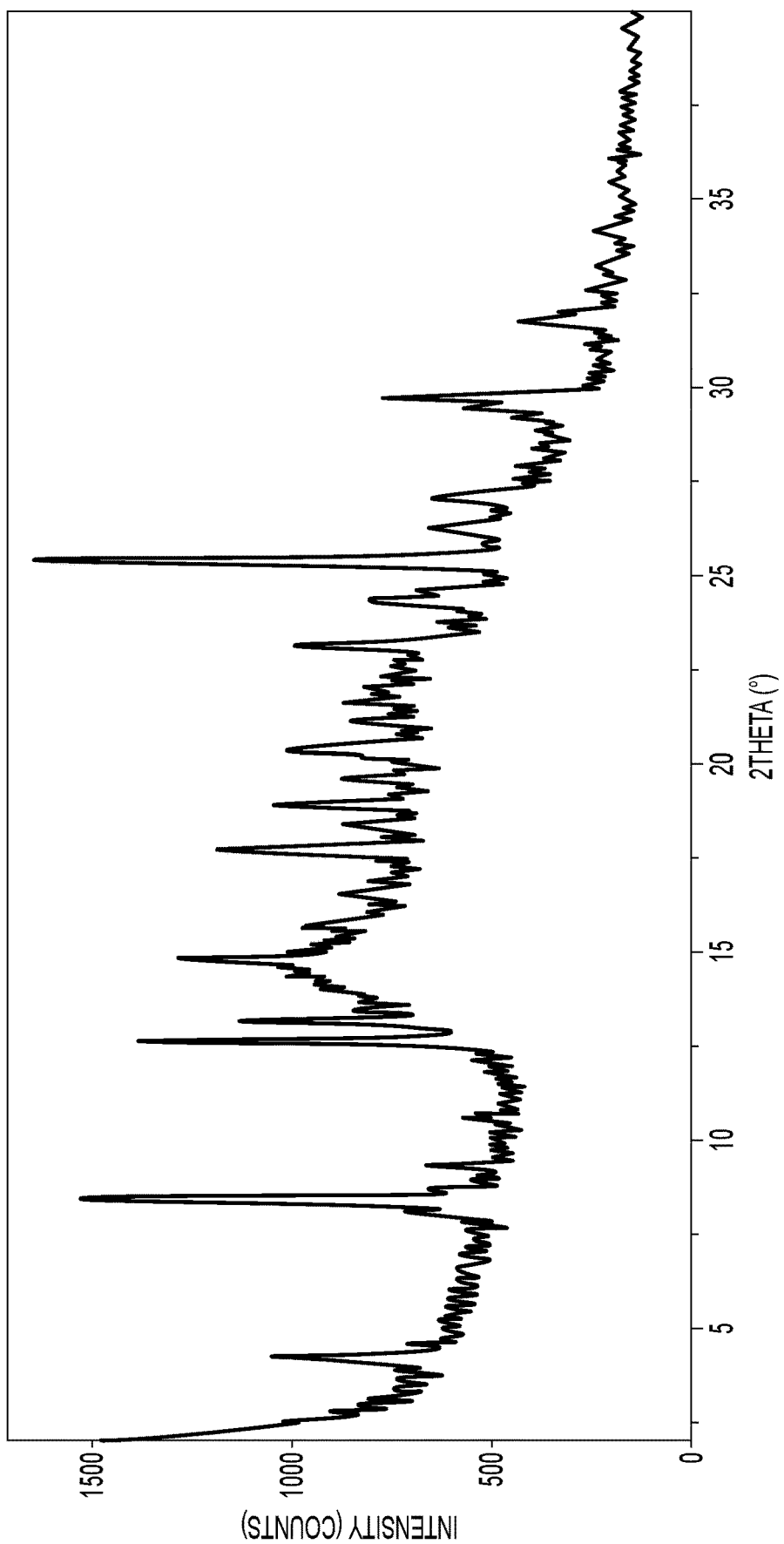
FIG. 118 depicts a PXRD pattern of Maleate Salt Form F of Compound 8.

In certain embodiments, a solid form of Compound 8 provided herein, e.g., Maleate Salt Form F, is substantially crystalline, as indicated by, e.g., X-ray powder diffraction measurements. In one embodiment, provided herein is a solid form of Compound 8 having an X-ray powder diffraction pattern (XRPD) substantially as shown in FIG. 118 (e.g., Maleate Salt Form F). In one embodiment, a solid form of Compound 8 provided herein, e.g., Maleate Salt Form F, has one or more characteristic X-ray powder diffraction peaks at approximately 4.3, 8.4, 9.3, 10.6, 12.6, 13.2, 13.5, 14.8, 15.7, 16.5, 17.7, 18.9, 19.6, 20.4, 23.1, 24.3, 25.4, 26.3, 27.0, 29.7, or 31.7° 2θ (±0.2° 2θ) or (±0.1° 2θ) as depicted in FIG. 118. In a specific embodiment, a solid form of Compound 8 provided herein, e.g., Maleate Salt Form F, has one, two, three, four, or five characteristic X-ray powder diffraction peaks at approximately 4.3, 8.4, 12.6, 13.2, 14.8, or 25.4° 2θ (±0.2° 2θ).

In certain embodiments, Maleate Salt Form F is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Maleate Salt Form F is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Malonate Salt Form A, Edisylate Salt Form A, Edisylate Salt Form B, Edisylate Salt Form C, Tosylate Salt Form A or Tosylate Salt Form B. In further embodiments, Maleate Salt Form F is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Maleate Salt Form F is substantially pure. In certain embodiments, the substantially pure Maleate Salt Form F is substantially free of other solid forms, including but not limited to amorphous solid. In certain embodiments, the purity of the substantially pure Maleate Salt Form F is no less than about 95%, no less than about 96%, no less than about 97%, no less than about 98%, no less than about 98.5%, no less than about 99%, no less than about 99.5%, or no less than about 99.8%.

(vii) Maleate Salt Form G

In one embodiment, the solid form of Compound 8 is Maleate Salt Form G. In one embodiment, Maleate Salt Form G is crystalline. In another embodiment, Maleate Salt Form G is moderately crystalline. In one embodiment, Maleate Salt Form G is solvated by 1,4-dioxane.

In certain embodiments, provided herein are methods for making Maleate Salt Form E comprising 1) combining Compound 1 with methanol and maleic acid (e.g., about 1.0 equivalent); 2) evaporating the solution to dryness under reduced pressure; 3) dissolving the solid in heptane (e.g., about 0.2 mL) and vortexing the sample; 4) adding 1,4-dioxane (e.g., about 0.2 mL) and stirring the solution at a temperature (e.g., ambient temperature); 5) cycling the temperature (e.g., between about 5° C. and about 40° C.; 1° C. per minute heating/cooling rate with an hour hold between each heating/cooling cycle) of the solution for a period of time (e.g., about 21 hours); 6) cooling the sample to 5° C. and isolating solids from the solution through vacuum filtration; 7) air-drying the solids for a period of time (e.g., one hour); and 8) oven drying the sample under reduced pressure to isolate Maleate Salt Form G of Compound 8.

Figure 123:
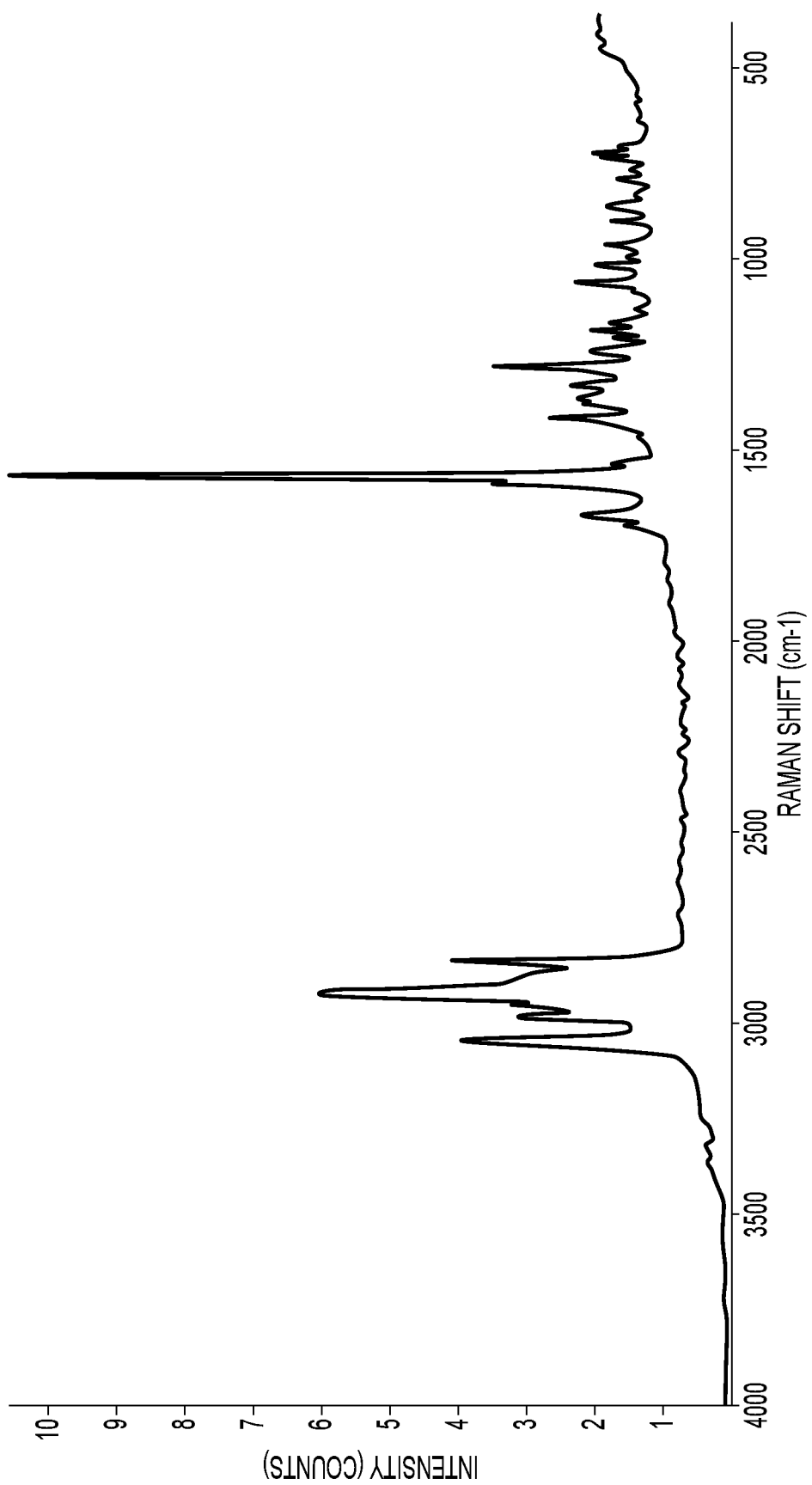
FIG. 123 depicts an FT-Raman spectrum of Maleate Salt Form G of Compound 8.

In one embodiment, provided herein is Maleate Salt Form G having an FT-Raman Spectrum as depicted in FIG. 123.

Figure 124:
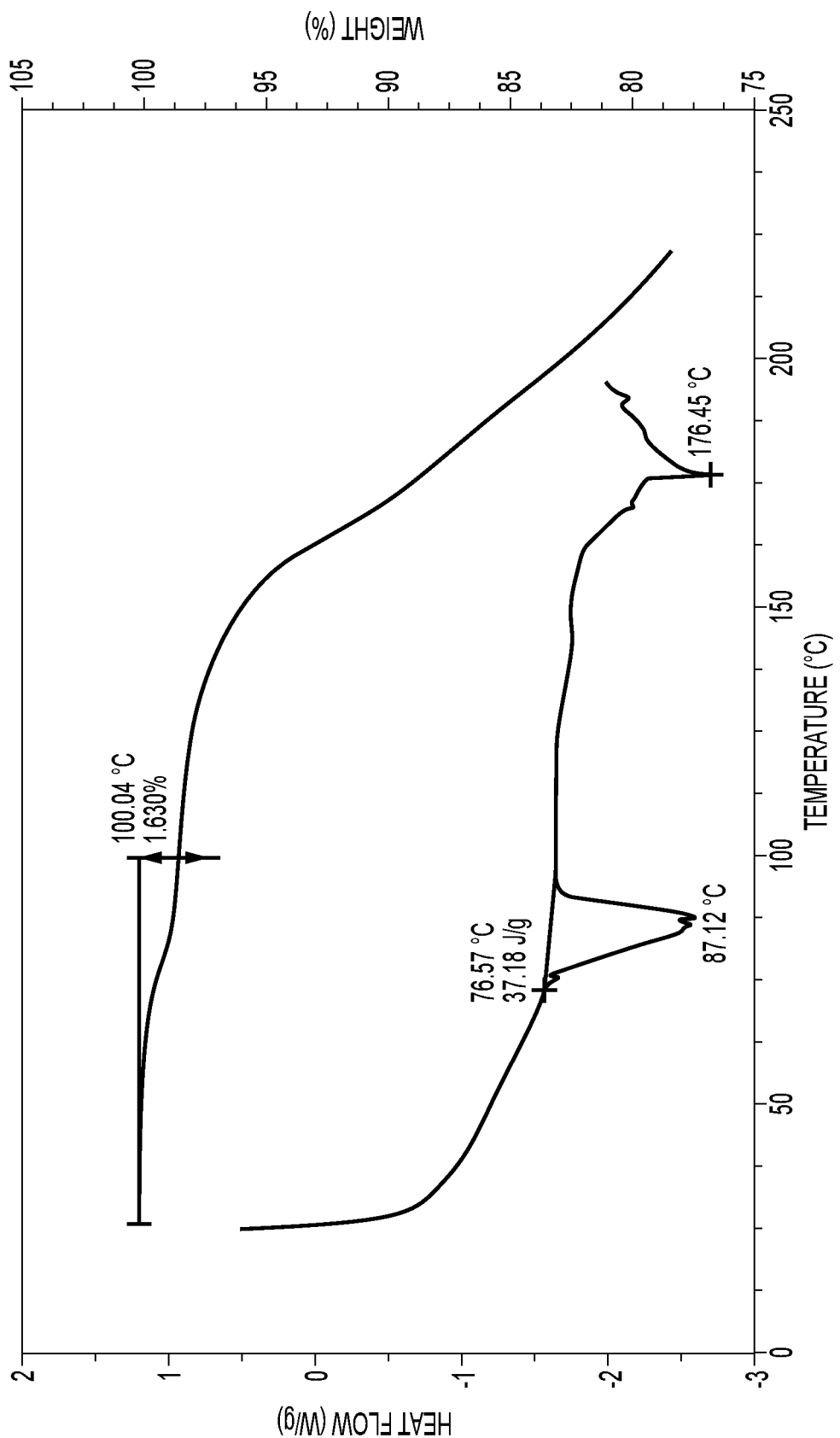
FIG. 124 depicts differential scanning calorimetry/thermal gravimetric analysis of Maleate Salt Form G of Compound 8.

In one embodiment, provided herein is a solid form of Compound 8, e.g., Maleate Salt Form G of Compound 8, having a DSC thermogram substantially as depicted in FIG. 124 comprising an endotherm with an onset temperature at approximately 77° C.

In one embodiment, provided herein is a solid form of Compound 8, e.g., Maleate Salt Form G of Compound 8, having a TGA thermogram corresponding substantially to the representative TGA thermogram as depicted in FIG. 124. In certain embodiments, the crystalline form exhibits a TGA thermogram comprising a total mass loss of approximately 1.6% of the total mass of the sample when heated from approximately 25° C. to approximately 100° C.

Figure 122:
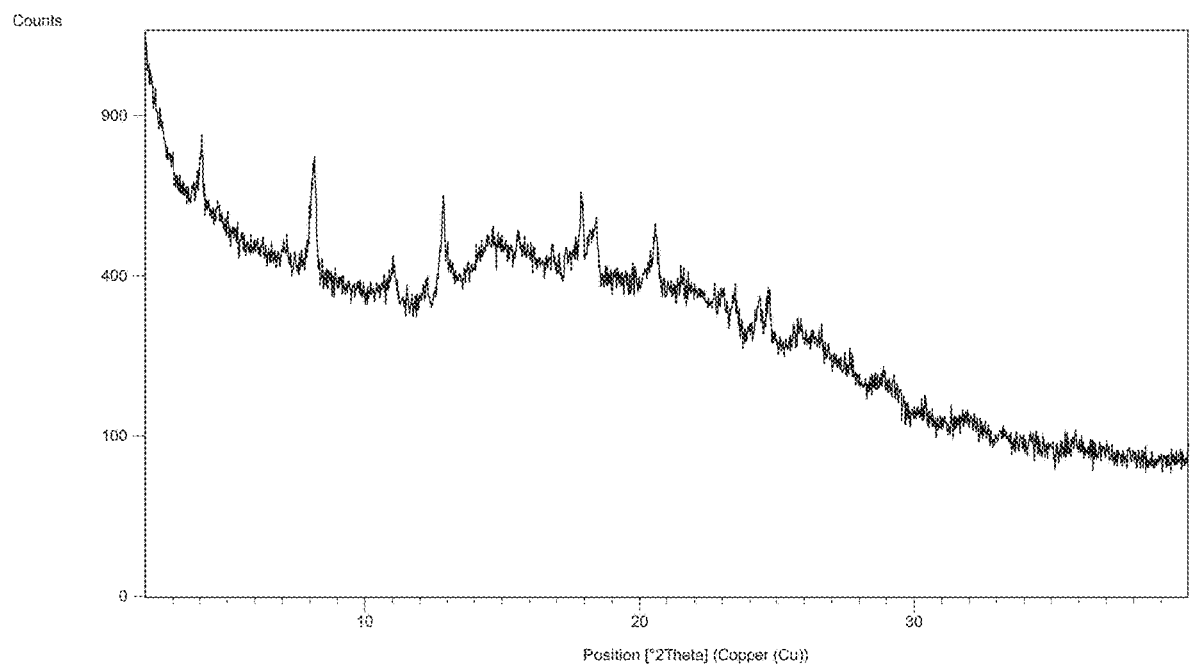
FIG. 122 depicts a PXRD pattern of Maleate Salt Form G of Compound 8.

In certain embodiments, a solid form of Compound 8 provided herein, e.g., Maleate Salt Form G, is substantially crystalline, as indicated by, e.g., X-ray powder diffraction measurements. In one embodiment, provided herein is a solid form of Compound 8 having an X-ray powder diffraction pattern (XRPD) substantially as shown in FIG. 122 (e.g., Maleate Salt Form G). In one embodiment, a solid form of Compound 8 provided herein, e.g., Maleate Salt Form G, has one or more characteristic X-ray powder diffraction peaks at approximately 4.1, 8.2, 11.0, 12.9, 17.9, 18.4, 20.6, or 24.7° 2θ (±0.2° 2θ) or (±0.1° 2θ) as depicted in FIG. 122. In a specific embodiment, a solid form of Compound 8 provided herein, e.g., Maleate Salt Form G, has one, two, three, four, or five characteristic X-ray powder diffraction peaks at approximately 4.1, 8.2, 12.9, 17.9, or 20.6° 2θ (±0.2° 2θ).

In certain embodiments, Maleate Salt Form G is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Maleate Salt Form G is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Malonate Salt Form A, Edisylate Salt Form A, Edisylate Salt Form B, Edisylate Salt Form C, Tosylate Salt Form A or Tosylate Salt Form B. In further embodiments, Maleate Salt Form G is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Maleate Salt Form G is substantially pure. In certain embodiments, the substantially pure Maleate Salt Form G is substantially free of other solid forms, including but not limited to amorphous solid. In certain embodiments, the purity of the substantially pure Maleate Salt Form G is no less than about 95%, no less than about 96%, no less than about 97%, no less than about 98%, no less than about 98.5%, no less than about 99%, no less than about 99.5%, or no less than about 99.8%.

(i) Solid Forms of Compound 9

In one embodiment, provided herein is a solid form of Compound 9.

(i) Malonate Salt Form A

In one embodiment, the solid form of Compound 9 is Malonate Salt Form A. In one embodiment, Malonate Salt Form A is crystalline. In one embodiment, Malonate Salt Form A is hydrated and solvated by methyl isobutyl ketone.

In certain embodiments, provided herein are methods for making Malonate Salt Form A, comprising 1) dispensing a solvent (e.g., about 250 µL) into a vial containing an amount of Compound 1 (e.g., about 20 mg); 2) adding a stoichiometric amount (e.g., 1.0 equivalent) of a 3 M solution of malonic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent, followed by temperature cycling (e.g., between about 5° C. and about 40° C.; 1° C. per minute heating/cooling rate with an hour hold between each heating/cooling cycle) of the solution for a period of time (e.g., about a day), and equilibrating the solution to a temperature (e.g., 20° C.) for a period of time (e.g., about one hour) at the end of temperature cycling; 7) adding an anti-solvent (e.g., 1:3 v/v solvent to anti-solvent ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) equilibrating the solution to a temperature (e.g., 20° C.) and evaporating the solvent slowly at room temperature to yield Malonate Salt Form A of Compound 9. In certain embodiments, the solution is evaporated under reduced pressure in a centrifuge evaporator. In certain other embodiments, the solution is evaporated under a slow bleed of inert gas such as nitrogen or argon gas. In certain embodiments, the solvent in step 1 is methyl isobutyl ketone and the anti-solvent in step 7 was hexane. In certain embodiments, the solvent in step 1 is isopropyl acetate and the anti-solvent in step 7 is diisopropyl ether.

In certain embodiments, provided herein are methods for making Malonate Salt Form A comprising 1) combining Compound 1 (e.g., about 102.4 mg) with methyl isobutyl ketone (e.g., about 1.25 mL) and malonic acid (e.g., about 1.0 equivalent of a 3 M solution in water); 2) heating the resulting mixture to a temperature (e.g., about 40° C.) for a period of time (e.g., about one hour); 3) adding seeds of crystalline malonate salt of Compound 1 to the solution (e.g., about 1 mg); 4) cycling the temperature (e.g., between about 5° C. and about 40° C.; 1° C. per minute heating/cooling rate with an hour hold between each heating/cooling cycle) of the solution for a period of time (e.g., about two days); 5) cooling the sample to a temperature (e.g., 5° C.) and holding the sample at that temperature for a period of time (e.g., three days); 5) isolating solids from the solution through vacuum filtration; 6) air-drying the solids for a period of time (e.g., one hour) and drying in a vacuum oven at a temperature (e.g., 40° C.) for a period of time (e.g., 5 hours) to yield Malonate Salt Form A of Compound 9.

Figure 73:
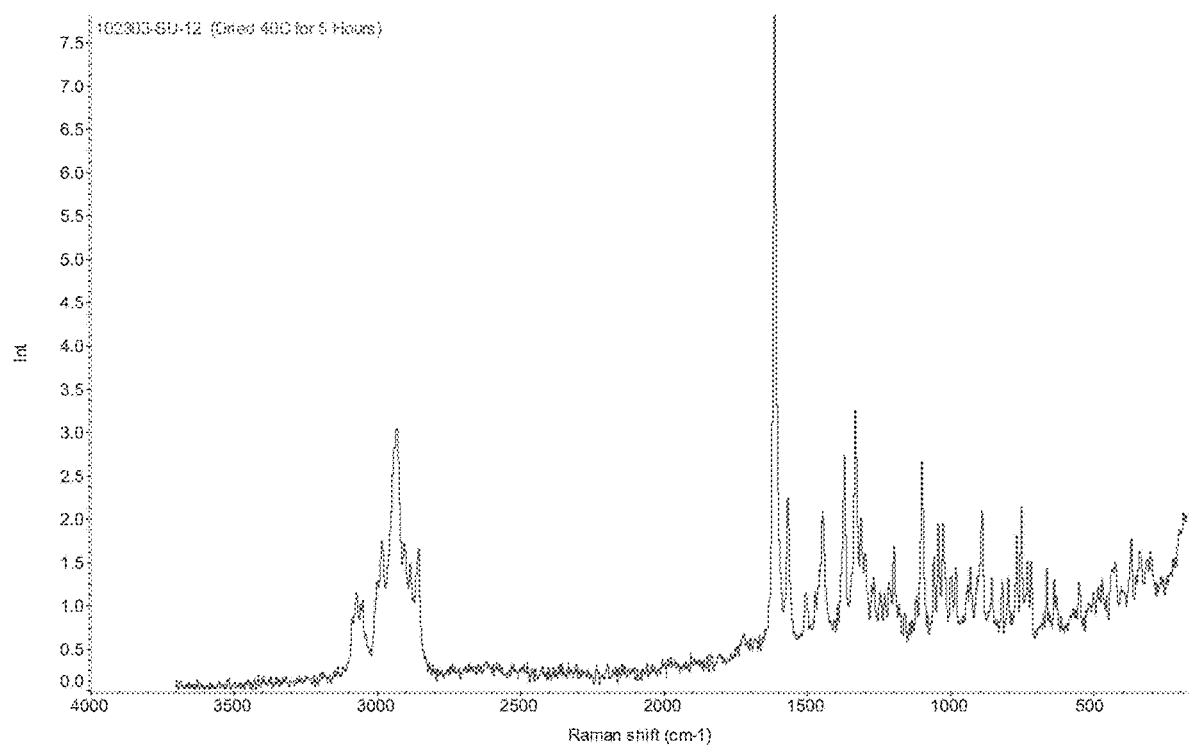
FIG. 73 depicts an FT-Raman spectrum of Malonate Salt Form A of Compound 9.

In one embodiment, provided herein is Malonate Salt Form A having an FT-Raman Spectrum as depicted in FIG. 73.

Figure 74:
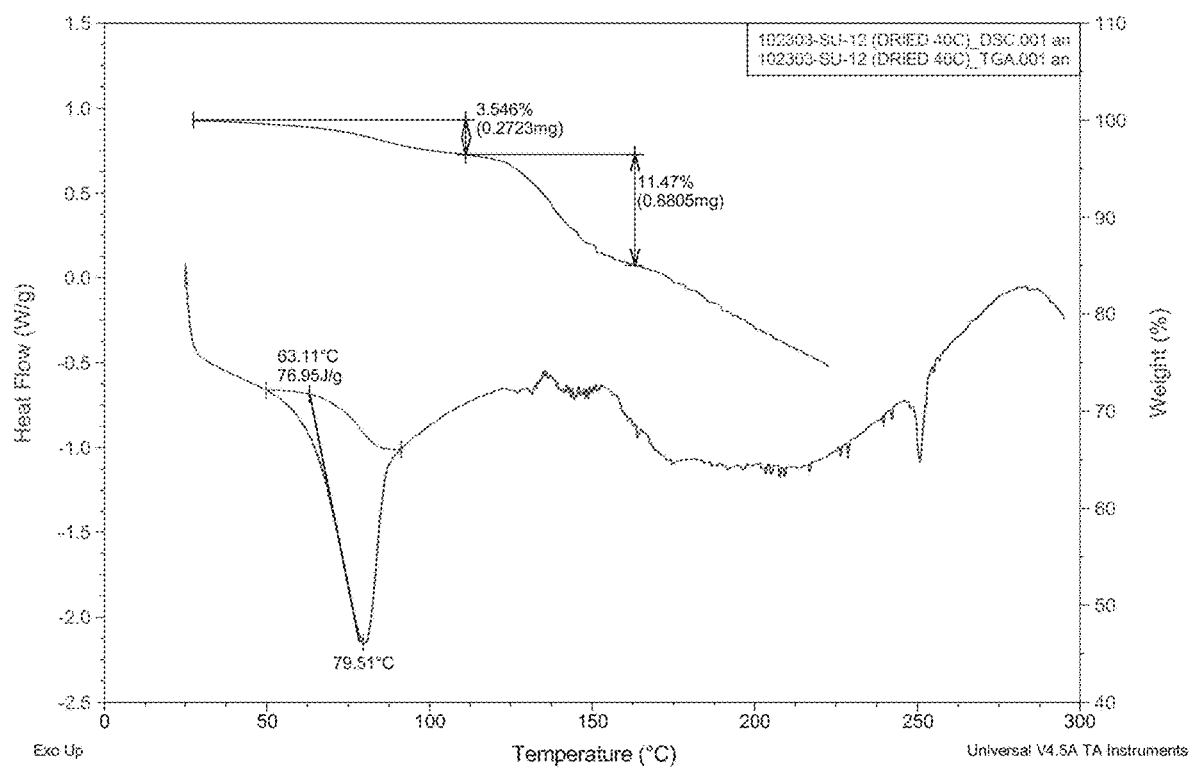
FIG. 74 depicts differential scanning calorimetry/thermal gravimetric analysis of Malonate Salt Form A of Compound 9.

In one embodiment, provided herein is a solid form of Compound 9, e.g., Malonate Salt Form A of Compound 9, having a DSC thermogram substantially as depicted in FIG. 74 comprising an endotherm with an onset temperature at 63.1° C.

In one embodiment, provided herein is a solid form of Compound 9, e.g., Malonate Salt Form A of Compound 9, having a TGA thermogram corresponding substantially to the representative TGA thermogram as depicted in FIG. 74. In certain embodiments, the crystalline form exhibits a TGA thermogram comprising a total mass loss of approximately 15% of the total mass of the sample when heated from approximately 25° C. to approximately 163° C.

Figure 72:
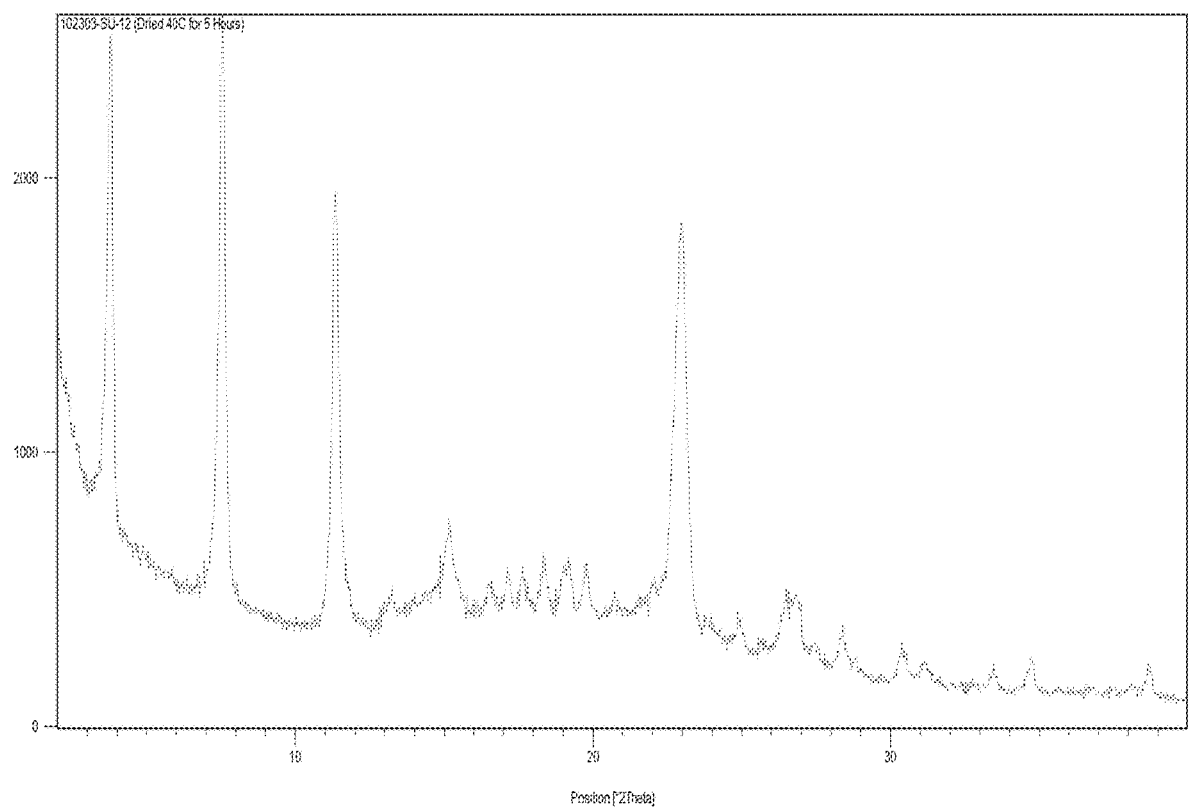
FIG. 72 depicts a PXRD pattern of Malonate Salt Form A of Compound 9.

In certain embodiments, a solid form of Compound 9 provided herein, e.g., Malonate Salt Form A, is substantially crystalline, as indicated by, e.g., X-ray powder diffraction measurements. In one embodiment, provided herein is a solid form of Compound 9 having an X-ray powder diffraction pattern (XRPD) substantially as shown in FIG. 72 (e.g., Form 11). In one embodiment, a solid form of Compound 9 provided herein, e.g., Malonate Salt Form A, has one or more characteristic X-ray powder diffraction peaks at approximately 3.8, 7.6, 11.3, 13.2, 15.2, 16.5, 17.2, 17.6, 18.4, 19.2, 19.8, 20.7, 23.0, 24.9, 26.5, 27.0, 27.5, 28.4, 30.4, 31.1, 33.4, 34.7, or 38.7° 2θ (±0.2° 2θ) or (±0.1° 2θ) as depicted in FIG. 72. In a specific embodiment, a solid form of Compound 9 provided herein, e.g., Malonate Salt Form A, has one, two, three, four, or five characteristic X-ray powder diffraction peaks at approximately 3.8, 7.6, 11.3, 15.2, or 23.0° 2θ (±0.2° 2θ).

In certain embodiments, Malonate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10, or Compound 11. In certain embodiments, Malonate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Edisylate Salt Form A, Edisylate Salt Form B, Edisylate Salt Form C, Tosylate Salt Form A or Tosylate Salt Form B. In further embodiments, Malonate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Malonate Salt Form A is substantially pure. In certain embodiments, the substantially pure Malonate Salt Form A is substantially free of other solid forms, including but not limited to amorphous solid. In certain embodiments, the purity of the substantially pure Malonate Salt Form A is no less than about 95%, no less than about 96%, no less than about 97%, no less than about 98%, no less than about 98.5%, no less than about 99%, no less than about 99.5%, or no less than about 99.8%.

(j) Solid Forms of Compound 10

In one embodiment, provided herein is a solid form of Compound 10.

(i) Edisylate Salt Form A

In one embodiment, the solid form of Compound 10 is Edisylate Salt Form A. In one embodiment, Edisylate Salt Form A is crystalline. In one embodiment, Edisylate Salt Form A is hydrated.

In certain embodiments, provided herein are methods for making Edisylate Salt Form A, comprising 1) dispensing acetonitrile (e.g., about 250 µL) into a vial containing an amount of Compound 1 (e.g., about 20 mg); 2) adding a stoichiometric amount (e.g., 1.0 equivalent) of a 3 M solution of ethane-1,2-disulfonic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in acetonitrile, followed by temperature cycling (e.g., between about 5° C. and about 40° C.; 1° C. per minute heating/cooling rate with an hour hold between each heating/cooling cycle) of the solution for a period of time (e.g., about a day); 7) equilibrating the solution to a temperature (e.g., 20° C.); 8) isolating solids from the solution; and 9) air-drying the solids for a period of time (e.g., one hour) followed by drying the solids in a vacuum oven at a temperature (e.g., 40° C.) for a period of time (e.g., 5 hours) to yield Edisylate Salt Form A of Compound 10. In certain embodiments, the solution is evaporated under reduced pressure in a centrifuge evaporator.

In certain other embodiments, the solution is evaporated under a slow bleed of inert gas such as nitrogen or argon gas.

Figure 77:
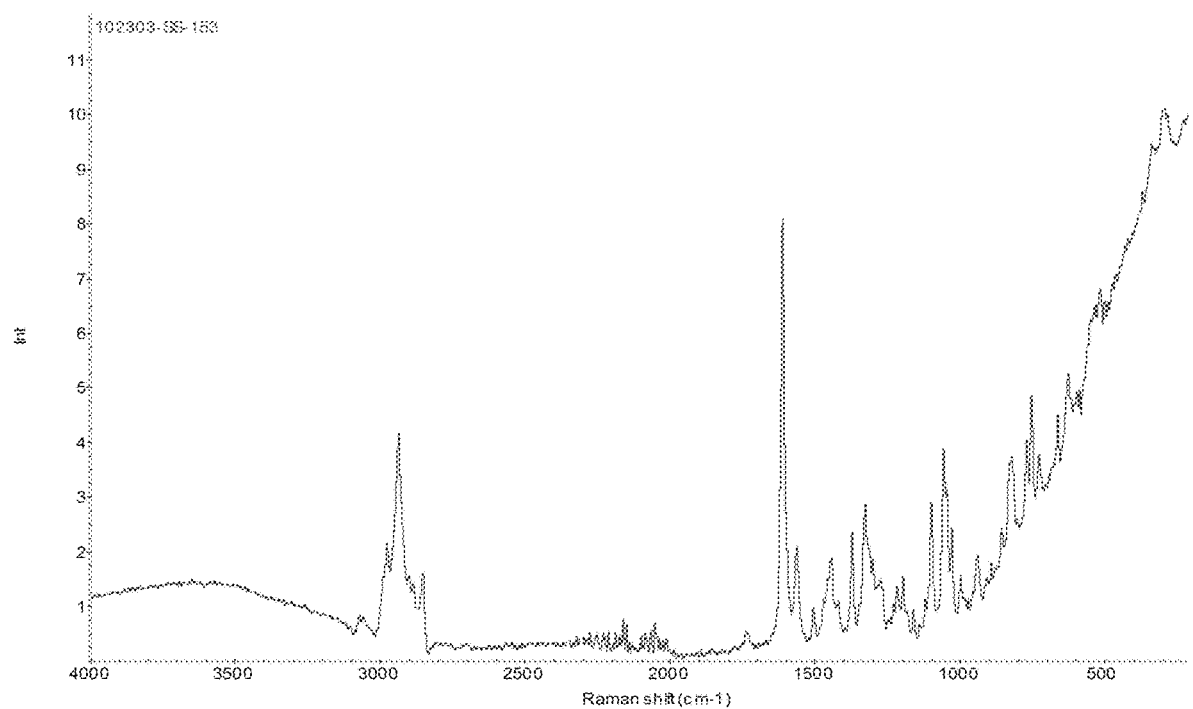
FIG. 77 depicts an FT-Raman spectrum of Edisylate Salt Form A of Compound 10.

In one embodiment, provided herein is Edisylate Salt Form A having an FT-Raman Spectrum as depicted in FIG. 77.

Figure 78:
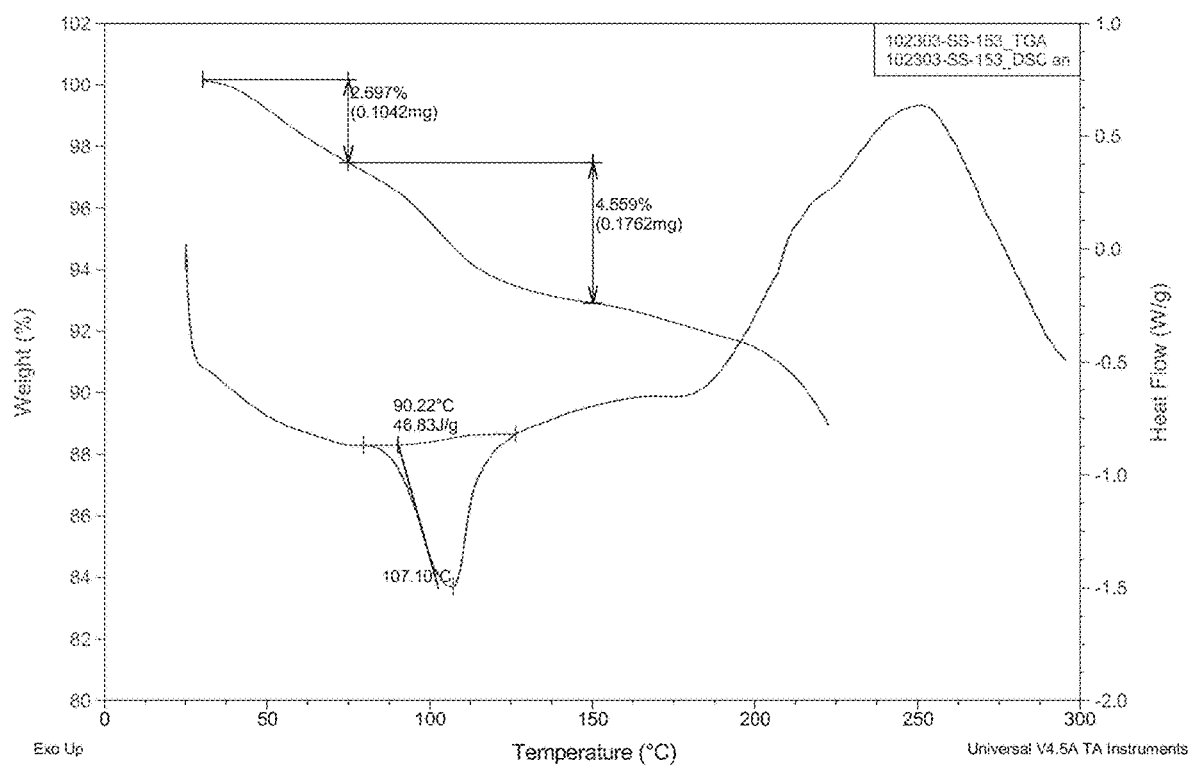
FIG. 78 depicts differential scanning calorimetry/thermal gravimetric analysis of Edisylate Salt Form A of Compound 10.

In one embodiment, provided herein is a solid form of Compound 10, e.g., Edisylate Salt Form A of Compound 10, having a DSC thermogram substantially as depicted in FIG. 78 comprising an endotherm with an onset temperature at 90.2° C.

In one embodiment, provided herein is a solid form of Compound 10, e.g., Edisylate Salt Form A of Compound 10, having a TGA thermogram corresponding substantially to the representative TGA thermogram as depicted in FIG. 78. In certain embodiments, the crystalline form exhibits a TGA thermogram comprising a total mass loss of approximately 7.3% of the total mass of the sample when heated from approximately 25° C. to approximately 150° C.

Figure 76:
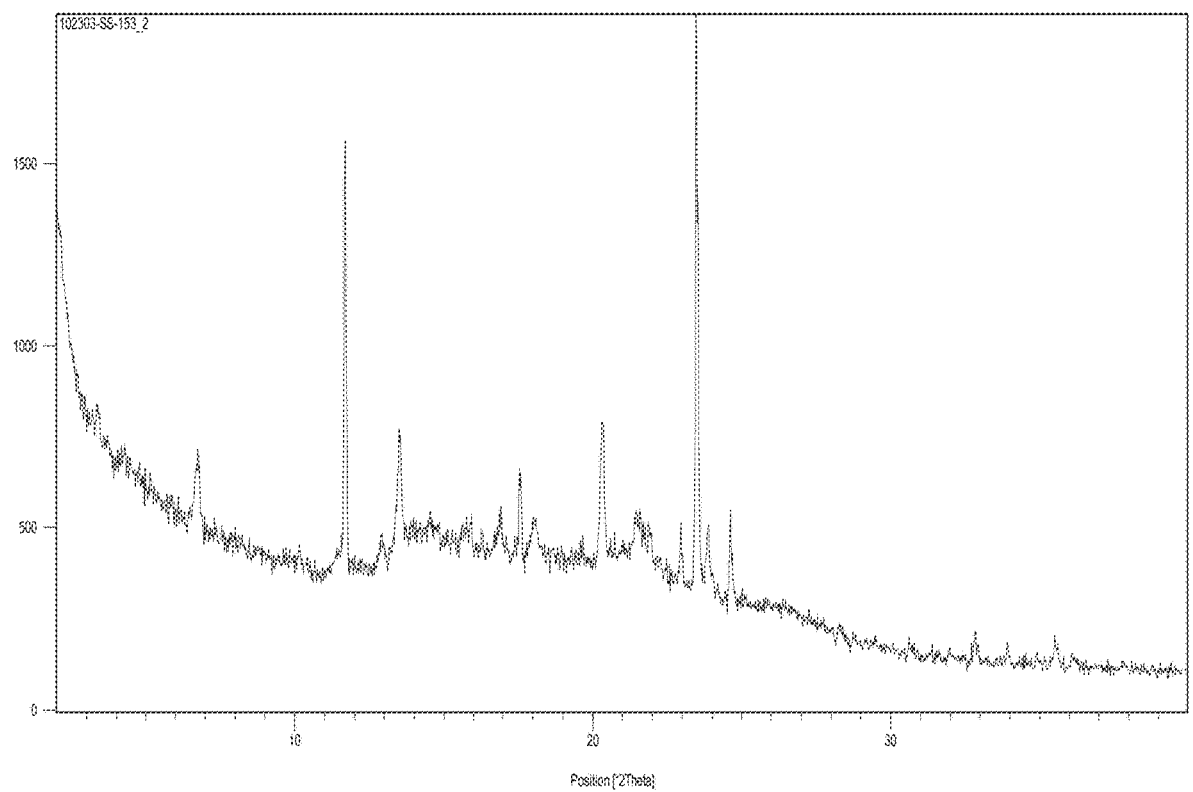
FIG. 76 depicts a PXRD pattern of Edisylate Salt Form A of Compound 10.

In certain embodiments, a solid form of Compound 10 provided herein, e.g., Edisylate Salt Form A, is substantially crystalline, as indicated by, e.g., X-ray powder diffraction measurements. In one embodiment, provided herein is a solid form of Compound 10 having an X-ray powder diffraction pattern (XRPD) substantially as shown in FIG. 76 (e.g., Edisylate Salt Form A). In one embodiment, a solid form of Compound 10 provided herein, e.g., Edisylate Salt Form A, has one or more characteristic X-ray powder diffraction peaks at approximately 6.8, 11.7, 13.5, 16.9, 17.6, 18.0, 20.3, 21.6, 23.0, 23.5, 23.9, 24.6, 32.8, or 35.5° 2θ (±0.2° 2θ) or (0.1° 2θ) as depicted in FIG. 76. In a specific embodiment, a solid form of Compound 10 provided herein, e.g., Edisylate Salt Form A, has one, two, three, four, or five characteristic X-ray powder diffraction peaks at approximately 6.8, 11.7, 13.5, 20.3, or 23.5° 2θ (±0.2° 2θ).

In certain embodiments, Edisylate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10 or Compound 11. In certain embodiments, Edisylate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form B, Edisylate Salt Form C, Tosylate Salt Form A or Tosylate Salt Form B. In further embodiments, Edisylate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Edisylate Salt Form A is substantially pure. In certain embodiments, the substantially pure Edisylate Salt Form A is substantially free of other solid forms, including but not limited to amorphous solid. In certain embodiments, the purity of the substantially pure Edisylate Salt Form A is no less than about 95%, no less than about 96%, no less than about 97%, no less than about 98%, no less than about 98.5%, no less than about 99%, no less than about 99.5%, or no less than about 99.8%.

(ii) Edisylate Salt Form B

In one embodiment, the solid form of Compound 10 is Edisylate Salt Form B. In one embodiment, Edisylate Salt Form B is crystalline. In one embodiment, Edisylate Salt Form B is hydrated and solvated by methyl isobutyl ketone.

In certain embodiments, provided herein are methods for making Edisylate Salt Form B, comprising 1) dispensing methyl isobutyl ketone (e.g., about 250 µL) into a vial containing an amount of Compound 1 (e.g., about 20 mg); 2) adding a stoichiometric amount (e.g., 1.0 equivalent) of a 3 M solution of ethane-1,2-disulfonic acid in water to the vial; 3) cycling the temperature (e.g., between about 5° C.

and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in methyl isobutyl ketone, followed by temperature cycling (e.g., between about 5° C. and about 40° C.; 1° C. per minute heating/cooling rate with an hour hold between each heating/cooling cycle) of the solution for a period of time (e.g., about a day), and equilibrating the solution to a temperature (e.g., 20° C.) for a period of time (e.g., about one hour) at the end of temperature cycling; 7) optionally heating the solution to a temperature (e.g., 40° C.) for a period of time (e.g., three hours); 8) cooling the solution to a temperature (e.g., 5° C.) and holding the solution at the temperature for a period of time (e.g., for one day); and 9) equilibrating the solution to a temperature (e.g., 20° C.) and evaporating the solvent slowly at room temperature to yield Edisylate Salt Form B of Compound 10. In certain embodiments, the solution is evaporated under reduced pressure in a centrifuge evaporator. In certain other embodiments, the solution is evaporated under a slow bleed of inert gas such as nitrogen or argon gas.

Figure 81:
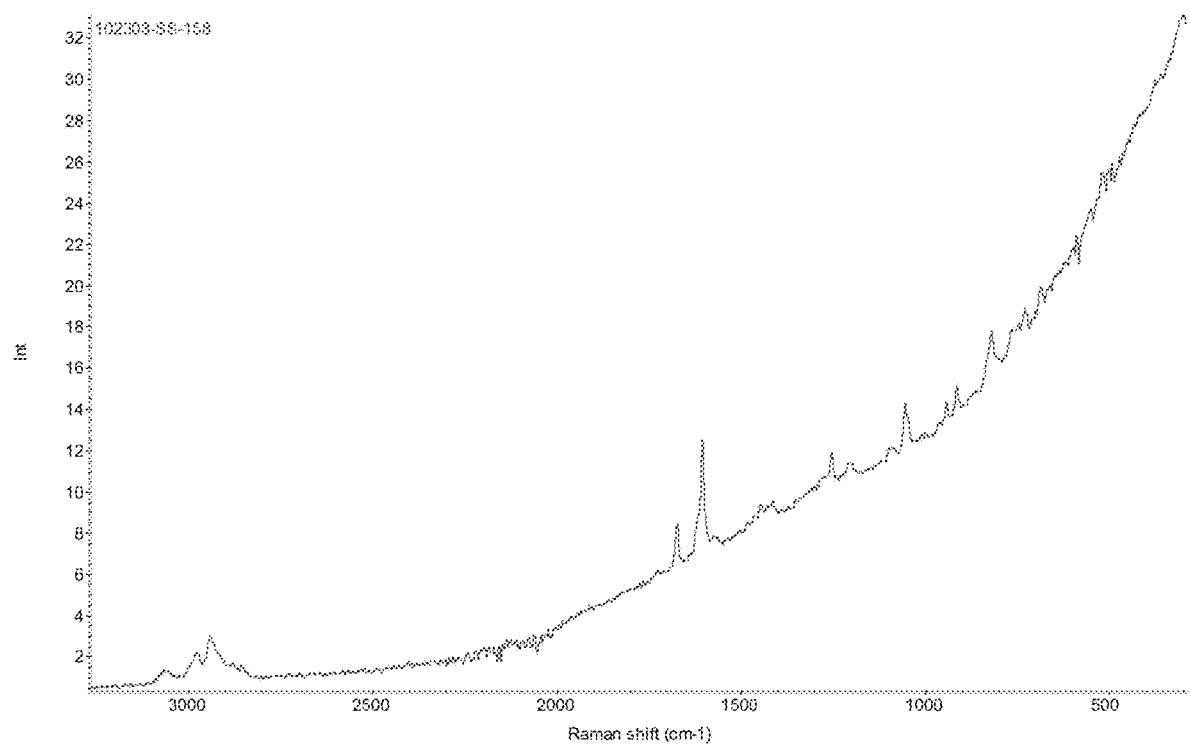
FIG. 81 depicts an FT-Raman spectrum of Edisylate Salt Form B of Compound 10.

In one embodiment, provided herein is Edisylate Salt Form B having an FT-Raman Spectrum as depicted in FIG. 81.

Figure 82:
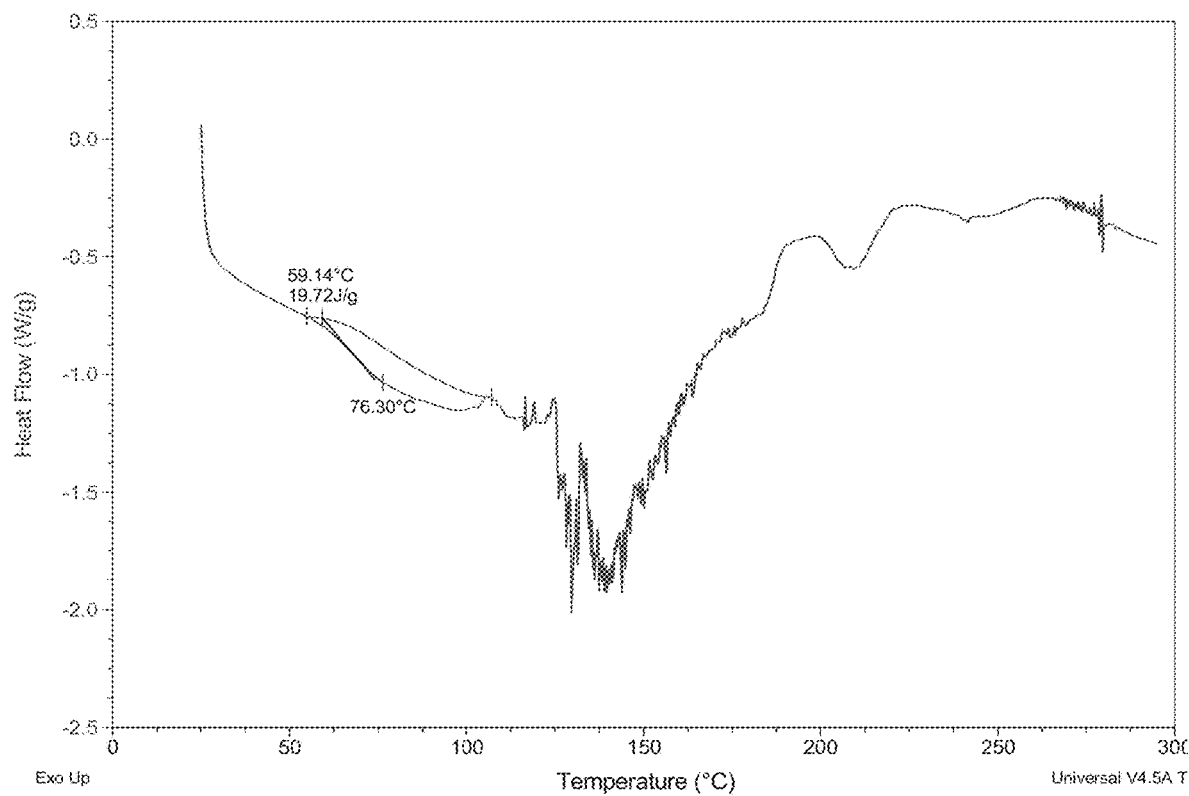
FIG. 82 depicts differential scanning calorimetry/thermal gravimetric analysis of Edisylate Salt Form B of Compound 10.

In one embodiment, provided herein is a solid form of Compound 10, e.g., Edisylate Salt Form B of Compound 10, having a DSC thermogram substantially as depicted in FIG. 82 comprising a broad endotherm between 50° C. and 106° C. with an onset temperature at 59.1° C.

Figure 80:
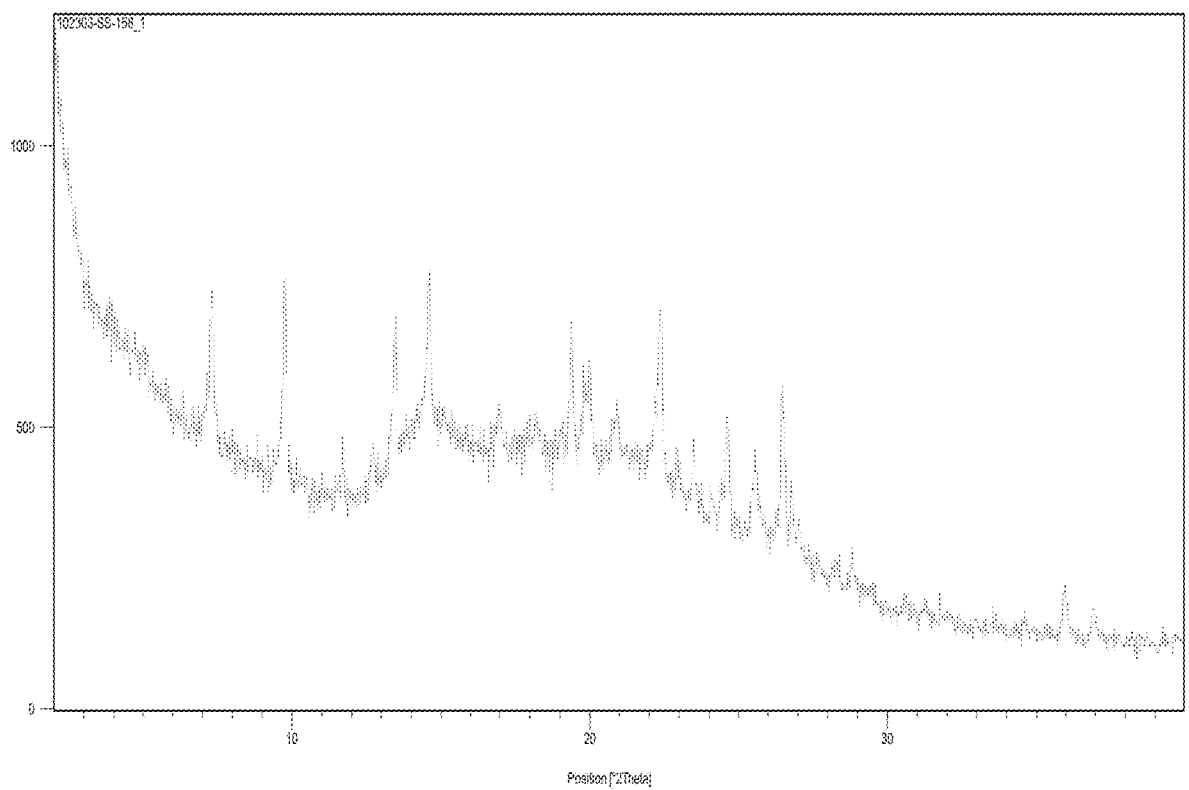
FIG. 80 depicts a PXRD pattern of Edisylate Salt Form B of Compound 10.

In certain embodiments, a solid form of Compound 10 provided herein, e.g., Edisylate Salt Form B, is substantially crystalline, as indicated by, e.g., X-ray powder diffraction measurements. In one embodiment, provided herein is a solid form of Compound 10 having an X-ray powder diffraction pattern (XRPD) substantially as shown in FIG. 80 (e.g., Edisylate Salt Form B). In one embodiment, a solid form of Compound 10 provided herein, e.g., Edisylate Salt Form B, has one or more characteristic X-ray powder diffraction peaks at approximately 7.3, 9.8, 11.7, 12.7, 13.5, 14.6, 17.0, 19.4, 20.0, 20.9, 22.4, 22.9, 23.5, 24.6, 25.6, 26.5, 26.8, 28.8, 36.0, or 36.9° 2θ (±0.2° 2θ) or (±0.1° 2θ) as depicted in FIG. 80. In a specific embodiment, a solid form of Compound 10 provided herein, e.g., Edisylate Salt Form B, has one, two, three, four, five or six characteristic X-ray powder diffraction peaks at approximately 7.3, 9.8, 13.5, 14.6, 22.4, or 26.5° 2θ (±0.2° 2θ).

In certain embodiments, Edisylate Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10 or Compound 11. In certain embodiments, Edisylate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In further embodiments, Edisylate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Edisylate Salt Form B is substantially pure. In certain embodiments, the substantially pure Edisylate Salt Form B is substantially free of other solid forms, including but not limited to amorphous solid. In certain embodiments, the purity of the substantially pure Edisylate Salt Form B is no less than about 95%, no less than about 96%, no less than about 97%, no less than about 98%, no less than about 98.5%, no less than about 99%, no less than about 99.5%, or no less than about 99.8%.

(iii) Edisylate Salt Form C

In one embodiment, the solid form of Compound 10 is Edisylate Salt Form C. In one embodiment, Edisylate Salt Form C is crystalline. In one embodiment, Edisylate Salt Form C is hydrated.

In certain embodiments, provided herein are methods for making Edisylate Salt Form C, comprising 1) dispensing a solvent (e.g., about 250 μL) into a vial containing an amount of Compound 1 (e.g., about 20 mg); 2) adding a stoichiometric amount (e.g., 1.0 equivalent) of a 3 M solution of ethane-1,2-disulfonic acid in water to the vial; 3) cycling the temperature (e.g., between about 5° C. and about 40° C.; 1° C. per minute heating/cooling rate with an hour hold between each heating/cooling cycle) of the solution for a period of time (e.g., about a day); 4) equilibrating the solution to a temperature (e.g., 20° C.) for a period of time (e.g., about one hour); 5) evaporating the solution to dryness; 6) suspending the dried sample in the solvent, followed by temperature cycling (e.g., between about 5° C. and about 40° C.; 1° C. per minute heating/cooling rate with an hour hold between each heating/cooling cycle) of the solution for a period of time (e.g., about a day), and equilibrating the solution to a temperature (e.g., 20° C.) for a period of time (e.g., about one hour) at the end of temperature cycling; 7) optionally adding an anti-solvent (e.g., 1:3 v/v solvent to anti-solvent ratio) at a temperature (e.g., 40° C.); 8) optionally heating the solution to a temperature (e.g., 40° C.) for a period of time (e.g., three hours); 9) cooling the solution to a temperature (e.g., 5° C.) and holding the solution at the temperature for a period of time (e.g., for one day); and 10) equilibrating the solution to a temperature (e.g., 20° C.) and evaporating the solvent slowly at room temperature to yield Edisylate Salt Form C of Compound 10. In certain embodiments, the solution is evaporated under reduced pressure in a centrifuge evaporator. In certain other embodiments, the solution is evaporated under a slow bleed of inert gas such as nitrogen or argon gas. In certain embodiments, the solvent in step 1 is methyl tert-butyl ether and an anti-solvent in step 7 was not used. In certain embodiments, the solvent in step 1 is isopropyl acetate and the anti-solvent in step 7 is diisopropyl ether.

In certain embodiments, provided herein are methods for making Edisylate Salt Form C comprising 1) combining Compound 1 (e.g., 103.4 mg) with acetonitrile (e.g., about 1.25 mL) and ethane-1,2-disulfonic acid (e.g. about 1.0 equivalent of a 3 M solution in water); 2) heating the resulting mixture to a temperature (e.g., about 40° C.) for a period of time (e.g., about one hour); 3) adding seeds of crystalline edisylate salt of Compound 1 (e.g., about 1 mg); 4) cycling the temperature (e.g., between about 5° C. and about 40° C.; 1° C. per minute heating/cooling rate with an hour hold between each heating/cooling cycle) for a period of time (e.g., about two days); 5) isolating solids from the sample via vacuum filtration; 6) air-drying the solids for a period of time (e.g., 90 minutes) and drying in a vacuum oven at a temperature (e.g., 40° C.) for a period of time (e.g., 5 hours) to yield Edisylate Salt Form C of Compound 10.

Figure 85:
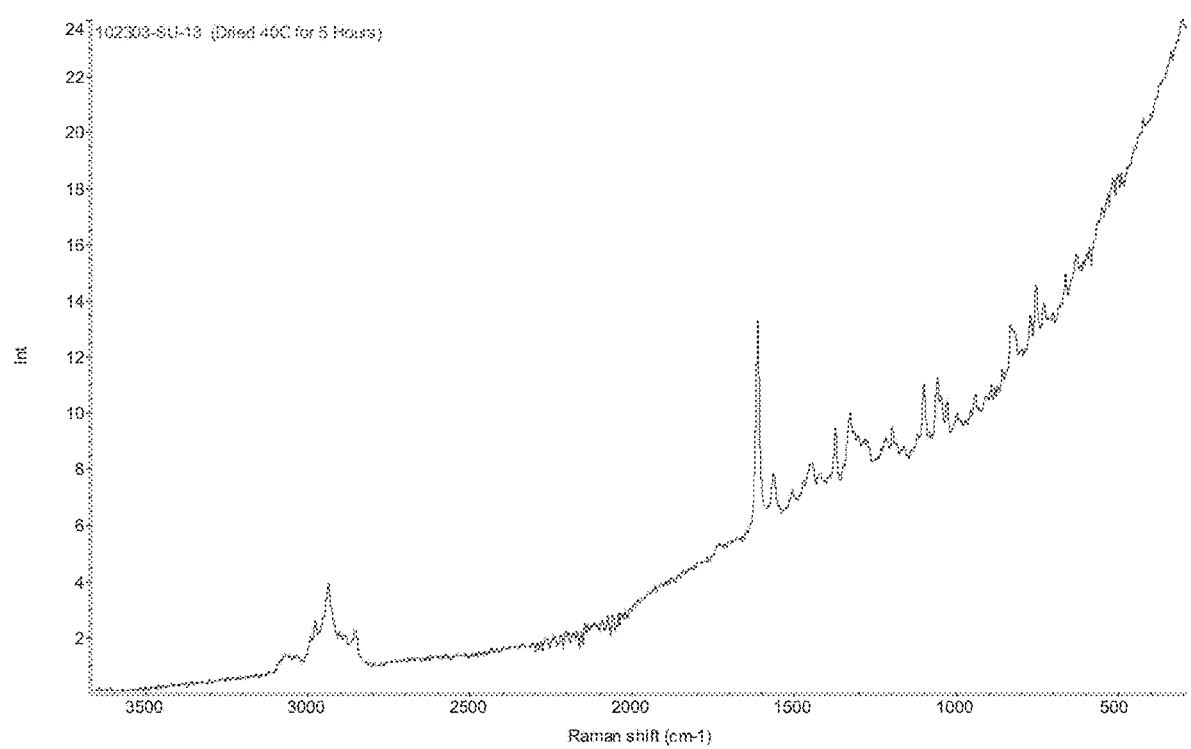
FIG. 85 depicts an FT-Raman spectrum of Edisylate Salt Form C of Compound 10.

In one embodiment, provided herein is Edisylate Salt Form C having an FT-Raman Spectrum as depicted in FIG. 85.

Figure 86:
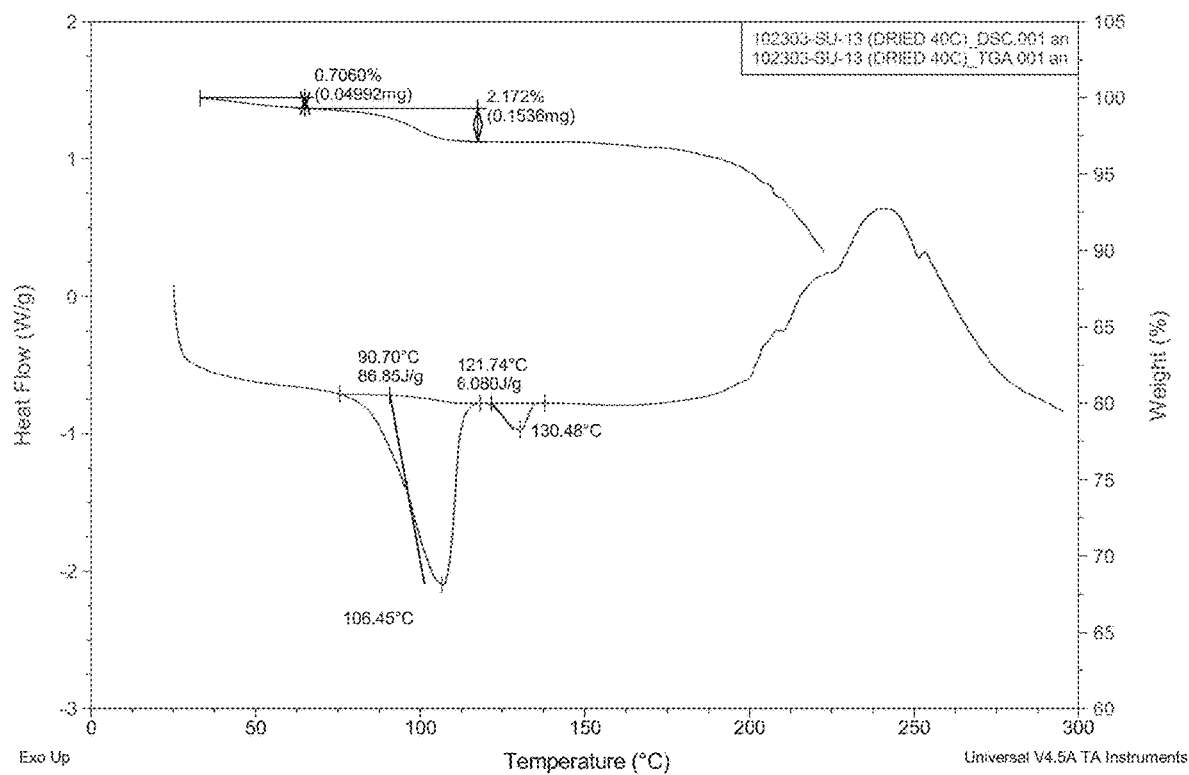
FIG. 86 depicts differential scanning calorimetry/thermal gravimetric analysis of Edisylate Salt Form C of Compound 10.

In one embodiment, provided herein is a solid form of Compound 10, e.g., Edisylate Salt Form C of Compound 10, having a DSC thermogram substantially as depicted in FIG. 86 comprising multiple endotherms with onset temperatures at 90.7° C. and 121.7° C., respectively.

In one embodiment, provided herein is a solid form of Compound 10, e.g., Edisylate Salt Form C of Compound 10, having a TGA thermogram corresponding substantially to the representative TGA thermogram as depicted in FIG. 86. In certain embodiments, the crystalline form exhibits a TGA thermogram comprising a total mass loss of approximately 2.9% of the total mass of the sample when heated from approximately 25° C. to approximately 118° C.

Figure 84:
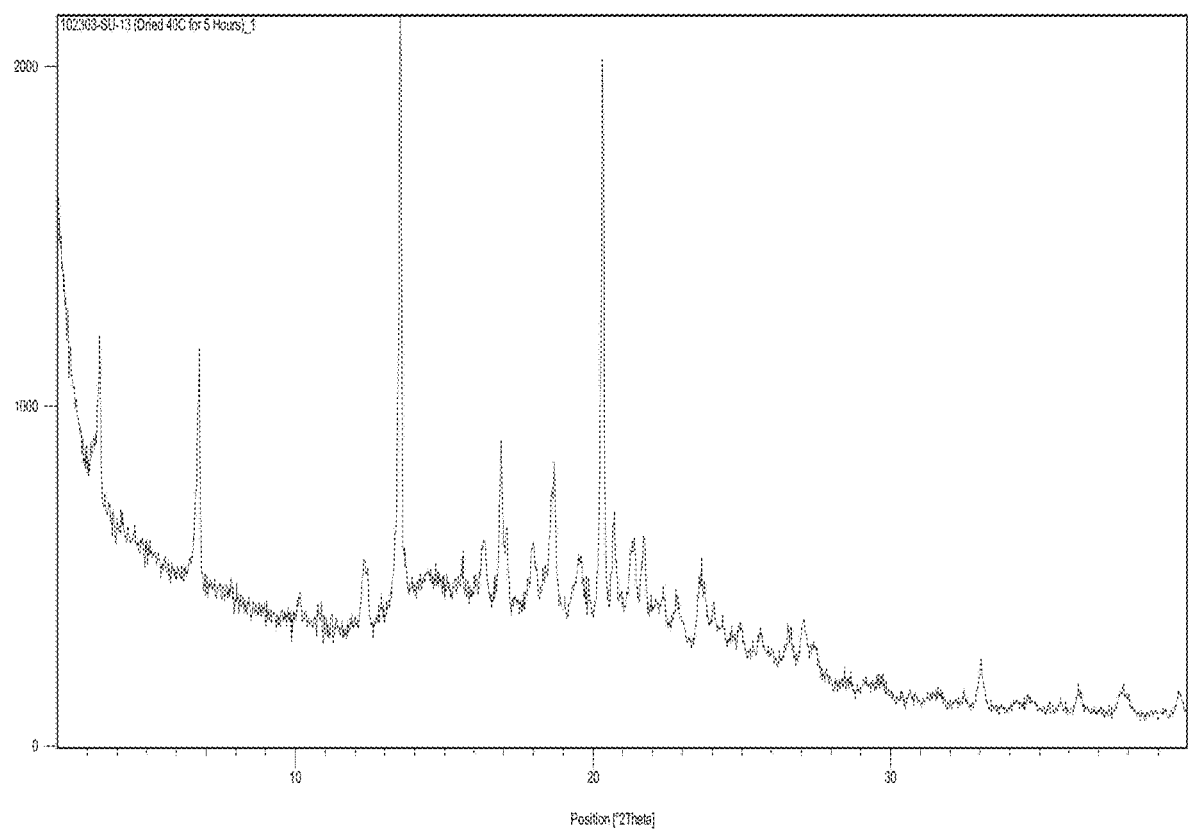
FIG. 84 depicts a PXRD pattern of Edisylate Salt Form C of Compound 10.

In certain embodiments, a solid form of Compound 10 provided herein, e.g., Edisylate Salt Form C, is substantially crystalline, as indicated by, e.g., X-ray powder diffraction measurements. In one embodiment, provided herein is a solid form of Compound 10 having an X-ray powder diffraction pattern (XRPD) substantially as shown in FIG. 84 (e.g., Edisylate Salt Form C). In one embodiment, a solid form of Compound 10 provided herein, e.g., Edisylate Salt Form C, has one or more characteristic X-ray powder diffraction peaks at approximately 3.4, 6.8, 12.3, 13.5, 16.3, 16.9, 18.0, 18.7, 19.5, 20.3, 20.7, 21.4, 21.7, 22.8, 23.6, 26.6, 27.1, 33.0, 36.3, or 37.8° 2θ (±0.2° 2θ) or (±0.1° 2θ) as depicted in FIG. 84. In a specific embodiment, a solid form of Compound 10 provided herein, e.g., Edisylate Salt Form C, has one, two, three, four, or five characteristic X-ray powder diffraction peaks at approximately 3.4, 6.8, 13.5, 16.9, or 20.3° 2θ (±0.2° 2θ).

In certain embodiments, Edisylate Salt Form C is mixed with other solid forms, including but not limited to an amorphous solid of Compound 1, Compound 2, Compound 3, Compound 4, Compound 5, Compound 6, Compound 7, Compound 8, Compound 9, Compound 10 or Compound 11. In certain embodiments, Edisylate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Tosylate Salt Form A, or Tosylate Salt Form B. In further embodiments, Edisylate Salt Form C is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Edisylate Salt Form C is substantially pure. In certain embodiments, the substantially pure Edisylate Salt Form C is substantially free of other solid forms, including but not limited to amorphous solid. In certain embodiments, the purity of the substantially pure Edisylate Salt Form C is no less than about 95%, no less than about 96%, no less than about 97%, no less than about 98%, no less than about 98.5%, no less than about 99%, no less than about 99.5%, or no less than about 99.8%.

(k) Solid Forms of Compound 11

In one embodiment, provided herein is a solid form of Compound 11.

(i) Tosylate Salt Form A

In one embodiment, the solid form of Compound 11 is Tosylate Salt Form A. In one embodiment, Tosylate Salt Form A is crystalline.

In certain embodiments, provided herein are methods for making Tosylate Salt Form A, comprising 1) dispensing a solution of Compound 1 in a solvent (e.g., a solution of about 126.25 mg/mL of Compound 1 in the solvent) into a vial 2) adding a stoichiometric amount (e.g., 1.0 equivalent) of a 0.225 M solution of p-toluenesulfonic acid in acetonitrile to the vial; 3) capping and shaking the vials at a frequency (e.g., about 200 rotations per minute) at a temperature (e.g., ambient temperature) for a period of time (e.g., about an hour); 4) uncapping and drying the sample under nitrogen purge; 5) mixing the sample with an amount of the solvent (e.g., about 600 µL); 6) recapping and stirring the sample at a temperature (e.g., ambient temperature) for a period of time (e.g., about two days); 7) filtering the sample using Nylon-membrane centrifuge tube filters; 8) recovering the solids and drying in a vacuum oven at a temperature (e.g. 30° C.) overnight to yield Tosylate Salt Form A of Compound 11. In certain embodiments, the solution is evaporated under reduced pressure in a centrifuge evaporator. In certain embodiments, the solvent used in step 1 is acetone. In certain embodiments, the solvent used in step 5 is isopropanol or isopropyl acetate.

Figure 89:
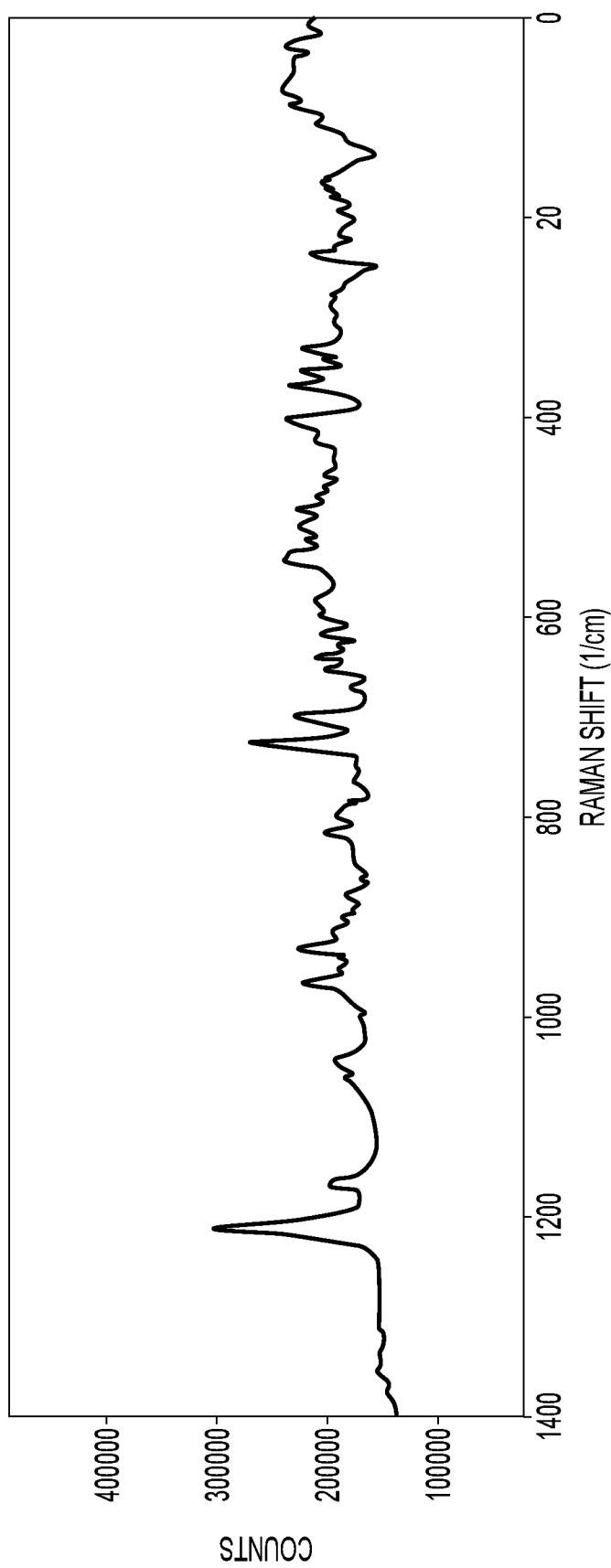
FIG. 89 depicts an FT-Raman spectrum of Tosylate Salt Form A of Compound 11.

In one embodiment, provided herein is Tosylate Salt Form A of Compound 11 having an FT-Raman Spectrum as depicted in FIG. 89.

Figure 90:
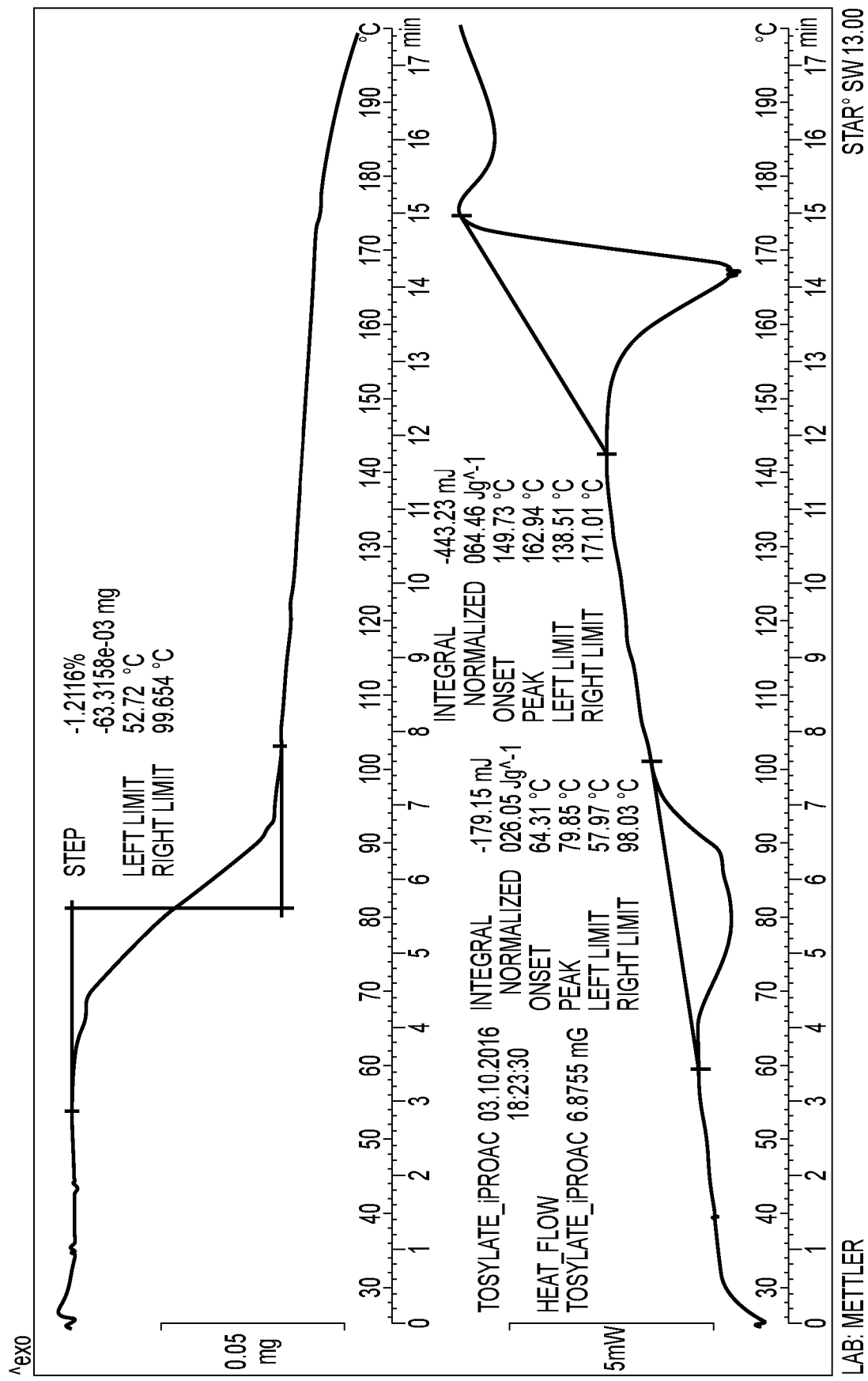
FIG. 90 depicts differential scanning calorimetry/thermal gravimetric analysis of Tosylate Salt Form A of Compound 11.

In one embodiment, provided herein is a solid form of Compound 11, e.g., Tosylate Salt Form A of Compound 11, having a DSC thermogram substantially as depicted in FIG. 90 comprising multiple endotherms with onset temperatures at 64.3° C. and 149.7° C., respectively.

In one embodiment, provided herein is a solid form of Compound 11, e.g., Tosylate Salt Form A of Compound 11, having a TGA thermogram corresponding substantially to the representative TGA thermogram as depicted in FIG. 90. In certain embodiments, the crystalline form exhibits a TGA thermogram comprising a total mass loss of approximately 1.21% of the total mass of the sample when heated from approximately 52.7° C. to approximately 99.6° C.

Figure 88:
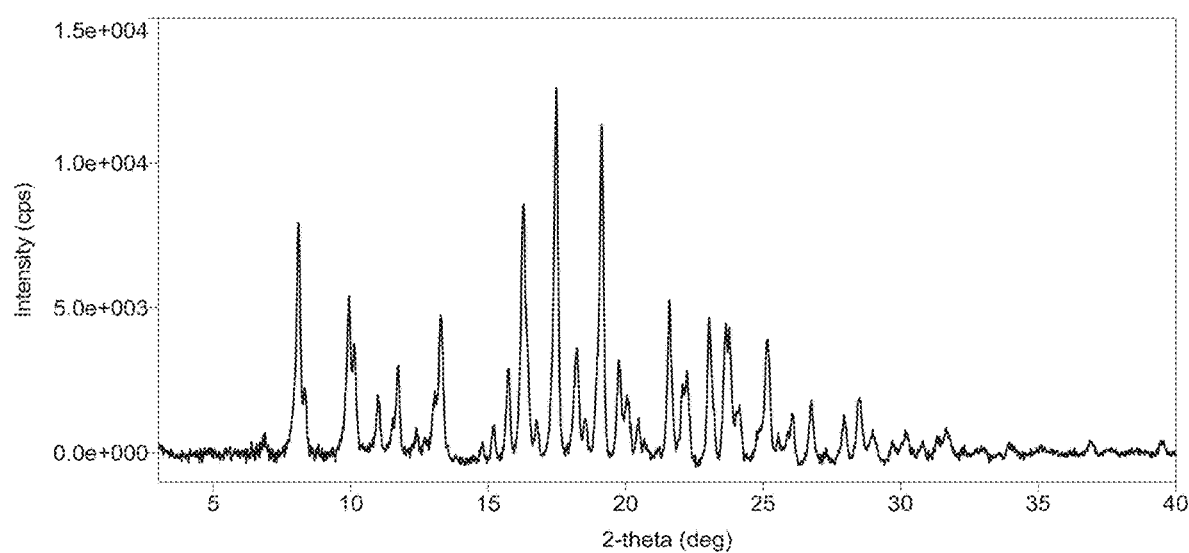
FIG. 88 depicts a PXRD pattern of Tosylate Salt Form A of Compound 11.

In certain embodiments, a solid form of Compound 11 provided herein, e.g., Tosylate Salt Form A, is substantially crystalline, as indicated by, e.g., X-ray powder diffraction measurements. In one embodiment, provided herein is a solid form of Compound 11 having an X-ray powder diffraction pattern (XRPD) substantially as shown in FIG. 88 (e.g., Tosylate Salt Form A). In one embodiment, a solid form of Compound 11 provided herein, e.g., Tosylate Salt Form A, has one or more characteristic X-ray powder diffraction peaks at approximately 6.9, 8.1, 8.3, 9.9, 10.2, 11.0, 11.7, 13.3, 15.8, 16.3, 17.5, 18.2, 19.1, 19.8, 20.1, 21.6, 22.0, 22.2, 23.0, 23.6, 25.2° 2θ (±0.2° 2θ) or (±0.1° 2θ) as depicted in FIG. 88. In a specific embodiment, a solid form of Compound 11 provided herein, e.g., Tosylate Salt Form A, has one, two, three, four, five, six, or seven characteristic X-ray powder diffraction peaks at approximately 8.1, 9.9, 13.3, 16.3, 17.5, 19.1, or 21.6° 2θ (±0.2° 2θ).

In certain embodiments, Tosylate Salt Form A is mixed with other solid forms, including but not limited to an amorphous solid of Compound 1, Compound 2, Compound 3, Compound 4, Compound 5, Compound 6, Compound 7, Compound 8, Compound 9, Compound 10 or Compound 11. In certain embodiments, Tosylate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C or Tosylate Salt Form B. In further embodiments, Tosylate Salt Form A is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment. Tosylate Salt Form A is substantially pure. In certain embodiments, the substantially pure Tosylate Salt Form A is substantially free of other solid forms, including but not limited to amorphous solid. In certain embodiments, the purity of the substantially pure Tosylate Salt Form A is no less than about 95%, no less than about 96%, no less than about 97%, no less than about 98%, no less than about 98.5%, no less than about 99%, no less than about 99.5%, or no less than about 99.8%.

(ii) Tosylate Salt Form B

In one embodiment, the solid form of Compound 11 is Tosylate Salt Form B. In one embodiment, Tosylate Salt Form B is crystalline.

In certain embodiments, provided herein are methods for making Tosylate Salt Form B, comprising 1) dispensing a solution of Compound 1 in a solvent (e.g., a solution of about 126.25 mg/mL of Compound 1 in the solvent) into a vial; 2) adding a stoichiometric amount (e.g., 1.0 equivalent) of a 0.225 M solution of p-toluenesulfonic acid in acetonitrile to the vial; 3) capping and shaking the vials at a frequency (e.g., about 200 rotations per minute) and at a temperature (e.g., ambient temperature) for a period of time (e.g., about an hour); 4) uncapping and drying the sample under nitrogen purge: 5) mixing the sample with an amount of a solvent or solvent system (e.g., about 600 μL); 6) recapping and stirring the sample at a temperature (e.g., ambient temperature) for a period of time (e.g., about two days); 7) filtering the sample using Nylon-membrane centrifuge tube filters; 8) recovering the solids an drying in a vacuum oven at a temperature (e.g., 30° C.) overnight to yield Tosylate Salt Form B of Compound 11. In certain embodiments, the solution is evaporated under reduced pressure in a centrifuge evaporator. In certain embodiments, the solvent used in step 1 is acetone. In certain embodiments, the solvent or solvent system used in step 5 is a 95:5 v/v mixture of acetone/water.

Figure 92:
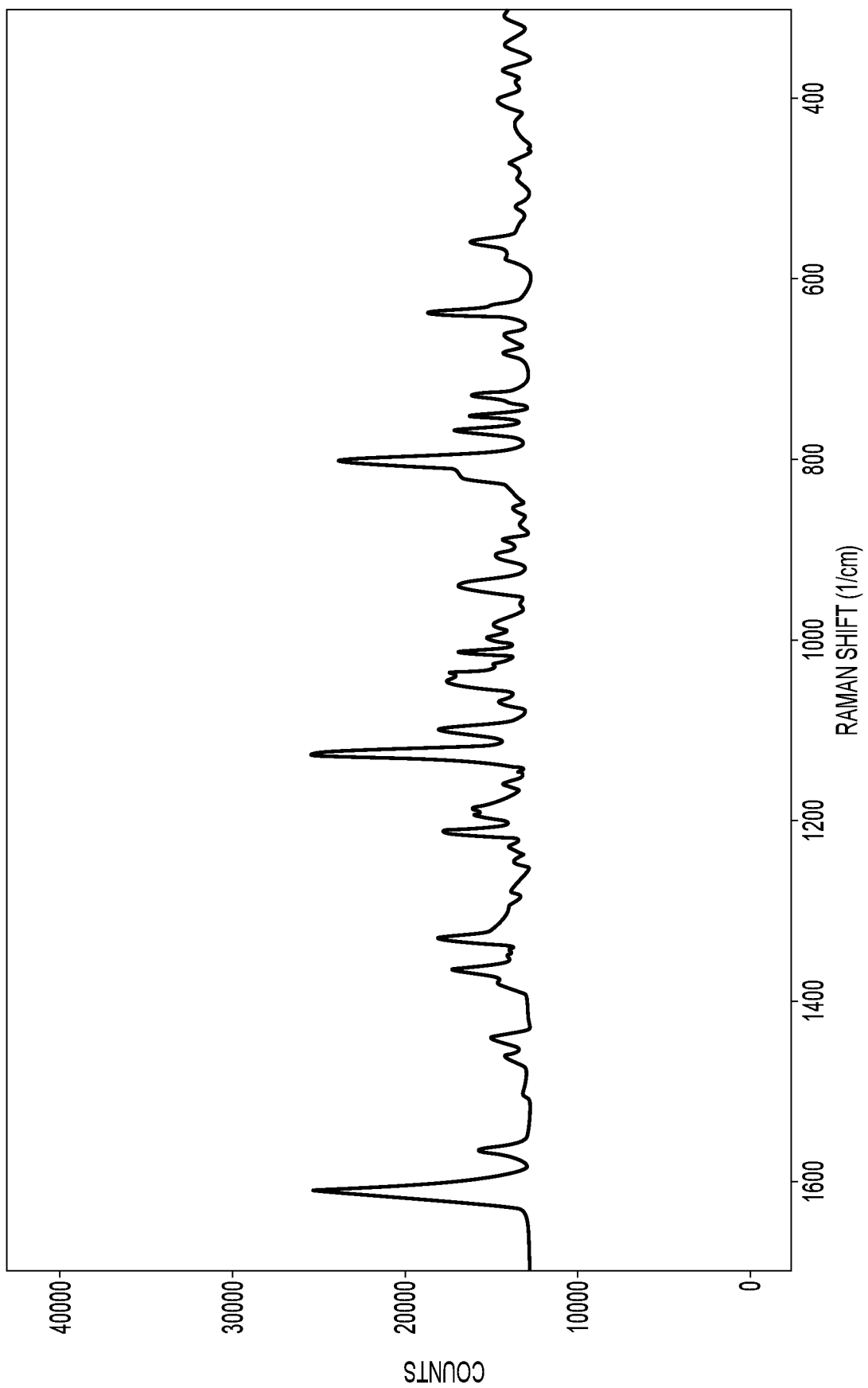
FIG. 92 depicts an FT-Raman spectrum of Tosylate Salt Form B of Compound 11.

In one embodiment, provided herein is Tosylate Salt Form B of Compound 11 having an FT-Raman Spectrum as depicted in FIG. 92.

Figure 93:
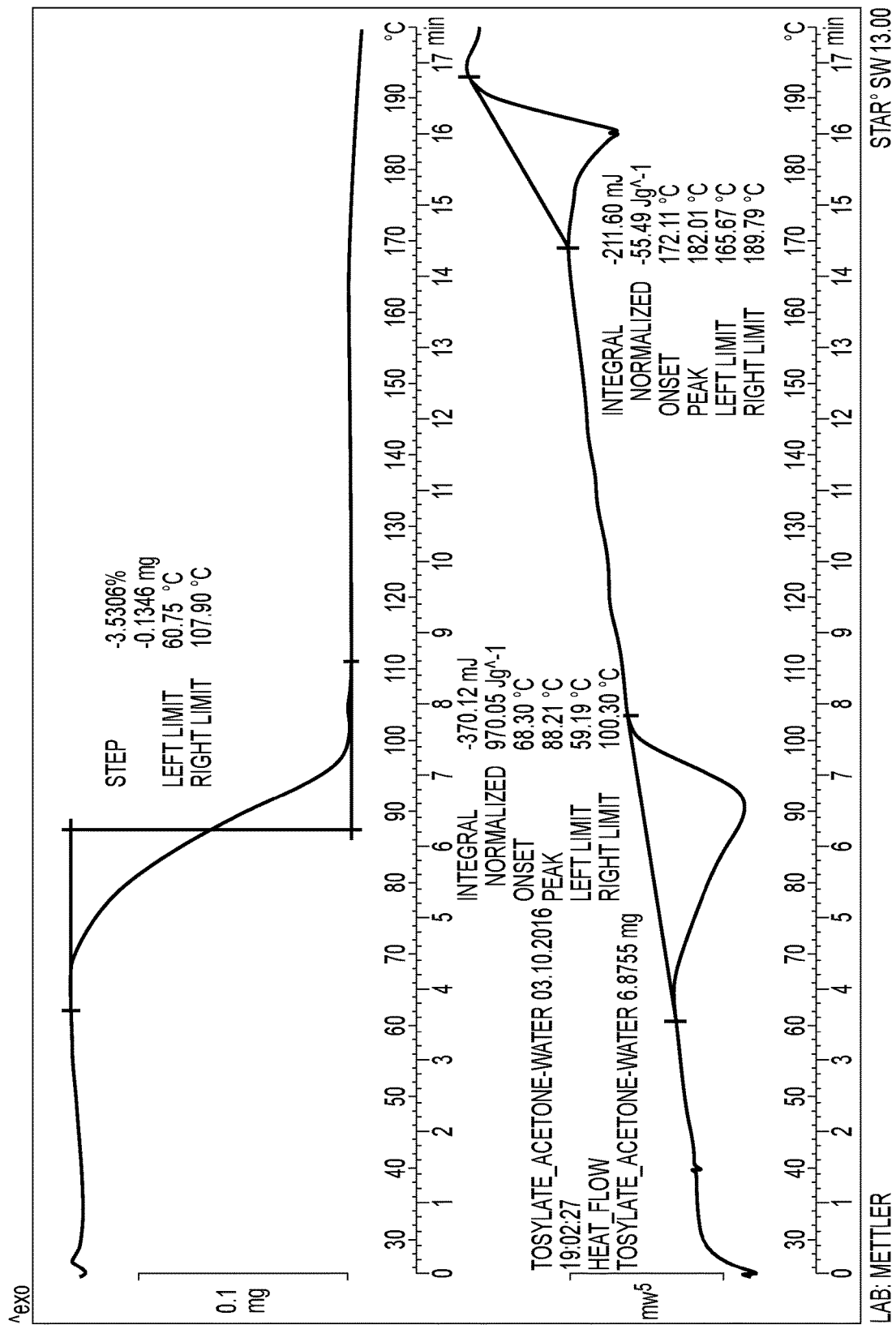
FIG. 93 depicts differential scanning calorimetry/thermal gravimetric analysis of Tosylate Salt Form B of Compound 11.

In one embodiment, provided herein is a solid form of Compound 11, e.g., Tosylate Salt Form B of Compound 11, having a DSC thermogram substantially as depicted in FIG. 93 comprising multiple endotherms with onset temperatures at 68.3° C. and 172.11° C., respectively.

In one embodiment, provided herein is a solid form of Compound 11, e.g., Tosylate Salt Form B of Compound 11, having a TGA thermogram corresponding substantially to the representative TGA thermogram as depicted in FIG. 93. In certain embodiments, the crystalline form exhibits a TGA thermogram comprising a total mass loss of approximately 3.53% of the total mass of the sample when heated from approximately 60.8° C. to approximately 107.9° C.

Figure 91:
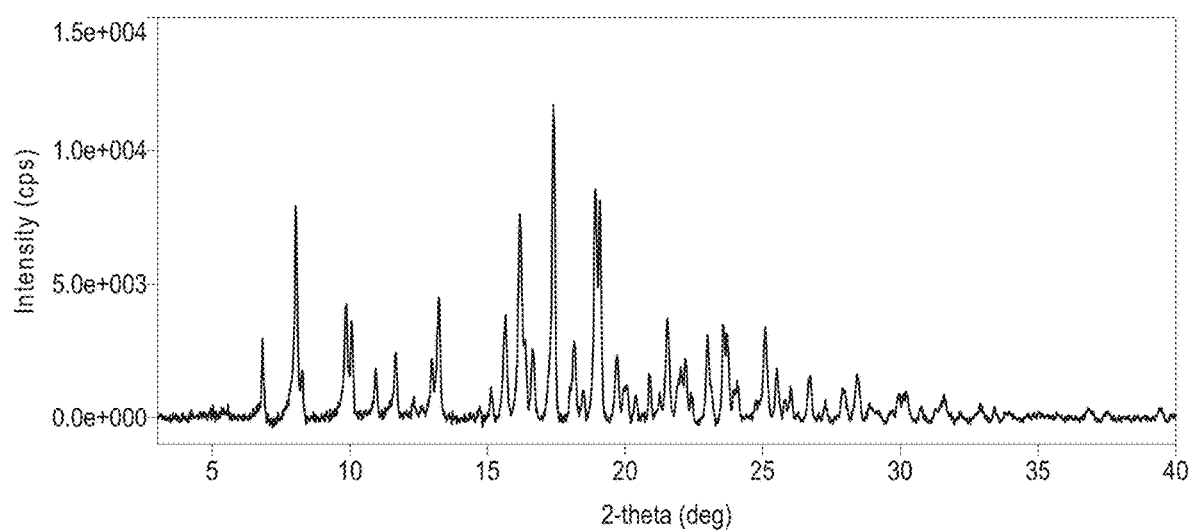
FIG. 91 depicts a PXRD pattern of Tosylate Salt Form B of Compound 11.

In certain embodiments, a solid form of Compound 11 provided herein, e.g., is Tosylate Salt Form B, is substantially crystalline, as indicated by, e.g., X-ray powder diffraction measurements. In one embodiment, provided herein is a solid form of Compound 11 having an X-ray powder diffraction pattern (XRPD) substantially as shown in FIG. 91 (e.g., Tosylate Salt Form B). In one embodiment, a solid form of Compound 11 provided herein, e.g., Tosylate Salt Form B, has one or more characteristic X-ray powder diffraction peaks at approximately 6.8, 8.0, 8.3, 9.8, 10.1, 10.9, 11.7, 13.2, 15.7, 16.2, 16.4, 16.6, 17.4, 18.2, 18.9, 19.1, 19.7, 20.9, 21.3, 21.5, 22.2, 22.4, 23.5, 25.1° 2θ (±0.2° 2θ) or (±0.1° 2θ) as depicted in FIG. 91. In a specific embodiment, a solid form of Compound 11 provided herein, e.g., Tosylate Salt Form B, has one, two, three, four, five, six, seven, eight, or nine characteristic X-ray powder diffraction peaks at approximately 6.8, 8.0, 9.8, 16.2, 17.4, 18.9, 19.1, 20.9, or 21.3° 2θ (±0.2° 2θ).

In certain embodiments, Tosylate Salt Form B is mixed with other solid forms, including but not limited to an amorphous solid of Compound 1, Compound 2, Compound 3, Compound 4, Compound 5, Compound 6, Compound 7, Compound 8, Compound 9, Compound 10 or Compound 11. In certain embodiments, Tosylate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C or Tosylate Salt Form A. In further embodiments, Tosylate Salt Form B is mixed with at least one of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form B, L-Tartrate Salt Form C, L-Tartrate Salt Form D, Hemifumarate Salt Form A, Hemifumarate Salt Form B, Hemifumarate Salt Form C, Hemifumarate Salt Form D, Hemifumarate Salt Form E, Hemifumarate Salt Form F, Hemifumarate Salt Form G, Hemifumarate Salt Form H, HBr Salt Form A, HBr Salt Form B, Maleate Salt Form A, Maleate Salt Form B, Maleate Salt Form C, Maleate Salt Form D, Maleate Salt Form E, Maleate Salt Form F, Maleate Salt Form G, Malonate Salt Form A, Edisylate Salt Form A, Edisylate Salt Form B, Edisylate Salt Form C, Tosylate Salt Form A or Tosylate Salt Form B.

In still another embodiment, Tosylate Salt Form B is substantially pure. In certain embodiments, the substantially pure Tosylate Salt Form B is substantially free of other solid forms, including but not limited to amorphous solid. In certain embodiments, the purity of the substantially pure Tosylate Salt Form B is no less than about 95%, no less than about 96%, no less than about 97%, no less than about 98%, no less than about 98.5%, no less than about 99%, no less than about 99.5%, or no less than about 99.8%.

5.4 Methods of Use

The solid forms and the pharmaceutical compositions comprising a Compound disclosed herein (e.g., Compound 1, Compound 2, Compound 3, Compound 4, Compound 5, Compound 6, Compound 7, Compound 8, Compound 9, Compound 10, Compound 11), or tautomers thereof, can be used in all the methods provided herein. The solid forms and the pharmaceutical compositions comprising a Compound disclosed herein, or a tautomer thereof, can be used in the treatment of all diseases, disorders or conditions provided herein.

Provided herein are methods for treating a subject suffering from or at risk for having an autoimmune disease or chronic inflammatory disorder, wherein the method comprises administering to said subject a solid form comprising a Compound disclosed herein, or a tautomer thereof, provided herein or a pharmaceutical composition thereof. In certain embodiments, the autoimmune or chronic inflammatory disorder is polymyositis, dermatomyositis, lupus nephritis, rheumatoid arthritis, Crohn's disease, ulcerative colitis, psoriasis, amyotrophic lateral sclerosis, autoimmune myositis, systemic lupus, Type 1 diabetes, biliary cirrhosis, bullous pemphigoid, sarcoidosis, Wegener's granulomatosis, ichthyosis, Graves' disease, or multiple sclerosis. In a preferred embodiment, the multiple sclerosis is relapsing-remitting multiple sclerosis, primary progressive multiple sclerosis, secondary progressive multiple sclerosis, or relapsing secondary progressive multiple sclerosis. In one embodiment, the solid form is selected from the group consisting of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In a further embodiment, the solid form is selected from the group consisting of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, or L-Tartrate Salt Form D.

In another embodiment, provided herein are methods for treating a subject suffering from or at risk for having a neurological disorder, wherein the method comprises administering to said subject a solid form comprising a Compound disclosed herein, or a tautomer thereof, provided herein or a pharmaceutical composition thereof. In one embodiment, the neurological disorder is Rett Syndrome. In one embodiment, the solid form is selected from the group consisting of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In a further embodiment, the solid form is selected from the group consisting of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, or L-Tartrate Salt Form D. In another embodiment, provided herein are methods for treating a subject suffering from or at risk for renal or hepatic impairment, wherein the method comprises administering to said subject a solid form comprising a Compound disclosed herein, or a tautomer thereof, provided herein or a pharmaceutical composition thereof. In one embodiment, the solid form is selected from the group consisting HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In a further embodiment, the solid form is selected from the group consisting of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, or L-Tartrate Salt Form D.

In another embodiment, provided herein are methods for treating a subject suffering from or at risk for a disease or disorder mediated by lymphocyte interactions, wherein the method comprises administering to said subject a solid form comprising a Compound disclosed herein, or a tautomer thereof, provided herein or a pharmaceutical composition thereof. In certain embodiments, the disease or disorder mediated by lymphocyte interactions is, for example, in transplantation, acute or chronic rejection of cell, tissue or organ allo- or xenografts or delayed graft function, graft versus host disease; autoimmune diseases, e.g., rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others; allergic diseases, e.g., allergic asthma, atopic dermatitis, allergic rhinitis/conjunctivitis, allergic contact dermatitis; inflammatory diseases optionally with underlying aberrant reactions, e.g., inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, inflammatory myopathy; myocarditis or hepatitis; ischemia/reperfusion injury, e.g., myocardial infarction, stroke, gut ischemia, renal failure or hemorrhage shock, traumatic shock; T cell lymphomas or T cell leukemias; infectious diseases, e.g., toxic shock (e.g., superantigen induced), septic shock, adult respiratory distress syndrome or viral infections, e.g., AIDS, viral hepatitis, chronic bacterial infection; muscle diseases, e.g., polymyositis; or senile dementia. Examples of cell, tissue or solid organ transplants include, e.g., pancreatic islets, stem cells, bone marrow, corneal tissue, neuronal tissue, heart, lung, combined heart-lung, kidney, liver, bowel, pancreas, trachea or oesophagus. In one embodiment, the solid form is selected from the group consisting of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In a further embodiment, the solid form is selected from the group consisting of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, or L-Tartrate Salt Form D.

In another embodiment, provided herein are methods for the treatment of a disease or disorder associated with sphingosine 1-phosphate, wherein the method comprises administering to said subject a solid form comprising a Compound disclosed herein, or a tautomer thereof, provided herein or a pharmaceutical composition thereof. In certain embodiments, the disease or disorder associated with sphingosine 1-phosphate is multiple sclerosis, relapse-remitting multiple sclerosis, systemic lupus, Type 1 diabetes, amyotrophic lateral sclerosis, refractory rheumatoid arthritis, inflammatory bowel disease, biliary cirrhosis, Crohn's disease, ulcerative colitis, bullous pemphigoid, sarcoidosis, psoriasis, autoimmune myositis, Wegener's granulomatosis, ichthyosis, or Graves' disease. In one embodiment, the solid form is selected from the group consisting of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In a further embodiment, the solid form is selected from the group consisting of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, or L-Tartrate Salt Form D.

In another embodiment, provided herein are methods for the treatment of a disease or disorder associated with the interferon alpha receptor 1, wherein the method comprises administering to said subject a solid form comprising a Compound disclosed herein, or a tautomer thereof, or a pharmaceutical composition thereof. In certain embodiments, the disease or disorder associated with the interferon alpha receptor is psoriasis, ulcerative colitis, systemic lupus, multiple sclerosis, or rheumatoid arthritis. In one embodiment, the solid form is selected from the group consisting of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B. In a further embodiment, the solid form is selected from the group consisting of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, or L-Tartrate Salt Form D.

The compounds, compositions, methods, and uses disclosed herein are not to be limited in scope by the specific embodiments described herein. Indeed, various modifications of the compounds, compositions, methods, and uses in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entities.

5.5 Pharmaceutical Compositions

Solid forms comprising a Compound disclosed herein (e.g., Compound 1, Compound 2, Compound 3, Compound 4, Compound 5, Compound 6, Compound 7, Compound 8, Compound 9, Compound 10, Compound 11), or a tautomer thereof, provided herein are useful for the preparation of pharmaceutical compositions, comprising an effective amount of a solid form comprising a Compound disclosed herein, or a tautomer thereof, and a pharmaceutically acceptable vehicle, carrier, diluent, or excipient, or a mixture thereof. In certain embodiments, the pharmaceutically acceptable carrier is hydroxypropyl methylcellulose. In some embodiments, the pharmaceutical compositions described herein are suitable for oral, parenteral, mucosal, transdermal or topical administration.

5.6 Oral Administration

The pharmaceutical compositions provided herein may be administered orally, for example in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, the pharmaceutically acceptable carrier or excipient is selected from the group consisting of lactose (e.g., as lactose monohydrate); microcrystalline cellulose; non-basic polymers (e.g., homopolymers of cross-linked N-vinyl-2-pyrrolidone (crospovidone), hypromellose (hydroxypropylmethyl cellulose), and ethyl cellulose); waxes; colloidal silicon dioxide; stearic acid; hydrogenated vegetable oil; mineral oil; polyethylene glycol (e.g., polyethylene glycol 4000-6000); glyceryl palmitostearate; and glyceryl behenate. In another embodiment, the pharmaceutically acceptable carrier or excipient is microcrystalline cellulose.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL® (Cabot Co. of Boston, MA); and mixtures thereof. The pharmaceutical compositions provided herein may contain about 0.1% to about 5% by weight of a lubricant.

Suitable glidants include, but are not limited to, colloidal silicon dioxide, CAB-O-SIL® (Cabot Co. of Boston, MA), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and L-tartaric acid. Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

In certain embodiments, pharmaceutical compositions provided herein for oral administration comprise 10 mg or less of a solid form comprising a Compound disclosed herein, 7.5 mg or less of a solid form of the compound, or 5 mg or less of a solid form comprising the compound. In certain embodiments, pharmaceutical compositions provided herein for oral administration comprise 0.1 mg or more of a solid form comprising a Compound disclosed herein, 0.2 mg or more of a solid form comprising the Compound, or 0.25 mg or more of a solid form comprising the compound. In certain embodiments, pharmaceutical compositions provided herein for oral administration comprise 0.1 mg to 10 mg of a solid form comprising a Compound disclosed herein, 0.2 mg to 7.5 mg of a solid form comprising the Compound, or 0.25 mg to 5 mg of a solid form comprising the Compound.

In one embodiment, the pharmaceutical compositions provided herein for oral administration are adapted to provide sustained release of a solid form comprising a Compound disclosed herein. In certain embodiments, the pharmaceutical compositions provided herein for oral administration comprise a sustained release component. In certain embodiments, the sustained release component is a polymer, or a combination of polymers. In one embodiment, an osmotic pump is used to obtain sustained release. In certain embodiments, the pharmaceutical compositions adapted for sustained release comprise about 4 mg to about 6 mg of a solid form comprising a Compound disclosed herein. In certain embodiments, the pharmaceutical compositions adapted for sustained release are provided as tablets.

In another embodiment, the pharmaceutical compositions provided herein for oral administration are adapted to provide immediate release of a solid form comprising a Compound disclosed herein. In certain embodiments, the pharmaceutical compositions provided herein for oral administration comprise 0.25 mg, 0.5 mg, 0.75 mg, 1.25 mg, 1.5 mg, 1.75, 2.0 mg, 2.25 mg, or 2.5 mg of a solid form comprising a Compound disclosed herein. In certain embodiments, the pharmaceutical compositions adapted for immediate release of a solid form comprising a Compound disclosed herein are provided as tablets for administration once daily.

5.7 Parenteral Administration

The pharmaceutical compositions provided herein can be administered parenterally, for example, by injection, infusion, or implantation techniques, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

6. EXAMPLES

The following Examples are presented by way of illustration, not limitation.

6.1 Analytical Methods

Powder X-ray diffraction (PXRD) patterns were obtained using a PANalytical X'Pert Pro diffractometer using Ni-filtered Cu Kα (45 kV/40 mA) radiation and a step size of 0.02° 2θ and X'celerator Real Time Multi-Strip (RTMS) detector. Configuration on the incidental beam side is a fixed divergence slit (0.25°), 0.04 radian Soller slits, anti-scatter slit (0.25°), and 10 mm beam mask. Configuration on the diffracted beam side is a fixed divergence slit (0.25°) and 0.04 radian Soller slit. Samples were mounted flat on zero-background Si wafers and covered with Kapton film to comply with safety policies.

Alternatively, powder X-ray diffraction (PXRD) patterns were obtained on a Rigaku SmartLab Guidance diffractometer with Cu—Kα radiation and D/teX Ultra detector. The powder samples were deposited on a zero-background polished silicon sample holder and were spun during measurement. Measurements were performed as follows: 40 kV/44 mA tube power, 0.02° 2θ step size, 5° 2θ/min scan rate, and 3-40° 2θ scan range. Data were processed using Rigaku PDXL2 software.

FT-Raman spectra were collected with a Nicolet NXR9650 or NXR 960 spectrometer (Thermo Electron) equipped with 1064 nm Nd:YVO$_4$ excitation laser, InGaAs and liquid-N$_2$ cooled Ge detectors, and a MicroStage. Spectra were acquired at 4 cm$^{-1}$ resolution, 64 scans, using Happ-Genzel apodization function and 2-level zero-filling.

Raman spectra were collected using a Raman Work Station (Kaiser Optical Systems, Inc, Ann Arbor, MI) with Holograms software. Data was acquired using 785 nm excitation laser with 300 mW in a reflection mode, 4 cm$^{-1}$ resolution through a 10× objective with 10 accumulations. Data were processed using Grams/AI software (Thermo Fisher Scientific Inc). Data may also be acquired using 785 nm excitation laser with 300 mW in a reflection mode, 4 cm$^{-1}$ resolution through a 10× objective.

Differential Scanning Calorimetry (DSC) was conducted with a TA Instruments Q100 differential scanning calorimeter equipped with an autosampler and a refrigerated cooling system under 40 mL/min nitrogen (N$_2$) purge. DSC thermograms were obtained at 15° C./min in crimped aluminum (Al) pans.

Polarized-light microscopy (PLM) photomicrographs were collected using an Olympus BX60 polarized-light microscope equipped with an Olympus DP70 camera.

Thermogravimetric Analysis (TGA) thermograms were obtained with a TA Instruments Q500 thermogravimetric analyzer under 40 mL/min N$_2$ purge at 15° C./min in Al pans.

Thermogravimetric Analysis with IR Off-Gas Detection (TGA-IR) was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N$_2$ flow and heating rate of 15° C./min in Al pans. IR spectra were collected at 4 cm$^{-1}$ resolution and 32 scans at each time point.

TGA/DSC data was obtained on a Mettler Toledo TGA/DSC 1 Star System. The samples were loaded on an Al sample pan and heated at a rate of 10° C./min.

Proton Nuclear Magnetic Resonance ($^1$H NMR) spectra were collected using an Agilent DD2 500 MHz spectrometer with tetramethylsilane reference. Samples were dissolved in deuterated dimethyl sulfoxide.

Proton Nuclear Magnetic Resonance (1H NMR) spectra were also collected using a Bruker UltraShield 300 MHz spectrometer with Topspin 3.2 software and tetramethylsilane reference. Samples were dissolved in deuterated dimethyl sulfoxide or deuterated methanol.

6.2 Preparation and Analysis of Solid Forms (a) HCl Salt Form A

Compound 1 (about 20 mg) was suspended in acetonitrile (about 250 µL) and a 3 M solution of HCl in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in acetonitrile and the temperature was cycled between about 5° C. and about 40° C. (1° C. per minute heating/cooling rate with an hour hold between each heating/cooling cycle) for a day. The sample was then equilibrated at 20° C. at the end of temperature cycling for at least an hour. After this time, the solids were isolated via vacuum filtration, air-dried for an hour and dried in a vacuum oven at 40° C. for 5 hours to yield HCl Salt Form A.

HCl Salt Form A has an FT-Raman Spectrum as depicted in FIG. 2. HCl Salt Form B has a DSC thermogram substantially as depicted in FIG. 3, an endotherm with an onset temperature at 132.9° C. HCl Salt Form A has a TGA thermogram as depicted in FIG. 3, comprising a total mass loss of approximately 1.6% of the total mass of the sample when heated from approximately 25° C. to approximately 115° C.

Figure 4:
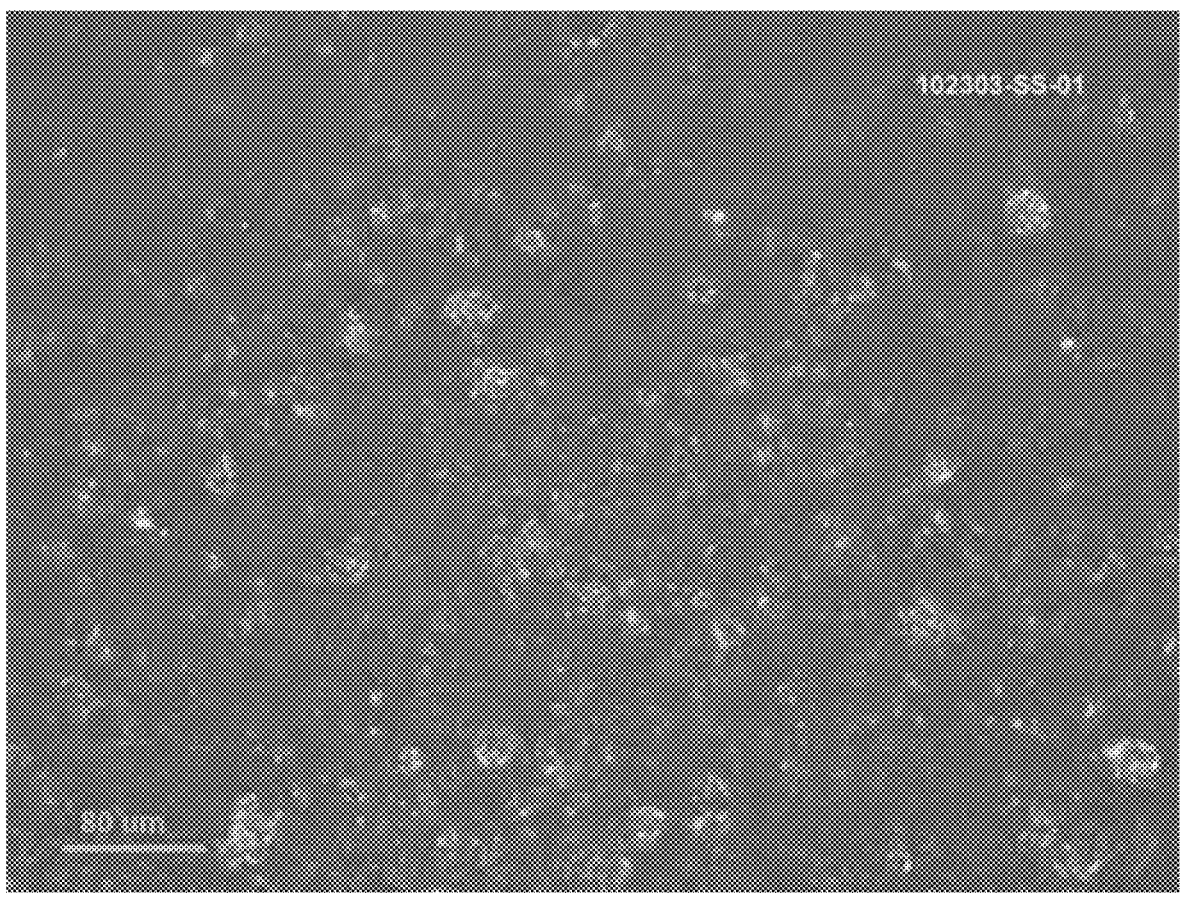
FIG. 4 depicts polarized-light microscopy of HCl Salt Form A of Compound 2.

FIG. 4 depicts polarized-light microscopy of HCl Salt Form A of Compound 2.

A list of X-Ray diffraction peaks for HCl Salt Form A is provided below in Table 1.

TABLE 1

X-Ray Diffraction Peaks for HCl Salt Form A.

| Two-theta angle (°) | d Space (Å) | Height (counts) |
|---|---|---|
| 8.2 | 10.845 | 84.8 |
| 11.5 | 7.676 | 64.9 |
| 12.3 | 7.212 | 122.6 |
| 13.3 | 6.679 | 86.7 |
| 15.8 | 5.619 | 97.9 |
| 16.4 | 5.420 | 112.1 |
| 16.5 | 5.368 | 80.4 |
| 17.7 | 5.020 | 118.6 |
| 18.9 | 4.706 | 161.7 |
| 19.6 | 4.524 | 163.4 |
| 21.3 | 4.180 | 138.7 |
| 22.1 | 4.026 | 220.9 |
| 22.5 | 3.946 | 147.8 |
| 23.1 | 3.844 | 75.0 |
| 23.8 | 3.735 | 157.7 |
| 24.8 | 3.585 | 139.5 |
| 25.5 | 3.496 | 68.0 |
| 26.8 | 3.323 | 71.9 |

(b) HCl Salt Form B

Compound 1 (about 20 mg) was suspended in methyl isobutyl ketone (about 250 µL) and a 3 M solution of HCl in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in methyl isobutyl ketone and the temperature was cycled between about 5° C. and about 40° C. (1° C. per minute heating/cooling rate with an hour hold between each heating/cooling cycle) for a day. The sample was then equilibrated at 20° C. at the end of temperature cycling for at least an hour. After this time, the sample was heated to 40° C. and hexane (about 750 µL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield HCl Salt Form B.

Alternatively, Compound 1 (101.9 mg) was combined with methyl isobutyl ketone (1.25 mL) and HCl (3 M solution in water, 1 equivalent), and the resulting product was heated to 40° C. and held at 40° C. for an hour. The solution was evaporated to dryness under reduced pressure and methyl isobutyl ketone (1.25 mL) was added to the resulting product. Seeds of a crystalline HCl salt of Compound 1 (about 1 mg) were added. The temperature of the suspension was cycled between 40° C. and 5° C. for two days (ramp rate of 1° C./min with an hour hold between each heating/cooling cycle) which led to a white suspension. The crystalline solids were isolated via vacuum filtration, air-dried for an hour and dried in a vacuum oven at 40° C. for 5 hours to yield HCl Salt Form B (85.4 mg).

HCl Salt Form B has an FT-Raman Spectrum as depicted in FIG. 6. HCl Salt Form B has a DSC thermogram substantially as depicted in FIG. 7, comprising multiple endotherms with onset temperatures at 32.7° C., 81.3° C., and 146.6° C. HCl Salt Form B has a TGA thermogram as depicted in FIG. 7, comprising a total mass loss of approximately 6.5% of the total mass of the sample when heated from approximately 25° C. to approximately 147° C.

Figure 8:
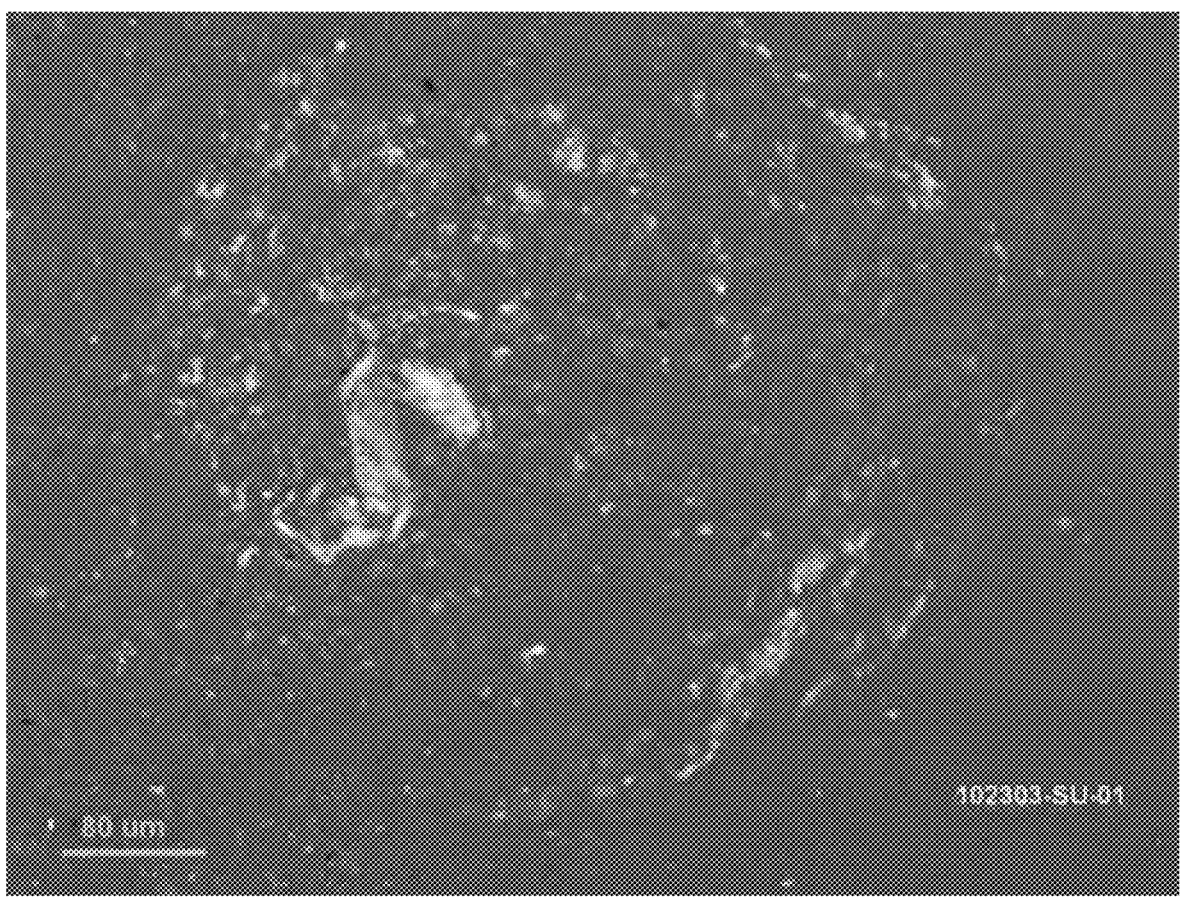
FIG. 8 depicts polarized-light microscopy of HCl Salt Form B of Compound 2.

FIG. 8 depicts polarized-light microscopy of HCl Salt Form B of Compound 2.

A list of X-Ray diffraction peaks for HCl Salt Form B is provided below in Table 2.

TABLE 2

X-Ray Diffraction Peaks for HCl Salt Form B.

| Two-theta angle (°) | d Space (Å) | Height (counts) |
|---|---|---|
| 8.2 | 10.801 | 854.0 |
| 12.3 | 7.214 | 1535.5 |
| 15.8 | 5.598 | 225.9 |
| 16.3 | 5.439 | 86.0 |
| 18.6 | 4.767 | 119.7 |
| 19.2 | 4.629 | 155.8 |
| 19.6 | 4.519 | 130.5 |
| 20.5 | 4.342 | 701.4 |
| 22.3 | 3.989 | 212.3 |
| 22.9 | 3.881 | 89.0 |
| 26.7 | 3.338 | 104.1 |

(c) L-Malate Salt Form A

Compound 1 (about 20 mg) was suspended in methyl tert-butyl ether (about 250 µL) and a 1 M solution of L-malic acid in THF (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl tert-butyl ether and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and hexane (about 750 µL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield L-Malate Salt Form A.

Alternatively, Compound 1 (about 20 mg) was suspended in isopropanol (about 250 µL) and a 1 M solution of L-malic acid in THF (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in isopropanol and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and cyclohexane (about 750 µL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield L-Malate Salt Form A.

Alternatively, Compound 1 (about 20 mg) was suspended in acetonitrile (about 250 µL) and a 1 M solution of L-malic acid in THF (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in acetonitrile and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. The sample was held at 40° C. for three hours, and then cooled to 5° C. and held at 5° C. for one day. The solution was warmed to 20° C. and the solvent was evaporated slowly at room temperature under a slow bleed of nitrogen gas to yield L-Malate Salt Form A.

Alternatively, Compound 1 (about 20 mg) was suspended in a mixture of ethyl acetate and toluene (about 250 µL of a 1:2 v/v mixture) and a 1 M solution of L-malic acid in THF (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in a mixture of ethyl acetate and toluene (about 250 µL of a 1:2 v/v mixture) and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the solids were isolated via vacuum filtration, air-dried for an hour and dried in a vacuum oven at 40° C. for 5 hours to yield L-Malate Salt Form A.

Alternatively, Compound 1 (97.9 mg) was combined with isopropyl acetate (1.25 mL) and L-malic acid (1 M solution in THF, 1 equivalent) and the resulting product was heated to 40° C. and held at 40° C. for an hour. The solvent was evaporated to dryness under reduced pressure and isopropyl acetate (1.25 mL) was added to the resulting product. Seeds of a crystalline L-malate salt of Compound 1 were added (about 1 mg). The temperature of the suspension was cycled between about 5° C. and about 40° C. for two days (ramp rate of 1° C./min with an hour hold between each heating/cooling cycle). The crystalline solids were isolated via vacuum filtration, air-dried for an hour and dried in a vacuum oven at 40° C. for 5 hours to yield L-Malate Salt Form A (35.6 mg).

L-Malate Salt Form A has an FT-Raman Spectrum as depicted in FIG. 10. L-Malate Salt Form A has a DSC thermogram substantially as depicted in FIG. 11, comprising an endotherm with an onset temperature at 91.6° C., followed by an endotherm at 153.6° C. L-Malate Salt Form A has a TGA thermogram as depicted in FIG. 11, comprising a total mass loss of approximately 2.7% of the total mass of the sample when heated from approximately 25° C. to approximately 145° C.

Figure 12:
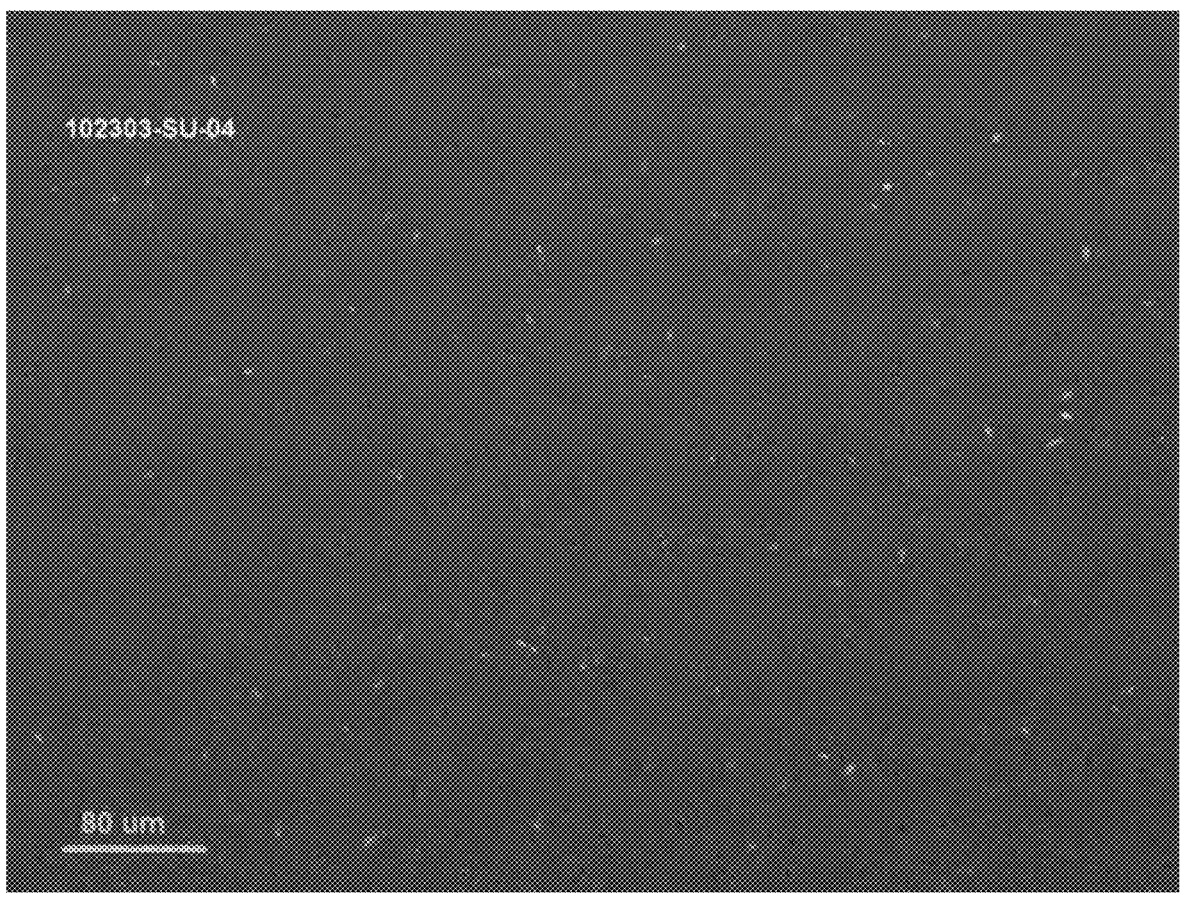
FIG. 12 depicts polarized-light microscopy of L-Malate Salt Form A of Compound 3.

FIG. 12 depicts polarized-light microscopy of L-Malate Salt Form A of Compound 3.

A list of X-Ray diffraction peaks for L-Malate Salt Form A is provided below in Table 3.

TABLE 3

X-Ray Diffraction Peaks for L-Malate Salt Form A.

| Two-theta angle (°) | d Space (Å) | Height (counts) |
| --- | --- | --- |
| 6.9 | 12.897 | 371.5 |
| 10.3 | 8.605 | 57.2 |
| 11.4 | 7.730 | 76.1 |
| 13.6 | 6.496 | 557.3 |
| 15.9 | 5.591 | 317.7 |
| 17.2 | 5.153 | 216.2 |
| 18.9 | 4.692 | 340.5 |
| 20.6 | 4.3123 | 733.4 |
| 21.7 | 4.089 | 257.6 |
| 24.0 | 3.701 | 359.7 |
| 26.3 | 3.395 | 50.6 |

(d) L-Malate Salt Form B

Compound 1 (about 20 mg) was suspended in isopropyl acetate (about 250 µL) and a 1 M solution of L-malic acid in THF (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in isopropyl acetate and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and diisopropyl ether (about 750 µL) was added. The sample was held at 40° C. for three hours, and then cooled to 5° C. and held at 5° C. for one day. After this time, the solids were isolated via vacuum filtration, air-dried for an hour and dried in a vacuum oven at 40° C. for 5 hours to yield L-Malate Salt Form B.

L-Malate Salt Form B has an FT-Raman Spectrum as depicted in FIG. 14. L-Malate Salt Form B has a DSC thermogram substantially as depicted in FIG. 15, comprising multiple endotherms with onset temperatures at 29.4° C., 95.9° C., 114.1° C., and 151.2° C. L-Malate Salt Form B has a TGA thermogram as depicted in FIG. 15, comprising a total mass loss of approximately 2.6% of the total mass of the sample when heated from approximately 30° C. to approximately 100° C.

Figure 16:
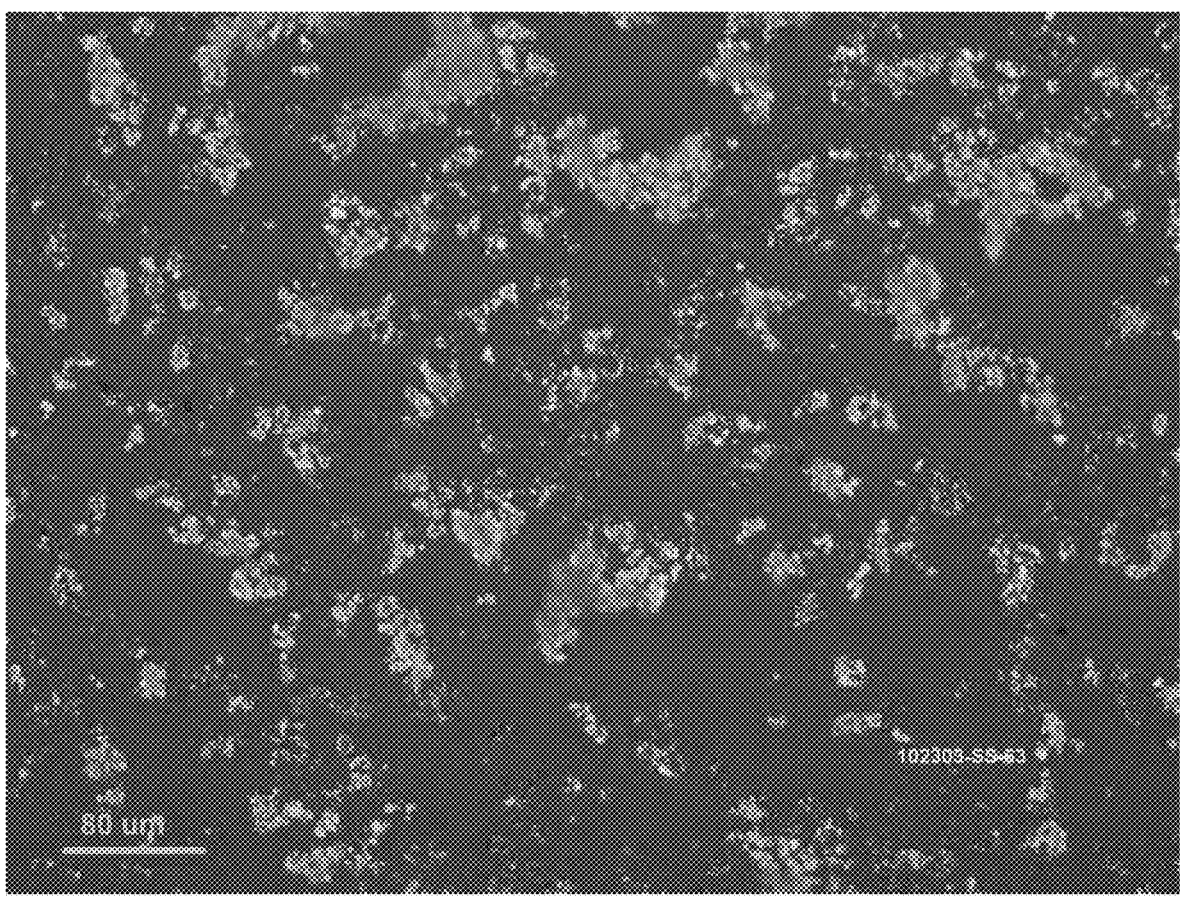
FIG. 16 depicts polarized-light microscopy of L-Malate Salt Form B of Compound 3.

FIG. 16 depicts polarized-light microscopy of L-Malate Salt Form B of Compound 3.

A list of X-Ray diffraction peaks for L-Malate Salt Form B is provided below in Table 4.

TABLE 4

X-Ray Diffraction Peaks for L-Malate Salt Form B.

| Two-theta angle (°) | d Space (Å) | Height (counts) |
|---|---|---|
| 6.4 | 13.760 | 70.6 |
| 12.9 | 6.881 | 46.7 |
| 15.8 | 5.600 | 150.8 |
| 17.4 | 5.103 | 71.6 |
| 18.9 | 4.684 | 107.1 |
| 20.7 | 4.284 | 36.9 |
| 21.7 | 4.093 | 119.7 |
| 24.0 | 3.708 | 135.4 |

(e) Oxalate Salt Form A

Compound 1 (about 20 mg) was suspended in methyl tert-butyl ether (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in methyl tert-butyl ether and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Oxalate Salt Form A.

Alternatively, Compound 1 (about 20 mg) was suspended in isopropanol (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in isopropanol and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Oxalate Salt Form A.

Alternatively, Compound 1 (about 20 mg) was suspended in a 95:5 v/v mixture of acetone/water (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in a 95:5 v/v mixture of acetone/water and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Oxalate Salt Form A.

Alternatively, Compound 1 (about 20 mg) was suspended in a 1:2 v/v mixture of ethyl acetate/toluene (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in a 1:2 v/v mixture of ethyl acetate/toluene and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Oxalate Salt Form A.

Alternatively, Compound 1 (about 20 mg) was suspended in methyl isobutyl ketone (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in methyl isobutyl ketone and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Oxalate Salt Form A.

Alternatively, Compound 1 (about 20 mg) was suspended in isopropyl acetate (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in isopropyl acetate and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Oxalate Salt Form A.

Oxalate Salt Form A has an FT-Raman Spectrum as depicted in FIG. 18. Oxalate Salt Form A has a DSC thermogram substantially as depicted in FIG. 19, comprising an endotherm with an onset temperature at 145.8° C. Oxalate Salt Form A has a TGA thermogram as depicted in FIG. 19, comprising a total mass loss of approximately 0.5% of the total mass of the sample when heated from approximately 30° C. to approximately 120° C.

Figure 20:
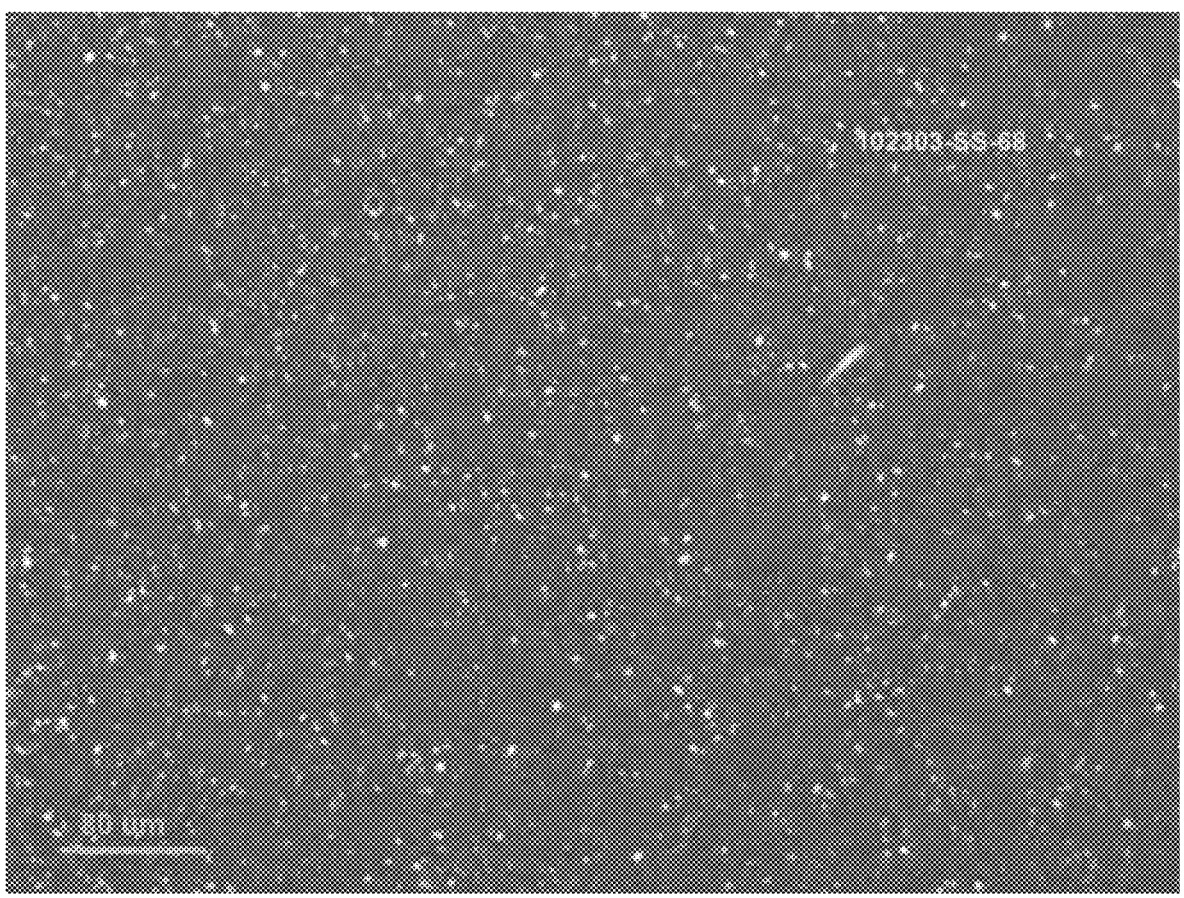
FIG. 20 depicts polarized-light microscopy of Oxalate Salt Form A of Compound 4.

FIG. 20 depicts polarized-light microscopy of Oxalate Salt Form A of Compound 4.

A list of X-Ray diffraction peaks for Oxalate Salt Form A is provided below in Table 5.

TABLE 5

X-Ray Diffraction Peaks for Oxalate Salt Form A.

| Two-theta angle (°) | d Space (Å) | Height (counts) |
| --- | --- | --- |
| 7.3 | 12.053 | 4156.1 |
| 9.3 | 9.482 | 75.6 |
| 9.9 | 8.902 | 105.0 |
| 12.5 | 7.100 | 81.3 |
| 14.7 | 6.020 | 174.5 |
| 15.5 | 5.722 | 65.0 |
| 16.1 | 5.514 | 117.2 |
| 18.1 | 4.895 | 922.5 |
| 18.4 | 4.823 | 246.0 |
| 19.1 | 4.651 | 91.8 |
| 19.8 | 4.476 | 64.2 |
| 21.4 | 4.158 | 543.7 |
| 22.2 | 4.003 | 767.0 |
| 23.0 | 3.860 | 53.0 |
| 23.4 | 3.794 | 90.5 |
| 24.0 | 3.701 | 137.9 |
| 24.8 | 3.589 | 52.6 |
| 25.9 | 3.435 | 193.9 |
| 28.1 | 3.171 | 222.9 |
| 29.7 | 3.009 | 84.2 |

(f) Oxalate Salt Form B

Compound 1 (about 20 mg) was suspended in acetonitrile (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in acetonitrile and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Oxalate Salt Form B.

Alternatively, Compound 1 (101.8 mg) was combined with acetonitrile (1.25 mL) and oxalic acid (0.5 M solution in water, 1 equivalent) and the resulting product was heated to 40° C. and held at 40° C. for an hour. The solvent was evaporated to dryness under reduced pressure and acetonitrile (1.25 mL) was added to the resulting product. Seeds of a crystalline oxalate salt of Compound 1 were added (about 1 mg). The temperature of the suspension was cycled between about 5° C. and about 40° C. for two days (ramp rate of 1° C./min with an hour hold between each heating/cooling cycle). A thick precipitate was obtained. Acetonitrile (1.0 mL) was added to enable proper stirring. The crystalline solids were isolated via vacuum filtration, air-dried for an hour and dried in a vacuum oven at 40° C. for 5 hours to yield Oxalate Salt Form B (79.3 mg).

Oxalate Salt Form B has an FT-Raman Spectrum as depicted in FIG. 22. Oxalate Salt Form B has a DSC thermogram substantially as depicted in FIG. 23, comprising multiple endotherms with onset temperatures at 102.6° C. and 139.2° C. Oxalate Salt Form B has a TGA thermogram as depicted in FIG. 23, comprising a total mass loss of approximately 0.3% of the total mass of the sample when heated from approximately 30° C. to approximately 140° C.

Figure 24:
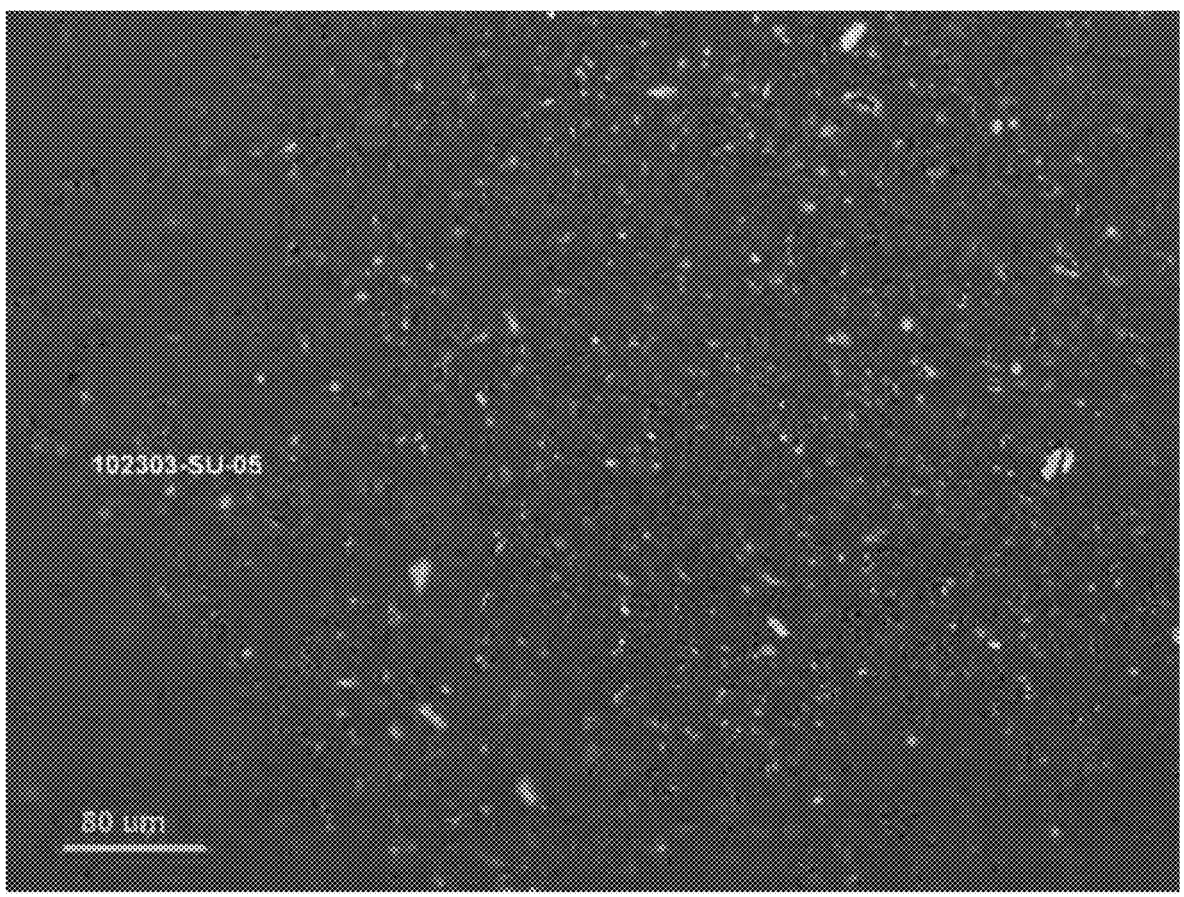
FIG. 24 depicts polarized-light microscopy of Oxalate Salt Form B of Compound 4.

FIG. 24 depicts polarized-light microscopy of Oxalate Salt Form B of Compound 4.

A list of X-Ray diffraction peaks for Oxalate Salt Form B is provided below in Table 6.

TABLE 6

X-Ray Diffraction Peaks for Oxalate Salt Form B.

| Two-theta angle (°) | d Space (Å) | Height (counts) |
| --- | --- | --- |
| 3.5 | 25.025 | 454.9 |
| 7.0 | 12.574 | 1405.4 |
| 9.9 | 8.921 | 80.1 |
| 16.1 | 5.507 | 158.5 |
| 18.1 | 4.890 | 251.4 |
| 28.2 | 3.168 | 76.0 |
| 30.1 | 2.965 | 112.9 |

(g) Oxalate Salt Form C

Compound 1 (about 20 mg) was suspended in an 4:1 v/v mixture of THF/water (about 250 μL) and a 0.5 M solution of oxalic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in an 4:1 v/v mixture of THF/water and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least an hour. The sample was cooled to 5° C. and held at 5° C. for one day. The solution was warmed to 20° C. and the solvent was evaporated slowly at room temperature under a slow bleed of nitrogen gas to yield Oxalate Salt Form C.

Oxalate Salt Form C has an FT-Raman Spectrum as depicted in FIG. 26. Oxalate Salt Form C has a DSC thermogram substantially as depicted in FIG. 27, comprising an endotherm with an onset temperature at 90.8° C. Oxalate Salt Form C has a TGA thermogram as depicted in FIG. 27, comprising a total mass loss of approximately 4.8% of the total mass of the sample when heated from approximately 25° C. to approximately 100° C.

Figure 28:
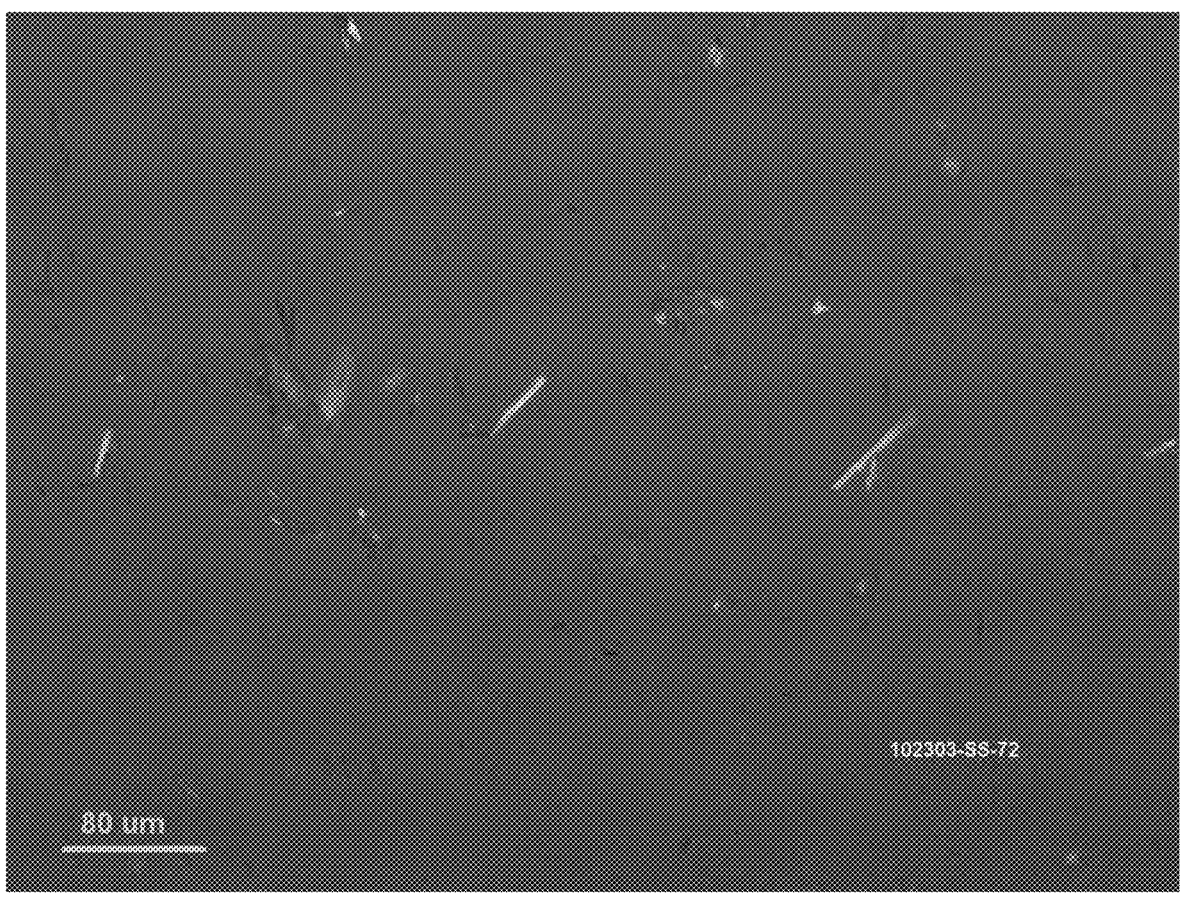
FIG. 28 depicts polarized-light microscopy of Oxalate Salt Form C of Compound 4.

FIG. 28 depicts polarized-light microscopy of Oxalate Salt Form C of Compound 4.

A list of X-Ray diffraction peaks for Oxalate Salt Form C is provided below in Table 7.

TABLE 7

X-Ray Diffraction Peaks for Oxalate Salt Form C.

| Two-theta angle (°) | d Space (Å) | Height (counts) |
| --- | --- | --- |
| 2.4 | 36.067 | 16719.0 |
| 4.8 | 18.367 | 2221.0 |
| 7.2 | 12.309 | 1367.4 |
| 9.6 | 9.248 | 3743.8 |
| 11.9 | 7.409 | 560.6 |
| 13.0 | 6.829 | 76.1 |
| 14.3 | 6.174 | 1179.4 |
| 15.4 | 5.765 | 143.3 |
| 16.7 | 5.302 | 188.8 |
| 18.1 | 4.892 | 208.3 |
| 19.2 | 4.629 | 227.8 |
| 21.6 | 4.121 | 1800.2 |
| 24.0 | 3.711 | 1316.8 |
| 25.9 | 3.444 | 162.6 |
| 26.4 | 3.374 | 966.2 |
| 28.1 | 3.176 | 233.6 |
| 30.4 | 2.944 | 206.0 |
| 32.7 | 2.739 | 77.0 |
| 33.8 | 2.650 | 174.3 |
| 36.3 | 2.475 | 100.3 |

(h) L-Tartrate Salt Form A

Compound 1 (about 20 mg) was suspended in acetonitrile (about 250 µL) and a 0.5 M solution of L-tartaric acid in tetrahydrofuran (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in acetonitrile and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and diisopropyl ether (about 750 µL) was added. The sample was held at 40° C. for three hours, and then cooled to 5° C. and held at 5° C. for one day. The solids were isolated via vacuum filtration, air-dried for an hour and dried in a vacuum oven at 40° C. for 5 hours to yield L-Tartrate Salt Form A.

Alternatively, Compound 1 (about 20 mg) was suspended in methyl tert-butyl ether (about 250 µL) and a 0.5 M solution of L-tartaric acid in tetrahydrofuran (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl tert-butyl ether and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the solids were isolated via vacuum filtration, air-dried for an hour and dried in a vacuum oven at 40° C. for 5 hours to yield L-Tartrate Salt Form A.

Alternatively, Compound 1 (e.g., about 95.9 mg) was combined with methyl tert-butyl ether (1.25 mL) and L-tartaric acid (0.5M solution in THF, 1 equivalent), and stirred at ambient temperature for one hour. The solution was evaporated to dryness under reduced pressure in a centrifuge evaporator and methyl tert-butyl ether (1 mL) was added to the dried sample. Seeds of a crystalline L-tartrate salt of Compound 1 (about 1 mg) were added to the resulting sample. The temperature of the mixture was cycled between 5° C. and 40° C. (1° C. per minute heating/cooling rate with an hour hold between each heating/cooling cycle) for a day. The sample was equilibrated at 5° C. and stirred at 5° C. for two days. The solids were isolated via vacuum filtration, air-dried for one hour, and followed by drying in a vacuum oven at 40° C. for 4 hours to yield L-Tartrate Salt Form A of Compound 5.

L-Tartrate Salt Form A has a FT-Raman Spectra as depicted in FIG. 30. L-Tartrate Salt Form A has a DSC thermogram substantially as depicted in FIG. 31, comprising an endothermic event with onset temperatures at 107.4° C. L-Tartrate Salt Form A has a TGA thermogram as depicted in FIG. 31, comprising a total mass loss of approximately 2% of the total mass of the sample when heated from approximately 28° C. to approximately 150° C.

Figure 32:
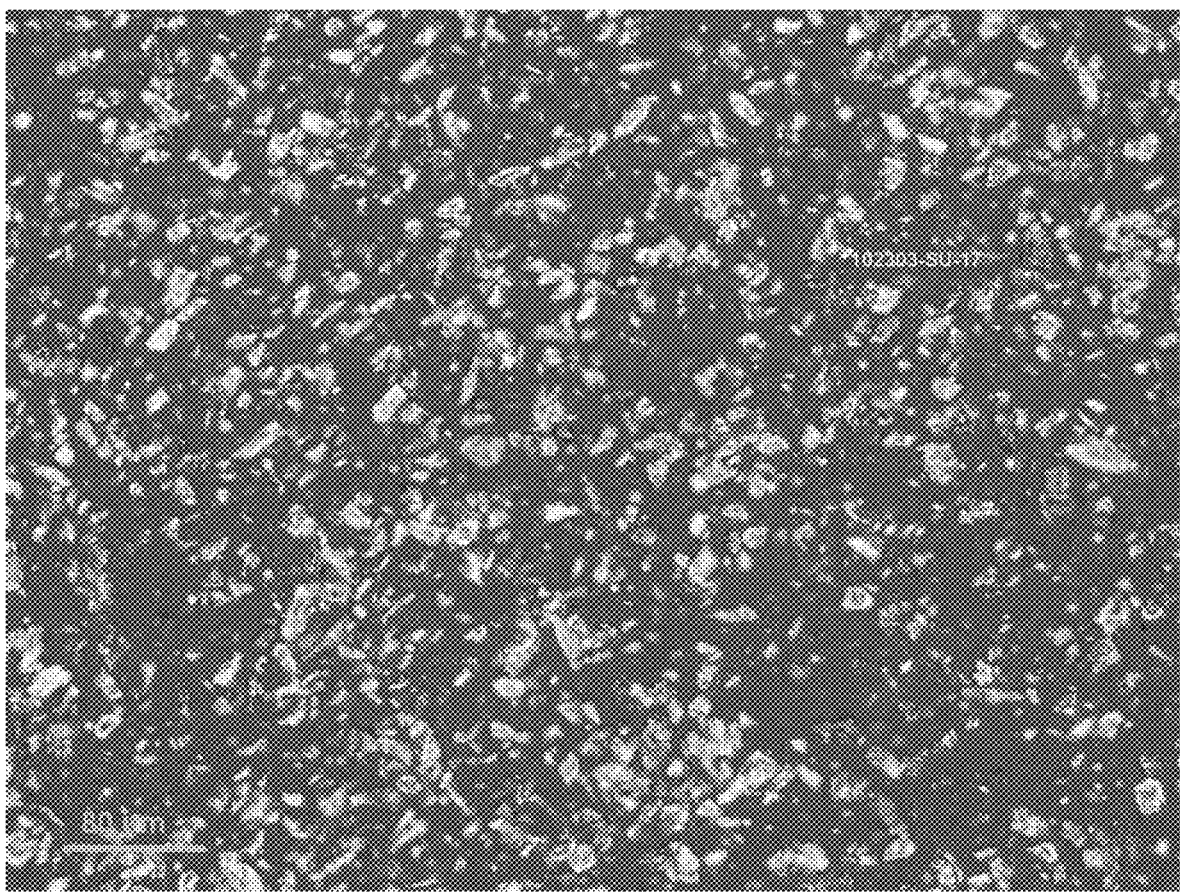
FIG. 32 depicts polarized-light microscopy of L-Tartrate Salt Form A of Compound 5.

FIG. 32 depicts polarized-light microscopy of L-Tartrate Salt Form A of Compound 5.

A list of X-Ray diffraction peaks for L-Tartrate Salt Form A is provided below in Table 8.

TABLE 8

X-Ray Diffraction Peaks for L-Tartrate Salt Form A.

| Two-theta angle (°) | d Space (Å) | Height (counts) |
| --- | --- | --- |
| 3.3 | 26.975 | 321.6 |
| 6.6 | 13.467 | 482.8 |
| 10.3 | 8.584 | 30.9 |
| 11.9 | 7.460 | 29.8 |
| 13.6 | 6.533 | 563.1 |
| 15.9 | 5.589 | 82.4 |
| 16.9 | 5.243 | 92.3 |
| 17.9 | 4.956 | 123.4 |
| 20.2 | 4.388 | 431.6 |
| 21.6 | 4.111 | 103.4 |
| 22.3 | 3.984 | 77.4 |
| 24.0 | 3.706 | 133.0 |
| 27.2 | 3.281 | 64.4 |

(i) L-Tartrate Salt Form B

Compound 1 (about 20 mg) was suspended in an 4:1 v/v mixture of THF/water (about 250 µL) and a 0.5 M solution of L-tartaric acid in tetrahydrofuran (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in an 4:1 v/v mixture of THF/water and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour, and the sample was then cooled to 5° C. and held at 5° C. for one day. The solution was warmed to 20° C. and the solvent was evaporated slowly at room temperature under a slow bleed of nitrogen gas to yield L-Tartrate Salt Form B.

L-Tartrate Salt Form B has a FT-Raman Spectra as depicted in FIG. 34. L-Tartrate Salt Form B has a DSC thermogram substantially as depicted in FIG. 35, comprising endothermic events with onset temperatures at 39° C. and 131° C., respectively. L-Tartrate Salt Form B has a TGA thermogram as depicted in FIG. 35, comprising a total mass loss of approximately 4.7% of the total mass of the sample when heated from approximately 25° C. to approximately 150° C.

Figure 36:
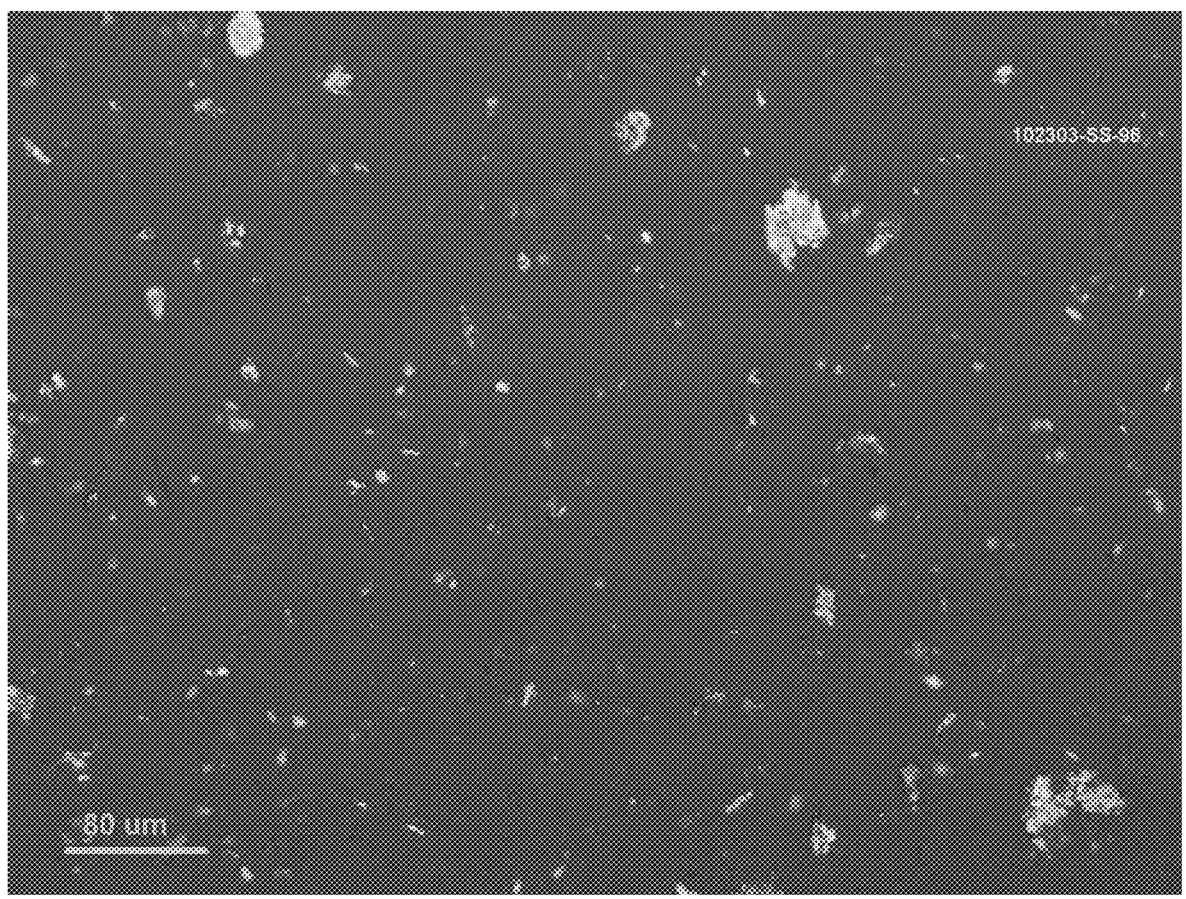
FIG. 36 depicts polarized-light microscopy of L-Tartrate Salt Form B of Compound 5.

FIG. 36 depicts polarized-light microscopy of L-Tartrate Salt Form B of Compound 5.

A list of X-Ray diffraction peaks for L-Tartrate Salt Form B is provided below in Table 9.

TABLE 9

X-Ray Diffraction Peaks for L-Tartrate Salt Form B.

| Two-theta angle (°) | d Space (Å) | Height (counts) |
|---|---|---|
| 2.7 | 32.929 | 3203.6 |
| 3.3 | 26.829 | 88.8 |
| 5.2 | 16.860 | 152.8 |
| 6.7 | 13.208 | 486.1 |
| 10.1 | 8.791 | 78.6 |
| 13.4 | 6.603 | 545.9 |
| 15.8 | 5.609 | 80.8 |
| 16.8 | 5.275 | 71.9 |
| 20.2 | 4.406 | 408.4 |
| 23.9 | 3.722 | 90.5 |

(j) Hemifumarate Salt Form A

Compound 1 (about 20 mg) was suspended in acetonitrile (about 250 μL) and a 0.2 M solution of fumaric acid in ethanol (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in acetonitrile and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Hemifumarate Salt Form A.

Alternatively, Compound 1 (about 20 mg) was suspended in methyl isobutyl ketone (about 250 μL) and a 0.2 M solution of fumaric acid in ethanol (1.0 equivalent) was added. The temperature of the mixture was cycled between about 5° C. and about 40° C. (1° C. per minute heating/ cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in methyl isobutyl ketone and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Hemifumarate Salt Form A.

Alternatively, Compound 1 (about 20 mg) was suspended in isopropyl acetate (about 250 μL) and a 0.2 M solution of fumaric acid in ethanol (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in isopropyl acetate and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Hemifumarate Salt Form A.

Alternatively, Compound 1 (about 20 mg) was suspended in isopropanol (about 250 μL) and a 0.2 M solution of fumaric acid in ethanol (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in isopropanol and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and cyclohexane (about 750 μL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield Hemifumarate Salt Form A.

Alternatively, Compound 1 (about 20 mg) was suspended in 4:1 v/v mixture of THF/water (about 250 μL) and a 0.2 M solution of fumaric acid in ethanol (1.0 equivalent) was added. The temperature of the mixture was cycled between about 5° C. and about 40° C. (1° C. per minute heating/ cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in 4:1 v/v mixture of THF/water and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. The sample was held at 40° C. for three hours, and then cooled to 5° C. and held at 5° C. for one day. The solution was warmed to 20° C. and the solvent was evaporated slowly at room temperature under a slow bleed of nitrogen gas to yield Hemifumarate Salt Form A.

Hemifumarate Salt Form A has an FT-Raman Spectrum as depicted in FIG. 38. Hemifumarate Salt Form A has a DSC thermogram substantially as depicted in FIG. 39, comprising multiple endotherms with an onset temperatures at 91.7° C. and 130° C. Hemifumarate Salt Form A has a TGA thermogram as depicted in FIG. 39, comprising a total mass loss of approximately 2.9% of the total mass of the sample when heated from approximately 25° C. to approximately 130° C.

Figure 40:
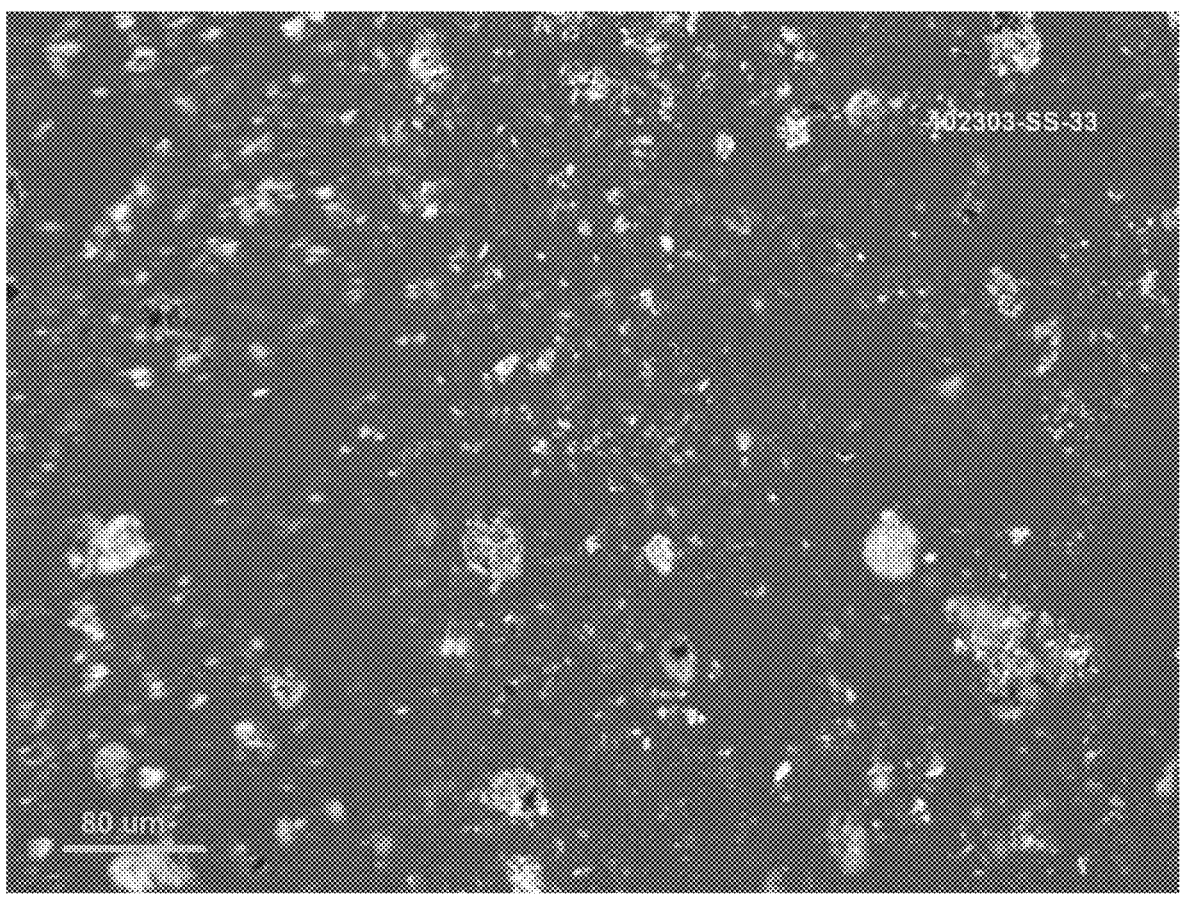
FIG. 40 depicts polarized-light microscopy of Hemifumarate Salt Form A of Compound 6.

FIG. 40 depicts polarized-light microscopy of Hemifumarate Salt Form A of Compound 6.

A list of X-Ray diffraction peaks for Hemifumarate Salt Form A is provided below in Table 10.

TABLE 10

X-Ray Diffraction Peaks for Hemifumarate Salt Form A.

| Two-theta angle (°) | d Space (Å) | Height (counts) |
|---|---|---|
| 7.1 | 12.430 | 309.5 |
| 10.7 | 8.302 | 168.1 |
| 11.7 | 7.569 | 65.2 |
| 12.1 | 7.320 | 113.8 |
| 13.6 | 6.529 | 129.8 |
| 14.2 | 6.245 | 242.1 |
| 15.1 | 5.869 | 111.2 |
| 16.4 | 5.403 | 160.0 |
| 17.9 | 4.968 | 304.9 |
| 18.3 | 4.835 | 270.5 |
| 21.4 | 4.144 | 407.4 |
| 23.9 | 3.723 | 116.0 |
| 24.4 | 3.653 | 134.6 |
| 25.4 | 3.509 | 139.6 |
| 26.6 | 3.350 | 63.9 |
| 28.9 | 3.087 | 90.8 |

(k) Hemifumarate Salt Form B

Compound 1 (about 20 mg) was suspended in methyl tert-butyl ether (about 250 µL) and a 0.2 M solution of fumaric acid in ethanol (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in methyl tert-butyl ether and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Hemifumarate Salt Form B.

Alternatively, Compound 1 (about 20 mg) was suspended in a 1:2 v/v mixture of ethyl acetate/toluene (about 250 µL) and a 0.2 M solution of fumaric acid in ethanol (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least an hour. The sample was evaporated to dryness under reduced pressure in a centrifuge evaporator. The sample was re-suspended in a 1:2 v/v mixture of ethyl acetate/toluene and the temperature was cycled between about 5° C. and about 40° C. (1° C. per minute heating/cooling rate with an hour hold between each heating/cooling cycle) for a period about a day, and the sample was cooled to 5° C. for one day. The solution was warmed to 20° C. and equilibrated at 20° C. for at least one hour. The crystalline solids were isolated via vacuum filtration, air-dried for an hour and dried in a vacuum oven at 40° C. for 5 hours to yield Hemifumarate Salt Form B.

Alternatively, Compound 1 (102.5 mg) was combined with methyl tert-butyl ether (1.25 mL) and fumaric acid (0.2 M solution in ethanol, 1 equivalent) and the resulting product was heated to 40° C. and held at 40° C. for an hour. The suspension was evaporated to dryness under reduced pressure and methyl tert-butyl ether (1.25 mL) was added to the resulting product. Seeds of a crystalline fumarate salt of Compound 1 (about 1 mg) were added. The temperature of the suspension was cycled between about 5° C. and about 40° C. for two days (ramp rate of 1° C./min with an hour hold between each heating/cooling cycle). The solids were isolated via vacuum filtration, air-dried for an hour and dried in a vacuum oven at 40° C. for 5 hours to provide Hemifumarate Salt Form B.

Hemifumarate Salt Form B has an FT-Raman Spectrum as depicted in FIG. 42. Hemifumarate Salt Form B has a DSC thermogram substantially as depicted in FIG. 43, comprising an endotherm with an onset temperature at 133.3° C. Hemifumarate Salt Form B has a TGA thermogram as depicted in FIG. 43, comprising a total mass loss of approximately 1.% of the total mass of the sample when heated from approximately 25° C. to approximately 150° C.

Figure 44:
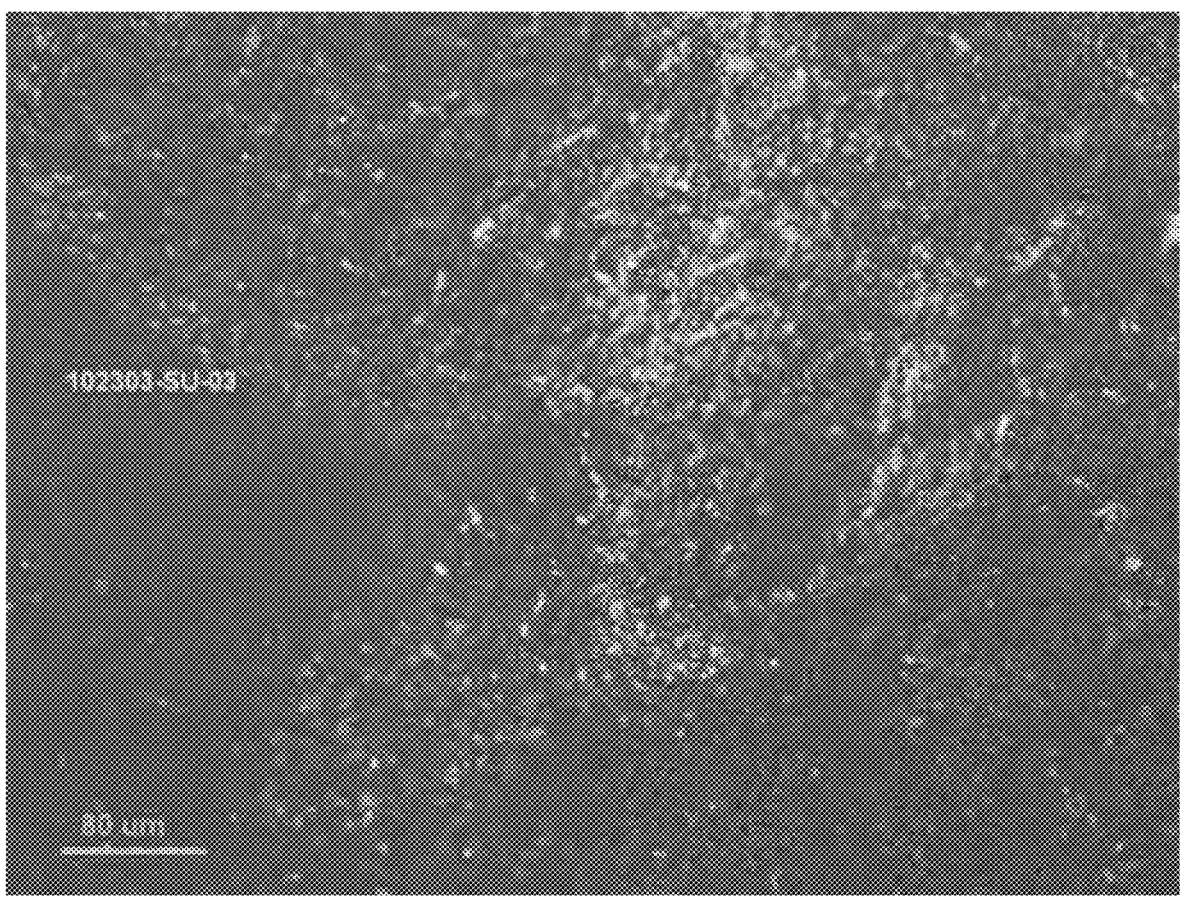
FIG. 44 depicts polarized-light microscopy of Hemifumarate Salt Form B of Compound 6.

FIG. 44 depicts polarized-light microscopy of Hemifumarate Salt Form B of Compound 6.

A list of X-Ray diffraction peaks for Hemifumarate Salt Form B is provided below in Table 11.

TABLE 11

X-Ray Diffraction Peaks for Hemifumarate Salt Form B.

| Two-theta angle (°) | d Space (Å) | Height (counts) |
|---|---|---|
| 3.5 | 24.972 | 87.1 |
| 7.0 | 12.656 | 3911.0 |
| 10.4 | 8.471 | 172.6 |
| 10.8 | 8.223 | 127.1 |
| 12.2 | 7.267 | 164.8 |
| 13.9 | 6.361 | 112.1 |
| 15.6 | 5.681 | 105.1 |
| 17.6 | 5.038 | 164.3 |
| 18.6 | 4.776 | 138.0 |
| 19.3 | 4.595 | 69.0 |
| 20.8 | 4.266 | 1152.3 |
| 21.7 | 4.093 | 372.9 |
| 22.2 | 4.012 | 78.4 |
| 23.1 | 3.845 | 113.6 |
| 24.0 | 3.706 | 543.7 |
| 24.5 | 3.633 | 66.1 |
| 25.0 | 3.567 | 163.5 |
| 27.4 | 3.259 | 376.1 |
| 28.0 | 3.181 | 71.9 |
| 28.7 | 3.110 | 74.9 |
| 29.9 | 2.989 | 60.7 |
| 30.7 | 2.910 | 179.3 |
| 31.7 | 2.826 | 62.6 |

(l) Hemifumarate Salt Form C

A solution of Compound 1 was prepared in acetone at 0.244 mmol/mL. A solution of fumaric acid was prepared in methanol at 0.207 mmol/mL. The solution of Compound 1 (500 µL) was mixed with 294.7 µL of fumaric acid solution in a 4 mL clear glass vial (0.5 equivalents). After mixing, the sample was capped and shaken at 200 RPM at room temperature for one hour. The samples were then uncapped and dried in fume hood under nitrogen purge. After drying, the sample was mixed with 600 µL of ethyl methyl ketone. The sample was re-capped and stirred with stirring bars at 200 RPM at room temperature for two days. The sample was filtered using Nylon-membraned centrifuge tube filter. The solids were recovered and dried in vacuum oven at 30° C. overnight to yield Hemifumarate Salt Form C.

Alternatively, a solution of Compound 1 was prepared in acetone at 0.244 mmol/mL. A solution of fumaric acid was prepared in methanol at 0.207 mmol/mL. The solution of Compound 1 (500 µL) was mixed with 294.7 µL of fumaric acid solution in a 4 mL clear glass vial (0.5 equivalents). After mixing, the sample was capped and shaken at 200 RPM at room temperature for one hour. The samples were then uncapped and dried in fume hood under nitrogen purge. After drying, the sample was mixed with 600 µL of dimethyl carbonate. The sample was re-capped and stirred with stirring bars at 200 RPM at room temperature for two days. The sample was filtered using Nylon-membraned centrifuge tube filter. The solids were recovered and dried in vacuum oven at 30° C. overnight to yield Hemifumarate Salt Form C.

Alternatively, a solution of Compound 1 was prepared in acetone at 0.244 mmol/mL. A solution of fumaric acid was prepared in methanol at 0.207 mmol/mL. The solution of Compound 1 (500 µL) was mixed with 294.7 µL of fumaric acid solution in a 4 mL clear glass vial (0.5 equivalents). After mixing, the sample was capped and shaken at 200 RPM at room temperature for one hour. The samples were then uncapped and dried in fume hood under nitrogen purge. After drying, the sample was mixed with 600 µL of ethyl methyl ketone. The sample was re-capped and stirred with stirring bars at 200 RPM at room temperature for two days. The sample was filtered using Nylon-membraned centrifuge tube filter. The solids were recovered and dried in vacuum oven at 30° C. overnight. The solids were then suspended in acetonitrile, allowed to stir at ambient temperature overnight, filtered, and dried in a vacuum oven at 30° C. overnight to yield Hemifumarate Salt Form C.

Hemifumarate Salt Form C has a Raman Spectrum as depicted in FIG. 46. Hemifumarate Salt Form C has a DSC thermogram substantially as depicted in FIG. 47, comprising an endotherm with an onset temperature at approximately 122.7° C. Hemifumarate Salt Form C has a TGA thermogram as depicted in FIG. 47, comprising a total mass loss of approximately 0.2% of the total mass of the sample when heated from approximately 34.5° C. to approximately 96.3° C.

A list of X-Ray diffraction peaks for Hemifumarate Salt Form C is provided below in Table 12.

TABLE 12

X-Ray Diffraction Peaks for Hemifumarate Salt Form C.

| Two-theta angle (°) | d Space (Å) | Height (counts) |
|---|---|---|
| 5.4 | 16.300 | 367 |
| 7.1 | 12.390 | 817 |
| 8.1 | 10.960 | 366 |
| 10.7 | 8.270 | 653 |
| 11.6 | 7.631 | 3169 |
| 12.1 | 7.313 | 2995 |
| 12.7 | 6.972 | 454 |
| 13.5 | 6.556 | 2376 |
| 13.8 | 6.415 | 1464 |
| 14.1 | 6.265 | 1664 |
| 15.8 | 5.619 | 2892 |
| 16.0 | 5.553 | 1088 |
| 16.4 | 5.385 | 804 |
| 16.8 | 5.260 | 84 |
| 17.5 | 5.058 | 5026 |
| 17.9 | 4.941 | 1923 |
| 18.4 | 4.821 | 1798 |
| 19.0 | 4.679 | 762 |
| 19.6 | 4.523 | 1259 |
| 20.2 | 4.391 | 2198 |
| 21.0 | 4.233 | 1814 |
| 21.4 | 4.155 | 5913 |
| 21.9 | 4.061 | 702 |
| 22.6 | 3.932 | 647 |
| 23.5 | 3.790 | 4377 |
| 23.9 | 3.728 | 1286 |
| 24.4 | 3.646 | 1678 |

TABLE 12-continued

X-Ray Diffraction Peaks for Hemifumarate Salt Form C.

| Two-theta angle (°) | d Space (Å) | Height (counts) |
|---|---|---|
| 24.9 | 3.572 | 447 |
| 25.1 | 3.552 | 839 |
| 25.4 | 3.510 | 1732 |
| 26.9 | 3.307 | 130 |
| 27.7 | 3.222 | 610 |
| 28.3 | 3.157 | 337 |
| 28.8 | 3.093 | 298 |
| 29.1 | 3.068 | 544 |
| 29.6 | 3.011 | 480 |
| 32.6 | 2.742 | 487 |

(m) HBr Salt Form A

Compound 1 (about 20 mg) was suspended in isopropanol (about 250 µL) and a 5 M solution of HBr in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in isopropanol and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. The solids were isolated from the solution via vacuum filtration, air-dried for one hour followed by drying in vacuum oven at a 40° C. for 5 hours to yield HBr Salt Form A.

Alternatively, Compound 1 (101.5 mg) was combined with isopropanol (1.25 mL) and HBr (5M solution in water, 1 equivalent) and the resulting product was heated to 40° C. and held at 40° C. for an hour. Seeds of a crystalline HBr salt of Compound 1 (about 1 mg) were added. The temperature of the suspension was cycled between about 5° C. and about 40° C. for two days (ramp rate of 1° C./min with an hour hold between each heating/cooling cycle) which led to a white precipitate. The solids were isolated via vacuum filtration, air-dried for 90 minutes and dried in a vacuum oven at 40° C. for 5 hours to provide HBr Salt Form A (14.1 mg).

HBr Salt Form A has an FT-Raman Spectrum as depicted in FIG. 49. HBr Salt Form A has a DSC thermogram substantially as depicted in FIG. 50, comprising an endotherm with an onset temperature at 114.7° C. HBr Salt Form A has a TGA thermogram as depicted in FIG. 50, comprising a total mass loss of approximately 5.5% of the total mass of the sample when heated from approximately 25° C. to approximately 141° C.

Figure 51:
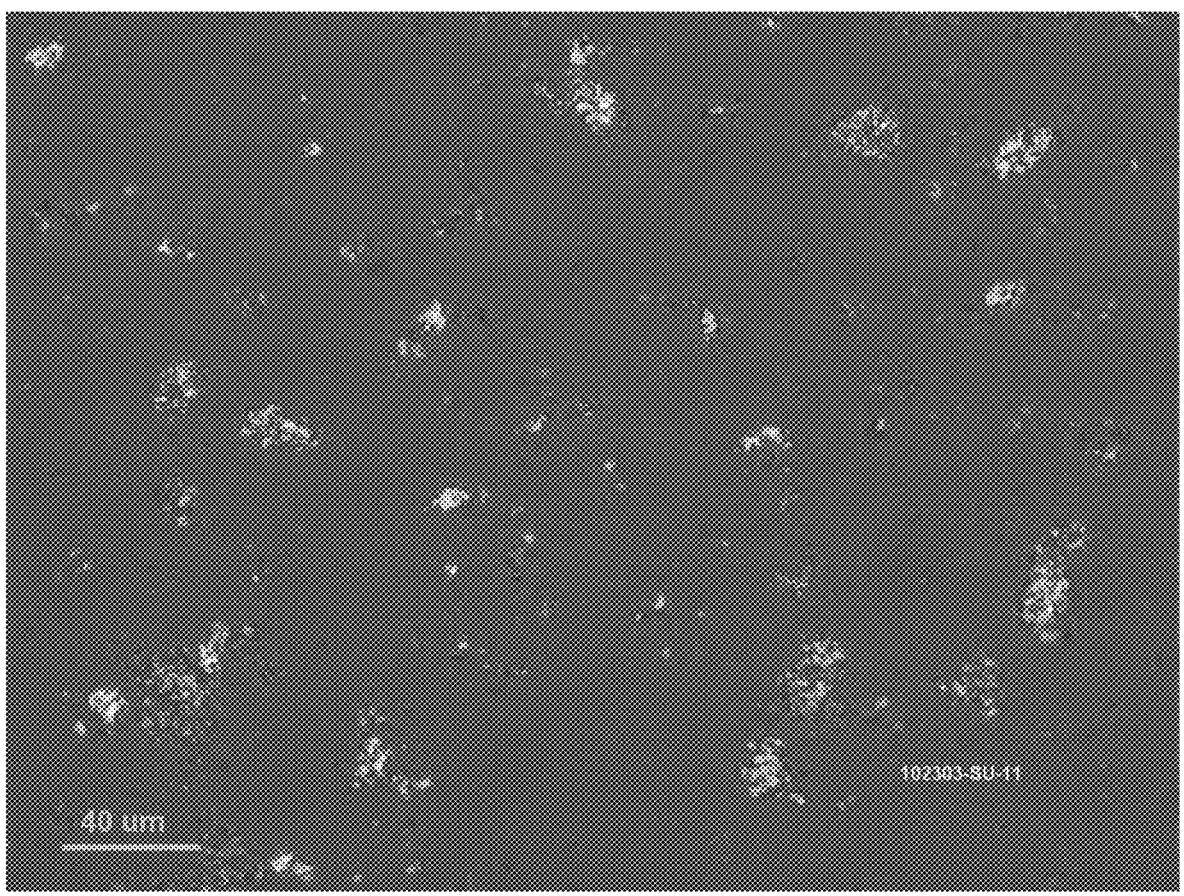
FIG. 51 depicts polarized-light microscopy of HBr Salt Form A of Compound 7.

FIG. 51 depicts polarized-light microscopy of HBr Salt Form A of Compound 7.

A list of X-Ray diffraction peaks for HBr Salt Form A is provided below in Table 13.

TABLE 13

X-Ray Diffraction Peaks for HBr Salt Form A.

| Two-theta angle (°) | d Space (Å) | Height (counts) |
|---|---|---|
| 4.1 | 21.726 | 166.6 |
| 6.1 | 14.414 | 320.2 |
| 8.2 | 10.821 | 311.7 |

TABLE 13-continued

X-Ray Diffraction Peaks for HBr Salt Form A.

| Two-theta angle (°) | d Space (Å) | Height (counts) |
|---|---|---|
| 20.5 | 4.336 | 221.6 |
| 22.6 | 3.940 | 188.4 |
| 26.8 | 3.330 | 67.6 |

(n) HBr Salt Form B

Compound 1 (about 20 mg) was suspended in methyl tert-butyl ether (about 250 µL) and a 5 M solution of HBr in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl tert-butyl ether and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and hexane (about 750 µL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield HBr Salt Form B.

Alternatively, Compound 1 (about 20 mg) was suspended in methyl isobutyl ketone (about 250 µL) and a 5 M solution of HBr in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl isobutyl ketone ether and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and hexane (about 750 µL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield HBr Salt Form B.

HBr Salt Form B has an FT-Raman Spectrum as depicted in FIG. 53. HBr Salt Form B has a DSC thermogram substantially as depicted in FIG. 54, comprising multiple endotherms with onset temperatures at 46.1° C., 91.1° C., and 125.8° C., respectively.

Figure 55:
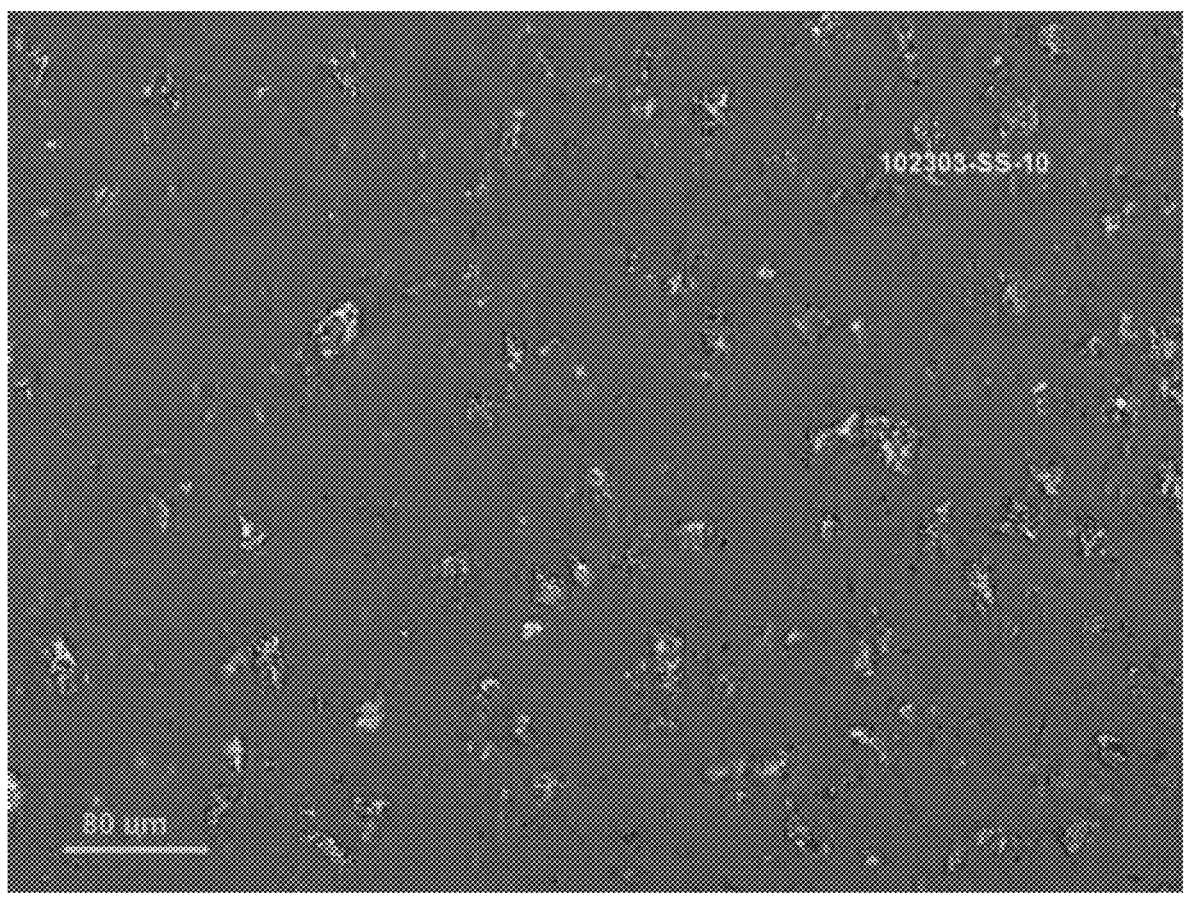
FIG. 55 depicts polarized-light microscopy of HBr Salt Form B of Compound 7.

FIG. 55 depicts polarized-light microscopy of HBr Salt Form B of Compound 7.

A list of X-Ray diffraction peaks for HBr Salt Form B is provided below in Table 14.

TABLE 14

X-Ray Diffraction Peaks for HBr Salt Form B.

| Two-theta angle (°) | d Space (Å) | Height (counts) |
|---|---|---|
| 2.3 | 38.105 | 290.6 |
| 8.1 | 10.921 | 147.9 |
| 10.2 | 8.691 | 91.5 |
| 12.2 | 7.244 | 160.5 |
| 15.7 | 5.638 | 99.5 |
| 17.5 | 5.054 | 80.4 |
| 18.7 | 4.739 | 135.6 |
| 19.5 | 4.559 | 88.0 |
| 23.6 | 3.763 | 71.3 |
| 24.6 | 3.620 | 65.6 |

(o) Maleate Salt Form A

Compound 1 (about 20 mg) was suspended in methyl tert-butyl ether (about 250 µL) and a 3 M solution of maleic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl tert-butyl ether and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. The solids were isolated via vacuum filtration, air-dried for one hour at room temperature to yield Maleate Salt Form A.

Maleate Salt Form A has an FT-Raman Spectrum as depicted in FIG. 57. Maleate Salt Form A has a DSC thermogram substantially as depicted in FIG. 58, comprising multiple endotherms with onset temperatures at 39.3° C., 67.6° C., and 100.4° C. Maleate Salt Form A has a TGA thermogram as depicted in FIG. 58, comprising a total mass loss of approximately 3.8% of the total mass of the sample when heated from approximately 25° C. to approximately 110° C., respectively.

Figure 59:
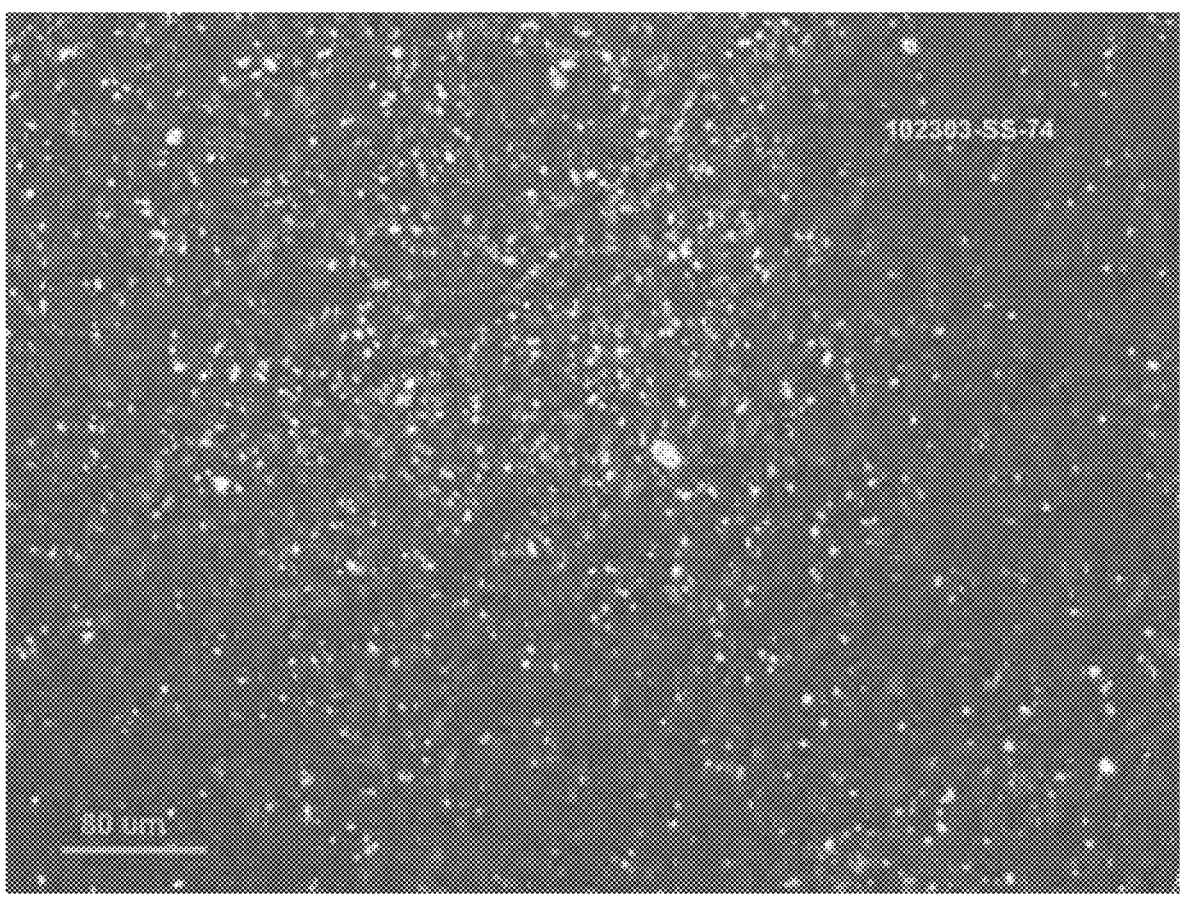
FIG. 59 depicts polarized-light microscopy of Maleate Salt Form A of Compound 8.

FIG. 59 depicts polarized-light microscopy of Maleate Salt Form A of Compound 8.

A list of X-Ray diffraction peaks for Maleate Salt Form A is provided below in Table 15.

TABLE 15

X-Ray Diffraction Peaks for Maleate Salt Form A.

| Two-theta angle (°) | d Space (Å) | Height (counts) |
|---|---|---|
| 4.1 | 21.639 | 421.8 |
| 7.5 | 11.731 | 236.3 |
| 8.2 | 10.809 | 1329.5 |
| 10.4 | 8.546 | 68.7 |
| 12.0 | 7.381 | 83.8 |
| 12.9 | 6.863 | 250.8 |
| 15.7 | 5.651 | 190.4 |
| 17.5 | 5.081 | 169.1 |
| 18.1 | 4.912 | 156.3 |
| 19.0 | 4.667 | 103.2 |
| 19.5 | 4.554 | 134.8 |
| 20.6 | 4.321 | 280.4 |
| 21.7 | 4.087 | 56.7 |
| 23.6 | 3.774 | 161.6 |
| 24.8 | 3.590 | 369.5 |
| 26.5 | 3.364 | 143.2 |
| 27.6 | 3.236 | 304.6 |
| 28.3 | 3.155 | 95.8 |

TABLE 15-continued

X-Ray Diffraction Peaks for Maleate Salt Form A.

| Two-theta angle (°) | d Space (Å) | Height (counts) |
|---|---|---|
| 29.0 | 3.081 | 82.2 |
| 30.6 | 2.923 | 71.9 |

(p) Maleate Salt Form B

Compound 1 (about 20 mg) was suspended in methyl isobutyl ketone (about 250 μL) and a 3 M solution of maleic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl isobutyl ketone and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and hexane (about 750 μL) was added. The sample was held at 40° C. for three hours, and then cooled to 5° C. for one day. The solution was warmed to 20° C. and the solvent was evaporated slowly at room temperature under a slow bleed of nitrogen gas to yield Maleate Salt Form B.

Maleate Salt Form B has an FT-Raman Spectrum as depicted in FIG. 61. Maleate Salt Form B has a DSC thermogram substantially as depicted in FIG. 62, comprising an endotherm with an onset temperature at 91.4° C. Maleate Salt Form B has a TGA thermogram as depicted in FIG. 62, comprising a total mass loss of approximately 2.5% of the total mass of the sample when heated from approximately 30° C. to approximately 110° C.

Figure 63:
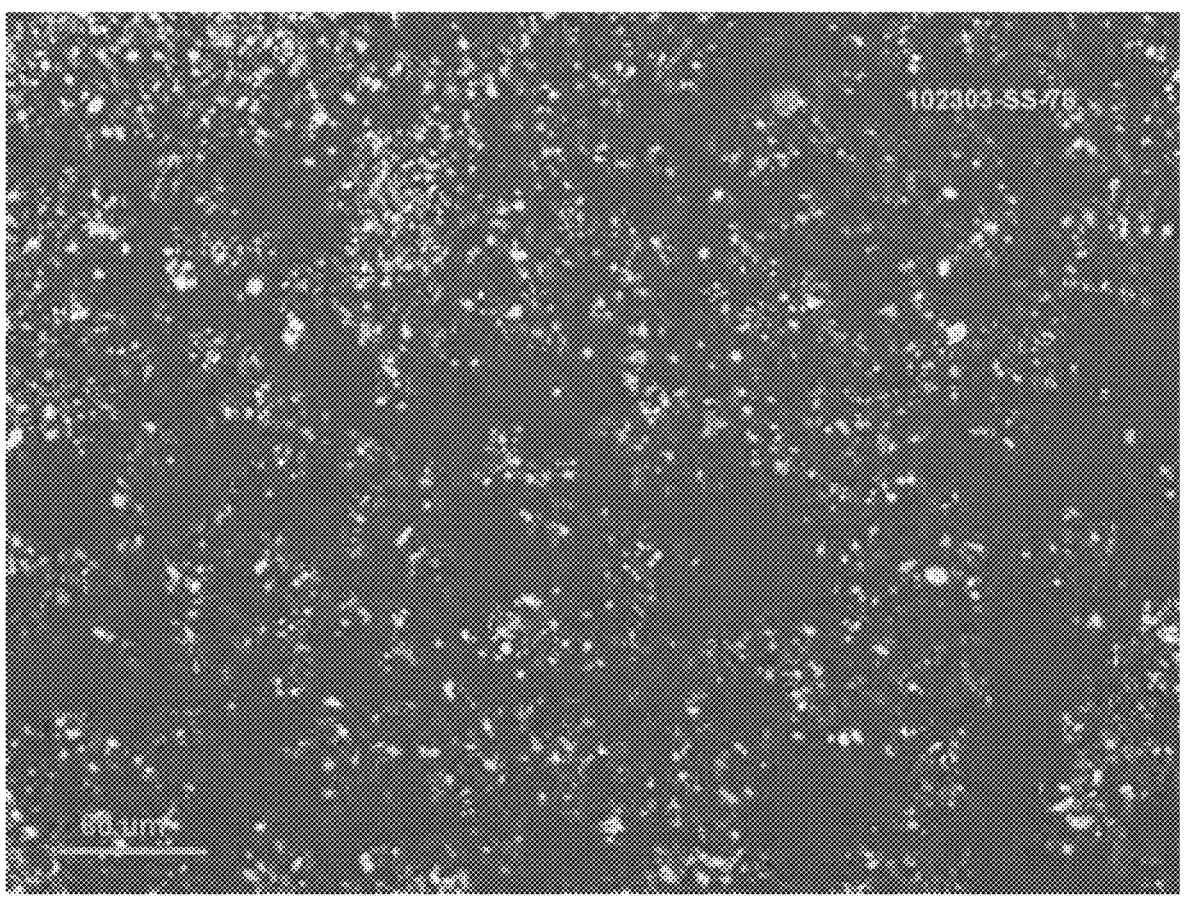
FIG. 63 depicts polarized-light microscopy of Maleate Salt Form B of Compound 8.

FIG. 63 depicts polarized-light microscopy of Maleate Salt Form B of Compound 8.

A list of X-Ray diffraction peaks for Maleate Salt Form B is provided below in Table 16.

TABLE 16

X-Ray Diffraction Peaks for Maleate Salt Form B.

| Two-theta angle (°) | d Space (Å) | Height (counts) |
|---|---|---|
| 6.9 | 12.743 | 311.4 |
| 10.4 | 8.498 | 258.6 |
| 11.4 | 7.741 | 79.6 |
| 13.9 | 6.382 | 216.0 |
| 15.8 | 5.593 | 149.2 |
| 18.9 | 4.704 | 139.7 |
| 19.1 | 4.642 | 134.1 |
| 20.9 | 4.255 | 415.8 |
| 23.9 | 3.731 | 75.1 |

(q) Maleate Salt Form C

Compound 1 (about 20 mg) was suspended in isopropyl acetate (about 250 μL) and a 3 M solution of maleic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in isopropyl acetate and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. The solids were isolated via vacuum filtration, air-dried for one hour at room temperature to yield Maleate Salt Form C.

Maleate Salt Form C has an FT-Raman Spectrum as depicted in FIG. 65. Maleate Salt Form C has a DSC thermogram substantially as depicted in FIG. 66, comprising multiple endotherms with onset temperatures at 68.6° C. and 123.3° C., respectively.

Figure 67:
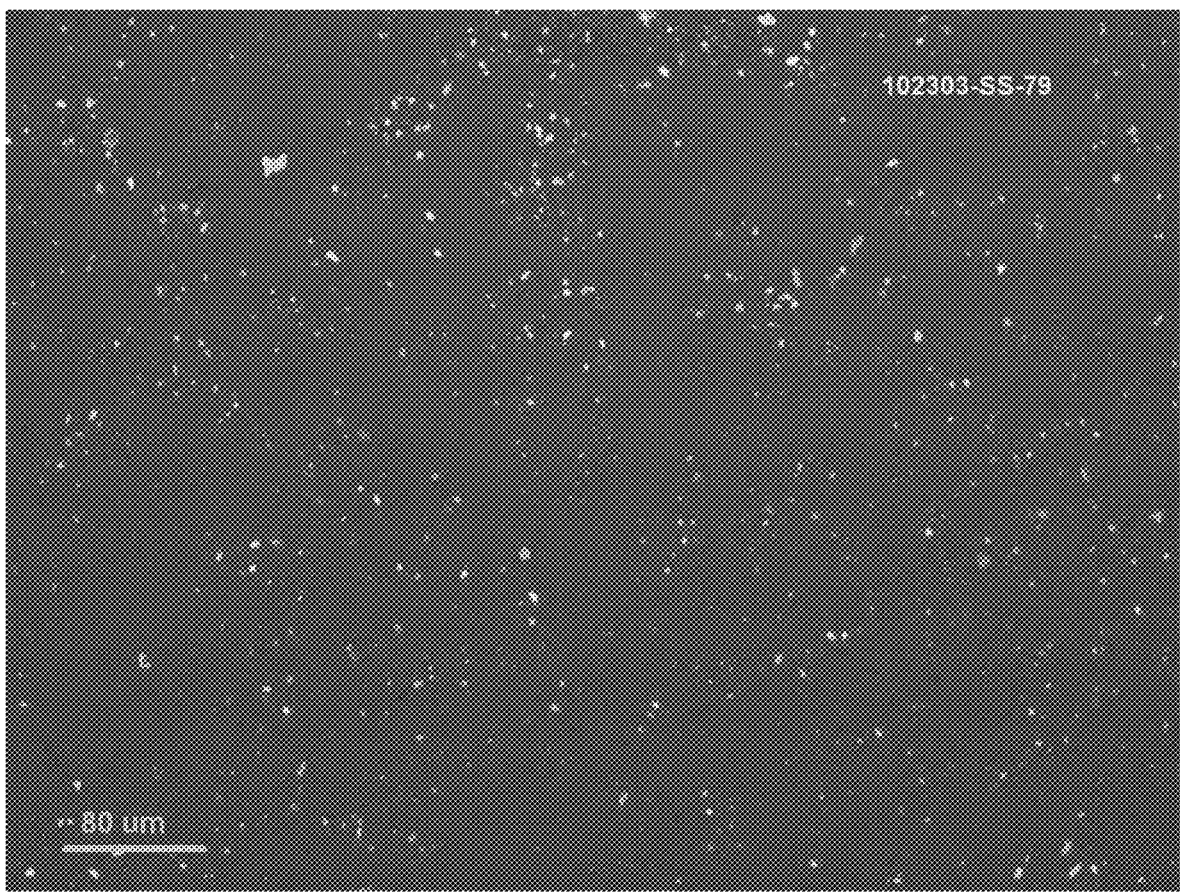
FIG. 67 depicts polarized-light microscopy of Maleate Salt Form C of Compound 8.

FIG. 67 depicts polarized-light microscopy of Maleate Salt Form C of Compound 8.

A list of X-Ray diffraction peaks for Maleate Salt Form C is provided below in Table 17.

TABLE 17

X-Ray Diffraction Peaks for Maleate Salt Form C.

| Two-theta angle (°) | d Space (Å) | Height (counts) |
|---|---|---|
| 4.1 | 21.769 | 398.7 |
| 8.1 | 10.911 | 781.3 |
| 10.9 | 8.149 | 64.9 |
| 12.1 | 7.302 | 87.7 |
| 16.2 | 5.484 | 116.2 |
| 20.3 | 4.379 | 197.4 |
| 24.4 | 3.647 | 186.3 |
| 26.0 | 3.434 | 89.0 |
| 26.5 | 3.359 | 92.8 |
| 27.6 | 3.233 | 175.7 |
| 28.6 | 3.125 | 155.9 |
| 30.6 | 2.920 | 55.0 |

(r) Maleate Salt Form D

Compound 1 (100 mg) was combined with methyl isobutyl ketone (1.25 mL) and maleic acid (3M solution in water, 1 equivalent) and the resulting product was heated to 40° C. and held at 40° C. for an hour. The solvent was evaporated to dryness under reduced pressure and methyl isobutyl ketone (1.25 mL) was added to the resulting product. Seeds of a crystalline maleate salt of Compound 1 (about 1 mg) were added. The temperature of the suspension was cycled between about 5° C. and about 40° C. for two days (ramp rate of 1° C./min with an hour hold between each heating/cooling cycle) which led to a white suspension. The suspension was filtered under vacuum and the solids were air-dried for an hour and dried in a vacuum oven at 40° C. for 5 hours to yield Maleate Salt Form D (47.5 mg).

Alternatively, Compound 1 (about 1.7 g) was combined with methanol (about 11 mL) and maleic acid (e.g., about 380.36 mg), and heated to 40° C. for one hour. An aliquot (about 0.21 mL) of the solution was dispersed to a vial and evaporated to dryness under reduced pressure, then dissolved in either a 1:9 mixture of 1-propanol and isopropyl ether, a 1:9 mixture of nitromethane and isopropyl ether, a 1:9 mixture of acetonitrile and isopropyl ether, toluene, dimethyl carbonate, methyl tert-butyl ether, isopropyl acetate, a 1:9 mixture of ethanol and isopropyl ether, a 1:2 mixture of ethyl acetate and cyclohexane, or a 1:2 mixture of methyl isobutyl ketone and heptane. The temperature of the resultant solution was cycled between 5° C. and 40° C. (1° C. per minute heating/cooling rate with an hour hold between each heating/cooling cycle) overnight. The solids were isolated through vacuum filtration to obtain Maleate Salt Form D of Compound 8.

Maleate Salt Form D has an FT-Raman Spectrum as depicted in FIG. 69. Maleate Salt Form D has a DSC thermogram substantially as depicted in FIG. 70, comprising multiple endotherms with peak maximum temperatures at 113.3° C. and 123.1° C., respectively. Maleate Salt Form D has a TGA thermogram as depicted in FIG. 70, comprising a total mass loss of approximately 2.5% of the total mass of the sample when heated from approximately 25° C. to approximately 123° C.

Figure 71:
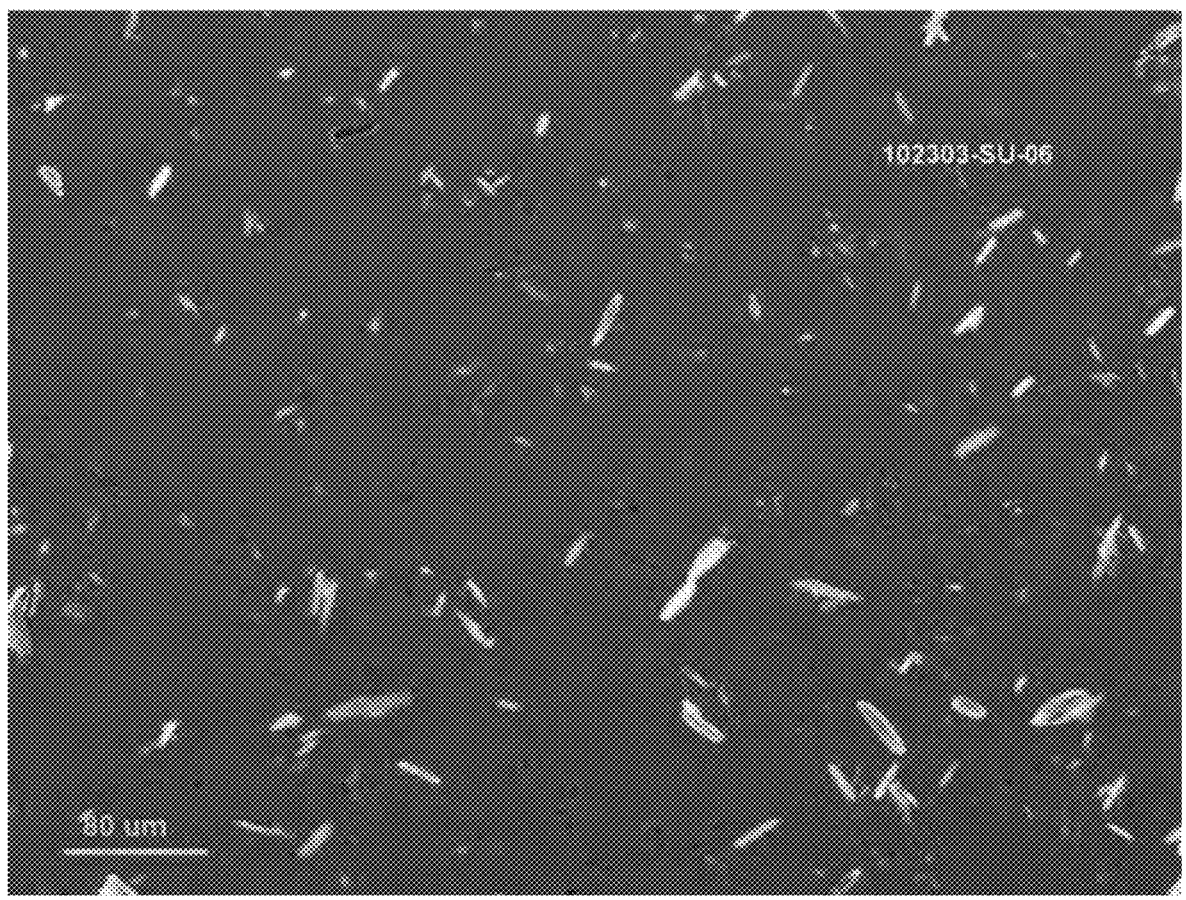
FIG. 71 depicts polarized-light microscopy of Maleate Salt Form D of Compound 8.

FIG. 71 depicts polarized-light microscopy of Maleate Salt Form D of Compound 8.

A list of X-Ray diffraction peaks for Maleate Salt Form D is provided below in Table 18.

TABLE 18

X-Ray Diffraction Peaks for Maleate Salt Form D.

| Two-theta angle (°) | d Space (Å) | Height (counts) |
|---|---|---|
| 3.7 | 23.848 | 1685.4 |
| 7.4 | 12.011 | 391.9 |
| 8.4 | 10.585 | 740.6 |
| 8.7 | 10.140 | 170.3 |
| 11.0 | 8.030 | 583.7 |
| 13.8 | 6.415 | 163.8 |
| 14.7 | 6.026 | 408.9 |
| 14.8 | 5.972 | 374.9 |
| 15.7 | 5.657 | 731.0 |
| 16.7 | 5.313 | 1106.5 |
| 17.5 | 5.077 | 641.4 |
| 17.6 | 5.041 | 957.6 |
| 18.5 | 4.795 | 716.6 |
| 19.5 | 4.542 | 823.7 |
| 20.3 | 4.366 | 198.0 |
| 20.7 | 4.286 | 491.3 |
| 21.2 | 4.194 | 356.6 |
| 22.1 | 4.022 | 618.6 |
| 23.2 | 3.836 | 466.4 |
| 23.8 | 3.732 | 165.8 |
| 24.3 | 3.657 | 339.3 |
| 25.2 | 3.537 | 125.1 |
| 25.9 | 3.446 | 225.2 |
| 26.3 | 3.385 | 127.2 |
| 27.0 | 3.298 | 83.1 |
| 27.9 | 3.193 | 200.4 |
| 29.4 | 3.034 | 168.5 |
| 30.2 | 2.959 | 77.1 |
| 31.0 | 2.881 | 80.9 |
| 31.6 | 2.835 | 127.0 |
| 32.6 | 2.748 | 75.2 |
| 34.3 | 2.616 | 62.3 |
| 34.8 | 2.576 | 62.4 |
| 37.2 | 2.414 | 98.7 |

(s) Malonate Salt Form A

Compound 1 (about 20 mg) was suspended in methyl isobutyl ketone (about 250 µL) and a 3 M solution of malonic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl isobutyl ketone and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and hexane (about 750 µL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield Malonate Salt Form A.

Alternatively, Compound 1 (102.4 mg) was combined with methyl isobutyl ketone (1.25 mL) and malonic acid (3 M solution in water, 1 equivalent) and the resulting product was heated to 40° C. and held at 40° C. for an hour. Seeds of a crystalline malonate salt of Compound 1 (about 1 mg) were added. The temperature of the suspension was cycled between about 5° C. and about 40° C. for two days (ramp rate of 1° C./min with an hour hold between each heating/cooling cycle) which led to a very thin suspension. The thin suspension was cooled to 5° C. and held at 5° C. for 3 days. The suspension was filtered via vacuum filtration and the solids were air-dried for an hour and dried in a vacuum oven at 40° C. for 5 hours to yield Malonate Salt Form A (58.5 mg).

Alternatively, Compound 1 (about 20 mg) was suspended in isopropyl acetate (about 250 µL) and a 3 M solution of malonic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in isopropyl acetate and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and diisopropyl ether (about 750 µL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield Malonate Salt Form A.

Malonate Salt Form A has an FT-Raman Spectrum as depicted in FIG. 73. Malonate Salt Form A has a DSC thermogram substantially as depicted in FIG. 74, comprising an endotherm with an onset temperature at 63.1° C. Malonate Salt Form A has a TGA thermogram as depicted in FIG. 74, comprising a mass loss of approximately 15% of the total mass of the sample when heated from approximately 25° C. to approximately 163° C.

Figure 75:
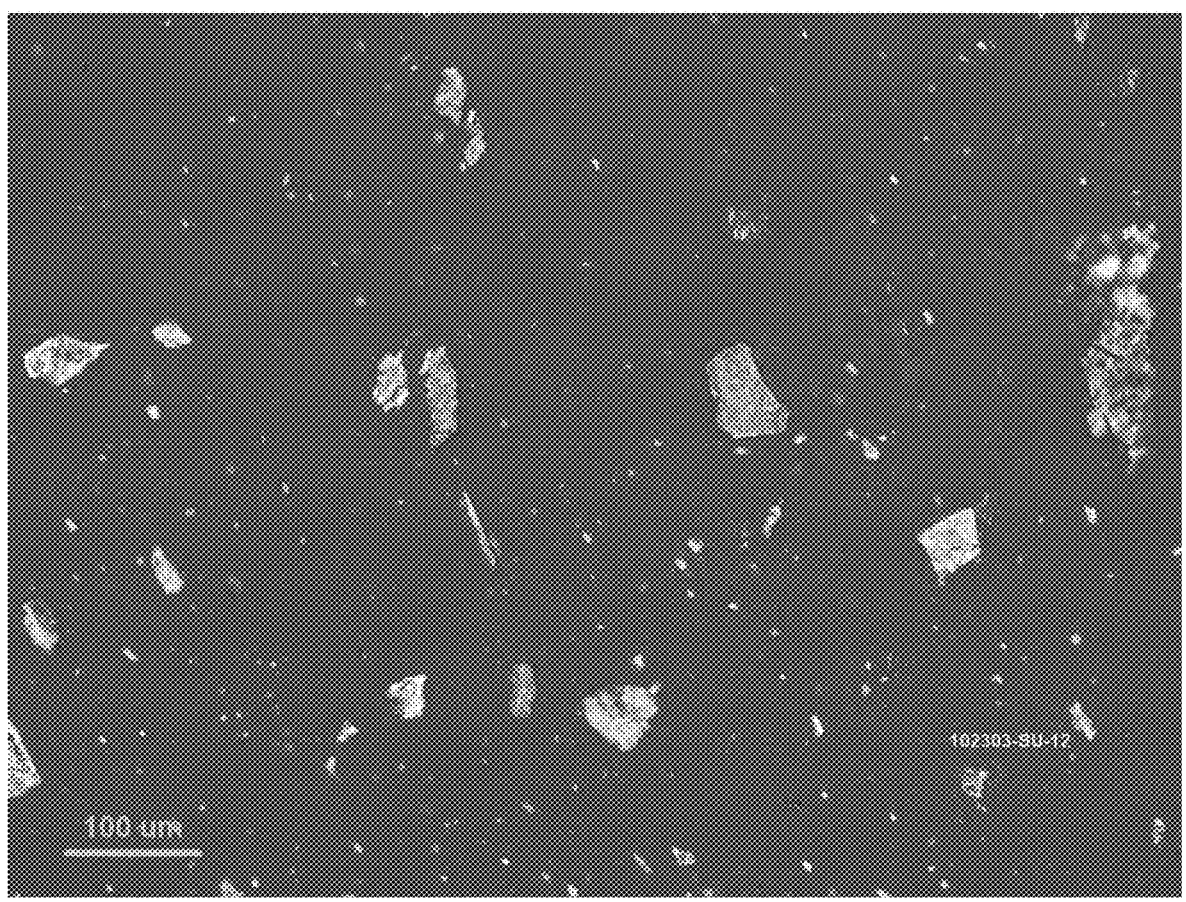
FIG. 75 depicts polarized-light microscopy of Malonate Salt Form A of Compound 9.

FIG. 75 depicts polarized-light microscopy of Malonate Salt Form A of Compound 9.

A list of X-Ray diffraction peaks for Malonate Salt Form A is provided below in Table 19.

TABLE 19

X-Ray Diffraction Peaks for Malonate Salt Form A.

| Two-theta angle (°) | d Space (Å) | Height (counts) |
|---|---|---|
| 3.8 | 23.271 | 1735.7 |
| 7.6 | 11.673 | 2126.7 |
| 11.3 | 7.826 | 1482.0 |
| 13.2 | 6.692 | 75.5 |
| 15.2 | 5.839 | 306.4 |
| 16.5 | 5.359 | 91.1 |
| 17.2 | 5.168 | 131.5 |
| 17.6 | 5.026 | 134.1 |
| 18.4 | 4.831 | 190.5 |
| 19.2 | 4.622 | 161.3 |
| 19.8 | 4.486 | 156.6 |
| 20.7 | 4.284 | 64.3 |

TABLE 19-continued

X-Ray Diffraction Peaks for Malonate Salt Form A.

| Two-theta angle (°) | d Space (Å) | Height (counts) |
|---|---|---|
| 23.0 | 3.860 | 1370.3 |
| 24.9 | 3.578 | 107.5 |
| 26.5 | 3.367 | 184.9 |
| 27.0 | 3.307 | 174.7 |
| 27.5 | 3.245 | 53.4 |
| 28.4 | 3.147 | 125.8 |
| 30.4 | 2.942 | 113.4 |
| 31.1 | 2.872 | 67.3 |
| 33.4 | 2.680 | 80.1 |
| 34.7 | 2.583 | 125.6 |
| 38.7 | 2.329 | 112.0 |

(t) Edisylate Salt Form A

Compound 1 (about 20 mg) was suspended in acetonitrile (about 250 µL) and a 3 M solution of ethane-1,2-disulfonic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in acetonitrile and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. The solids were isolated via vacuum filtration, air-dried for one hour to yield Edisylate Salt Form A.

Edisylate Salt Form A has an FT-Raman Spectrum as depicted in FIG. 77. Edisylate Salt Form A has a DSC thermogram substantially as depicted in FIG. 78, comprising an endotherm with an onset temperature at 90.2° C. Edisylate Salt Form A has a TGA thermogram as depicted in FIG. 78, comprising a total mass loss of approximately 7.3% of the total mass of the sample when heated from approximately 25° C. to approximately 150° C.

Figure 79:
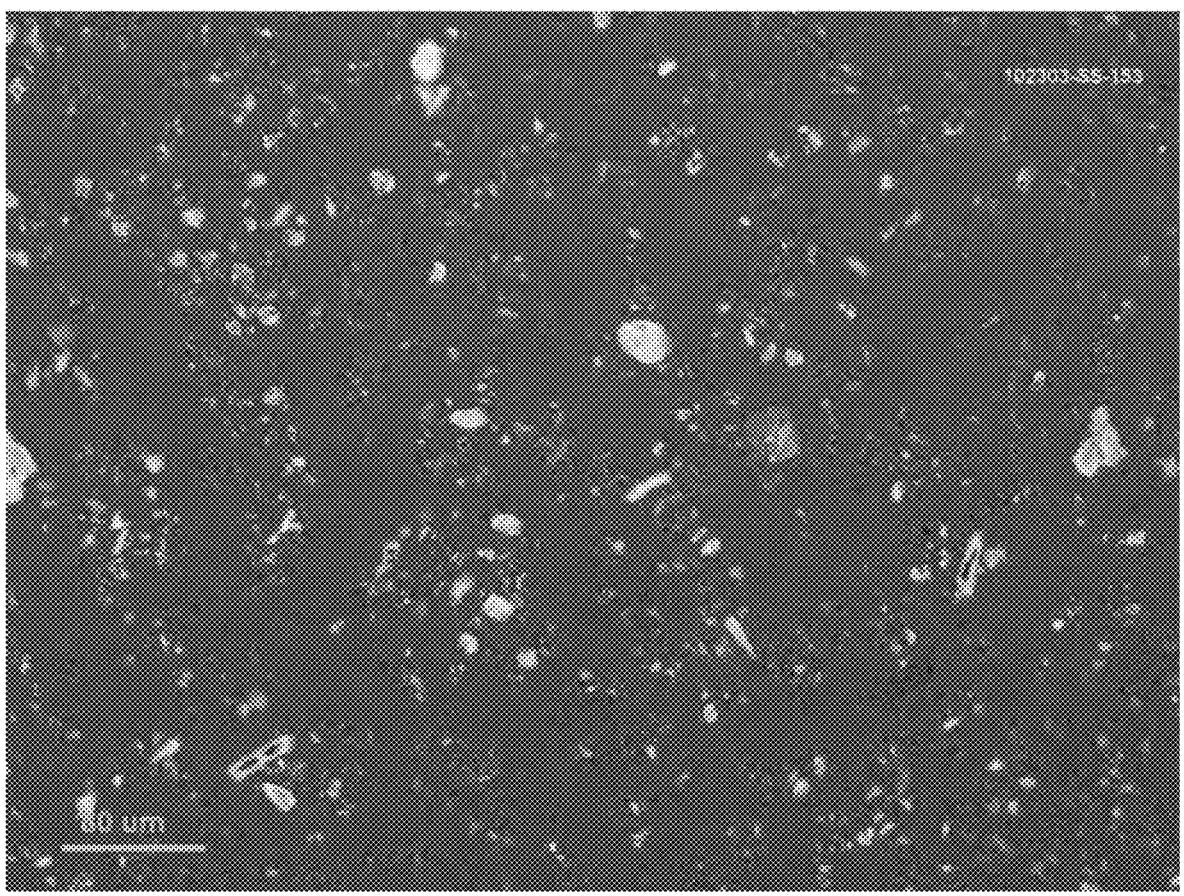
FIG. 79 depicts polarized-light microscopy of Edisylate Salt Form A of Compound 10.

FIG. 79 depicts polarized-light microscopy of Edisylate Salt Form A of Compound 10.

A list of X-Ray diffraction peaks for Edisylate Salt Form A is provided below in Table 20.

TABLE 20

X-Ray Diffraction Peaks for Edisylate Salt Form A.

| Two-theta angle (°) | d Space (Å) | Height (counts) |
|---|---|---|
| 6.8 | 13.087 | 199.9 |
| 11.7 | 7.574 | 1174.1 |
| 13.5 | 6.545 | 337.4 |
| 16.9 | 5.253 | 90.7 |
| 17.6 | 5.049 | 189.9 |
| 18.0 | 4.915 | 104.7 |
| 20.3 | 4.365 | 386.5 |
| 21.6 | 4.113 | 121.5 |
| 23.0 | 3.873 | 131.0 |
| 23.5 | 3.791 | 1633.8 |
| 23.9 | 3.730 | 167.3 |
| 24.6 | 3.618 | 224.7 |
| 32.8 | 2.728 | 65.7 |
| 35.5 | 2.526 | 61.8 |

(u) Edisylate Salt Form B

Compound 1 (about 20 mg) was suspended in methyl isobutyl ketone (about 250 µL) and a 3 M solution of ethane-1,2-disulfonic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl isobutyl ketone and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. The sample was heated to 40° C., held at 40° C. for three hours, and cooled to 5° C. and held at 5° C. for one day. The solution was warmed to 20° C. and the solvent was evaporated slowly at room temperature under a slow bleed of nitrogen gas to yield Edisylate Salt Form B.

Edisylate Salt Form B has an FT-Raman Spectrum as depicted in FIG. 81. Edisylate Salt Form B has a DSC thermogram substantially as depicted in FIG. 82, comprising an endotherm between with an onset temperature at approximately 59.1° C.

Figure 83:
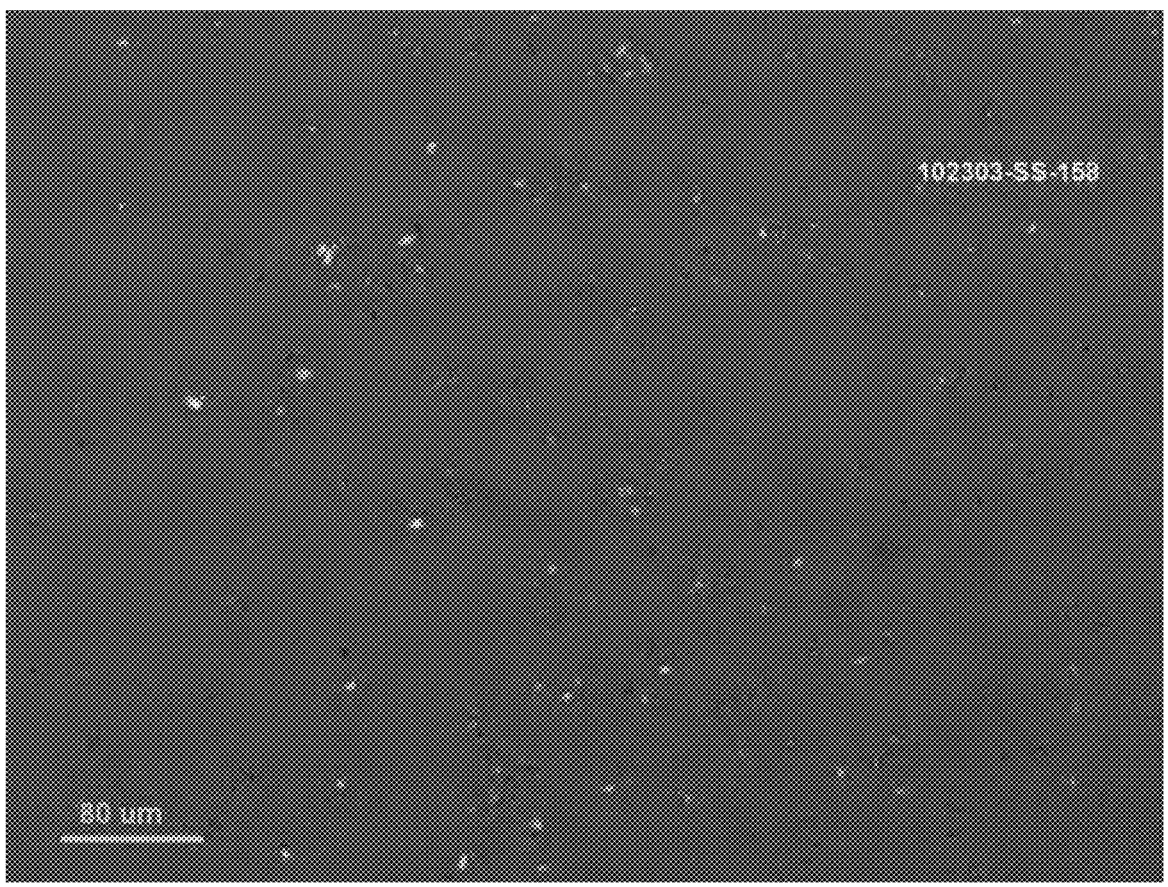
FIG. 83 depicts polarized-light microscopy of Edisylate Salt Form B of Compound 10.

FIG. 83 depicts polarized-light microscopy of Edisylate Salt Form B of Compound 10.

A list of X-Ray diffraction peaks for Edisylate Salt Form B is provided below in Table 21.

TABLE 21

X-Ray Diffraction Peaks for Edisylate Salt Form B.

| Two-theta angle (°) | d Space (Å) | Height (counts) |
|---|---|---|
| 7.3 | 12.070 | 281.7 |
| 9.8 | 9.063 | 363.7 |
| 11.7 | 7.568 | 116.8 |
| 12.7 | 6.966 | 71.4 |
| 13.5 | 6.575 | 276.4 |
| 14.6 | 6.071 | 305.3 |
| 17.0 | 5.224 | 69.2 |
| 19.4 | 4.578 | 220.4 |
| 20.0 | 4.441 | 168.5 |
| 20.9 | 4.258 | 73.6 |
| 22.4 | 3.970 | 298.5 |
| 22.9 | 3.876 | 73.6 |
| 23.5 | 3.791 | 101.9 |
| 24.6 | 3.614 | 172.4 |
| 25.6 | 3.482 | 124.7 |
| 26.5 | 3.368 | 261.7 |
| 26.8 | 3.327 | 116.3 |
| 28.8 | 3.097 | 65.3 |
| 36.0 | 2.497 | 95.0 |
| 36.9 | 2.435 | 65.1 |

(v) Edisylate Salt Form C

Compound 1 (about 20 mg) was suspended in methyl tert-butyl ether (about 250 µL) and a 3 M solution of ethane-1,2-disulfonic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in methyl tert-butyl ether and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. The sample was heated to 40° C. and held at 40° C. for three hours. The sample was cooled to 5° C. and held at 5° C. for one day. The solution was warmed to 20° C. and the solvent was evaporated slowly at room temperature under a slow bleed of nitrogen gas to yield Edisylate Salt Form C.

Alternatively, Compound 1 (about 20 mg) was suspended in isopropyl acetate (about 250 μL) and a 3 M solution of ethane-1,2-disulfonic acid in water (1.0 equivalent) was added. The temperature of the mixture was cycled between about 5° C. and about 40° C. (1° C. per minute heating/cooling rate with an hour hold between each heating/cooling cycle) for a day. The sample was equilibrated at 20° C. at the end of temperature cycling for at least one hour. The sample was evaporated to dryness under reduced pressure in a centrifuge evaporator. The sample was re-suspended in isopropyl acetate and the temperature was cycled between about 5° C. and about 40° C. (1° C. per minute heating/cooling rate with an hour hold between each heating/cooling cycle) for a period about a day. The sample was equilibrated at 20° C. at the end of temperature cycling for at least one hour. After this time, the sample was heated to 40° C. and diisopropyl ether (about 750 μL) was added. The sample was held at 40° C. for three hours, and then cooled to 5° C. and held at 5° C. for one day. The solution was warmed to 20° C. and the solvent was evaporated slowly at room temperature under a slow bleed of nitrogen gas to yield Edisylate Salt Form C.

Alternatively, Compound 1 (103.4 mg) was combined with acetonitrile (1.25 mL) and ethane-1,2-disulfonic acid (3 M solution in water, 1 equivalent) and the resulting product was heated to 40° C. and held at 40° C. for an hour. Seeds of a crystalline edisylate salt of Compound 1 (about 1 mg) were added. The temperature of the suspension was cycled between about 5° C. and about 40° C. for two days (ramp rate of 1° C./min with an hour hold between each heating/cooling cycle) which led to a white precipitate. The solids were isolated via vacuum filtration, air-dried for 90 minutes and dried in a vacuum oven at 40° C. for 5 hours to yield Edisylate Salt Form C (32.8 mg).

Edisylate Salt Form C has an FT-Raman Spectrum as depicted in FIG. 85. Edisylate Salt Form C has a DSC thermogram substantially as depicted in FIG. 86, comprising multiple endotherms with onset temperatures at 90.7° C. and 121.7° C. Edisylate Salt Form C has a TGA thermogram as depicted in FIG. 86, comprising a total mass loss of approximately 2.9% of the total mass of the sample when heated from approximately 25° C. to approximately 118° C., respectively.

Figure 87:
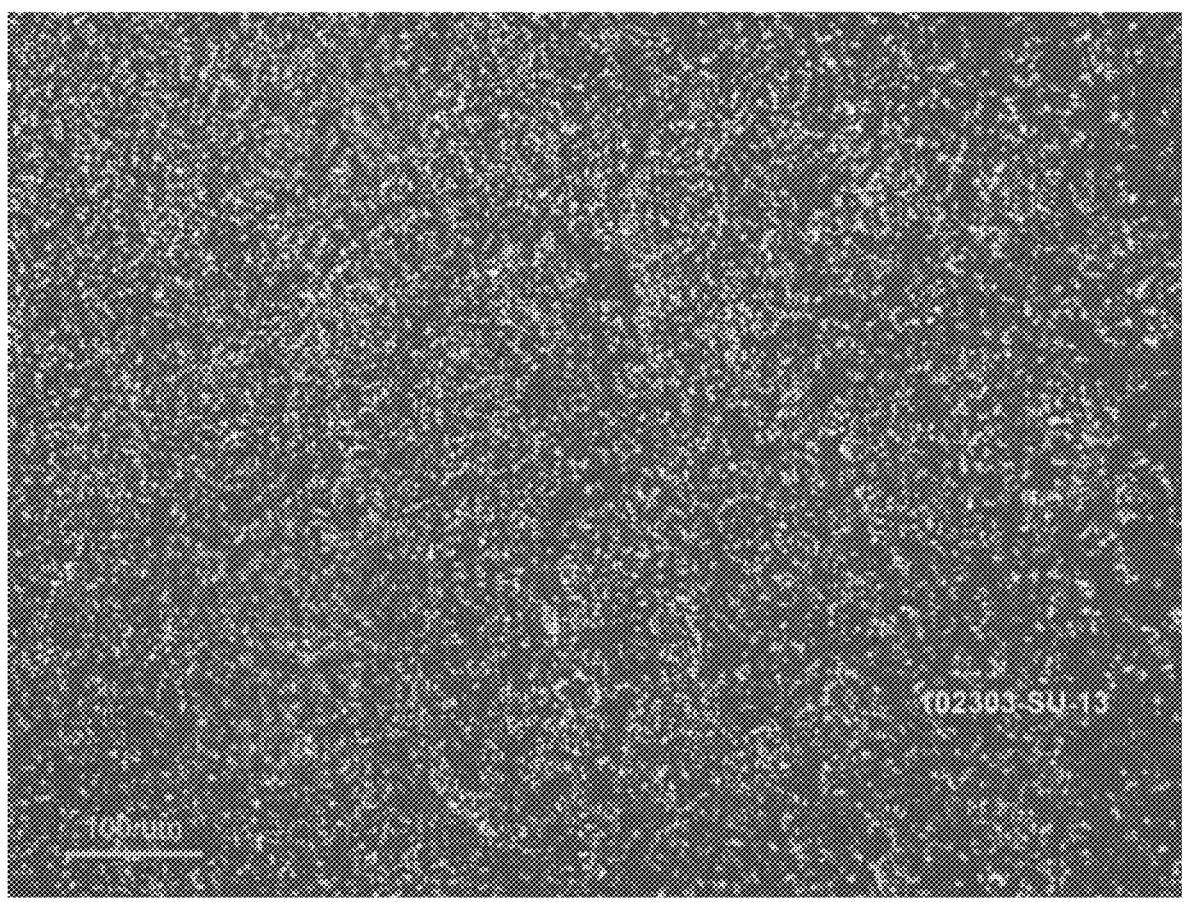
FIG. 87 depicts polarized-light microscopy of Edisylate Salt Form C of Compound 10.

FIG. 87 depicts polarized-light microscopy of Edisylate Salt Form C of Compound 10.

A list of X-Ray diffraction peaks for Edisylate Salt Form C is provided below in Table 22.

TABLE 22

X-Ray Diffraction Peaks for Edisylate Salt Form C.

| Two-theta angle (°) | d Space (Å) | Height (counts) |
|---|---|---|
| 3.4 | 25.891 | 474.0 |
| 6.8 | 13.039 | 679.0 |
| 12.3 | 7.205 | 173.3 |
| 13.5 | 6.547 | 1710.6 |
| 16.3 | 5.424 | 176.0 |
| 16.9 | 5.239 | 443.7 |
| 18.0 | 4.934 | 186.0 |
| 18.7 | 4.748 | 384.4 |

TABLE 22-continued

X-Ray Diffraction Peaks for Edisylate Salt Form C.

| Two-theta angle (°) | d Space (Å) | Height (counts) |
|---|---|---|
| 19.5 | 4.541 | 151.9 |
| 20.3 | 4.369 | 1641.4 |
| 20.7 | 4.291 | 281.3 |
| 21.4 | 4.158 | 213.8 |
| 21.7 | 4.094 | 239.3 |
| 22.8 | 3.895 | 100.9 |
| 23.6 | 3.771 | 181.2 |
| 26.6 | 3.351 | 100.3 |
| 27.1 | 3.294 | 142.0 |
| 33.0 | 2.712 | 129.6 |
| 36.3 | 2.472 | 63.2 |
| 37.8 | 2.381 | 70.8 |

(w) Tosylate Salt Form A

A solution of Compound 1 was prepared in acetone at 0.244 mmole/mL. A solution of p-toluenesulfonic acid monohydrate was prepared in acetonitrile at 0.225 mmole/mL. The solution of Compound 1 (500 μL) was mixed with 543.1 μL of p-toluenesulfonic acid solution in a 4 mL clear glass vial (1.0 equivalent). After mixing, the sample was capped and shaken at 200 RPM at room temperature for one hour. The samples were then uncapped and dried in fume hood under nitrogen purge. After drying, the sample was mixed with 600 μL of isopropanol. The sample was re-capped and stirred with stirring bars at 200 RPM at room temperature for two days. The sample was filtered using Nylon-membraned centrifuge tube filter. The solids were recovered and dried in vacuum oven at 30° C. overnight to yield Tosylate Salt Form A.

Alternatively, a solution of Compound 1 was prepared in acetone at 0.244 mmole/mL. A solution of p-toluenesulfonic acid monohydrate was prepared in acetonitrile at 0.225 mmole/mL. The solution of Compound 1 (500 μL) was mixed with 543.1 μL of p-toluenesulfonic acid solution in a 4 mL clear glass vial (1.0 equivalent). After mixing, the sample was capped and shaken at 200 RPM at room temperature for one hour. The sample was then uncapped and dried in fume hood under nitrogen purge. After drying, the sample was mixed with 600 μL of isopropyl acetate. The sample was re-capped and stirred with stirring bars at 200 RPM at room temperature for two days. The sample was filtered using Nylon-membraned centrifuge tube filter. The solids were recovered and dried in vacuum oven at 30° C. overnight to yield Tosylate Salt Form A.

Tosylate Salt Form A has an FT-Raman Spectrum as depicted in FIG. 89. Tosylate Salt Form A has a DSC thermogram substantially as depicted in FIG. 90, comprising multiple endotherms with onset temperatures at 64.3° C. and 149.7° C., respectively. Tosylate Salt Form A has a TGA thermogram as depicted in FIG. 90, comprising a total mass loss of approximately 1.2% of the total mass of the sample when heated from approximately 52.7° C. to approximately 99.6° C.

A list of X-Ray diffraction peaks for Tosylate Salt Form A is provided below in Table 23.

TABLE 23

X-Ray Diffraction Peaks for Tosylate Salt Form A.

| Two-theta angle (°) | d Space (Å) | Height (counts) |
|---|---|---|
| 6.9 | 12.840 | 561 |
| 8.1 | 10.897 | 5191 |

TABLE 23-continued

X-Ray Diffraction Peaks for Tosylate Salt Form A.

| Two-theta angle (°) | d Space (Å) | Height (counts) |
|---|---|---|
| 8.3 | 10.604 | 1454 |
| 9.9 | 8.897 | 3305 |
| 10.2 | 8.708 | 2151 |
| 11.0 | 8.032 | 1277 |
| 11.7 | 7.557 | 2063 |
| 13.3 | 6.675 | 3229 |
| 15.8 | 5.622 | 2008 |
| 16.3 | 5.432 | 6571 |
| 17.5 | 5.074 | 8595 |
| 18.2 | 4.865 | 2299 |
| 19.1 | 4.646 | 8840 |
| 19.8 | 4.491 | 2127 |
| 20.1 | 4.418 | 1227 |
| 21.6 | 4.112 | 3586 |
| 22.0 | 4.033 | 1207 |
| 22.2 | 4.000 | 1799 |
| 23.0 | 3.865 | 2932 |
| 23.6 | 3.765 | 2942 |
| 25.2 | 3.538 | 2762 |

(x) Tosylate Salt Form B

A solution of Compound 1 was prepared in acetone at 0.244 mmole/mL. A solution of p-toluenesulfonic acid monohydrate was prepared in acetonitrile at 0.225 mmole/mL. The solution of Compound 1 (500 µL) was mixed with 543.1 µL of p-toluenesulfonic acid solution in a 4 mL clear glass vial (1.0 equivalent). After mixing, the sample was capped and shaken at 200 RPM at room temperature for one hour. The sample was then uncapped and dried in fume hood under nitrogen purge. After drying, the sample was mixed with 600 µL of a 95/5 v/v mixture of acetone/water. The sample was re-capped and stirred with stirring bars at 200 RPM at room temperature for two days. The sample was filtered using Nylon-membraned centrifuge tube filter. The solids were recovered and dried in vacuum oven at 30° C. overnight to yield Tosylate Salt Form B.

Tosylate Salt Form B has an FT-Raman Spectrum as depicted in FIG. 92. Tosylate Salt Form B has a DSC thermogram substantially as depicted in FIG. 93, comprising multiple endotherms with onset temperatures at 68.3° C. and 172.11° C., respectively. Tosylate Salt Form B has a TGA thermogram as depicted in FIG. 93, comprising a total mass loss of approximately 3.5% of the total mass of the sample when heated from approximately 60.8° C. to approximately 107.9° C.

A list of X-Ray diffraction peaks for Tosylate Salt Form B is provided below in Table 24.

TABLE 24

X-Ray Diffraction Peaks for Tosylate Salt Form B.

| Two-theta angle (°) | d Space (Å) | Height (counts) |
|---|---|---|
| 6.8 | 12.909 | 2021 |
| 8.0 | 10.985 | 4964 |
| 8.3 | 10.674 | 1233 |
| 9.8 | 8.974 | 2736 |
| 10.1 | 8.790 | 2473 |
| 10.9 | 8.084 | 1270 |
| 11.7 | 7.581 | 1702 |
| 13.2 | 6.696 | 3143 |
| 15.7 | 5.656 | 2396 |
| 16.2 | 5.480 | 5067 |
| 16.4 | 5.408 | 1773 |
| 16.6 | 5.323 | 1846 |
| 17.4 | 5.097 | 8642 |
| 18.2 | 4.880 | 1805 |

TABLE 24-continued

X-Ray Diffraction Peaks for Tosylate Salt Form B.

| Two-theta angle (°) | d Space (Å) | Height (counts) |
|---|---|---|
| 18.9 | 4.690 | 5959 |
| 19.1 | 4.651 | 5874 |
| 19.7 | 4.505 | 1659 |
| 20.9 | 4.254 | 1693 |
| 21.3 | 4.177 | 562 |
| 21.5 | 4.126 | 2572 |
| 22.2 | 4.005 | 1651 |
| 22.4 | 3.969 | 823 |
| 23.5 | 3.775 | 2781 |
| 25.1 | 3.547 | 2437 |

(y) L-Tartrate Salt Form C

Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in water. The temperature of the mixture was cycled between about 5° C. and about 40° C. (1° C. per minute heating/cooling rate with an hour hold between each heating/cooling cycle) for about two days. The solids were isolated through vacuum filtration under nitrogen to yield L-Tartrate Salt Form C.

Alternatively, Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in a 1:4 mixture of dimethylsulfoxide and water. The temperature of the mixture was cycled between about 5° C. and about 40° C. (1° C. per minute heating/cooling rate with an hour hold between each heating/cooling cycle) for about two days. The solids were isolated through vacuum filtration under nitrogen to yield L-Tartrate Salt Form C.

Alternatively, Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in a 1:1 mixture of acetone and water. The temperature of the mixture was cycled between about 5° C. and about 40° C. (1° C. per minute heating/cooling rate with an hour hold between each heating/cooling cycle) for about two days. The solids were isolated through vacuum filtration under nitrogen to yield L-Tartrate Salt Form C.

Alternatively, Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in a 1:9 mixture of 1,4-dioxane and water. The temperature of the mixture was cycled between about 5° C. and about 40° C. (1° C. per minute heating/cooling rate with an hour hold between each heating/cooling cycle) for about two days. The solids were isolated through vacuum filtration under nitrogen to yield L-Tartrate Salt Form C.

Alternatively, Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in a 1:9 mixture of acetone and water. The temperature of the mixture was cycled between about 5° C. and about 40° C. (1° C. per minute heating/cooling rate with an hour hold between each heating/cooling cycle) for about two days. The solids were isolated through vacuum filtration under nitrogen to yield L-Tartrate Salt Form C.

Alternatively, Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in a 3:7 mixture of tetrahydrofuran and water at 40° C., and filtered while hot. The filtrate was stored at 4° C. for 5 days. The solids were isolated through vacuum filtration under nitrogen to yield L-Tartrate Salt Form C.

Alternatively, Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in a 9:1 mixture of acetonitrile and water at 40° C., and filtered while hot. The filtrate was stored at 4° C. for 5 days. The solids were isolated through vacuum filtration under nitrogen to yield L-Tartrate Salt Form C.

Alternatively, Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in a 9:1 mixture of isopropanol and water at 40° C., and filtered while hot. The filtrate was stored at 4° C. for 5 days. The solids were isolated through vacuum filtration under nitrogen to yield L-Tartrate Salt Form C.

L-Tartrate Salt Form C has a FT-Raman Spectra as depicted in FIG. 95. L-Tartrate Salt Form C has a DSC thermogram substantially as depicted in FIG. 96, comprising an endotherm with an onset temperature at 65° C. L-Tartrate Salt Form C has a TGA thermogram as depicted in FIG. 96, comprising a total mass loss of approximately 3.7% of the total mass of the sample when heated from approximately 22.6° C. to approximately 110° C.

Figure 97:
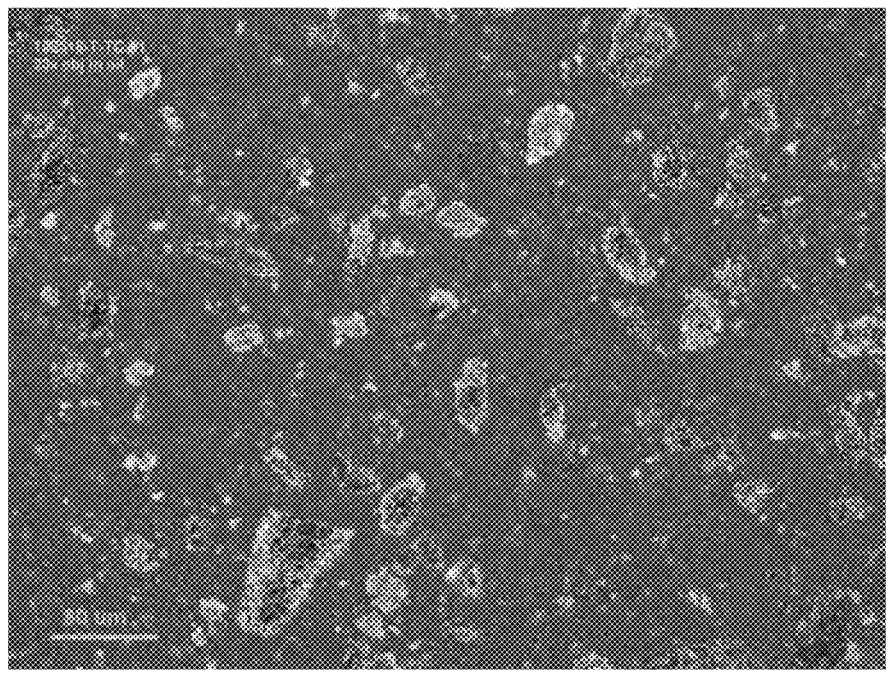
FIG. 97 depicts polarized-light microscopy of L-Tartrate Salt Form C of Compound 5.

FIG. 97 depicts polarized-light microscopy of L-Tartrate Salt Form C of Compound 5.

A list of X-Ray diffraction peaks for L-Tartrate Salt Form C is provided below in Table 25.

TABLE 25

X-Ray Diffraction Peaks for L-Tartrate Salt Form C.

| Two-theta angle (°) | d Space (Å) | Height (counts) |
|---|---|---|
| 2.6 | 34.413 | 269 |
| 3.4 | 25.633 | 134 |
| 6.9 | 12.743 | 928 |
| 10.5 | 8.462 | 517 |
| 11.5 | 7.680 | 168 |
| 13.9 | 6.380 | 431 |
| 14.8 | 5.974 | 98 |
| 16.0 | 5.554 | 283 |
| 18.4 | 4.819 | 228 |
| 19.2 | 4.630 | 182 |
| 20.8 | 4.262 | 734 |

(z) L-Tartrate Salt Form D

Compound 1 (about 2.5 g) was suspended in methyl tert-butyl ether (about 25 mL) and a 0.5 M solution of L-tartaric acid in tetrahydrofuran (1.0 equivalent) was added. An aliquot of the solution was dispensed into a vial, and the solution was allowed to evaporate. The resulting sample was dissolved in an 8:2 mixture of isopropanol/water (0.4 mL) and mixed at 40° C. for 30 min along with seeds of L-Tartrate Salt Form D. The temperature of the sample was cycled between 40° C. and 5° C. for five days. The crystalline solids were isolated by vacuum filtration under nitrogen to yield L-Tartrate Salt Form D.

L-Tartrate Salt Form D has an FT-Raman Spectra as depicted in FIG. 99. L-Tartrate Salt Form D has a DSC thermogram substantially as depicted in FIG. 100, comprising comprising an endotherm with an onset temperature at 107° C. L-Tartrate Salt Form D has a TGA thermogram as depicted in FIG. 100, comprising a total mass loss of approximately 14% of the total mass of the sample.

Figure 101:
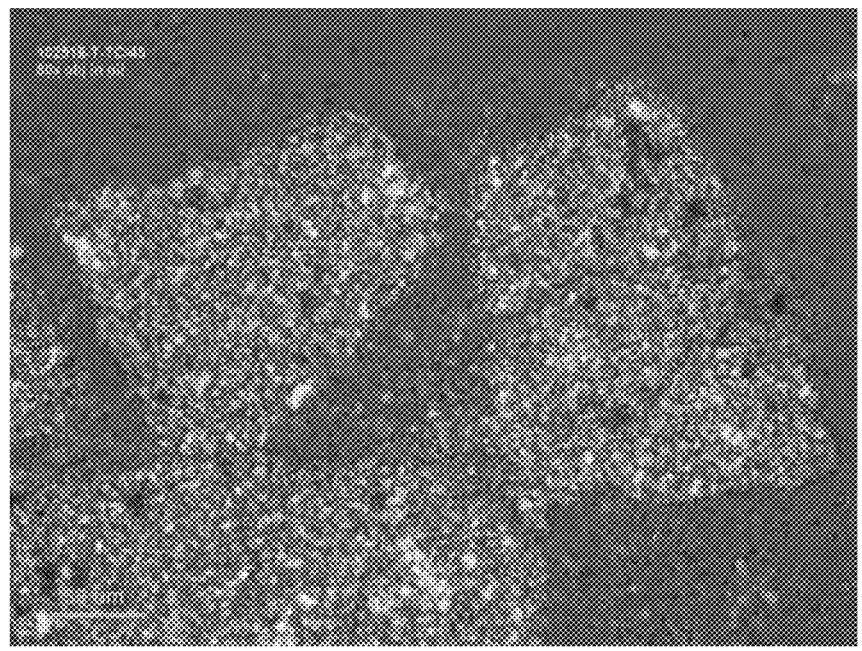
FIG. 101 depicts polarized-light microscopy of L-Tartrate Salt Form D of Compound 5.

FIG. 101 depicts polarized-light microscopy of L-Tartrate Salt Form D of Compound 5.

A list of X-Ray diffraction peaks for L-Tartrate Salt Form D is provided below in Table 26.

TABLE 26

X-Ray Diffraction Peaks for L-Tartrate Salt Form D.

| Two-theta angle (°) | d Space (Å) | Height (counts) |
|---|---|---|
| 12.5 | 7.065 | 144 |
| 13.8 | 6.439 | 827 |
| 14.8 | 5.980 | 850 |
| 16.8 | 5.270 | 1051 |
| 18.7 | 4.757 | 179 |
| 19.5 | 4.550 | 180 |
| 21.8 | 4.077 | 281 |
| 23.8 | 3.736 | 424 |
| 24.5 | 3.629 | 356 |
| 25.2 | 3.539 | 348 |
| 27.6 | 3.230 | 310 |
| 28.3 | 3.156 | 298 |
| 30.9 | 2.889 | 324 |
| 31.0 | 2.884 | 324 |
| 33.6 | 2.665 | 336 |
| 34.0 | 2.635 | 160 |
| 36.4 | 2.471 | 161 |
| 37.7 | 2.383 | 244 |

(aa) Hemifumarate Salt Form D

Hemifumarate Salt Form B was suspended in 1,4-dioxane (about 250 μL). The temperature of the mixture was cycled between about 5° C. and about 40° C. (1° C. per minute heating/cooling rate with an hour hold between each heating/cooling cycle) for two days. The solids were isolated via vacuum filtration to yield Hemifumarate Salt Form D.

Alternatively, Hemifumarate Salt Form B was suspended in a 10% mixture of water in 1,4-dioxane (about 250 μL). The temperature of the mixture was cycled between about 5° C. and about 40° C. (1° C. per minute heating/cooling rate with an hour hold between each heating/cooling cycle) for two days. The solids were isolated via vacuum filtration to yield Hemifumarate Salt Form D.

Alternatively, Hemifumarate Salt Form B was suspended in 1,4-dioxane (about 250 μL). The solvent was allowed to slowly evaporate through a loosened cap on the vial for 7 days at ambient temperature. The cap was removed and the solvent was allowed to evaporate for a further 7 days. The remaining solution was evaporated under reduced pressure for 24 hours to yield Hemifumarate Salt Form D.

Hemifumarate Salt Form D has an FT-Raman Spectrum as depicted in FIG. 103. Hemifumarate Salt Form D has a DSC thermogram substantially as depicted in FIG. 104, comprising multiple endotherms with an endotherm between 50° C. and 110° C., with a peak temperature at 91° C.; and a large endotherm with an onset temperature at 143° C. Hemifumarate Salt Form D has a TGA thermogram as depicted in FIG. 104, comprising a total mass loss of approximately 10.1% of the total mass of the sample when heated from approximately 27° C. to approximately 106° C.

Figure 105:
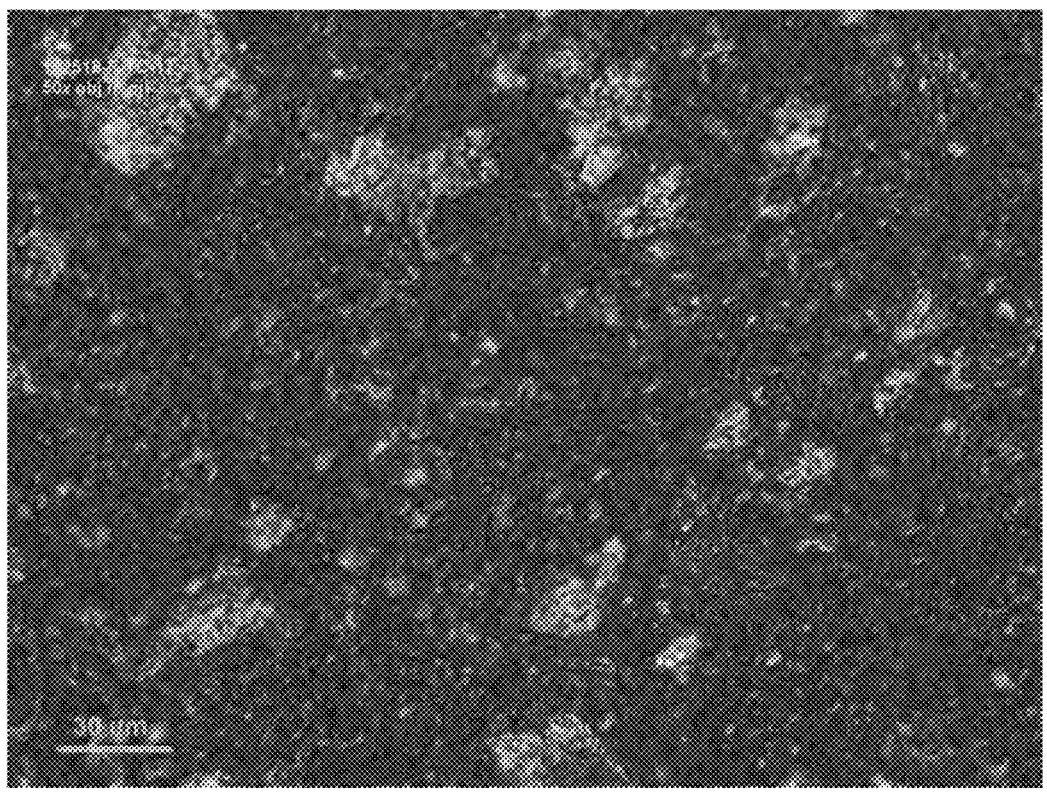
FIG. 105 depicts polarized-light microscopy of Hemifumarate Salt Form D of Compound 6.

FIG. 105 depicts polarized-light microscopy of Hemifumarate Salt Form D of Compound 6.

A list of X-Ray diffraction peaks for Hemifumarate Salt Form D is provided below in Table 27.

TABLE 27

X-Ray Diffraction Peaks for Hemifumarate Salt Form D.

| Two-theta angle (°) | d Space (Å) | Height (counts) |
|---|---|---|
| 2.8 | 31.564 | 4945 |
| 5.6 | 15.922 | 336 |
| 8.3 | 10.636 | 241 |
| 11.1 | 7.989 | 269 |
| 13.1 | 6.757 | 133 |
| 13.8 | 6.399 | 291 |
| 15.1 | 5.853 | 295 |
| 16.6 | 5.333 | 306 |
| 19.4 | 4.574 | 1271 |
| 19.9 | 4.470 | 226 |
| 20.8 | 4.266 | 993 |
| 22.3 | 3.984 | 1030 |
| 23.4 | 3.809 | 981 |
| 25.0 | 3.556 | 318 |
| 26.0 | 3.432 | 151 |
| 27.9 | 3.202 | 319 |
| 30.7 | 2.912 | 205 |

(bb) Hemifumarate Salt Form E

Hemifumarate Salt Form B was suspended in methanol (about 250 μL). The solvent was allowed to slowly evaporate through a loosened cap on the vial for 7 days at ambient temperature. The cap was removed and the solvent was allowed to evaporate for a further 7 days. The remaining solution was evaporated under reduced pressure for 24 hours to yield Hemifumarate Salt Form E.

Alternatively, Hemifumarate Salt Form B was suspended in a 51% mixture of water in methanol (about 250 μL). The solvent was allowed to slowly evaporate through a loosened cap on the vial for 7 days at ambient temperature. The cap was removed and the solvent was allowed to evaporate for a further 7 days. The remaining solution was evaporated under reduced pressure for 24 hours to yield Hemifumarate Salt Form E.

Alternatively, Hemifumarate Salt Form B was suspended in a 10% mixture of dimethylsulfoxide in isopropanol (about 250 μL). The solvent was allowed to slowly evaporate through a loosened cap on the vial for 7 days at ambient temperature. The cap was removed and the solvent was allowed to evaporate for a further 7 days. The remaining solution was evaporated under reduced pressure for 24 hours to yield Hemifumarate Salt Form E.

Alternatively, Hemifumarate Salt Form B was suspended in a 10% mixture of water in methanol (about 250 μL). The solvent was allowed to slowly evaporate through a loosened cap on the vial for 7 days at ambient temperature. The cap was removed and the solvent was allowed to evaporate for a further 7 days. The remaining solution was evaporated under reduced pressure for 24 hours to yield Hemifumarate Salt Form E.

Alternatively, Hemifumarate Salt Form B (61.9 mg) was combined with a 5% mixture of water in methanol (3 mL) at 30° C. for 60 minutes, yielding a thin suspension. The suspension was filtered through a 0.22 μm PTFE filter into a new vial. Seeds of Hemifumarate Form E (about 1 mg) were added at the surface of the filtrate, and the cap was loosened to permit slow evaporation to yield Hemifumarate Salt Form E.

Hemifumarate Salt Form E has an FT-Raman Spectrum as depicted in FIG. 107. Hemifumarate Salt Form E has a DSC thermogram substantially as depicted in FIG. 108, comprising an endotherm with an onset temperature at 134° C. Hemifumarate Salt Form E has a TGA thermogram as depicted in FIG. 108, comprising a total mass loss of approximately 0.7% of the total mass of the sample when heated from approximately 27° C. to approximately 159° C.

Figure 109:
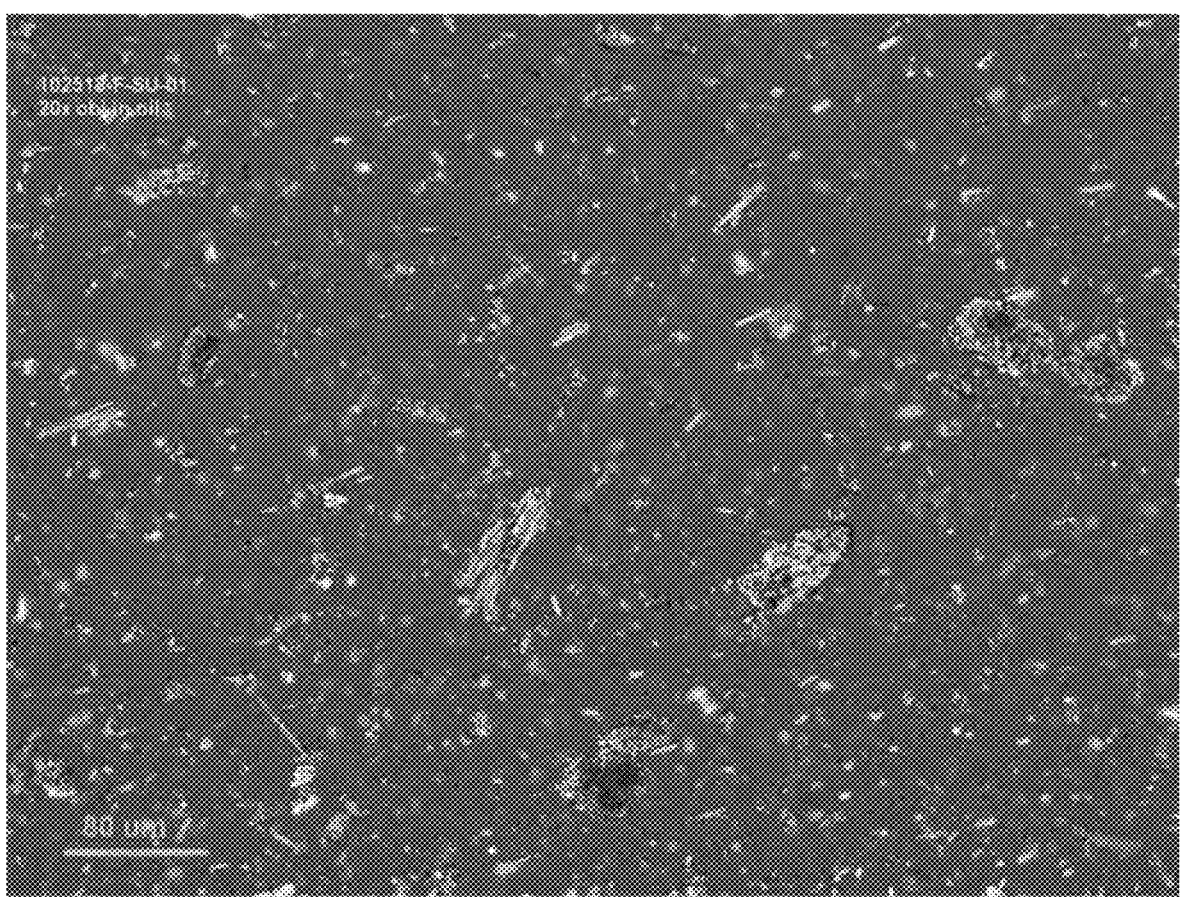
FIG. 109 depicts polarized-light microscopy of Hemifumarate Salt Form E of Compound 6.

FIG. 109 depicts polarized-light microscopy of Hemifumarate Salt Form E of Compound 6.

A list of X-Ray diffraction peaks for Hemifumarate Salt Form E is provided below in Table 28.

TABLE 28

X-Ray Diffraction Peaks for Hemifumarate Salt Form E.

| Two-theta angle (°) | d Space (Å) | Height (counts) |
|---|---|---|
| 3.6 | 24.709 | 131 |
| 7.0 | 12.551 | 1149 |
| 9.7 | 9.156 | 420 |
| 10.7 | 8.265 | 201 |
| 11.4 | 7.747 | 344 |
| 12.6 | 7.015 | 248 |
| 13.9 | 6.373 | 146 |
| 15.3 | 5.803 | 301 |
| 16.3 | 5.429 | 349 |
| 16.8 | 5.269 | 264 |
| 17.0 | 5.208 | 335 |
| 17.7 | 5.021 | 123 |
| 18.1 | 4.904 | 888 |
| 18.6 | 4.764 | 161 |
| 19.5 | 4.555 | 1283 |
| 19.9 | 4.462 | 528 |
| 20.1 | 4.417 | 268 |
| 20.5 | 4.343 | 298 |
| 20.9 | 4.256 | 330 |
| 21.5 | 4.133 | 1005 |
| 22.0 | 4.047 | 506 |
| 23.1 | 3.848 | 181 |
| 23.8 | 3.732 | 122 |
| 24.8 | 3.588 | 241 |
| 26.4 | 3.378 | 434 |
| 26.8 | 3.326 | 228 |
| 27.3 | 3.266 | 348 |
| 28.2 | 3.167 | 128 |
| 29.8 | 3.003 | 126 |
| 30.5 | 2.933 | 114 |

(cc) Hemifumarate Salt Form F

Hemifumarate Salt Form B was suspended in a 20% mixture of water in acetone (about 250 μL). The solvent was allowed to slowly evaporate through a loosened cap on the vial for 7 days at ambient temperature. The cap was removed and the solvent was allowed to evaporate for a further 7 days. The remaining solution was evaporated under reduced pressure for 24 hours to yield Hemifumarate Salt Form F.

Hemifumarate Salt Form F has an FT-Raman Spectrum as depicted in FIG. 111. Hemifumarate Salt Form F has a DSC thermogram substantially as depicted in FIG. 112, comprising an endotherm between 45° C. and 140° C. with a peak temperature at 106° C. Hemifumarate Salt Form F has a TGA thermogram as depicted in FIG. 112, comprising a total mass loss of approximately 1.5% of the total mass of the sample when heated from approximately 22° C. to approximately 139° C.

Figure 113:
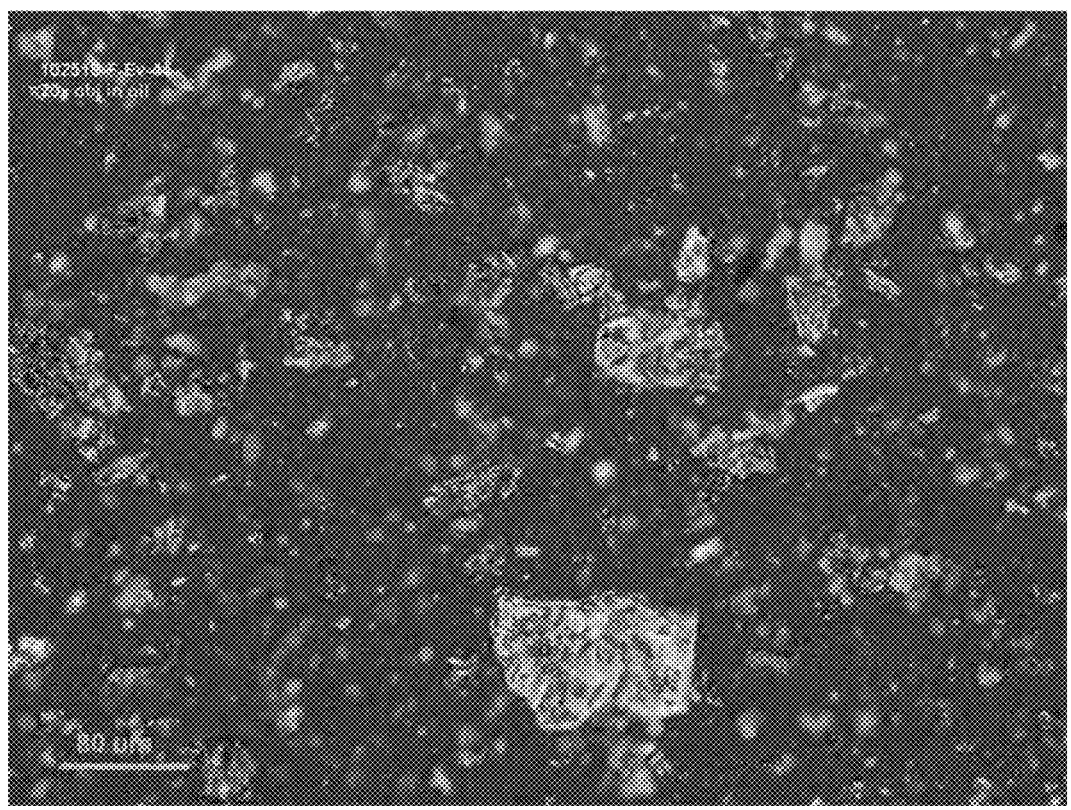
FIG. 113 depicts polarized-light microscopy of Hemifumarate Salt Form F of Compound 6.

FIG. 113 depicts polarized-light microscopy of Hemifumarate Salt Form F of Compound 6.

A list of X-Ray diffraction peaks for Hemifumarate Salt Form F is provided below in Table 29.

TABLE 29

X-Ray Diffraction Peaks for Hemifumarate Salt Form F.

| Two-theta angle (°) | d Space (Å) | Height (counts) |
|---|---|---|
| 7.0 | 12.627 | 269 |
| 15.8 | 5.611 | 274 |
| 17.6 | 5.030 | 300 |
| 21.8 | 4.076 | 385 |
| 23.9 | 3.716 | 238 |
| 29.7 | 3.007 | 137 |

(dd) Hemifumarate Salt Form G

Compound 1 (5 g) was combined with methyl tert-butyl ether (62.5 mL) and mixed at 40° C. for 30 minutes. Fumaric acid (99.5+%, about 0.5 equivalents) was added to the mixture at 40° C. and the mixture was seeded with Hemifumarate Salt Form B. The mixture was stirred for about 2 hours at 40° C. The mixture was slowly cooled to ambient temperature. The mixture was stirred at ambient temperature for 3 days. The solids were filtered by vacuum filtration for 1.5 hours. A portion of the solids was mixed with 20% water in isopropanol to create a slurry. The temperature of the mixture was cycled between about 5° C. and about 40° C. (1° C. per minute heating/cooling rate with an hour hold between each heating/cooling cycle) for two days. The solids were isolated via vacuum filtration to yield Hemifumarate Salt Form G of Compound 6.

Hemifumarate Salt Form G has an FT-Raman Spectrum as depicted in FIG. 127. Hemifumarate Salt Form G has a DSC thermogram substantially as depicted in FIG. 128, comprising multiple endotherms with onset temperatures at 80.4 C and 149.7° C. Hemifumarate Salt Form G has a TGA thermogram as depicted in FIG. 128, comprising a total mass loss of approximately 0.3% of the total mass of the sample when heated from approximately 27° C. to approximately 163° C.

Figure 129:
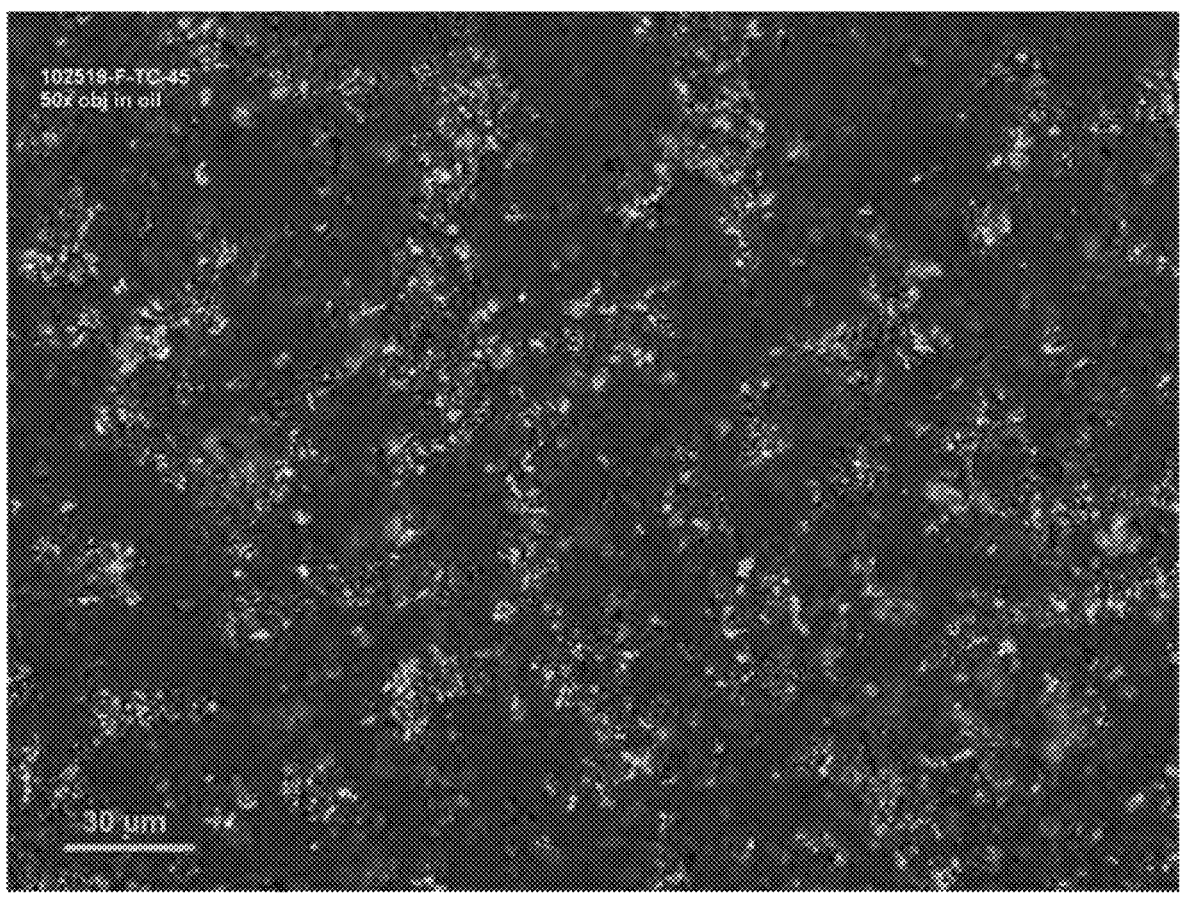
FIG. 129 depicts polarized-light microscopy of Hemifumarate Salt Form G of Compound 6.

FIG. 129 depicts polarized-light microscopy of Hemifumarate Salt Form G of Compound 6.

A list of X-Ray diffraction peaks for Hemifumarate Salt Form G is provided below in Table 30.

TABLE 30

X-Ray Diffraction Peaks for Hemifumarate Salt Form G.

| Two-theta angle (°) | d Space (Å) | Height (counts) |
|---|---|---|
| 7.0 | 12.718 | 3908 |
| 9.1 | 9.716 | 99 |
| 10.2 | 8.686 | 788 |
| 10.7 | 8.281 | 1013 |
| 12.2 | 7.256 | 852 |
| 15.7 | 5.629 | 621 |
| 15.9 | 5.558 | 661 |
| 16.3 | 5.453 | 454 |
| 17.0 | 5.230 | 131 |
| 17.6 | 5.041 | 1235 |
| 17.8 | 4.973 | 400 |
| 18.1 | 4.892 | 656 |
| 18.3 | 4.850 | 498 |
| 18.6 | 4.782 | 549 |
| 19.3 | 4.606 | 276 |
| 19.4 | 4.573 | 319 |
| 19.8 | 4.486 | 356 |
| 20.4 | 4.348 | 753 |
| 20.8 | 4.279 | 1965 |
| 21.0 | 4.230 | 1008 |
| 21.5 | 4.141 | 346 |

TABLE 30-continued

X-Ray Diffraction Peaks for Hemifumarate Salt Form G.

| Two-theta angle (°) | d Space (Å) | Height (counts) |
|---|---|---|
| 21.7 | 4.099 | 526 |
| 22.1 | 4.025 | 620 |
| 23.1 | 3.854 | 341 |
| 23.6 | 3.776 | 115 |
| 24.0 | 3.707 | 700 |
| 24.5 | 3.641 | 140 |
| 24.9 | 3.576 | 199 |
| 25.8 | 3.448 | 154 |
| 27.3 | 3.265 | 615 |
| 29.8 | 2.999 | 102 |
| 30.4 | 2.941 | 186 |
| 30.7 | 2.911 | 243 |

(ee) Hemifumarate Salt Form H

Compound 1 (100 mg) was dissolved in a mixture of acetone (0.5 mL) and methanol (0.8 mL), and filtered via 0.2 μm PTFE-membraned syringe filter. Solution of fumaric acid was prepared in methanol at 0.084 M. The filtered solution was mixed with the fumaric acid solution in a 4 mL clear glass vial (0.49 equivalent). After mixed, the sample was capped and shaken at 200 RPM at room temperature for one hour. The sample was then un-capped and dried in fume hood under nitrogen purge. After dried, the sample was mixed with 300 μL of ethyl methyl ketone, re-capped and stirred with a stirring bar at 300 RPM at room temperature overnight. The sample was filtered using Nylon-membraned centrifuge tube filter. The solids were recovered and dried in vacuum oven at 35° C. for about 24 hours. A portion of the solids after vacuum oven drying was slurried in acetonitrile at ambient temperature via stirring for three days. Afterwards, the sample was filtered using Nylon-membraned centrifuge tube filter. The solids were recovered and dried in vacuum oven at 35° C. overnight prior to analysis to yield Hemifumarate Salt Form H of Compound 6.

Hemifumarate Salt Form H has a Raman Spectrum as depicted in FIG. 131. Hemifumarate Salt Form H has a DSC thermogram substantially as depicted in FIG. 132, comprising an endotherm with a peak temperature of approximately 140.9° C. Hemifumarate Salt Form H has a TGA thermogram as depicted in FIG. 132, comprising a total mass loss of approximately 0.4% of the total mass of the sample when heated to approximately 100° C.

A list of X-Ray diffraction peaks for Hemifumarate Salt Form H is provided below in Table 31.

TABLE 31

X-Ray Diffraction Peaks for Hemifumarate Salt Form H.

| Two-theta angle (°) | d Space (Å) | Height (counts) |
|---|---|---|
| 8.0 | 11.050 | 781 |
| 11.6 | 7.617 | 3992 |
| 12.0 | 7.378 | 3333 |
| 13.5 | 6.549 | 3187 |
| 13.8 | 6.406 | 1510 |
| 14.1 | 6.256 | 1298 |
| 15.8 | 5.617 | 4760 |
| 16.2 | 5.476 | 794 |
| 17.6 | 5.049 | 7693 |
| 19.0 | 4.665 | 1327 |
| 19.3 | 4.597 | 1084 |
| 19.7 | 4.513 | 1934 |
| 20.2 | 4.382 | 2560 |
| 21.0 | 4.217 | 2310 |
| 21.4 | 4.155 | 6379 |
| 22.5 | 3.956 | 621 |

TABLE 31-continued

X-Ray Diffraction Peaks for Hemifumarate Salt Form H.

| Two-theta angle (°) | d Space (Å) | Height (counts) |
|---|---|---|
| 23.5 | 3.789 | 6187 |
| 25.1 | 3.548 | 967 |
| 27.8 | 3.202 | 700 |
| 29.6 | 3.014 | 791 |
| 8.0 | 11.050 | 781 |
| 11.6 | 7.617 | 3992 |
| 12.0 | 7.378 | 3333 |
| 13.5 | 6.549 | 3187 |
| 13.8 | 6.406 | 1510 |
| 14.1 | 6.256 | 1298 |
| 15.8 | 5.617 | 4760 |
| 16.2 | 5.476 | 794 |
| 17.6 | 5.049 | 7693 |
| 19.0 | 4.665 | 1327 |
| 19.3 | 4.597 | 1084 |
| 19.7 | 4.513 | 1934 |
| 20.2 | 4.382 | 2560 |
| 21.0 | 4.217 | 2310 |
| 21.4 | 4.155 | 6379 |
| 22.5 | 3.956 | 621 |
| 23.5 | 3.789 | 6187 |

(f) Maleate Salt Form E

Compound 1 (251.9 mg) was combined with methanol (1.0 mL) and maleic acid (56.6 mg, 1 equivalent) and the resulting product was heated to 40° C. and held at 40° C. for an hour. The solvent was evaporated to dryness under reduced pressure. The sample was mixed with heptanes (about 0.2 mL) and vortexed. 1,4-dioxane (0.2 mL) was added and the mixture was allowed to stir at ambient temperature. The temperature of the suspension was cycled between about 5° C. and about 40° C. for 21 hours (ramp rate of 1° C./min with an hour hold between each heating/cooling cycle). The sample was cooled to 5° C. and the solids were isolated from the solution through vacuum filtration and were air-dried for one hour to yield Maleate Salt Form E.

Maleate Salt Form E has an FT-Raman Spectrum as depicted in FIG. 115. Maleate Salt Form E has a DSC thermogram substantially as depicted in FIG. 116, comprising an endotherm with onset temperature at approximately 85'C. Maleate Salt Form E has a TGA thermogram as depicted in FIG. 116, comprising a total mass loss of approximately 2.4% of the total mass of the sample when heated from approximately 25° C. to approximately 130° C.

Figure 117:
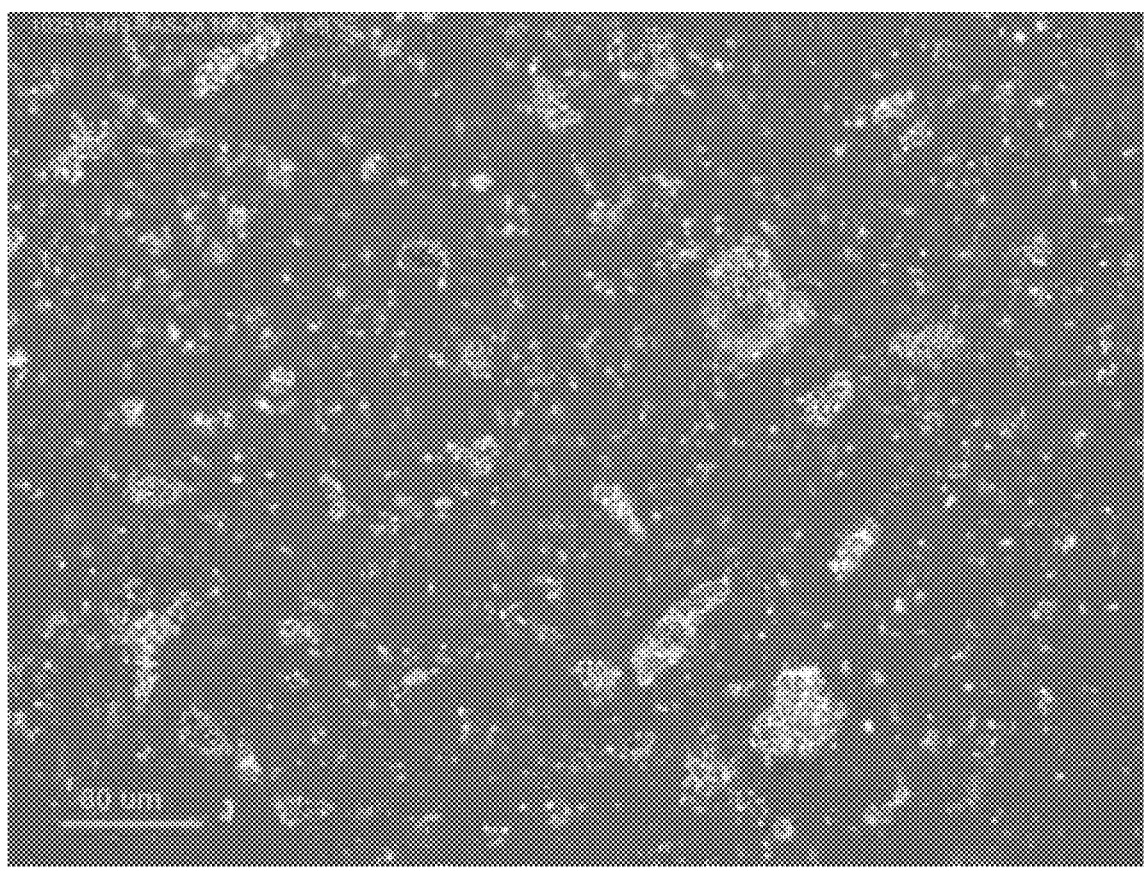
FIG. 117 depicts polarized-light microscopy of Maleate Salt Form E of Compound 8.

FIG. 117 depicts polarized-light microscopy of Maleate Salt Form E of Compound 8.

A list of X-Ray diffraction peaks for Maleate Salt Form E is provided below in Table 32.

TABLE 32

X-Ray Diffraction Peaks for Maleate Salt Form E.

| Two-theta angle (°) | d Space (Å) | Height (counts) |
|---|---|---|
| 4.0 | 21.883 | 153.4 |
| 7.2 | 12.197 | 106.7 |
| 8.1 | 10.945 | 872.9 |
| 10.7 | 8.293 | 232.8 |
| 12.1 | 7.288 | 173.4 |
| 12.8 | 6.937 | 313.1 |
| 13.2 | 6.699 | 277.7 |
| 15.6 | 5.666 | 625.3 |
| 16.9 | 5.241 | 205.0 |
| 17.7 | 5.016 | 617.8 |
| 17.9 | 4.954 | 1001.8 |
| 18.3 | 4.841 | 418.5 |
| 20.3 | 4.369 | 413.2 |
| 20.5 | 4.322 | 318.2 |
| 22.1 | 4.024 | 353.2 |
| 23.0 | 3.873 | 489.7 |
| 24.3 | 3.656 | 626.7 |
| 25.7 | 3.469 | 218.7 |
| 26.0 | 3.430 | 359.2 |
| 27.5 | 3.242 | 260.5 |
| 28.5 | 3.133 | 368.5 |
| 29.2 | 3.062 | 188.4 |
| 31.8 | 2.818 | 162.4 |
| 32.7 | 2.743 | 106.8 |
| 35.8 | 2.507 | 94.1 |

(gg) Maleate Salt Form F

Compound 1 (251.9 mg) was combined with methanol (1. mL) and maleic acid (56.6 mg, 1 equivalent) and the resulting product was heated to 40° C. and held at 40° C. for an hour. The solvent was evaporated to dryness under reduced pressure and heptane (0.2 mL) was added to the resulting product and the sample was vortexed. THF (0.2 mL) was added. The temperature of the suspension was cycled between about 5° C. and about 40° C. for 21 hours (ramp rate of 1° C./min with an hour hold between each heating/cooling cycle). The sample was cooled to 5° C. and the solids were isolated from the solution through vacuum filtration and were air-dried for one hour to yield Maleate Salt Form F.

Maleate Salt Form F has an FT-Raman Spectrum as depicted in FIG. 119. Maleate Salt Form F has a DSC thermogram substantially as depicted in FIG. 120, comprising an endotherm with an onset temperature at 85° C. and a broad endotherm between 95° C. to 125° C. Maleate Salt Form F has a TGA thermogram as depicted in FIG. 120, comprising a total mass loss of approximately 0.5% of the total mass of the sample when heated from approximately 25° C. to approximately 94° C.

Figure 121:
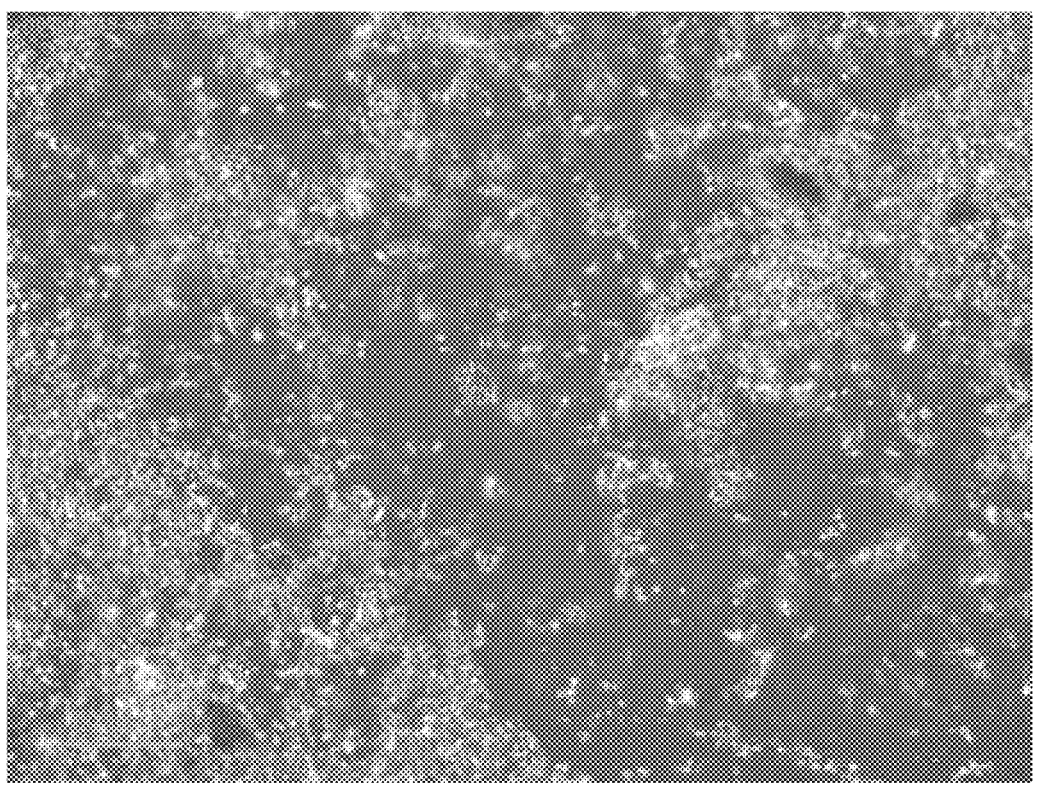
FIG. 121 depicts polarized-light microscopy of Maleate Salt Form F of Compound 8.

FIG. 121 depicts polarized-light microscopy of Maleate Salt Form F of Compound 8.

A list of X-Ray diffraction peaks for Maleate Salt Form F is provided below in Table

TABLE 33

X-Ray Diffraction Peaks for Maleate Salt Form F.

| Two-theta angle (°) | d Space (Å) | Height (counts) |
|---|---|---|
| 4.3 | 20.735 | 377.4 |
| 8.4 | 10.482 | 1008.2 |
| 9.3 | 9.503 | 145.6 |
| 10.6 | 8.368 | 99.4 |
| 12.6 | 7.004 | 791.8 |
| 13.2 | 6.728 | 541.0 |
| 13.5 | 6.583 | 250.7 |
| 14.8 | 5.982 | 626.1 |
| 15.7 | 5.636 | 231.4 |
| 16.5 | 5.359 | 165.2 |
| 17.7 | 5.006 | 472.9 |
| 18.9 | 4.687 | 346.1 |
| 19.6 | 4.532 | 180.3 |
| 20.4 | 4.357 | 346.5 |
| 23.1 | 3.848 | 385.0 |
| 24.3 | 3.657 | 283.0 |

TABLE 33-continued

X-Ray Diffraction Peaks for Maleate Salt Form F.

| Two-theta angle (°) | d Space (Å) | Height (counts) |
|---|---|---|
| 25.4 | 3.506 | 1181.6 |
| 26.3 | 3.387 | 182.1 |
| 27.0 | 3.297 | 239.7 |
| 29.7 | 3.003 | 483.7 |
| 31.7 | 2.820 | 213.4 |

(hh) Maleate Salt Form G

Compound 1 (251.9 mg) was combined with methanol (1. mL) and maleic acid (56.6 mg, 1 equivalent) and the resulting product was heated to 40° C. and held at 40° C. for an hour. The solvent was evaporated to dryness under reduced pressure. The sample was dissolved in heptanes (about 0.2 mL) and vortexed. 1,4-dioxane (0.2 mL) was added and the mixture was allowed to stir at ambient temperature. The temperature of the suspension was cycled between about 5° C. and about 40° C. for 21 hours (ramp rate of 1° C./min with an hour hold between each heating/cooling cycle). The sample was cooled to 5° C. and the solids were isolated from the solution through vacuum filtration and were air-dried for one hour to yield Maleate Salt Form E. Maleate Salt Form E was dried in vacuum oven to yield Maleate Salt Form G.

Maleate Salt Form G has an FT-Raman Spectrum as depicted in FIG. 123. Maleate Salt Form G has a DSC thermogram substantially as depicted in FIG. 124, comprising an endotherm with an onset temperature at 77° C. Maleate Salt Form G has a TGA thermogram as depicted in FIG. 124, comprising a total mass loss of approximately 1.6% of the total mass of the sample when heated from approximately 25° C. to approximately 100° C.

Figure 125:
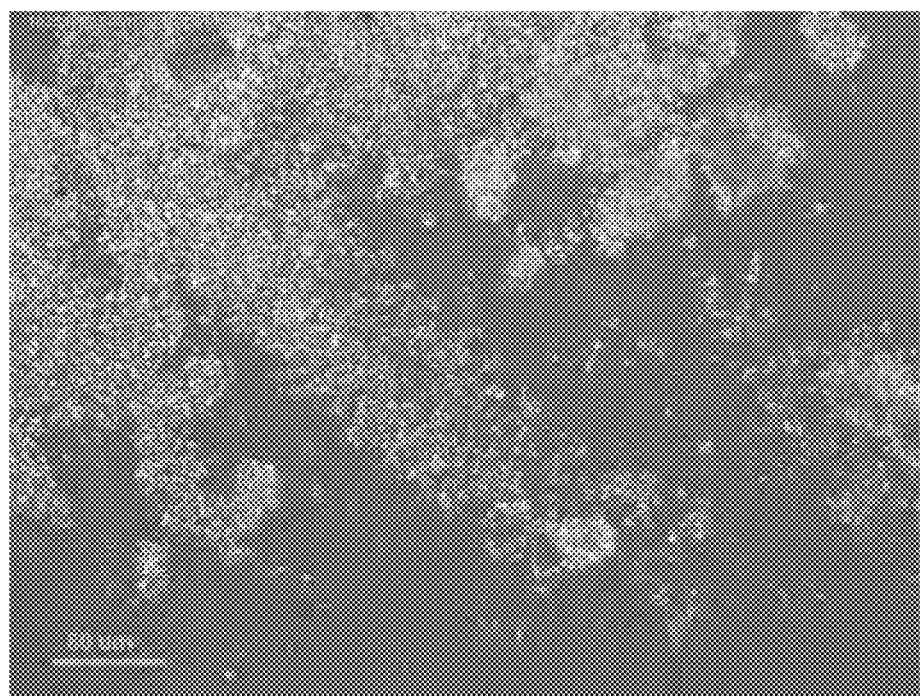
FIG. 125 depicts polarized-light microscopy of Maleate Salt Form G of Compound 8.

FIG. 125 depicts polarized-light microscopy of Maleate Salt Form G of Compound 8.

A list of X-Ray diffraction peaks for Maleate Salt Form G is provided below in Table 34.

TABLE 34

X-Ray Diffraction Peaks for Maleate Salt Form G.

| Two-theta angle (°) | d Space (Å) | Height (counts) |
|---|---|---|
| 4.1 | 21.602 | 195.8 |
| 8.2 | 10.792 | 290.8 |
| 11.0 | 8.010 | 89.5 |
| 12.9 | 6.881 | 245.4 |
| 17.9 | 4.963 | 238.6 |
| 18.4 | 4.815 | 156.7 |
| 20.6 | 4.317 | 166.6 |
| 24.7 | 3.602 | 107.9 |

6.3 Evaluation of Solid Forms (a) Solubility Measurements

A weighed sample of each of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B is treated with aliquots of the test solvent at ambient temperature or elevated temperature. Complete dissolution of the test material is determined by visual inspection. Solubility was estimated based on the total solvent used to provide complete dissolution of the sample. The actual solubility may be greater than the value calculated because of the use of solvent aliquots that were too large or due to a slow rate of dissolution.

In addition, a weighed sample of each of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, and L-Tartrate Salt Form D is treated with aliquots of the test solvent at ambient temperature or elevated temperature. Complete dissolution of the test material is determined by visual inspection. Solubility was estimated based on the total solvent used to provide complete dissolution of the sample. The actual solubility may be greater than the value calculated because of the use of solvent aliquots that were too large or due to a slow rate of dissolution.

(b) Stability Measurements

Stability of each of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B is determined by exposing the sample to a 40° C./75% relative humidity (RH) environment for four weeks or 11% RH at ambient temperature for four days.

In addition, stability of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, and L-Tartrate Salt Form D is determined by exposing the sample to a 40° C./75% relative humidity (RH) environment for four weeks or 11% RH at ambient temperature for four days.

6.4 Biological Evaluation (a) S1P1 Assays

The compounds are useful in the treatment of a variety of S1P1 receptor-mediated clinical conditions, including autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas. Therefore, the compounds of the invention may be assayed for their ability to modulate the S1P1 receptor activity.

(i) In Vitro Binding Assay

The solid forms described herein (e.g., HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B) are evaluated using a [$^{35}$S]-GTPgammaS binding assay to monitor dose-dependent selectivity against S1P1 receptors. The assay is completed with sample solid forms subjected to an eight-point, four-fold dose response curve with starting concentration of 10 µM. Selectivity is determined upon initial addition of solid forms followed by an incubation period. Following compound incubation, bounded [35S]-GTPgammaS is determined by filtration and scintillation counting. Percentage activation and inhibition values are determined relative to the reference agonist at S1P1.

In addition, Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, and L-Tartrate Salt Form D are evaluated using a [$^{35}$S]-GTPgammaS binding assay to monitor dose-dependent selectivity against S1P1 receptors. The assay is completed with sample solid forms subjected to an eight-point, four-fold dose response curve with starting concentration of 10 µM. Selectivity is determined upon initial addition of solid forms followed by an incubation period. Following compound incubation, bounded [35S]-GTPgammaS is determined by filtration and scintillation counting. Percentage activation and inhibition values are determined relative to the reference agonist at S1P1.

(ii) In Vivo Blood Lymphocyte Depletion Assay

In addition to their S1P1 binding properties, modulators of the S1P1 receptor also have accelerating lymphocyte homing properties. These properties may be measured using a blood lymphocyte depletion assay. The solid forms described herein (e.g HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B) are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms.

In addition, Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, and L-Tartrate Salt Form D are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms.

(b) In Vitro Metabolic Disposition in Liver Microsomal Fractions

The stability of each of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B is determined according to standard procedures known in the art. For example, stability of each of HCl Salt Form A, HCl Salt Form B, L-Malate Salt Form A, L-Malate Salt Form B, Oxalate Salt Form A, Oxalate Salt Form B, Oxalate Salt Form C, L-Tartrate Salt Form A, L-Tartrate Salt Form B, Hemifumarate Salt Form A, Hemifumarate Salt Form B, Hemifumarate Salt Form C, HBr Salt Form A, HBr Salt Form B, Maleate Salt Form A, Maleate Salt Form B, Maleate Salt Form C, Maleate Salt Form D, Malonate Salt Form A, Edisylate Salt Form A, Edisylate Salt Form B, Edisylate Salt Form C, Tosylate Salt Form A or Tosylate Salt Form B is established by an in vitro assay. An in vitro hepatic microsome stability assay measures the stability of one or more subject compounds when reacting with mouse, rat or human microsomes.

In addition, the stability of each of Maleate Salt Form E, Maleate Salt Form F, Maleate Salt Form G, Hemifumarate Salt Form D, Hemifumarate Salt Form E, Hemifumarate Salt Form F, Hemifumarate Salt Form G, Hemifumarate Salt Form H, L-Tartrate Salt Form C, and L-Tartrate Salt Form D is established by an in vitro assay. An in vitro hepatic microsome stability assay measures the stability of one or more subject compounds when reacting with mouse, rat or human microsomes.

Incubations with liver microsomes are conducted in a final volume of 0.1 mL per incubation time point. 10 µM of the subject compound from a stock solution in DMSO (final DMSO concentration of 0.1%) is incubated at 37° C. from 0-60 min with pooled microsomal protein (1.0 mg/mL), suspended in incubation buffer (0.1 M potassium phosphate, pH 7.4, 5 mM MgCl2, and 0.1 mM EDTA). The microsomal reaction is initiated by the addition of NADPH (3 mM final concentration). Incubations with (a) no protein or (b) no NADPH serve as controls. Reactions are terminated by the addition of 0.2 mL of stop solution (acetonitrile). The samples are vortex-mixed for 30 sec and then centrifuged at 10,000×g for 10 min. The supernatant is dried using a Labconco CentriVap concentrator and the dry residue reconstituted in water, transferred to an HPLC glass vial and analyzed by HPLC-UV. The disappearance of the subject compound is used to evaluate the in vitro metabolism thereof.

What is claimed is:

1. A crystalline solid form comprising an HBr salt of (E)-1-(4-(1-(((4-cyclohexyl-3-(trifluoromethyl)benzyl)oxy)imino)ethyl)-2-ethylbenzyl)azetidine-3-carboxylic acid (Compound 1) or a tautomer thereof.

2. A method of treating a disease selected from multiple sclerosis, psoriasis, and polymyositis, wherein the method comprises administering to a patient in need thereof a therapeutically effective amount of the crystalline solid form of claim 1.

3. A crystalline solid form comprising a maleate salt of (E)-1-(4-(1-(((4-cyclohexyl-3-(trifluoromethyl)benzyl)oxy)imino)ethyl)-2-ethylbenzyl)azetidine-3-carboxylic acid (Compound 1), or tautomer thereof.

4. A method of treating a disease selected from multiple sclerosis, psoriasis, and polymyositis, wherein the method comprises administering to a patient in need thereof a therapeutically effective amount of the crystalline solid form of claim 3.

5. A crystalline solid form comprising a malonate salt of (E)-1-(4-(1-(((4-cyclohexyl-3-(trifluoromethyl)benzyl)oxy)imino)ethyl)-2-ethylbenzyl)azetidine-3-carboxylic acid (Compound 1), or a tautomer thereof.

6. A method of treating a disease selected from multiple sclerosis, psoriasis, and polymyositis, wherein the method comprises administering to a patient in need thereof a therapeutically effective amount of the crystalline solid form of claim 5.

7. A crystalline solid form comprising an edisylate salt of (E)-1-(4-(1-(((4-cyclohexyl-3-(trifluoromethyl)benzyl)oxy)imino)ethyl)-2-ethylbenzyl)azetidine-3-carboxylic acid (Compound 1), or a tautomer thereof.

8. A method of treating a disease selected from multiple sclerosis, psoriasis, and polymyositis, wherein the method comprises administering to a patient in need thereof a therapeutically effective amount of the crystalline solid form of claim 7.

9. A crystalline solid form comprising a tosylate salt of (E)-1-(4-(1-(((4-cyclohexyl-3-(trifluoromethyl)benzyl)oxy)imino)ethyl)-2-ethylbenzyl)azetidine-3-carboxylic acid (Compound 1), or a tautomer thereof.

10. The crystalline solid form according to claim 9 having an x-ray powder diffraction pattern substantially as shown in FIG. 88.

11. The crystalline solid form according to claim 9 having an x-ray powder diffraction pattern substantially as shown in FIG. 91.

12. A method of treating a disease selected from multiple sclerosis, psoriasis, and polymyositis, wherein the method comprises administering to a patient in need thereof a therapeutically effective amount of the crystalline solid form of claim 9.

13. The crystalline solid form of claim 1, wherein the crystalline solid form has an X-ray powder diffraction pattern comprising at least three characteristic peaks selected from 4.1, 6.1, 8.2, 20.5, and 22.6° 2θ (±0.2° 2θ).

14. The crystalline solid form of claim 1, wherein the solid crystalline form has an X-ray powder diffraction pattern comprising at least three characteristic peaks 2.3, 8.1, 12.2, 15.7, and 18.7° 2θ (±0.2° 2θ).

15. The crystalline solid form of claim 3, wherein the crystalline solid form has an X-ray powder diffraction pattern comprising at least three characteristic peaks selected from 4.1, 8.2, 12.9, 20.6, and 24.8° 2θ (±0.2° 2θ).

16. The crystalline solid form of claim 3, wherein the crystalline solid form has an X-ray powder diffraction pattern comprising at least three characteristic peaks selected from 6.9, 10.4, 13.9, 18.9, and 20.9° 2θ (±0.2° 2θ).

17. The crystalline solid form of claim 3, wherein the crystalline solid form has an X-ray powder diffraction pattern comprising at least three characteristic peaks selected from 4.1, 8.1, 20.3, 24.4, and 27.6° 2θ (±0.2° 2θ).

18. The crystalline solid form of claim 3, wherein the solid crystalline form has an X-ray powder diffraction pattern comprising at least three characteristic peaks selected from 3.7, 8.4, 11.0, 16.7, and 22.1° 2θ (±0.2° 2θ).

19. The crystalline solid form of claim 3, wherein the solid crystalline form has an X-ray powder diffraction pattern comprising at least three characteristic peaks selected from 4.3, 8.4, 12.6, 13.2, 14.8, and 25.4° 2θ (±0.2° 2θ).

20. The crystalline solid form of claim 3, wherein the solid crystalline form has an X-ray powder diffraction pattern comprising at least three characteristic peaks selected from 4.0, 8.1, 15.6, 17.9, 23.0, and 24.3° 2θ (±0.2° 2θ).

21. The crystalline solid form of claim 5, wherein the solid crystalline form has an X-ray powder diffraction pattern comprising at least three characteristic peaks selected from 3.8, 7.6, 11.3, 15.2, and 23.0° 2θ (±0.2° 2θ).

22. The crystalline solid form of claim 7, wherein the solid crystalline form has an X-ray powder diffraction pattern comprising at least three characteristic peaks selected from 6.8, 11.7, 13.5, 20.3, and 23.5° 2θ (±0.2° 2θ).

23. The crystalline solid form of claim 7, wherein the solid crystalline form has an X-ray powder diffraction pattern comprising at least three characteristic peaks selected from 7.3, 9.8, 13.5, 14.6, 22.4, and 26.5° 2θ (±0.2° 2θ).

24. The crystalline solid form of claim 7, wherein the solid crystalline form has an X-ray powder diffraction pattern comprising at least three characteristic peaks selected from 3.4, 6.8, 13.5, 16.9, and 20.3° 2θ (±0.2° 2θ).

25. The crystalline solid form of claim 9, wherein the solid crystalline form has an X-ray powder diffraction pattern comprising at least three characteristic peaks selected from 8.1, 9.9, 13.3, 16.3, 17.5, 19.1, and 21.6° 2θ (±0.2° 2θ).

26. The crystalline solid form of claim 9, wherein the solid crystalline form has an X-ray powder diffraction pattern comprising at least three characteristic peaks selected from 6.8, 8.0, 9.8, 16.2, 17.4, 18.9, 19.1, 20.9, and 21.3° 2θ (±0.2° 2θ).

27. The crystalline solid form of claim 1, wherein the crystalline solid form has an X-ray powder diffraction pattern comprising at least three peaks selected from 4.1, 6.1, 8.2, 20.5, 22.6, and 26.8° 2θ (±0.2° 2θ).

28. The crystalline solid form of claim 1, wherein the solid crystalline form has an X-ray powder diffraction pattern comprising at least three peaks 2.3, 8.1, 10.2, 12.2, 15.7, 17.5, 18.7, 19.5, 23.6, and 24.6° 2θ (±0.2° 2θ).

29. The crystalline solid form of claim 3, wherein the crystalline solid form has an X-ray powder diffraction pattern comprising at least three peaks selected from 4.1, 7.5, 8.2, 10.4, 12.0, 12.9, 15.7, 17.5, 18.1, 19.0, 19.5, 20.6, 21.7, 23.6, 24.8, 26.5, 27.6, 28.3, 29.0, and 30.6° 2θ (±0.2° 2θ).

30. The crystalline solid form of claim 3, wherein the crystalline solid form has an X-ray powder diffraction pattern comprising at least three peaks selected from 6.9, 10.4, 11.4, 13.9, 15.8, 18.9, 19.1, 20.9, and 23.9° 2θ (±0.2° 2θ).

31. The crystalline solid form of claim 3, wherein the crystalline solid form has an X-ray powder diffraction pattern comprising at least three peaks selected from 4.1, 8.1, 10.9, 12.1, 16.2, 20.3, 24.4, 26.0, 26.5, 27.6, 28.6, and 30.6° 2θ (±0.2° 2θ).

32. The crystalline solid form of claim 3, wherein the solid crystalline form has an X-ray powder diffraction pattern comprising at least three peaks selected from 3.7, 7.4, 8.4, 8.7, 11.0, 13.8, 14.7, 14.8, 15.7, 16.7, 17.5, 17.6, 18.5, 19.5, 20.3, 20.7, 21.2, 22.1, 23.2, 23.8, 24.3, 25.2, 25.9, 26.3, 27.0, 27.9 29.4, 30.2, 31.0, 31.6, 32.6, 34.3, 34.8, and 37.2° 2θ (±0.2° 2θ).

33. The crystalline solid form of claim 5, wherein the solid crystalline form has an X-ray powder diffraction pattern comprising at least three peaks selected from 3.8, 7.6, 11.3, 13.2, 15.2, 16.5, 17.2, 17.6, 18.4, 19.2, 19.8, 20.7, 23.0, 24.9, 26.5, 27.0, 27.5, 28.4, 30.4, 31.1, 33.4, 34.7, and 38.7° 2θ (±0.2° 2θ).

34. The crystalline solid form of claim 7, wherein the solid crystalline form has an X-ray powder diffraction pattern comprising at least three peaks selected from 6.8, 11.7, 13.5, 16.9, 17.6, 18.0, 20.3, 21.6, 23.5, 23.9, 24.6, 32.8, and 35.5° 2θ (±0.2° 2θ).

35. The crystalline solid form of claim 7, wherein the solid crystalline form has an X-ray powder diffraction pattern comprising at least three peaks selected from 7.3, 9.8, 11.7, 12.7, 13.5, 14.6, 17.0, 19.4, 20.0, 20.9, 22.4, 22.9, 23.5, 24.6, 25.6, 26.5, 26.8, 28.8, 36.0, and 36.9° 2θ (±0.2° 2θ).

36. The crystalline solid form of claim 7, wherein the solid crystalline form has an X-ray powder diffraction pattern comprising at least three peaks selected from 3.4, 6.8, 12.3, 13.5, 16.3, 16.9, 18.0, 18.7, 19.5, 20.3, 20.7, 21.4, 21.7, 22.8, 23.6, 26.6, 27.1, 33.0, 36.3, and 37.8° 2θ (±0.2° 2θ).

37. The crystalline solid form of claim 9, wherein the solid crystalline form has an X-ray powder diffraction pattern comprising at least three peaks selected from 6.9, 8.1, 8.3, 9.9, 10.2, 11.0, 11.7, 13.3, 15.8, 16.3, 17.5, 18.2, 19.1, 19.8, 20.1, 21.6, 22.0, 22.2, 23.0, 23.6, and 25.2° 2θ (±0.2° 2θ).

38. The crystalline solid form of claim 9, wherein the solid crystalline form has an X-ray powder diffraction pattern comprising at least three peaks selected from 6.8, 8.0, 8.3, 9.8, 10.1, 10.9, 11.7, 13.2, 15.7, 16.2, 16.4, 16.6, 17.4, 18.2, 18.9, 19.1, 19.7, 20.9, 21.3, 21.5, 22.2, 22.4, 23.5, and 25.1° 2θ (±0.2° 2θ).

* * * * *